(12) United States Patent
Weiner et al.

(10) Patent No.: US 7,348,140 B1
(45) Date of Patent: Mar. 25, 2008

(54) CLINICAL INDICATIONS FOR GENOTYPING POLYMORPHIC VARIANTS OF G-PROTEIN COUPLED RECEPTORS

(75) Inventors: David M. Weiner, San Diego, CA (US); Mark R. Brann, Del Mar, CA (US); Ethan S. Burstein, San Diego, CA (US); Jakob L. Hansen, Copenhagen (DK); Fabrice Piu, San Diego, CA (US); Andria Lee, San Diego, CA (US)

(73) Assignee: Acadia Pharmaceuticals, Inc., San Diego, CA (US)

( * ) Notice: Subject to any disclaimer, the term of this patent is extended or adjusted under 35 U.S.C. 154(b) by 184 days.

(21) Appl. No.: 10/206,858

(22) Filed: Jul. 25, 2002

Related U.S. Application Data

(60) Provisional application No. 60/308,037, filed on Jul. 25, 2001, provisional application No. 60/323,206, filed on Sep. 12, 2001, provisional application No. 60/347,053, filed on Jan. 8, 2002, provisional application No. 60/348,633, filed on Jan. 14, 2002, provisional application No. 60/372,703, filed on Apr. 15, 2002.

(51) Int. Cl.
 *C12Q 1/68* (2006.01)
 *G01N 33/53* (2006.01)
 *G01N 33/68* (2006.01)

(52) U.S. Cl. .............................. 435/6; 435/7.1; 436/86; 436/89; 436/94

(58) Field of Classification Search ...................... None
See application file for complete search history.

(56) References Cited

U.S. PATENT DOCUMENTS

| | | | |
|---|---|---|---|
| 5,143,854 | A | 9/1992 | Pirrung et al. |
| 5,510,270 | A | 4/1996 | Fodor et al. |
| 5,539,083 | A | 7/1996 | Cook et al. |
| 5,556,752 | A | 9/1996 | Lockhart et al. |
| 5,578,832 | A | 11/1996 | Trulson et al. |
| 5,677,195 | A | 10/1997 | Winkler et al. |
| 6,040,138 | A | 3/2000 | Lockhart et al. |

FOREIGN PATENT DOCUMENTS

| | | |
|---|---|---|
| WO | WO 90/15070 | 12/1990 |
| WO | WO 92/10092 | 6/1992 |
| WO | WO 93/09668 | 5/1993 |
| WO | WO 01/38576 | * 5/2001 |

OTHER PUBLICATIONS

Dobutamine: Side Effects & Drug Interactions. Available via url: <rxlist.com/cgi/generic/dobutamine_ad.htm.*
Phenylephrine. Drug Information Online. Available via url: <drugs.com/cdi/phenylephrine>.*
Oxymetazoline. Drug Information Online. Available via url: <drugs.com/cons/oxymetazoline-nasal.html>.*
Dobutamine Injection. Drug Information Online. available via url: <drugs.com/pro/dobutamine.html>.*
Blanchard et al., High-density oligonucleotide arrays, Biosensors & Bioelectronics 11:687 (1996).
Egholm et al., PNA hybridizes to complementary oligonucleotides obeying the Watson-Crick hydrogen-bonding rules, Nature 365:566 (1993).
Ferguson et al., A fiber-optic DNA biosensor microarray for the analysis of gene expression, Nature Biotech. 14:1681 (1996).
Fitzgerald et al., Total chemical synthesis and catalytic properties of the enzyme enantiomers L- and D-4- oxalocrotonate tautomerase, J.A.C.S. 117:11075 (1995).
Fodor et al., Light-directed, spatially addressable parallel chemical synthesis, Science 251:767 (1991).
Froehler et al., Synthesis of DNA via deoxynucleoside H-phosphonate intermediates, Nucleic Acid. Res. 14:5399 (1986).
Gram et al., In vitro selection and affinity maturation of antibodies from a naive combinatorial immunoglobulin library, Proc. Natl. Acad. Sci. USA 89:3576-80 (1992).
Lóckhart et al., Expression monitoring by hybridization to high-density oligonucleotide arrays, Nature Biotech. 14:1675 (1996).
McBride et al., An investigation of several deoxynucleoside phosphoramidites useful for synthesizing deoxyoligonucleotides, Tetrahedron Lett. 24:245 (1983).
Pease et al., Light-generated oligonucleotide arrays for rapid DNA sequence analysis, Proc. Natl. Acad. Sci. USA 91:5022 (1994).
Shalon et al., A DNA microarray system for analyzing complex DNA samples using two-color fluorescent probe hybridization, Genome Research 6:639 (1996).
Horan and Flowers. *Am. Fam. Physician*. 60:1727-34 (1999).
Pea et al. *J. Antimicrob. Chemotherapy*. 45:329-335 (2000).
Ruffolo and Waddell. *J. Pharmacol. and Exp. Ther*. 222:29-36 (1982).

* cited by examiner

*Primary Examiner*—Carla Myers
(74) *Attorney, Agent, or Firm*—Knobbe, Martens, Olson & Bear LLP

(57) ABSTRACT

The invention provides compositions and methods for screening individuals for the presence of G-protein coupled receptor (GPCR) variants. The compositions and methods are useful for determining clinical outcome of drug therapy or for tailoring drug therapy for the individual based upon the presence or absence of one or more GPCR variants in the subject.

4 Claims, 10 Drawing Sheets

SEQUENCE LISTING

<160> NUMBER OF SEQ ID NOS: 112

<210> SEQ ID NO 1
<211> LENGTH: 2289
<212> TYPE: DNA
<213> ORGANISM: Homo sapiens
<220> FEATURE:
<221> NAME/KEY: misc_feature
<222> LOCATION: 1141
<223> OTHER INFORMATION: n = A,T,C or G

<400> SEQUENCE: 1

```
gaattccgaa tcatgtgcag aatgctgaat cttcccccag ccaggacgaa taagacagcg      60
cggaaaagca gattctcgta attctggaat tgcatgttgc aaggagtctc ctggatcttc     120
gcacccagct tcgggtaggg agggagtccg ggtcccgggc taggccagcc cggcaggtgg     180
agagggtccc cggcagcccc cgcgcgcccct ggccatgtct ttaatgccct gccccttcat    240
gtggccttct gagggttccc agggctggcc agggttgttt cccacccgcg cgcgcgctct     300
cacccccagc caaacccacc tggcagggct ccctccagcc gagacctttt gattcccggc     360
tcccgcgctc ccgcctccgc gccagcccgg gaggtggccc tggacagccg gacctcgccc     420
ggccccggct gggaccatgg tgtttctctc gggaaatgct tccgacagct ccaactgcac     480
ccaaccgccg gcaccggtga acatttccaa ggccattctg ctcgggtga tcttgggggg     540
cctcattctt ttcggggtgc tgggtaacat cctagtgatc ctctccgtag cctgtcaccg     600
acacctgcac tcagtcacgc actactacat cgtcaacctg gcggtggccg acctcctgct     660
cacctccacg gtgctgccct tctccgccat cttcgaggtc taggctact gggccttcgg     720
cagggtcttc tgcaacatct gggcggcagt ggatgtgctg tgctgcaccg cgtccatcat     780
gggcctctgc atcatctcca tcgaccgcta catcggcgtg agctaccgc tgcgctaccc     840
aaccatcgtc acccagagga ggggtctcat ggctctgctc tgcgtctggg cactctccct     900
ggtcatatcc attggacccc tgttcggctg gaggcagccg gcccccgagg acgagaccat     960
ctgccagatc aacgaggagc cgggctacgt gctcttctca gcgctgggct ccttctacct    1020
gcctctggcc atcatcctgg tcatgtactg ccgcgtctac gtggtggcca agagggagag    1080
ccgggggcctc aagtctggcc tcaagaccga caagtcggac tcggagcaag tgacgctccg    1140
natccatcgg aaaacgcccc cggcaggagg cagcgggatg ccagcgcca agaccaagac     1200
gcacttctca gtgaggctcc tcaagttctc ccgggagaag aaagcggcca aaacgctggg    1260
catcgtggtc ggctgcttcg tcctctgctg gctgccttttt ttcttagtca tgcccattgg   1320
gtctttcttc cctgatttca gccctctga aacagttttt aaaatagtat tttggctcgg     1380
atatctaaac agctgcatca acccccatcat atacccatgc tccagccaag agttcaaaaa    1440
ggcctttcag aatgtcttga atccagtg tctccgcaga aagcagtctt ccaaacatgc      1500
cctgggctac accctgcacc cgcccagcca ggccgtggaa gggcaacaca aggacatggt    1560
gcgcatcccc gtgggatcaa gagagacctt ctacaggatc tccaagacgg atggcgtttg    1620
tgaatggaaa ttttctctctt ccatgccccg tggatctgcc aggattacag tgtccaaaga  1680
ccaatcctcc tgtaccacag cccgggtgag aagtaaaagc ttttttggagg tctgctgctg  1740
tgtagggccc tcaacccccca gccttgacaa gaaccatcaa gttccaacca ttaaggtcca  1800
caccatctcc ctcagtgaga acggggagga agtctaggac aggaaagatg cagaggaaag   1860
gggaataatc ttaggtaccc accccacttc cttctcggaa ggccagctct tcttggagga   1920
```

| | | |
|---|---|---|
| caagacagga ccaatcaaag aggggacctg ctgggaatgg ggtgggtggt agacccaact | 1980 | |
| catcaggcag cgggtagggc acagggaaga gggagggtgt ctcacaacca accagttcaa | 2040 | |
| atgatacgga acagcatttc cctgcagcta atgctttctt ggtcactctg tgcccacttc | 2100 | |
| aacgaaaacc accatgggaa acagaatttc atgcacaatc caaaagacta taaatatagg | 2160 | |
| attatgattt catcatgaat attttgagca cacactctaa gtttggagct atttcttgat | 2220 | |
| ggaagtgagg ggatttttatt ttcaggctca acctactgac agccacattt gacatttatg | 2280 | |
| ccggaattc | 2289 | |

<210> SEQ ID NO 2
<211> LENGTH: 2289
<212> TYPE: DNA
<213> ORGANISM: Homo sapiens
<220> FEATURE:
<221> NAME/KEY: misc_feature
<222> LOCATION: 1141
<223> OTHER INFORMATION: n = A,T,C or G

<400> SEQUENCE: 2

| | | |
|---|---|---|
| gaattccgaa tcatgtgcag aatgctgaat cttcccccag ccaggacgaa taagacagcg | 60 | |
| cggaaaagca gattctcgta attctggaat tgcatgttgc aaggagtctc ctggatcttc | 120 | |
| gcacccagct tcgggtaggg agggagtccg ggtcccgggc taggccagcc cggcaggtgg | 180 | |
| agagggtccc cggcagcccc gcgcgcccct ggccatgtct ttaatgccct gccccttcat | 240 | |
| gtggccttct gagggttccc agggctggcc agggttgttt cccacccgcg cgcgcgctct | 300 | |
| cacccccagc caaacccacc tggcagggct ccctccagcc gagaccttt gattcccggc | 360 | |
| tcccgcgctc ccgcctccgc gccagcccgg gaggtggccc tggacagccg gacctcgccc | 420 | |
| ggccccggct gggaccatgg tgtttctctc gggaaatgct ccgacagct ccaactgcac | 480 | |
| ccaaccgccg gcaccggtga acatttccaa ggccattctg ctcggggtga tcttgggggg | 540 | |
| cctcattctt ttcggggtgc tggttaacat cctagtgatc ctctccgtag cctgtcaccg | 600 | |
| acacctgcac tcagtcacgc actactacat cgtcaacctg gcggtggccg acctcctgct | 660 | |
| cacctccacg gtgctgccct tctccgccat cttcgaggtc ctaggctact gggccttcgg | 720 | |
| cagggtcttc tgcaacatct gggcggcagt ggatgtgctg tgctgcaccg cgtccatcat | 780 | |
| gggcctctgc atcatctcca tcgaccgcta catcggcgtg agctaccgc tgcgctaccc | 840 | |
| aaccatcgtc acccagagga ggggtctcat ggctctgctc tgcgtctggg cactctccct | 900 | |
| ggtcatatcc attggacccc tgttcggctg gaggcagccg gcccccgagg acgagaccat | 960 | |
| ctgccagatc aacgaggagc cgggctacgt gctcttctca gcgctgggct ccttctacct | 1020 | |
| gcctctggcc atcatcctgg tcatgtactg ccgcgtctac gtggtggcca gagggagag | 1080 | |
| ccggggcctc aagtctggcc tcaagaccga caagtcggac tcggagcaag tgacgctccg | 1140 | |
| natccatcgg aaaacgcccc cggcaggagg cagcgggatg ccagcgcca agaccaagac | 1200 | |
| gcacttctca gtgaggctcc tcaagttctc ccgggagaag aaagcggcca aaacgctggg | 1260 | |
| catcgtggtc ggctgcttcg tcctctgctg gctgccttt ttcttagtca tgcccattgg | 1320 | |
| gtctttcttc cctgatttca gcccctctga aacagttttt aaaatagtat tttggctcgg | 1380 | |
| atatctaaac agctgcatca accccatcat ataccatgc tccagccaag agttcaaaaa | 1440 | |
| ggccttttcag aatgtcttga gaatccagtg tctccgcaga aagcagtctt ccaaacatgc | 1500 | |
| cctgggctac accctgcacc cgcccagcca ggccgtggaa gggcaacaca aggacatggt | 1560 | |

```
gcgcatcccc gtgggatcaa gagagacctt ctacaggatc tccaagacgg atggcgtttg    1620
tgaatggaaa ttttttctctt ccatgccccg tggatctgcc aggattacag tgtccaaaga    1680
ccaatcctcc tgtaccacag cccgggtgag aagtaaaagc ttttttggagg tctgctgctg    1740 tgtagggccc tcaacccccca gccttgacaa gaaccatcaa gttccaacca ttaaggtcca    1800
caccatctcc ctcagtgaga acggggagga agtctaggac aggaaagatg cagaggaaag    1860
gggaataatc ttaggtaccc accccacttc cttctcggaa ggccagctct tcttggagga    1920
caagacagga ccaatcaaag aggggacctg ctgggaatgg ggtgggtggt agacccaact    1980
catcaggcag cgggtagggc acaggaagaa gggagggtgt ctcacaacca accagttcaa    2040
atgatacgga acagcatttc cctgcagcta atgctttctt ggtcactctg tgcccacttc    2100
aacgaaaacc accatgggaa acagaatttc atgcacaatc caaaagacta taaatatagg    2160
attatgattt catcatgaat attttgagca cacactctaa gtttggagct atttcttgat    2220
ggaagtgagg ggattttatt ttcaggctca acctactgac agccacattt gacatttatg    2280
ccggaattc                                                             2289

<210> SEQ ID NO 3
<211> LENGTH: 2289
<212> TYPE: DNA
<213> ORGANISM: Homo sapiens
<220> FEATURE:
<221> NAME/KEY: misc_feature
<222> LOCATION: 1141
<223> OTHER INFORMATION: n = A,T,C or G

<400> SEQUENCE: 3
gaattccgaa tcatgtgcag aatgctgaat cttcccccag ccaggacgaa taagacagcg      60
cggaaaagca gattctcgta attctggaat tgcatgttgc aaggagtctc ctggatcttc     120
gcacccagct tcgggtaggg agggagtccg ggtcccgggc taggccagcc cggcaggtgg     180
agagggtccc cggcagcccc gcgcgcccct ggccatgtct ttaatgccct gccccttcat     240
gtggccttct gagggttccc agggctggcc agggttgttt cccacccgcg cgcgcgctct     300
cacccccagc caaacccacc tggcagggct ccctccagcc gagaccttt tgattcccggc     360 tcccgcgctc ccgcctccgc gccagcccgg gaggtggccc tggacagccg gacctcgccc     420
ggccccggct gggaccatgg tgtttctctc gggaaatgct tccgacagct ccaactgcac     480
ccaaccgccg gcaccggtga acatttccaa ggccattctg ctcggggtga tcttgggggg     540
cctcattctt ttcggggtgc tggttaacat cctagtgatc ctctccgtag cctgtcaccg     600
acacctgcac tcagtcacgc actactacat cgtcaacctg gcggtggccg acctcctgct     660
cacctccacg gtgctgccct tctccgccat cttcgaggtc ctaggctact gggccttcgg    720
cagggtcttc tgcaacatct gggcggcagt ggatgtgctg tgctgcaccg cgtccatcat    780
gggcctctgc atcatctcca tcgaccgcta catcggcgtg agctaccccg tcgctaccc     840 aaccatcgtc acccagagga gggtctcat ggctctgctc tgcgtctggg cactctccct    900
ggtcatatcc attggacccc tgttcggctg gaggcagccg gccccgagg acgagaccat    960 ctgccagatc aacgaggagc cgggctacgt gctcttctca gcgctgggct ccttctaccct    1020 gcctctggcc atcagcctgg tcatgtactg ccgcgtctac gtggtggcca agagggagag    1080
ccggggcctc aagtctggcc tcaagaccga caagtcggac tcggagcaag tgacgctccg    1140
natccatcgg aaaaacgccc cggcaggagg cagcgggatg gccagcgcca agaccaagac    1200
gcacttctca gtgaggctcc tcaagttctc ccgggagaag aaagcggcca aaacgctggg    1260
```

```
catcgtggtc ggctgcttcg tcctctgctg gctgccttt  ttcttagtca tgcccattgg   1320
gtctttcttc cctgatttca gccctctga  aacagttttt aaaatagtat tttggctcgg   1380
atatctaaac agctgcatca accccatcat atacccatgc tccagccaag agttcaaaaa   1440
ggcctttcag aatgtcttga gaatccagtg tctccgcaga aagcagtctt ccaaacatgc   1500
cctgggctac accctgcacc cgcccagcca ggccgtggaa gggcaacaca aggacatggt   1560
gcgcatcccc gtgggatcaa gagagacctt ctacaggatc tccaagacgg atggcgtttg   1620
tgaatggaaa tttttctctt ccatgccccg tggatctgcc aggattacag tgtccaaaga   1680
ccaatcctcc tgtaccacag cccgggtgag aagtaaaagc ttttggagg  tctgctgctg   1740 tgtagggccc tcaacccca  gccttgacaa gaaccatcaa gttccaacca ttaaggtcca   1800
caccatctcc ctcagtgaga cggggagga  agtctaggac aggaaagatg cagaggaaag   1860
gggaataatc ttaggtaccc accccacttc cttctcggaa ggccagctct tcttggagga   1920
caagacagga ccaatcaaag aggggacctg ctgggaatgg ggtgggtggt agacccaact   1980
catcaggcag cgggtagggc acagggaaga gggagggtgt ctcacaacca accagttcaa   2040
atgatacgga acagcatttc cctgcagcta atgctttctt ggtcactctg tgcccacttc   2100
aacgaaaacc accatgggaa acagaatttc atgcacaatc caaaagacta taaatatagg   2160
attatgattt catcatgaat attttgagca cacactctaa gtttggagct atttcttgat   2220
ggaagtgagg ggattttatt ttcaggctca acctactgac agccacattt gacatttatg   2280
ccggaattc                                                          2289

<210> SEQ ID NO 4
<211> LENGTH: 464
<212> TYPE: PRT
<213> ORGANISM: Homo sapiens

<400> SEQUENCE: 4

Met Val Phe Leu Ser Gly Asn Ala Ser Asp Ser Ser Asn Cys Thr Gln
  1               5                  10                  15

Pro Pro Ala Pro Val Asn Ile Ser Lys Ala Ile Leu Leu Gly Val Ile
             20                  25                  30

Leu Gly Gly Leu Ile Leu Phe Gly Val Leu Gly Asn Ile Leu Val Ile
         35                  40                  45

Leu Ser Val Ala Cys His Arg His Leu His Ser Val Thr His Tyr Tyr
     50                  55                  60

Ile Val Asn Leu Ala Val Ala Asp Leu Leu Leu Thr Ser Thr Val Leu
 65                  70                  75                  80

Pro Phe Ser Ala Ile Phe Glu Val Leu Gly Tyr Trp Ala Phe Gly Arg
                 85                  90                  95

Val Phe Cys Asn Ile Trp Ala Ala Val Asp Val Leu Cys Cys Thr Ala
            100                 105                 110

Ser Ile Met Gly Leu Cys Ile Ile Ser Ile Asp Arg Tyr Ile Gly Val
        115                 120                 125

Ser Tyr Pro Leu Arg Tyr Pro Thr Ile Val Thr Gln Arg Arg Gly Leu
    130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
```

-continued

```
                180             185             190
Phe Tyr Leu Pro Leu Ala Ile Ile Leu Val Met Tyr Cys Arg Val Tyr
            195                 200                 205
Val Val Ala Lys Arg Glu Ser Arg Gly Leu Lys Ser Gly Leu Lys Thr
        210                 215                 220
Asp Lys Ser Asp Ser Glu Gln Val Thr Leu Arg Ile His Arg Lys Asn
225                 230                 235                 240
Ala Pro Ala Gly Gly Ser Gly Met Ala Ser Ala Lys Thr Lys Thr His
                245                 250                 255
Phe Ser Val Arg Leu Leu Lys Phe Ser Arg Glu Lys Lys Ala Ala Lys
            260                 265                 270
Thr Leu Gly Ile Val Val Gly Cys Phe Val Leu Cys Trp Leu Pro Phe
        275                 280                 285
Phe Leu Val Met Pro Ile Gly Ser Phe Phe Pro Asp Phe Lys Pro Ser
        290                 295                 300
Glu Thr Val Phe Lys Ile Val Phe Trp Leu Gly Tyr Leu Asn Ser Cys
305                 310                 315                 320
Ile Asn Pro Ile Ile Tyr Pro Cys Ser Ser Gln Glu Phe Lys Lys Ala
                325                 330                 335
Phe Gln Asn Val Leu Arg Ile Gln Cys Leu Arg Arg Lys Gln Ser Ser
            340                 345                 350
Lys His Ala Leu Gly Tyr Thr Leu His Pro Pro Ser Gln Ala Val Glu
        355                 360                 365
Gly Gln His Lys Asp Met Val Arg Ile Pro Val Gly Ser Arg Glu Thr
        370                 375                 380
Phe Tyr Arg Ile Ser Lys Thr Asp Gly Val Cys Glu Trp Lys Phe Phe
385                 390                 395                 400
Ser Ser Met Pro Arg Gly Ser Ala Arg Ile Thr Val Ser Lys Asp Gln
                405                 410                 415
Ser Ser Cys Thr Thr Ala Arg Val Arg Ser Lys Ser Phe Leu Glu Val
            420                 425                 430
Cys Cys Cys Val Gly Pro Ser Thr Pro Ser Leu Asp Lys Asn His Gln
        435                 440                 445
Val Pro Thr Ile Lys Val His Thr Ile Ser Leu Ser Glu Asn Gly Glu
        450                 455                 460
```

<210> SEQ ID NO 5
<211> LENGTH: 464
<212> TYPE: PRT
<213> ORGANISM: Homo sapiens

<400> SEQUENCE: 5

```
Met Val Phe Leu Ser Gly Asn Ala Ser Asp Ser Ser Asn Cys Thr Gln
1               5                   10                  15
Pro Pro Ala Pro Val Asn Ile Ser Lys Ala Ile Leu Leu Gly Val Ile
                20                  25                  30
Leu Gly Gly Leu Ile Leu Phe Gly Val Leu Gly Asn Ile Leu Val Ile
            35                  40                  45
Leu Ser Val Ala Cys His Arg His Leu His Ser Val Thr His Tyr Tyr
        50                  55                  60
Ile Val Asn Leu Ala Val Ala Asp Leu Leu Leu Thr Ser Thr Val Leu
65                  70                  75                  80
Pro Phe Ser Ala Ile Phe Glu Val Leu Gly Tyr Trp Ala Phe Gly Arg
                85                  90                  95
```

-continued

```
Val Phe Cys Asn Ile Trp Ala Ala Val Asp Val Leu Cys Cys Thr Ala
                100                 105                 110

Ser Ile Met Gly Leu Cys Ile Ile Ser Ile Asp Arg Tyr Ile Gly Val
            115                 120                 125

Ser Tyr Pro Leu Arg Tyr Pro Thr Ile Val Thr Gln Arg Arg Gly Leu
        130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
            180                 185                 190

Phe Tyr Leu Pro Leu Ala Ile Ser Leu Val Met Tyr Cys Arg Val Tyr
        195                 200                 205

Val Val Ala Lys Arg Glu Ser Arg Gly Leu Lys Ser Gly Leu Lys Thr
    210                 215                 220

Asp Lys Ser Asp Ser Glu Gln Val Thr Leu Arg Ile His Arg Lys Asn
225                 230                 235                 240

Ala Pro Ala Gly Gly Ser Gly Met Ala Ser Ala Lys Thr Lys Thr His
                245                 250                 255

Phe Ser Val Arg Leu Leu Lys Phe Ser Arg Glu Lys Lys Ala Ala Lys
            260                 265                 270

Thr Leu Gly Ile Val Val Gly Cys Phe Val Leu Cys Trp Leu Pro Phe
        275                 280                 285

Phe Leu Val Met Pro Ile Gly Ser Phe Phe Pro Asp Phe Lys Pro Ser
    290                 295                 300

Glu Thr Val Phe Lys Ile Val Phe Trp Leu Gly Tyr Leu Asn Ser Cys
305                 310                 315                 320

Ile Asn Pro Ile Ile Tyr Pro Cys Ser Ser Gln Glu Phe Lys Lys Ala
                325                 330                 335

Phe Gln Asn Val Leu Arg Ile Gln Cys Leu Arg Arg Lys Gln Ser Ser
            340                 345                 350

Lys His Ala Leu Gly Tyr Thr Leu His Pro Pro Ser Gln Ala Val Glu
        355                 360                 365

Gly Gln His Lys Asp Met Val Arg Ile Pro Val Gly Ser Arg Glu Thr
    370                 375                 380

Phe Tyr Arg Ile Ser Lys Thr Asp Gly Val Cys Glu Trp Lys Phe Phe
385                 390                 395                 400

Ser Ser Met Pro Arg Gly Ser Ala Arg Ile Thr Val Ser Lys Asp Gln
                405                 410                 415

Ser Ser Cys Thr Thr Ala Arg Val Arg Ser Lys Ser Phe Leu Glu Val
            420                 425                 430

Cys Cys Cys Val Gly Pro Ser Thr Pro Ser Leu Asp Lys Asn His Gln
        435                 440                 445

Val Pro Thr Ile Lys Val His Thr Ile Ser Leu Ser Glu Asn Gly Glu
    450                 455                 460
```

<210> SEQ ID NO 6
<211> LENGTH: 464
<212> TYPE: PRT
<213> ORGANISM: Homo sapiens

<400> SEQUENCE: 6

```
Met Val Phe Leu Ser Gly Asn Ala Ser Asp Ser Ser Asn Cys Thr Gln
1               5                   10                  15
```

-continued

```
Pro Pro Ala Pro Val Asn Ile Ser Lys Ala Ile Leu Leu Gly Val Ile
            20                  25                  30
Leu Gly Gly Leu Ile Leu Phe Gly Val Leu Cys Asn Ile Leu Val Ile
        35                  40                  45
Leu Ser Val Ala Cys His Arg His Leu His Ser Val Thr His Tyr Tyr
        50                  55                  60
Ile Val Asn Leu Ala Val Ala Asp Leu Leu Thr Ser Thr Val Leu
65                  70                  75                  80
Pro Phe Ser Ala Ile Phe Glu Val Leu Gly Tyr Trp Ala Phe Gly Arg
                85                  90                  95
Val Phe Cys Asn Ile Trp Ala Ala Val Asp Val Leu Cys Cys Thr Ala
            100                 105                 110
Ser Ile Met Gly Leu Cys Ile Ile Ser Ile Asp Arg Tyr Ile Gly Val
        115                 120                 125
Ser Tyr Pro Leu Arg Tyr Pro Thr Ile Val Thr Gln Arg Arg Gly Leu
    130                 135                 140
Met Ala Leu Leu Cys Val Trp Ala Leu Ser Leu Val Ile Ser Ile Gly
145                 150                 155                 160
Pro Leu Phe Gly Trp Arg Gln Pro Ala Pro Glu Asp Glu Thr Ile Cys
                165                 170                 175
Gln Ile Asn Glu Glu Pro Gly Tyr Val Leu Phe Ser Ala Leu Gly Ser
            180                 185                 190
Phe Tyr Leu Pro Leu Ala Ile Ile Leu Val Met Tyr Cys Arg Val Tyr
        195                 200                 205
Val Val Ala Lys Arg Glu Ser Arg Gly Leu Lys Ser Gly Leu Lys Thr
    210                 215                 220
Asp Lys Ser Asp Ser Glu Gln Val Thr Leu Arg Ile His Arg Lys Asn
225                 230                 235                 240
Ala Pro Ala Gly Gly Ser Gly Met Ala Ser Ala Lys Thr Lys Thr His
                245                 250                 255
Phe Ser Val Arg Leu Leu Lys Phe Ser Arg Glu Lys Lys Ala Ala Lys
            260                 265                 270
Thr Leu Gly Ile Val Val Gly Cys Phe Val Leu Cys Trp Leu Pro Phe
        275                 280                 285
Phe Leu Val Met Pro Ile Gly Ser Phe Phe Pro Asp Phe Lys Pro Ser
    290                 295                 300
Glu Thr Val Phe Lys Ile Val Phe Trp Leu Gly Tyr Leu Asn Ser Cys
305                 310                 315                 320
Ile Asn Pro Ile Ile Tyr Pro Cys Ser Ser Gln Glu Phe Lys Lys Ala
                325                 330                 335
Phe Gln Asn Val Leu Arg Ile Gln Cys Leu Arg Arg Lys Gln Ser Ser
            340                 345                 350
Lys His Ala Leu Gly Tyr Thr Leu His Pro Pro Ser Gln Ala Val Glu
        355                 360                 365
Gly Gln His Lys Asp Met Val Arg Ile Pro Val Gly Ser Arg Glu Thr
    370                 375                 380
Phe Tyr Arg Ile Ser Lys Thr Asp Gly Val Cys Glu Trp Lys Phe Phe
385                 390                 395                 400
Ser Ser Met Pro Arg Gly Ser Ala Arg Ile Thr Val Ser Lys Asp Gln
                405                 410                 415
Ser Ser Cys Thr Thr Ala Arg Val Arg Ser Lys Ser Phe Leu Glu Val
            420                 425                 430
```

```
Cys Cys Cys Val Gly Pro Ser Thr Pro Ser Leu Asp Lys Asn His Gln
        435                 440                 445

Val Pro Thr Ile Lys Val His Thr Ile Ser Leu Ser Glu Asn Gly Glu
        450                 455                 460

<210> SEQ ID NO 7
<211> LENGTH: 3683
<212> TYPE: DNA
<213> ORGANISM: Homo sapiens

<400> SEQUENCE: 7
agatctcacc aagctgaggt cttgggagag gagatactgg ctgagcccta ttacttaatt        60 taaaataccct taggggaggc cacccaagtg gatgcggggc tcctgtgaat cctttgcttg      120
actccagcgg gttacctttg cctctgatac ataaagggtg gggatgggag cgctctcctc      180
tctccttccc ctgccttgct gtgggaactt ctgggaaagg aggtgcaggg ctccaggaag      240
ccagtgccca gggagtgcta tgctgagtcc aggagcctgg ccacggcagg ggtggacaga      300
tggtggcaga ggaaccacgg tgtcccttcc tccagattta gctaaaggaa acgtggagca      360
tcccattggc catcctcccc actctccaat tcggctccag aggcccctcc agactatagg      420
cagctgcccc tttaagcgtc gctactcctc ccccaagagc ggtggcaccg agggagttgg      480 ggtggggggga ggctgagcgc tctggctggg acagctagaa aagatggccc aggctgggga      540
agtcgctctc atgccttgct gtcccctccc ctgagccagg tgatttggga gaccccctcc      600
ttccttcttt ccctaccgcc ccacgcgcga cccggggatg gctccgtggc ctcacgagaa      660
cagctctctt gccccatggc cggacctccc caccctggcg cccaataccg ccaacaccag      720
tgggctgcca ggggttccgt gggaggcggc cctagccggg gccctgctgg cgctggcggt      780
gctggccacc gtgggaggca acctgctggt catcgtggcc atcgcctgga ctccgagact      840
ccagaccatg accaacgtgt tcgtgacttc gctggccgca gccgacctgg tgatgggact      900
cctggtggtg ccgccggcgg ccaccttggc gctgactggc cactggccgt gggcgccac      960 tggctgcgag ctgtggacct cggtggacgt gctgtgtgtg accgccagca tcgaaaccct     1020
gtgcgccctg gccgtggacc gctacctggc tgtgaccaac ccgctgcgtt acggcgcact     1080
ggtcaccaag cgctgcgccc ggacagctgt ggtcctggtg tgggtcgtgt cggccgcgt     1140 gtcgtttgcg cccatcatga ccagtggtg gcgcgtaggg gccgacgccg aggcgcagcg     1200
ctgccactcc aacccgcgct gctgtgcctt cgcctccaac atgccctacg tgctgctgtc     1260
ctcctccgtc tccttctacc ttcctcttct cgtgatgctc ttcgtctacg cgcgggtttt     1320
cgtggtggct acgcgccagc tgcgcttgct gcgcggggag ctgggccgct ttccgcccga     1380
ggagtctccg ccggcgccgt cgcgctctct ggccccggcc ccgtggggga cgtgcgctcc     1440
gcccgaaggg gtgcccgcct gcggccggcg gcccgcgcgc ctcctgcctc tcgggaaca     1500 ccgggccctg tgcaccttgg gtctcatcat gggcaccttc actctctgct ggttgccctt     1560
ctttctggcc aacgtgctgc gcgccctggg gggccctct ctagtccgg gcccggcttt     1620 ccttgccctg aactggctag ttatgccaa ttctgccttc aacccgctca tctactgccg     1680
cagcccggac tttcgcagcg ccttccgccg tcttctgtgc cgctgcggcc gtcgcctgcc     1740
tccggagccc tgcgccgccg cccgcccggc cctcttcccc tcgggcgttc ctgcggcccg     1800
gagcagccca gcgcagccca ggctttgcca acggtcgac gggtaggtaa ccggggcaga     1860
gggaccggcg gctcagggtc gggaagcatg cgatgtgtcc gtgggtcaac ttttttgagtg     1920 tggagtttat taagagaagg tgggatggct ttgcttggag agaaaaggga acgaggagta     1980
```

-continued

```
gcgaaccaaa atgggaccca gggtccttt ctttccggat ccagtcacta gggtagaagc    2040
aaaggagggc gagcgggccg tcgttcctca cccaaggacc caaggtgcgc caccggaaag    2100
cgctgcggtg tcccgaggac tctcgcctcg cctggtcggc tttagggatt tttttttt     2160 ttaaatagag acagggtttc gtctctgtcg cccacgcggg aatgcagtgg tgcgatctca    2220
gctcactgca gtcttgaact cctggctcct gggctcaagc gatcctccca cctcagcctc    2280
ctgagtatct gggactacag gcgagcccca ccaatcccag ctatttttaa aatttcttgt    2340
agagatgggg tcttgctatg ttgcccaggc ttgtcttgaa cttctggcct caagtgatcc    2400
ttctgcctca gccttccaaa gcattaggat tacaggccgg agccagggcg ccgggtcggc    2460
tctagttttg gttttccagc tcagttcttt gcccccctcc cccgatttct tgccatcact    2520
agacctggct cggacttgaa ggcagggcta gtgcccccc acccgccccc caagccctcg    2580
gcctcagttc tgggttttct caaaggtttg acagctgtgg aggtgagaat ccacttccgg    2640
tatgaagtac agttgtgagt gaggagcctg tgagtgcaga tgtgtgccct cccgctccct    2700
gggctgggtt ggagtaggga tggggtgggg cgtgtgtggc tgggtggtgc cctggcgttt    2760
ttgtgtaact aaatatgcgt tccagggtct ctgatctctg tcattcccct cagtgcacct    2820
gttgctcctt tcaccccagg gtctattatc tccacttttt ttcccagggc ttcttgggga    2880
gtttcttagg cctgaaggac aagaagcaac aactctgttg atcagaacct gtggaaaacc    2940
tctggcctct gttcagaatg agtcccatgg gattccccgg ctgtgacact ctaccctcca    3000
gaacctgacg actgggccat gtgacccaag gagggatcct taccaagtgg gttttcacca    3060
tcctcttgct ctctgtctga gagatgtttt ctaaacccca gccttgaact tcactcctcc    3120
ctcagtggta gtgtccaggt gccgtggagc agcaggctgg ctttggtagg ggcacccatc    3180
acccggcttg cctgtgcagt cagtgagtgc ttagggcaaa gagagctccc ctggttccat    3240
tccttctgcc acccaaaccc tgatgagacc ttagtgttct ccaggctctg tggcccaggc    3300
tgagagcagc agggtagaaa agaccaagat ttggggtttt atctctggtt cccttattac    3360
tgctctcaag cagtggcctc tctcacttta gccatggaat ggctccgatc tacctcacag    3420
cagtgtcaga aggacttcgc cagggttttg ggagctccag ggttcataag aaggtgaacc    3480
attagaacag atcccttctt ttccttttgc aatcagataa ataaatatca ctgaatgcag    3540
ttcatcctcg gccccctttc cctccgtttg ttttctttc ataatccact tactcccttc    3600
ccttctactc tgctggcttt tgacagaggc gtaaattagg cctaatcctc actctttct    3660 tcctaatgtt catcaaagaa aaa                                            3683
```

<210> SEQ ID NO 8
<211> LENGTH: 3683
<212> TYPE: DNA
<213> ORGANISM: Homo sapiens

<400> SEQUENCE: 8

```
agatctcacc aagctgaggt cttgggagag gagatactgg ctgagcccta ttacttaatt     60 taaaataccct taggggaggc cacccaagtg gatgcgggc tcctgtgaat cctttgcttg    120
actccagcgg gttacctttg cctctgatac ataaagggtg gggatgggag cgctctcctc    180
tctccttccc ctgccttgct gtgggaactt ctgggaaagg aggtgcaggg ctccaggaag    240
ccagtgccca gggagtgcta tgctgagtcc aggagcctgg ccacggcagg ggtggacaga    300
tggtggcaga ggaaccacgg tgtcccttcc tccagattta gctaaaggaa acgtggagca    360
```

```
tcccattggc catcctcccc actctccaat tcggctccag aggcccctcc agactatagg      420
cagctgcccc tttaagcgtc gctactcctc ccccaagagc ggtggcaccg agggagttgg      480
ggtgggggga ggctgagcgc tctggctggg acagctagag aagatgggcc aggctgggga      540
agtcgctctc atgccttgct gtcccctccc ctgagccagg tgatttggga gacccctcc       600 ttccttctt  ccctaccgcc ccacgcgcga cccggggatg gctccgtggc ctcacgagaa      660
cagctctctt gccccatggc cggacctccc caccctggcg cccaataccg ccaacaccag      720
tgggctgcca ggggttccgt gggaggcggc cctagccggg gccctgctgg cgctggcggt      780
gctggccacc gtgggaggca acctgctggt catcgtggcc atcgcctgga ctccgagact      840
ccagaccatg accaacgtgt tcgtgacttt gctggccgca gccgacctgg tgatgggact      900
cctggtggtg ccgccggcgg ccaccttggc gctgactggc cactggccgt tgggcgccac      960
tggctgcgag ctgtggacct cggtggacgt gctgtgtgtg accgccagca tcgaaaccct     1020
gtgcgccctg gccgtggacc gctacctggc tgtgaccaac ccgctgcgtt acggcgcact     1080
ggtcaccaag cgctgcgccc ggacagctgt ggtcctggtg tgggtcgtgt cggccgcggt     1140
gtcgtttgcg cccatcatga gccagtggtg gcgcgtaggg gccgacgccg aggcgcagcg     1200
ctgccactcc aacccgcgct gctgtgcctt cgcctccaac atgccctacg tgctgctgtc     1260
ctcctccgtc tccttctacc ttcctcttct cgtgatgctc ttcgtctacg cgcgggtttt     1320
cgtggtggct acgcgccagc tgcgcttgct gcgcggggag ctgggccgct tccgcccga      1380 ggagtctccg ccggcgccgt cgcgctctct ggccccggcc ccggtgggga cgtgcgctcc     1440
gcccgaaggg gtgcccgcct gcggccggcg gcccgcgcgc ctcctgcctc tcgggaaca     1500 ccgggccctg tgcaccttgg gtctcatcat gggcaccttc actctctgct ggttgccctt     1560 cttctctggcc aacgtgctgc gcgccctggg gggcccctct ctagtcccgg gcccggcttt     1620
ccttgccctg aactggctag ttatgccaa ttctgccttc aacccgctca tctactgccg      1680
cagcccggac tttcgcagcg ccttccgccg tcttctgtgc cgctgcggcc gtcgcctgcc     1740
tccggagccc tgcgccgccg cccgcccggc cctcttcccc tcgggcgttc ctgcggcccg     1800
gagcagccca gcgcagccca ggctttgcca acggctcgac gggtaggtaa ccggggcaga     1860
gggaccggcg gctcagggtc gggaagcatg cgatgtgtcc gtgggtcaac ttttgagtg      1920 tggagtttat taagagaagg tgggatggct ttgcttggag agaaaggga acgaggagta      1980 gcgaaccaaa atgggaccca gggtcctttt ctttccggat ccagtcacta gggtagaagc     2040
aaaggagggc gagcgggccg tcgttcctca cccaaggacc caaggtgcgc caccggaaag     2100
cgctgcggtg tcccgaggac tctcgcctcg cctggtcggc tttagggatt ttttttttt      2160 ttaaatagag acagggtttc gtctctgtcg cccacgcggg aatgcagtgg tgcgatctca     2220
gctcactgca gtcttgaact cctggctcct gggctcaagc gatcctccca cctcagcctc     2280
ctgagtatct gggactacag gcgagcccca ccaatcccag ctatttttaa aatttcttgt     2340
agagatgggg tcttgctatg ttgcccaggc ttgtcttgaa cttctggcct caagtgatcc     2400
ttctgcctca gccttccaaa gcattaggat tacaggccgg agccagggcg ccgggtcggc     2460
tctagttttg gttttccagc tcagttcttt gcccccctcc cccgatttct tgccatcact     2520
agacctggct cggacttgaa ggcagggcta gtgcccccc acccgccccc caagccctcg     2580
gcctcagttc tgggttttct caaaggtttg acagctgtgg aggtgagaat ccacttccgg     2640
tatgaagtac agttgtgagt gaggagcctg tgagtgcaga tgtgtgccct cccgctccct     2700
gggctgggtt ggagtaggga tggggtgggg cgtgtgtggc tgggtggtgc cctggcgttt     2760
```

-continued

```
ttgtgtaact aaatatgcgt tccagggtct ctgatctctg tcattcccct cagtgcacct    2820
gttgctcctt tcaccccagg gtctattatc tccactttt ttcccagggc ttcttgggga    2880
gtttcttagg cctgaaggac aagaagcaac aactctgttg atcagaacct gtggaaaacc    2940
tctggcctct gttcagaatg agtcccatgg gattccccgg ctgtgacact ctaccctcca    3000
gaacctgacg actgggccat gtgacccaag gagggatcct taccaagtgg gttttcacca    3060
tcctcttgct ctctgtctga gagatgtttt ctaaacccca gccttgaact tcactcctcc    3120
ctcagtggta gtgtccaggt gccgtggagc agcaggctgg ctttggtagg ggcacccatc    3180
acccggcttg cctgtgcagt cagtgagtgc ttagggcaaa gagagctccc ctggttccat    3240
tccttctgcc acccaaaccc tgatgagacc ttagtgttct ccaggctctg tggcccaggc    3300
tgagagcagc agggtagaaa agaccaagat ttggggtttt atctctggtt cccttattac    3360
tgctctcaag cagtggcctc tctcacttta gccatggaat ggctccgatc tacctcacag    3420
cagtgtcaga aggacttcgc cagggttttg ggagctccag ggttcataag aaggtgaacc    3480
attagaacag atcccttctt ttccttttgc aatcagataa ataaatatca ctgaatgcag    3540
ttcatcctcg gccccctttc cctccgtttg ttttcttttc ataatccact tactcccttc    3600
ccttctactc tgctggcttt tgacagaggc gtaaattagg cctaatcctc actcttttct    3660
tcctaatgtt catcaaagaa aaa                                            3683

<210> SEQ ID NO 9
<211> LENGTH: 408
<212> TYPE: PRT
<213> ORGANISM: Homo sapiens

<400> SEQUENCE: 9

Met Ala Pro Trp Pro His Glu Asn Ser Ser Leu Ala Pro Trp Pro Asp
  1               5                  10                  15

Leu Pro Thr Leu Ala Pro Asn Thr Ala Asn Thr Ser Gly Leu Pro Gly
             20                  25                  30

Val Pro Trp Glu Ala Ala Leu Ala Gly Ala Leu Leu Ala Leu Ala Val
         35                  40                  45

Leu Ala Thr Val Gly Gly Asn Leu Leu Val Ile Val Ala Ile Ala Trp
     50                  55                  60

Thr Pro Arg Leu Gln Thr Met Thr Asn Val Phe Val Thr Ser Leu Ala
 65                  70                  75                  80

Ala Ala Asp Leu Val Met Gly Leu Leu Val Val Pro Pro Ala Ala Thr
                 85                  90                  95

Leu Ala Leu Thr Gly His Trp Pro Leu Gly Ala Thr Gly Cys Glu Leu
            100                 105                 110

Trp Thr Ser Val Asp Val Leu Cys Val Thr Ala Ser Ile Glu Thr Leu
        115                 120                 125

Cys Ala Leu Ala Val Asp Arg Tyr Leu Ala Val Thr Asn Pro Leu Arg
    130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                165                 170                 175

Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
        195                 200                 205
```

-continued

```
Ser Ser Val Ser Phe Tyr Leu Pro Leu Leu Val Met Leu Phe Val Tyr
    210                 215                 220

Ala Arg Val Phe Val Val Ala Thr Arg Gln Leu Arg Leu Leu Arg Gly
225                 230                 235                 240

Glu Leu Gly Arg Phe Pro Glu Glu Ser Pro Pro Ala Pro Ser Arg
                245                 250                 255

Ser Leu Ala Pro Ala Pro Val Gly Thr Cys Ala Pro Glu Gly Val
                260                 265                 270

Pro Ala Cys Gly Arg Arg Pro Ala Arg Leu Leu Pro Leu Arg Glu His
            275                 280                 285

Arg Ala Leu Cys Thr Leu Gly Leu Ile Met Gly Thr Phe Thr Leu Cys
290                 295                 300

Trp Leu Pro Phe Phe Leu Ala Asn Val Leu Ala Leu Gly Gly Pro
305                 310                 315                 320

Ser Leu Val Pro Gly Pro Ala Phe Leu Ala Leu Asn Trp Leu Gly Tyr
                325                 330                 335

Ala Asn Ser Ala Phe Asn Pro Leu Ile Tyr Cys Arg Ser Pro Asp Phe
            340                 345                 350

Arg Ser Ala Phe Arg Arg Leu Leu Cys Arg Cys Gly Arg Arg Leu Pro
            355                 360                 365

Pro Glu Pro Cys Ala Ala Ala Arg Pro Ala Leu Phe Pro Ser Gly Val
    370                 375                 380

Pro Ala Ala Arg Ser Ser Pro Ala Gln Pro Arg Leu Cys Gln Arg Leu
385                 390                 395                 400

Asp Gly Ala Ser Trp Gly Val Ser
                405

<210> SEQ ID NO 10
<211> LENGTH: 408
<212> TYPE: PRT
<213> ORGANISM: Homo sapiens

<400> SEQUENCE: 10

Met Ala Pro Trp Pro His Glu Asn Ser Ser Leu Ala Pro Trp Pro Asp
  1               5                  10                  15

Leu Pro Thr Leu Ala Pro Asn Thr Ala Asn Thr Ser Gly Leu Pro Gly
                20                  25                  30

Val Pro Trp Glu Ala Ala Leu Ala Gly Ala Leu Leu Ala Leu Ala Val
                35                  40                  45

Leu Ala Thr Val Gly Gly Asn Leu Leu Val Ile Val Ala Ile Ala Trp
    50                  55                  60

Thr Pro Arg Leu Gln Thr Met Thr Asn Val Phe Val Thr Leu Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
                100                 105                 110

Trp Thr Ser Val Asp Val Leu Cys Val Thr Ala Ser Ile Glu Thr Leu
            115                 120                 125

Cys Ala Leu Ala Val Asp Arg Tyr Leu Ala Val Thr Asn Pro Leu Arg
            130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
```

```
                    165                 170                 175
Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
        195                 200                 205

Ser Ser Val Ser Phe Tyr Leu Pro Leu Leu Val Met Leu Phe Val Tyr
    210                 215                 220

Ala Arg Val Phe Val Val Ala Thr Arg Gln Leu Arg Leu Leu Arg Gly
225                 230                 235                 240

Glu Leu Gly Arg Phe Pro Pro Glu Glu Ser Pro Pro Ala Pro Ser Arg
                245                 250                 255

Ser Leu Ala Pro Ala Pro Val Gly Thr Cys Ala Pro Pro Glu Gly Val
            260                 265                 270

Pro Ala Cys Gly Arg Arg Pro Ala Arg Leu Leu Pro Leu Arg Glu His
        275                 280                 285

Arg Ala Leu Cys Thr Leu Gly Leu Ile Met Gly Thr Phe Thr Leu Cys
    290                 295                 300

Trp Leu Pro Phe Phe Leu Ala Asn Val Leu Arg Ala Leu Gly Gly Pro
305                 310                 315                 320

Ser Leu Val Pro Gly Pro Ala Phe Leu Ala Leu Asn Trp Leu Gly Tyr
                325                 330                 335

Ala Asn Ser Ala Phe Asn Pro Leu Ile Tyr Cys Arg Ser Pro Asp Phe
            340                 345                 350

Arg Ser Ala Phe Arg Arg Leu Leu Cys Arg Cys Gly Arg Arg Leu Pro
        355                 360                 365

Pro Glu Pro Cys Ala Ala Ala Arg Pro Ala Leu Phe Pro Ser Gly Val
    370                 375                 380

Pro Ala Ala Arg Ser Ser Pro Ala Gln Pro Arg Leu Cys Gln Arg Leu
385                 390                 395                 400

Asp Gly Ala Ser Trp Gly Val Ser
                405

<210> SEQ ID NO 11
<211> LENGTH: 1705
<212> TYPE: DNA
<213> ORGANISM: Homo sapiens

<400> SEQUENCE: 11
ttcaggggct ttctggtgcc cttgacagtg acctgcagca agggagtcag aagacagatg      60
tagaaatcaa gagtgaccat ccacgggatt gacttggatt gccactcaag cggtcctctc     120
atggaatgtt ggtgaggccc tctgccaggg aagcaatctg ctgtgcaaa gtgctgcctg      180 gtggggagga ctcctggaaa tctgactgac cctattccc tgcttgggaa cttgaggggt      240
gtcagagccc ctgatgtgct ttctcttagg aagatgagga ctctgaacac ctctgccatg     300
gacgggactg ggctggtggt ggagagggac ttctctgttc gtatcctcac tgcctgtttc     360
ctgtcgctgc tcatcctgtc cacgctcctg ggaacacgc tggtctgtgc tgccgttatc     420
aggttccgac acctgcggtc caaggtgacc aacttctttg tcatctcctt ggctgtgtca     480
gatctcttgg tggccgtcct ggtcatgccc tggaaggcag tggctgagat tgctggcttc     540
tggccctttg ggtccttctg taacatctgg gtggcctttg acatcatgtg ctccactgca     600
tccatcctca acctctgtgt gatcagcgtg acaggtatt ggctatctc cagcccttc       660 cggtatgaga gaaagatgac ccccaaggca gccttcatcc tgatcagtgt ggcatggacc     720
```

```
ttgtctgtac tcatctcctt catcccagtg cagctcagct ggcacaaggc aaaacccaca      780
agcccctctg atggaaatgc cacttccctg gctgagacca tagacaactg tgactccagc      840
ctcagcagga catatgccat ctcatcctct gtaataagct tttacatccc tgtggccatc      900
atgattgtca cctacaccag gatctacagg attgctcaga aacaaatacg gcgcattgcg      960
gccttggaga gggcagcagt ccacgccaag aattgccaga ccaccacagg taatggaaag     1020
cctgtcgaat gttctcaacc ggaaagttct tttaagatgt ccttcaaaag agaaactaaa     1080
gtcctgaaga ctctgtcggt gatcatgggt gtgtttgtgt gctgttggct acctttcttc     1140
atcttgaact gcattttgcc cttctgtggg tctggggaga cgcagccctt ctgcattgat     1200
tccaacacct ttgacgtgtt tgtgtggttt gggtgggcta attcatcctt gaacccatc      1260 atttatgcct ttaatgctga ttttcggaag gcattttcaa ccctcttagg atgctacaga     1320
ctttgccctg cgacgaataa tgccatagag acggtgagta tcaataacaa tggggccgcg     1380
atgttttcca gccatcatga gccacgaggc tccatctcca aggagtgcaa tctggtttac     1440
ctgatcccac atgctgtggg ctcctctgag gacctgaaaa aggaggaggc agctggcatc     1500
gccagaccct tggagaagct gtccccagcc ctatcggtca tattggacta tgacactgac     1560
gtctctctgg agaagatcca acccatcaca caaaacggtc agcacccaac ctgaactcgc     1620
agatgaatcc tgccacacat gctcatccca aaagctagag gagattgctc tggggtttgc     1680
tattaagaaa ctaaggtacg gtgag                                           1705

<210> SEQ ID NO 12
<211> LENGTH: 1705
<212> TYPE: DNA
<213> ORGANISM: Homo sapiens

<400> SEQUENCE: 12
ttcaggggct ttctggtgcc cttgacagtg acctgcagca agggagtcag aagacagatg       60
tagaaatcaa gagtgaccat ccacgggatt gacttggatt gccactcaag cggtcctctc      120
atggaatgtt ggtgaggccc tctgccaggg aagcaatctg gctgtgcaaa gtgctgcctg      180
gtggggagga ctcctggaaa tctgactgac ccctattccc tgcttgggaa cttgaggggt      240
gtcagagccc ctgatgtgct ttctcttagg aagatgagga ctctgaacac ctctgccatg      300
gacgggactg ggctggtggt ggagagggac ttctctgttc gtatcctcac tgcctgtttc      360
ctgtcgctgc tcatcctgtc cccgctcctg gggaacacgc tggtctgtgc tgccgttatc      420
aggttccgac acctgcggtc caaggtgacc aacttctttg tcatctcctt ggctgtgtca      480
gatctcttgg tggccgtcct ggtcatgccc tggaaggcag tggctgagat tgctggcttc      540 tggcccttg ggtccttctg taacatctgg gtggcctttg acatcatgtg ctccactgca      600
tccatcctca acctctgtgt gatcagcgtg acaggtatt gggctatctc cagcccttc      660 cggtatgaga gaaagatgac ccccaaggca gccttcatcc tgatcagtgt ggcatggacc      720
ttgtctgtac tcatctcctt catcccagtg cagctcagct ggcacaaggc aaaacccaca      780
agcccctctg atggaaatgc cacttccctg gctgagacca tagacaactg tgactccagc      840
ctcagcagga catatgccat ctcatcctct gtaataagct tttacatccc tgtggccatc      900
atgattgtca cctacaccag gatctacagg attgctcaga aacaaatacg gcgcattgcg      960
gccttggaga gggcagcagt ccacgccaag aattgccaga ccaccacagg taatggaaag     1020
cctgtcgaat gttctcaacc ggaaagttct tttaagatgt ccttcaaaag agaaactaaa     1080
gtcctgaaga ctctgtcggt gatcatgggt gtgtttgtgt gctgttggct acctttcttc     1140
```

-continued

```
atcttgaact gcattttgcc cttctgtggg tctggggaga cgcagccctt ctgcattgat    1200
tccaacacct ttgacgtgtt tgtgtggttt gggtgggcta attcatcctt gaaccccatc    1260
atttatgcct ttaatgctga ttttcggaag gcattttcaa ccctcttagg atgctacaga    1320
ctttgccctg cgacgaataa tgccatagag acggtgagta tcaataacaa tggggccgcg    1380
atgttttcca gccatcatga gccacgaggc tccatctcca aggagtgcaa tctggtttac    1440
ctgatcccac atgctgtggg ctcctctgag gacctgaaaa aggaggaggc agctggcatc    1500
gccagaccct tggagaagct gtccccagcc ctatcggtca tattggacta tgacactgac    1560
gtctctctgg agaagatcca acccatcaca caaaacggtc agcacccaac ctgaactcgc    1620
agatgaatcc tgccacacat gctcatccca aaagctagag gagattgctc tggggtttgc    1680
tattaagaaa ctaaggtacg gtgag                                          1705
```

<210> SEQ ID NO 13
<211> LENGTH: 1705
<212> TYPE: DNA
<213> ORGANISM: Homo sapiens

<400> SEQUENCE: 13

```
ttcaggggct ttctggtgcc cttgacagtg acctgcagca agggagtcag aagacagatg      60
tagaaatcaa gagtgaccat ccacgggatt gacttggatt gccactcaag cggtcctctc     120
atggaatgtt ggtgaggccc tctgccaggg aagcaatctg gctgtgcaaa gtgctgcctg     180
gtggggagga ctcctggaaa tctgactgac ccctattccc tgcttgggaa cttgagggggt     240 gtcagagccc ctgatgtgct ttctcttagg aagatgagga ctctgaacac ctctgccatg     300
gacgggactg ggctggtggt ggagagggac ttctctgttc gtatcctcac tgcctgtttc     360
ctgtcgctgc tcatcctgtc ccggctcctg gggaacacgc tggtctgtgc tgccgttatc     420
aggttccgac acctgcggtc caaggtgacc aacttctttg tcatctcctt ggctgtgtca     480
gatctcttgg tggccgtcct ggtcatgccc tggaaggcag tggctgagat tgctggcttc     540
tggccctttg ggtccttctg taacatctgg gtggcctttg acatcatgtg ctccactgca     600
tccatcctca acctctgtgt gatcagcgtg gacaggtatt gggctatctc cagccctttc     660
cggtatgaga gaaagatgac ccccaaggca gccttcatcc tgatcagtgt ggcatggacc     720
ttgtctgtac tcatctcctt catcccagtg cagctcagct ggcacaaggc aaaacccaca     780
agcccctctg atgaaatgc cacttccctg gctgagacca tagacaactg tgactccagc     840
ctcagcagga catatgccat ctcatcctct gtaataagct tttacatccc tgtggccatc     900
atgattgtca cctacaccag gatctacagg attgctcaga acaaatacg gcgcattgcg      960 gccttggaga gggcagcagt ccacgccaag aattgccaga ccaccacagg taatggaaag    1020
cctgtcgaat gttctcaacc ggaaagttct tttaagatgt ccttcaaaag agaaactaaa    1080
gtcctgaaga ctctgtcggt gatcatgggt gtgtttgtgt gctgttggct accttcttc    1140 atcttgaact gcattttgcc cttctgtggg tctggggaga cgcagccctt ctgcattgat    1200
tccaacacct ttgacgtgtt tgtgtggttt gggtgggcta attcatcctt gaaccccatc    1260
atttatgcct ttaatgctga ttttcggaag gcattttcaa ccctcttagg atgctacaga    1320
ctttgccctg cgacgaataa tgccatagag acggtgagta tcaataacaa tggggccgcg    1380
atgttttcca gccatcatga gccacgaggc tccatctcca aggagtgcaa tctggtttac    1440
ctgatcccac atgctgtggg ctcctctgag gacctgaaaa aggaggaggc agctggcatc    1500
```

```
gccagaccct tggagaagct gtccccagcc ctatcggtca tattggacta tgacactgac    1560
gtctctctgg agaagatcca acccatcaca caaaacggtc agcacccaac ctgaactcgc    1620
agatgaatcc tgccacacat gctcatccca aaagctagag gagattgctc tggggtttgc    1680
tattaagaaa ctaaggtacg gtgag                                          1705

<210> SEQ ID NO 14
<211> LENGTH: 1705
<212> TYPE: DNA
<213> ORGANISM: Homo sapiens

<400> SEQUENCE: 14
ttcaggggct ttctggtgcc cttgacagtg acctgcagca agggagtcag aagacagatg      60
tagaaatcaa gagtgaccat ccacgggatt gacttggatt gccactcaag cggtcctctc     120
atggaatgtt ggtgaggccc tctgccaggg aagcaatctg gctgtgcaaa gtgctgcctg     180
gtggggagga ctcctggaaa tctgactgac ccctattccc tgcttgggaa cttgaggggt     240
gtcagagccc ctgatgtgct ttctcttagg aagatgagga ctctgaacac ctctgccatg     300
gacgggactg ggctggtggt ggagagggac ttctctgttc gtatcctcac tgcctgtttc     360
ctgtcgctgc tcatcctgtc cacgctcctg ggaacacgc tggtctgtgc tgccgttatc      420
aggttccgac acctgcggtc caaggtgacc aacttctttg tcatctcctt ggctgtgtca     480
gatctcttgg tggccgtcct ggtcatgctc tggaaggcag tggctgagat tgctggcttc     540
tggccctttg ggtccttctg taacatctgg gtggcctttg acatcatgtg ctccactgca     600
tccatcctca acctctgtgt gatcagcgtg acaggtatt gggctatctc cagcccttc      660 cggtatgaga gaaagatgac ccccaaggca gccttcatcc tgatcagtgt ggcatggacc     720 tgtctgtac tcatctcctt catcccagtg cagctcagct ggcacaaggc aaaacccaca     780
agcccctctg atggaaatgc cacttccctg gctgagacca tagacaactg tgactccagc     840
ctcagcagga catatgccat ctcatcctct gtaataagct tttacatccc tgtggccatc     900
atgattgtca cctacaccag gatctacagg attgctcaga aacaaatacg gcgcattgcg     960
gccttggaga gggcagcagt ccacgccaag aattgccaga ccaccacagg taatggaaag    1020
cctgtcgaat gttctcaacc ggaaagttct tttaagatgt ccttcaaaag agaaactaaa    1080
gtcctgaaga ctctgtcggt gatcatgggt gtgtttgtgt gctgttggct accttttcttc   1140 atcttgaact gcattttgcc cttctgtggg tctggggaga cgcagcccct ctgcattgat    1200
tccaacacct ttgacgtgtt tgtgtggttt gggtgggcta attcatcctt gaaccccatc    1260
atttatgcct ttaatgctga ttttcggaag gcattttcaa ccctcttagg atgctacaga    1320
ctttgccctg cgacgaataa tgccatagag acggtagta tcaataacaa tggggccgcg     1380
atgttttcca gccatcatga gccacgaggc tccatctcca aggagtgcaa tctggtttac    1440
ctgatcccac atgctgtggg ctcctctgag gacctgaaaa aggaggaggc agctggcatc    1500
gccagaccct tggagaagct gtccccagcc ctatcggtca tattggacta tgacactgac    1560
gtctctctgg agaagatcca acccatcaca caaaacggtc agcacccaac ctgaactcgc    1620
agatgaatcc tgccacacat gctcatccca aaagctagag gagattgctc tggggtttgc    1680
tattaagaaa ctaaggtacg gtgag                                          1705

<210> SEQ ID NO 15
<211> LENGTH: 1705
<212> TYPE: DNA
<213> ORGANISM: Homo sapiens
```

<400> SEQUENCE: 15

```
ttcaggggct ttctggtgcc cttgacagtg acctgcagca agggagtcag aagacagatg      60
tagaaatcaa gagtgaccat ccacgggatt gacttggatt gccactcaag cggtcctctc     120
atggaatgtt ggtgaggccc tctgccaggg aagcaatctg gctgtgcaaa gtgctgcctg     180
gtggggagga ctcctggaaa tctgactgac ccctattccc tgcttgggaa cttgaggggt     240
gtcagagccc ctgatgtgct ttctcttagg aagatgagga ctctgaacac ctctgccatg     300
gacgggactg gctggtggt ggagagggac ttctctgttc gtatcctcac tgcctgtttc      360
ctgtcgctgc tcatcctgtc cacgctcctg ggaacacgc tggtctgtgc tgccgttatc      420
aggttccgac acctgcggtc caaggtgacc aacttctttg tcatctcctt ggctgtgtca     480
gatctcttgg tggccgtcct ggtcatgccc tggaaggcag tggctgagat tgctggcttc     540
tggccctttg ggtccttctg taacatctgg gtggcctttg acatcatgtg ctccactgca     600
tccatcctca acctctgtgt gatcagcgtg gacaggtatt gggctatctc cagcccttc     660
cggtatgaga gaaagatgac ccccaaggca gccttcatcc tgatcagtgt ggcatggacc     720
ttgtctgtac tcatctcctt catcccagtg cagctcagct ggcacaaggc aaaacccaca     780
agccctctg atggaaatgc cacttccctg gctgagacca tagacaactg tgactccagc     840
ctcagcagga catatgccat ctcatcccgt gtaataagct tttacatccc tgtggccatc     900
atgattgtca cctacaccag gatctacagg attgctcaga acaaatacg gcgcattgcg     960
gccttggaga gggcagcagt ccacgccaag aattgccaga ccaccacagg taatggaaag    1020
cctgtcgaat gttctcaacc ggaaagttct tttaagatgt ccttcaaaag agaaactaaa    1080
gtcctgaaga ctctgtcggt gatcatgggt gtgtttgtgt gctgttggct acctttcttc    1140
atcttgaact gcattttgcc cttctgtggg tctggggaga cgcagcccct ctgcattgat    1200
tccaacacct ttgacgtgtt tgtgtggttt gggtgggcta attcatcctt gaaccccatc    1260
atttatgcct ttaatgctga ttttcggaag gcattttcaa ccctcttagg atgctacaga    1320
cttttgccctg cgacgaataa tgccatagag acggtgagta tcaataacaa tggggccgcg    1380
atgttttcca gccatcatga gccacgaggc tccatctcca aggagtgcaa tctggtttac    1440
ctgatcccac atgctgtggg ctcctctgag gacctgaaaa aggaggaggc agctggcatc    1500
gccagaccct tggagaagct gtccccagcc ctatcggtca tattggacta tgacactgac    1560
gtctctctgg agaagatcca acccatcaca caaaacggtc agcacccaac ctgaactcgc    1620
agatgaatcc tgccacacat gctcatccca aaagctagag gagattgctc tggggtttgc    1680
tattaagaaa ctaaggtacg gtgag                                          1705
```

<210> SEQ ID NO 16
<211> LENGTH: 446
<212> TYPE: PRT
<213> ORGANISM: Homo sapiens

<400> SEQUENCE: 16

```
Met Arg Thr Leu Asn Thr Ser Ala Met Asp Gly Thr Gly Leu Val Val
 1               5                  10                  15

Glu Arg Asp Phe Ser Val Arg Ile Leu Thr Ala Cys Phe Leu Ser Leu
            20                  25                  30

Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
```

```
                50                  55                  60
Ser Leu Ala Val Ser Asp Leu Val Ala Val Leu Val Met Pro Trp
 65                  70                  75                  80

Lys Ala Val Ala Glu Ile Ala Gly Phe Trp Pro Phe Gly Ser Phe Cys
                     85                  90                  95

Asn Ile Trp Val Ala Phe Asp Ile Met Cys Ser Thr Ala Ser Ile Leu
                100                 105                 110

Asn Leu Cys Val Ile Ser Val Asp Arg Tyr Trp Ala Ile Ser Ser Pro
                115                 120                 125

Phe Arg Tyr Glu Arg Lys Met Thr Pro Lys Ala Ala Phe Ile Leu Ile
130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
                180                 185                 190

Thr Tyr Ala Ile Ser Ser Ser Val Ile Ser Phe Tyr Ile Pro Val Ala
                195                 200                 205

Ile Met Ile Val Thr Tyr Thr Arg Ile Tyr Arg Ile Ala Gln Lys Gln
                210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
                260                 265                 270

Thr Leu Ser Val Ile Met Gly Val Phe Val Cys Cys Trp Leu Pro Phe
                275                 280                 285

Phe Ile Leu Asn Cys Ile Leu Pro Phe Cys Gly Ser Gly Glu Thr Gln
                290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
                340                 345                 350

Ala Thr Asn Asn Ala Ile Glu Thr Val Ser Ile Asn Asn Asn Gly Ala
                355                 360                 365

Ala Met Phe Ser Ser His His Glu Pro Arg Gly Ser Ile Ser Lys Glu
                370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
                420                 425                 430

Glu Lys Ile Gln Pro Ile Thr Gln Asn Gly Gln His Pro Thr
                435                 440                 445

<210> SEQ ID NO 17
<211> LENGTH: 446
<212> TYPE: PRT
<213> ORGANISM: Homo sapiens
```

<400> SEQUENCE: 17

Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
            20                  25                  30

Leu Ile Leu Ser Pro Leu Leu Gly Asn Thr Leu Val Cys Ala Ala Val
        35                  40                  45

Ile Arg Phe Arg His Leu Arg Ser Lys Val Thr Asn Phe Phe Val Ile
50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
    290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu

```
                    405                 410                 415
Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
        435                 440                 445

<210> SEQ ID NO 18
<211> LENGTH: 446
<212> TYPE: PRT
<213> ORGANISM: Homo sapiens

<400> SEQUENCE: 18

Met Arg Thr Leu Asn Thr Ser Ala Met Asp Gly Thr Gly Leu Val Val
 1               5                  10                  15

Glu Arg Asp Phe Ser Val Arg Ile Leu Thr Ala Cys Phe Leu Ser Leu
                20                  25                  30

Leu Ile Leu Ser Arg Leu Leu Gly Asn Thr Leu Val Cys Ala Ala Val
            35                  40                  45

Ile Arg Phe Arg His Leu Arg Ser Lys Val Thr Asn Phe Phe Val Ile
50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
        130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
        210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
        290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335
```

-continued

Phe Arg Lys Ala Phe Ser Thr Leu Leu Gly Cys Tyr Arg Leu Cys Pro
                340                 345                 350

Ala Thr Asn Asn Ala Ile Glu Thr Val Ser Ile Asn Asn Asn Gly Ala
            355                 360                 365

Ala Met Phe Ser Ser His His Glu Pro Arg Gly Ser Ile Ser Lys Glu
        370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
                435                 440                 445

<210> SEQ ID NO 19
<211> LENGTH: 446
<212> TYPE: PRT
<213> ORGANISM: Homo sapiens

<400> SEQUENCE: 19

Met Arg Thr Leu Asn Thr Ser Ala Met Asp Gly Thr Gly Leu Val Val
1                   5                   10                  15

Glu Arg Asp Phe Ser Val Arg Ile Leu Thr Ala Cys Phe Leu Ser Leu
                20                  25                  30

Leu Ile Leu Ser Thr Leu Leu Gly Asn Thr Leu Val Cys Ala Ala Val
            35                  40                  45

Ile Arg Phe Arg His Leu Arg Ser Lys Val Thr Asn Phe Phe Val Ile
        50                  55                  60

Ser Leu Ala Val Ser Asp Leu Val Ala Val Leu Val Met Ser Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

-continued

Thr Leu Ser Val Ile Met Gly Val Phe Val Cys Cys Trp Leu Pro Phe
         275                 280                 285

Phe Ile Leu Asn Cys Ile Leu Pro Phe Cys Gly Ser Gly Glu Thr Gln
         290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                 325                 330                 335

Phe Arg Lys Ala Phe Ser Thr Leu Leu Gly Cys Tyr Arg Leu Cys Pro
                 340                 345                 350

Ala Thr Asn Asn Ala Ile Glu Thr Val Ser Ile Asn Asn Asn Gly Ala
                 355                 360                 365

Ala Met Phe Ser Ser His His Glu Pro Arg Gly Ser Ile Ser Lys Glu
                 370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                 405                 410                 415

Ser Pro Ala Leu Ser Val Ile Leu Asp Tyr Asp Thr Asp Val Ser Leu
                 420                 425                 430

Glu Lys Ile Gln Pro Ile Thr Gln Asn Gly Gln His Pro Thr
                 435                 440                 445

<210> SEQ ID NO 20
<211> LENGTH: 446
<212> TYPE: PRT
<213> ORGANISM: Homo sapiens

<400> SEQUENCE: 20

Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
                20                  25                  30

Leu Ile Leu Ser Thr Leu Leu Gly Asn Thr Leu Val Cys Ala Ala Val
            35                  40                  45

Ile Arg Phe Arg His Leu Arg Ser Lys Val Thr Asn Phe Phe Val Ile
        50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ala Val Ile Ser Phe Tyr Ile Pro Val Ala

```
                195                 200                 205
Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
                260                 265                 270

Thr Leu Ser Val Ile Met Gly Val Phe Val Cys Cys Trp Leu Pro Phe
            275                 280                 285

Phe Ile Leu Asn Cys Ile Leu Pro Phe Cys Gly Ser Gly Glu Thr Gln
        290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
        435                 440                 445

<210> SEQ ID NO 21
<211> LENGTH: 2100
<212> TYPE: DNA
<213> ORGANISM: Homo sapiens

<400> SEQUENCE: 21
gaattccgag agccccggcg ggcagcagcc ggcgccgtct ctgccccggg gcgccctatg      60
gcttgaagag cctggccacc cagtggctcc accgccctga tggatccact gaatctgtcc     120
tggtatgatg atgatctgga gaggcagaac tggagccggc ccttcaacgg gtcagacggg     180
aaggcggaca gacccactaa caactactat gccacactgc tcaccctgct catcgctgtc     240
atcgtcttcg gcaacgtgct ggtgtgcatg gctgtgtcta gagagaaggc gctgcagacc     300
accaccaact acctgatcgt cagcctcgca gtggccgacc tcctcgtcgc cacactggtc     360
atgccctggg ttgtctacct ggaggtggta ggtgagtgga aattcagcag gattcactgt     420
gacatcttcg tcactctgga cgtcatgatg tgcacggcga catcctgaa cttgtgtgcc     480 atcagcatcg acaggtacac agctgtggcc atgcccatgc tgtacaatac gcgctacagc     540
tccaagcgcc gggtcaccgt catgatctcc atcgtctggg tcctgtcctt caccatctcc     600
tgcccactcc tcttcggact caataacgca gaccagaacg agtgcatcat tgccaacccg     660
gccttcgtgg tctactcctc catcgtctcc ttctacgtgc ccttcattgt cacccttgctg     720
```

| | |
|---|---|
| gtctacatca agatctacat tgtcctccgc agacgccgca agcgagtcaa caccaaacgc | 780 |
| agcagccgag ctttcagggc ccacctgagg gctccactaa aggaggctgc ccggcgagcc | 840 |
| caggagctgg agatggagat gctctccagc accagcccac ccgagaggac ccggtacagc | 900 |
| cccatcccac ccagccacca ccagctgact ctccccgacc cgtcccacca tggtctccac | 960 |
| agcactcccg acagcccgc caaaccagag aagaatgggc atgccaaaga ccaccccaag | 1020 |
| attgccaaga tctttgagat ccagaccatg cccaatggca aaacccggac ctccctcaag | 1080 |
| accatgagcc gtaggaagct ctcccagcag aaggagaaga agccactca gatgcttgcc | 1140 |
| attgttctcg gtgtgttcat catctgctgg ctgcccttct tcatcacaca catcctgaat | 1200 |
| atacactgtg actgcaacat cccgcctgtc ctgtacagcg ccttcacgtg gctgggctat | 1260 |
| gtcaacagcg ccgtgaaccc catcatctac accaccttca acattgagtt ccgcaaggcc | 1320 |
| ttcctgaaga tcctccactg ctgactctgc tgcctgcccg cacagcagcc tgcttcccac | 1380 |
| ctccctgccc aggccggcca gccgtcaccc ttgcgaaccg tgagcaggaa ggcctgggtg | 1440 |
| gatcggcctc ctcttcaccc cggcagccct gcagtgttcg cttggctcca tgctcctcac | 1500 |
| tgcccgcaca ccctcactct gccagggcag tgctagtgag ctgggcatgg taccagccct | 1560 |
| ggggctggcc ccccagctca ggggcagctc atagagtccc ccctcccacc tccagtcccc | 1620 |
| ctatccttgg caccaaagat cgagccgcct tccttgacct tcctctgggc tctagggttg | 1680 |
| ctggagcctg agtcagggcc cagaggctga gttttctctt tgtggggctt ggcgtggagc | 1740 |
| aggcggtggg gagagatgga cagttcacac cctgcaaggc ccacaggagg caagcaagct | 1800 |
| ctcttgccga ggagccaggc aacttcagtc ctgggagacc catgtaaata ccagactgca | 1860 |
| ggttggaccc cagagattcc caagccaaaa accttagctc cctcccgcac ccgatgtgg | 1920 |
| acctctactt tccaggctag tccggaccca cctcaccccg ttacagctcc ccaagtggtt | 1980 |
| tccacatgct ctgagaagag gagccctcat cttgaagggc caggagggtc tatggggaga | 2040 |
| ggaactcctt ggcctagccc accctgctgc cttctgacgg ccctgcaatg tatcccttct | 2100 |

<210> SEQ ID NO 22
<211> LENGTH: 2100
<212> TYPE: DNA
<213> ORGANISM: Homo sapiens

<400> SEQUENCE: 22

| | |
|---|---|
| gaattccgag agccccggcg ggcagcagcc ggcgccgtct ctgccccggg gcgccctatg | 60 |
| gcttgaagag cctggccacc cagtggctcc accgccctga tggatccact gaatctgtcc | 120 |
| tggtatgatg atgatctgga gaggcagaac tggagccggc ccttcaacgg gtcagacggg | 180 |
| aaggcggaca gaccccacta caactactat gccacacggc tcaccctgct catcgctgtc | 240 |
| atcgtcttcg gcaacgtgct ggtgtgcatg gctgtgtcta gagagaaggc gctgcagacc | 300 |
| accaccaact acctgatcgt cagcctcgca gtggccgacc tcctcgtcgc cacactggtc | 360 |
| atgccctggg ttgtctacct ggaggtggta ggtgagtgga aattcagcag gattcactgt | 420 |
| gacatcttcg tcactctgga cgtcatgatg tgcacggcga gcatcctgaa cttgtgtgcc | 480 |
| atcagcatcg acaggtacac agctgtggcc atgcccatgc tgtacaatac gcgctacagc | 540 |
| tccaagcgcc gggtcaccgt catgatctcc atcgtctggg tcctgtcctt caccatctcc | 600 |
| tgcccactcc tcttcggact caataacgca gaccagaacg agtgcatcat tgccaacccg | 660 |
| gccttcgtgg tctactcctc catcgtctcc ttctacgtgc ccttcattgt caccctgctg | 720 |
| gtctacatca agatctacat tgtcctccgc agacgccgca agcgagtcaa caccaaacgc | 780 |

-continued

| | |
|---|---|
| agcagccgag ctttcagggc ccacctgagg gctccactaa aggaggctgc ccggcgagcc | 840 |
| caggagctgg agatggagat gctctccagc accagcccac ccgagaggac ccggtacagc | 900 |
| cccatcccac ccagccacca ccagctgact ctccccgacc cgtcccacca tggtctccac | 960 |
| agcactcccg acagccccgc caaaccagag aagaatgggc atgccaaaga ccaccccaag | 1020 |
| attgccaaga tctttgagat ccagaccatg cccaatggca aaacccggac ctccctcaag | 1080 |
| accatgagcc gtaggaagct ctcccagcag aaggagaaga aagccactca gatgcttgcc | 1140 |
| attgttctcg gtgtgttcat catctgctgg ctgcccttct tcatcacaca catcctgaat | 1200 |
| atacactgtg actgcaacat cccgcctgtc ctgtacagcg ccttcacgtg gctgggctat | 1260 |
| gtcaacagcg ccgtgaaccc catcatctac accaccttca acattgagtt ccgcaaggcc | 1320 |
| ttcctgaaga tcctccactg ctgactctgc tgcctgcccg cacagcagcc tgcttcccac | 1380 |
| ctccctgccc aggccggcca gccgtcaccc ttgcgaaccg tgagcaggaa ggcctgggtg | 1440 |
| gatcggcctc ctcttcaccc cggcagccct gcagtgttcg cttggctcca tgctcctcac | 1500 |
| tgcccgcaca ccctcactct gccagggcag tgctagtgag ctgggcatgg taccagccct | 1560 |
| ggggctggcc ccccagctca ggggcagctc atagagtccc ccctcccacc tccagtcccc | 1620 |
| ctatccttgg caccaaagat cgagccgcct tccttgacct tcctctgggc tctagggttg | 1680 |
| ctggagcctg agtcagggcc cagaggctga gttttctctt tgtggggctt ggcgtggagc | 1740 |
| aggcggtggg gagagatgga cagttcacac cctgcaaggc ccacaggagg caagcaagct | 1800 |
| ctcttgccga ggagccaggc aacttcagtc ctgggagacc catgtaaata ccagactgca | 1860 |
| ggttggaccc cagagattcc caagccaaaa accttagctc cctccgcac cccgatgtgg | 1920 |
| acctctactt tccaggctag tccggaccca cctcaccccg ttacagctcc ccaagtggtt | 1980 |
| tccacatgct ctgagaagag gagccctcat cttgaagggc caggagggtc tatggggaga | 2040 |
| ggaactcctt ggcctagccc accctgctgc cttctgacgg ccctgcaatg tatcccttct | 2100 |

<210> SEQ ID NO 23
<211> LENGTH: 2100
<212> TYPE: DNA
<213> ORGANISM: Homo sapiens

<400> SEQUENCE: 23

| | |
|---|---|
| gaattccgag agccccggcg ggcagcagcc ggcgccgtct ctgccccggg gcgccctatg | 60 |
| gcttgaagag cctggccacc cagtggctcc accgccctga tggatccact gaatctgtcc | 120 |
| tggtatgatg atgatctgga gaggcagaac tggagccggc ccttcaacgg gtcagacggg | 180 |
| aaggcggaca daccccacta caactactat gccacactgc tcaccctgct catcgctgtc | 240 |
| atcgtcttcg gcaacgtgct ggtgtgcatg gctgtgtcta gagagaaggc gctgcagacc | 300 |
| accaccaact acctgatcgt cagcctcgca gtggccgacc tcctcgtcgc cacactggtc | 360 |
| atgccctggg ttgtctacct ggaggtggta ggtgagtgga aattcagcag gattcactgt | 420 |
| gacatcttcg tcactctgga cgtcatgatg tgcacggcga gcatcctgaa cttgtgtgcc | 480 |
| atcagcatcg acaggtacac agctgtggcc atgcccatgc tgtacaatac gcgctacagc | 540 |
| tccaagcgcc gggtcaccgt catgatctcc atcgtctggg tcctgtcctt caccatctcc | 600 |
| tgcccactcc tcttcggact caataacgca gaccagaacg agtgcatcat tgccaacccg | 660 |
| gccttcgtgg tctactcctc catcgtctcc ttctacgtgc ccttcattgt caccctgctg | 720 |
| ctctacatca agatctacat tgtcctccgc agacgccgca agcgagtcaa caccaaacgc | 780 |

```
agcagccgag ctttcagggc ccacctgagg gctccactaa aggaggctgc ccggcgagcc      840
caggagctgg agatggagat gctctccagc accagcccac ccgagaggac ccggtacagc      900
cccatcccac ccagccacca ccagctgact ctccccgacc cgtcccacca tggtctccac      960
agcactcccg acagccccgc caaaccagag aagaatgggc atgccaaaga ccaccccaag     1020
attgccaaga tctttgagat ccagaccatg cccaatggca aaccccggac ctccctcaag     1080
accatgagcc gtaggaagct ctcccagcag aaggagaaga agccactca gatgcttgcc      1140 attgttctcg gtgtgttcat catctgctgg ctgcccttct tcatcacaca catcctgaat     1200
atacactgtg actgcaacat cccgcctgtc ctgtacagcg ccttcacgtg gctgggctat     1260
gtcaacagcg ccgtgaaccc catcatctac accaccttca acattgagtt ccgcaaggcc     1320
ttcctgaaga tcctccactg ctgactctgc tgcctgcccg cacagcagcc tgcttcccac     1380
ctccctgccc aggccggcca gccgtcaccc ttgcgaaccg tgagcaggaa ggcctgggtg     1440
gatcggcctc ctcttcaccc cggcagccct gcagtgttcg cttggctcca tgctcctcac     1500
tgcccgcaca ccctcactct gccagggcag tgctagtgag ctgggcatgg taccagccct     1560
ggggctggcc ccccagctca ggggcagctc atagagtccc ccctcccacc tccagtcccc     1620
ctatccttgg caccaaagat cgagccgcct tccttgacct tcctctgggc tctagggttg     1680
ctggagcctg agtcagggcc cagaggctga gttttctctt tgtggggctt ggcgtggagc     1740
aggcggtggg gagagatgga cagttcacac cctgcaaggc ccacaggagg caagcaagct     1800
ctcttgccga ggagccaggc aacttcagtc ctgggagacc catgtaaata ccagactgca     1860
ggttggaccc cagagattcc caagccaaaa accttagctc cctcccgcac ccgatgtgg     1920 acctctactt tccaggctag tccggaccca cctcaccccg ttacagctcc caagtggtt     1980 tccacatgct ctgagaagag gagccctcat cttgaagggc caggagggtc tatggggaga     2040
ggaactcctt ggcctagccc accctgctgc cttctgacgg ccctgcaatg tatcccttct     2100
```

<210> SEQ ID NO 24
<211> LENGTH: 414
<212> TYPE: PRT
<213> ORGANISM: Homo sapiens

<400> SEQUENCE: 24

```
Met Asp Pro Leu Asn Leu Ser Trp Tyr Asp Asp Leu Glu Arg Gln
 1               5                  10                  15

Asn Trp Ser Arg Pro Phe Asn Gly Ser Asp Gly Lys Ala Asp Arg Pro
             20                  25                  30

His Tyr Asn Tyr Tyr Ala Thr Leu Leu Thr Leu Leu Ile Ala Val Ile
         35                  40                  45

Val Phe Gly Asn Val Leu Val Cys Met Ala Val Ser Arg Glu Lys Ala
     50                  55                  60

Leu Gln Thr Thr Thr Asn Tyr Leu Ile Val Ser Leu Ala Val Ala Asp
 65                  70                  75                  80

Leu Leu Val Ala Thr Leu Val Met Pro Trp Val Val Tyr Leu Glu Val
                 85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
        115                 120                 125

Ser Ile Asp Arg Tyr Thr Ala Val Ala Met Pro Met Leu Tyr Asn Thr
    130                 135                 140
```

```
Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Arg Arg Arg Lys Arg Val Asn
210                 215                 220

Thr Lys Arg Ser Ser Arg Ala Phe Arg Ala His Leu Arg Ala Pro Leu
225                 230                 235                 240

Lys Glu Ala Ala Arg Arg Ala Gln Glu Leu Glu Met Glu Met Leu Ser
                245                 250                 255

Ser Thr Ser Pro Pro Glu Arg Thr Arg Tyr Ser Pro Ile Pro Pro Ser
                260                 265                 270

His His Gln Leu Thr Leu Pro Asp Pro Ser His His Gly Leu His Ser
            275                 280                 285

Thr Pro Asp Ser Pro Ala Lys Pro Glu Lys Asn Gly His Ala Lys Asp
290                 295                 300

His Pro Lys Ile Ala Lys Ile Phe Glu Ile Gln Thr Met Pro Asn Gly
305                 310                 315                 320

Lys Thr Arg Thr Ser Leu Lys Thr Met Ser Arg Arg Lys Leu Ser Gln
                325                 330                 335

Gln Lys Glu Lys Lys Ala Thr Gln Met Leu Ala Ile Val Leu Gly Val
            340                 345                 350

Phe Ile Ile Cys Trp Leu Pro Phe Phe Ile Thr His Ile Leu Asn Ile
        355                 360                 365

His Cys Asp Cys Asn Ile Pro Pro Val Leu Tyr Ser Ala Phe Thr Trp
    370                 375                 380

Leu Gly Tyr Val Asn Ser Ala Val Asn Pro Ile Ile Tyr Thr Thr Phe
385                 390                 395                 400

Asn Ile Glu Phe Arg Lys Ala Phe Leu Lys Ile Leu His Cys
                405                 410

<210> SEQ ID NO 25
<211> LENGTH: 414
<212> TYPE: PRT
<213> ORGANISM: Homo sapiens

<400> SEQUENCE: 25

Met Asp Pro Leu Asn Leu Ser Trp Tyr Asp Asp Leu Glu Arg Gln
1                   5                   10                  15

Asn Trp Ser Arg Pro Phe Asn Gly Ser Asp Gly Lys Ala Asp Arg Pro
                20                  25                  30

His Tyr Asn Tyr Tyr Ala Thr Arg Leu Thr Leu Leu Ile Ala Val Ile
            35                  40                  45

Val Phe Gly Asn Val Leu Val Cys Met Ala Val Ser Arg Glu Lys Ala
        50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
                100                 105                 110
```

-continued

Leu Asp Val Met Met Cys Thr Ala Ser Ile Leu Asn Leu Cys Ala Ile
            115                 120                 125

Ser Ile Asp Arg Tyr Thr Ala Val Ala Met Pro Met Leu Tyr Asn Thr
        130                 135                 140

Arg Tyr Ser Ser Lys Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Arg Arg Arg Lys Arg Val Asn
210                 215                 220

Thr Lys Arg Ser Ser Arg Ala Phe Arg Ala His Leu Arg Ala Pro Leu
225                 230                 235                 240

Lys Glu Ala Ala Arg Arg Ala Gln Glu Leu Glu Met Glu Met Leu Ser
                245                 250                 255

Ser Thr Ser Pro Pro Glu Arg Thr Arg Tyr Ser Pro Ile Pro Pro Ser
            260                 265                 270

His His Gln Leu Thr Leu Pro Asp Pro Ser His His Gly Leu His Ser
        275                 280                 285

Thr Pro Asp Ser Pro Ala Lys Pro Glu Lys Asn Gly His Ala Lys Asp
290                 295                 300

His Pro Lys Ile Ala Lys Ile Phe Glu Ile Gln Thr Met Pro Asn Gly
305                 310                 315                 320

Lys Thr Arg Thr Ser Leu Lys Thr Met Ser Arg Arg Lys Leu Ser Gln
                325                 330                 335

Gln Lys Glu Lys Lys Ala Thr Gln Met Leu Ala Ile Val Leu Gly Val
            340                 345                 350

Phe Ile Ile Cys Trp Leu Pro Phe Phe Ile Thr His Ile Leu Asn Ile
        355                 360                 365

His Cys Asp Cys Asn Ile Pro Pro Val Leu Tyr Ser Ala Phe Thr Trp
370                 375                 380

Leu Gly Tyr Val Asn Ser Ala Val Asn Pro Ile Ile Tyr Thr Thr Phe
385                 390                 395                 400

Asn Ile Glu Phe Arg Lys Ala Phe Leu Lys Ile Leu His Cys
                405                 410

<210> SEQ ID NO 26
<211> LENGTH: 414
<212> TYPE: PRT
<213> ORGANISM: Homo sapiens

<400> SEQUENCE: 26

Met Asp Pro Leu Asn Leu Ser Trp Tyr Asp Asp Asp Leu Glu Arg Gln
1               5                   10                  15

Asn Trp Ser Arg Pro Phe Asn Gly Ser Asp Gly Lys Ala Asp Arg Pro
            20                  25                  30

His Tyr Asn Tyr Tyr Ala Thr Leu Leu Thr Leu Leu Ile Ala Val Ile
        35                  40                  45

Val Phe Gly Asn Val Leu Val Cys Met Ala Val Ser Arg Glu Lys Ala
    50                  55                  60

Leu Gln Thr Thr Thr Asn Tyr Leu Ile Val Ser Leu Ala Val Ala Asp

```
                65                  70                  75                  80
Leu Leu Val Ala Thr Leu Val Met Pro Trp Val Val Tyr Leu Glu Val
                    85                  90                  95
Val Gly Glu Trp Lys Phe Ser Arg Ile His Cys Asp Ile Phe Val Thr
                100                 105                 110
Leu Asp Val Met Met Cys Thr Ala Ser Ile Leu Asn Leu Cys Ala Ile
                115                 120                 125
Ser Ile Asp Arg Tyr Thr Ala Val Ala Met Pro Met Leu Tyr Asn Thr
            130                 135                 140
Arg Tyr Ser Ser Lys Arg Val Thr Val Met Ile Ser Ile Val Trp
145                 150                 155                 160
Val Leu Ser Phe Thr Ile Ser Cys Pro Leu Leu Phe Gly Leu Asn Asn
                    165                 170                 175
Ala Asp Gln Asn Glu Cys Ile Ile Ala Asn Pro Ala Phe Val Val Tyr
                180                 185                 190
Ser Ser Ile Val Ser Phe Tyr Val Pro Phe Ile Val Thr Leu Leu Leu
                195                 200                 205
Tyr Ile Lys Ile Tyr Ile Val Leu Arg Arg Arg Lys Arg Val Asn
                210                 215                 220
Thr Lys Arg Ser Ser Arg Ala Phe Arg Ala His Leu Arg Ala Pro Leu
225                 230                 235                 240
Lys Glu Ala Ala Arg Arg Ala Gln Glu Leu Glu Met Glu Met Leu Ser
                    245                 250                 255
Ser Thr Ser Pro Pro Glu Arg Thr Arg Tyr Ser Pro Ile Pro Pro Ser
                260                 265                 270
His His Gln Leu Thr Leu Pro Asp Pro Ser His His Gly Leu His Ser
                275                 280                 285
Thr Pro Asp Ser Pro Ala Lys Pro Glu Lys Asn Gly His Ala Lys Asp
            290                 295                 300
His Pro Lys Ile Ala Lys Ile Phe Glu Ile Gln Thr Met Pro Asn Gly
305                 310                 315                 320
Lys Thr Arg Thr Ser Leu Lys Thr Met Ser Arg Arg Lys Leu Ser Gln
                    325                 330                 335
Gln Lys Glu Lys Lys Ala Thr Gln Met Leu Ala Ile Val Leu Gly Val
                340                 345                 350
Phe Ile Ile Cys Trp Leu Pro Phe Phe Ile Thr His Ile Leu Asn Ile
                355                 360                 365
His Cys Asp Cys Asn Ile Pro Pro Val Leu Tyr Ser Ala Phe Thr Trp
            370                 375                 380
Leu Gly Tyr Val Asn Ser Ala Val Asn Pro Ile Ile Tyr Thr Thr Phe
385                 390                 395                 400
Asn Ile Glu Phe Arg Lys Ala Phe Leu Lys Ile Leu His Cys
                    405                 410

<210> SEQ ID NO 27
<211> LENGTH: 1203
<212> TYPE: DNA
<213> ORGANISM: Homo sapiens

<400> SEQUENCE: 27
atggcatctc tgagtcagct gagtagccac ctgaactaca cctgtggggc agagaactcc      60
acaggtgcca gccaggcccg cccacatgcc tactatgccc tctcctactg cgcgctcatc     120
ctggccatcg tcttcggcaa tggcctggtg tgcatggctg tgctgaagga gcgggccctg     180
```

```
cagactacca ccaactactt agtagtgagc ctggctgtgg cagacttgct ggtggccacc      240
ttggtgatgc cctgggtggt atacctggag gtgacaggtg gagtctggaa tttcagccgc      300
atttgctgtg atgttttgt cacctggat gtcatgatgt gtacagccag catccttaat        360
ctctgtgcca tcagcataga caggtacact gcagtggtca tgcccgttca ctaccagcat      420
ggcacgggac agagctcctg tcggcgcgtg gccctcatga tcacggccgt ctgggtactg      480
gcctttgctg tgtcctgccc tcttctgttt ggctttaata ccacagggga ccccactgtc      540
tgctccatct ccaaccctga ttttgtcatc tactcttcag tggtgtcctt ctacctgccc      600
tttggagtga ctgtccttgt ctatgccaga atctatgtgg tgctgaaaca aaggagacgg      660
aaaaggatcc tcactcgaca gaacagtcag tgcaacagtg tcaggcctgg cttcccccaa      720
caaaccctct ctcctgaccc ggcacatctg gagctgaagc gttactacag catctgccag      780
gacactgcct tgggtggacc aggcttccaa gaaagaggag gagagttgaa aagagaggag      840
aagactcgga attccctgag tcccaccata gcgcccaagc tcagcttaga agttcgaaaa      900
ctcagcaatg gcagattatc gacatctttg aagctggggc ccctgcaacc tcggggagtg      960
ccacttcggg agaagaaggc aacccaaaatg gtggccattg tgcttgggc cttcattgtc     1020 tgctggctgc ccttcttctt gacccatgtt ctcaataccc actgccagac atgccacgtg     1080
tccccagagc tttacagtgc cacgacatgg ctgggctacg tgaatagcgc cctcaaccct     1140
gtgatctata ccaccttcaa tatcgagttc cggaaagcct tcctcaagat cctgtcttgc     1200
tga                                                                   1203
```

<210> SEQ ID NO 28
<211> LENGTH: 1203
<212> TYPE: DNA
<213> ORGANISM: Homo sapiens

<400> SEQUENCE: 28

```
atggcatctc tgagtcagct gagtagccac ctgaactaca cctgtggggc agagaactcc       60
acaggtgcca gccaggcccg cccacatgcc tactatgccc tctcctactg cgcgctcatc      120
ctggccatcg tcttcggcaa tggcctgctg tgcatggctg tgctgaagga gcgggccctg      180
cagactacca ccaactactt agtagtgagc ctggctgtgg cagacttgct ggtggccacc      240
ttggtgatgc cctgggtggt atacctggag gtgacaggtg gagtctggaa tttcagccgc      300
atttgctgtg atgttttgt cacctggat gtcatgatgt gtacagccag catccttaat        360
ctctgtgcca tcagcataga caggtacact gcagtggtca tgcccgttca ctaccagcat      420
ggcacgggac agagctcctg tcggcgcgtg gccctcatga tcacggccgt ctgggtactg      480
gcctttgctg tgtcctgccc tcttctgttt ggctttaata ccacagggga ccccactgtc      540
tgctccatct ccaaccctga ttttgtcatc tactcttcag tggtgtcctt ctacctgccc      600
tttggagtga ctgtccttgt ctatgccaga atctatgtgg tgctgaaaca aaggagacgg      660
aaaaggatcc tcactcgaca gaacagtcag tgcaacagtg tcaggcctgg cttcccccaa      720
caaaccctct ctcctgaccc ggcacatctg gagctgaagc gttactacag catctgccag      780
gacactgcct tgggtggacc aggcttccaa gaaagaggag gagagttgaa aagagaggag      840
aagactcgga attccctgag tcccaccata gcgcccaagc tcagcttaga agttcgaaaa      900
ctcagcaatg gcagattatc gacatctttg aagctggggc ccctgcaacc tcggggagtg      960
ccacttcggg agaagaaggc aacccaaaatg gtggccattg tgcttgggc cttcattgtc     1020 tgctggctgc ccttcttctt gacccatgtt ctcaataccc actgccagac atgccacgtg     1080
```

-continued

```
tccccagagc tttacagtgc cacgacatgg ctgggctacg tgaatagcgc cctcaaccct    1140
gtgatctata ccaccttcaa tatcgagttc cggaaagcct tcctcaagat cctgtcttgc    1200
tga                                                                  1203
```

<210> SEQ ID NO 29
<211> LENGTH: 400
<212> TYPE: PRT
<213> ORGANISM: Homo sapiens

<400> SEQUENCE: 29

```
Met Ala Ser Leu Ser Gln Leu Ser Ser His Leu Asn Tyr Thr Cys Gly
1               5                   10                  15

Ala Glu Asn Ser Thr Gly Ala Ser Gln Ala Arg Pro His Ala Tyr Tyr
            20                  25                  30

Ala Leu Ser Tyr Cys Ala Leu Ile Leu Ala Ile Val Phe Gly Asn Gly
        35                  40                  45

Leu Val Cys Met Ala Val Leu Lys Glu Arg Ala Leu Gln Thr Thr Thr
    50                  55                  60

Asn Tyr Leu Val Val Ser Leu Ala Val Ala Asp Leu Leu Val Ala Thr
65                  70                  75                  80

Leu Val Met Pro Trp Val Val Tyr Leu Glu Val Thr Gly Gly Val Trp
                85                  90                  95

Asn Phe Ser Arg Ile Cys Cys Asp Val Phe Val Thr Leu Asp Val Met
            100                 105                 110

Met Cys Thr Ala Ser Ile Leu Asn Leu Cys Ala Ile Ser Ile Asp Arg
        115                 120                 125

Tyr Thr Ala Val Val Met Pro Val His Tyr Gln His Gly Thr Gly Gln
    130                 135                 140

Ser Ser Cys Arg Arg Val Ala Leu Met Ile Thr Ala Val Trp Val Leu
145                 150                 155                 160

Ala Phe Ala Val Ser Cys Pro Leu Leu Phe Gly Phe Asn Thr Thr Gly
                165                 170                 175

Asp Pro Thr Val Cys Ser Ile Ser Asn Pro Asp Phe Val Ile Tyr Ser
            180                 185                 190

Ser Val Val Ser Phe Tyr Leu Pro Phe Gly Val Thr Val Leu Val Tyr
        195                 200                 205

Ala Arg Ile Tyr Val Val Leu Lys Gln Arg Arg Arg Lys Arg Ile Leu
    210                 215                 220

Thr Arg Gln Asn Ser Gln Cys Asn Ser Val Arg Pro Gly Phe Pro Gln
225                 230                 235                 240

Gln Thr Leu Ser Pro Asp Pro Ala His Leu Glu Leu Lys Arg Tyr Tyr
                245                 250                 255

Ser Ile Cys Gln Asp Thr Ala Leu Gly Gly Pro Gly Phe Gln Glu Arg
            260                 265                 270

Gly Gly Glu Leu Lys Arg Glu Glu Lys Thr Arg Asn Ser Leu Ser Pro
        275                 280                 285

Thr Ile Ala Pro Lys Leu Ser Leu Glu Val Arg Lys Leu Ser Asn Gly
    290                 295                 300

Arg Leu Ser Thr Ser Leu Lys Leu Gly Pro Leu Gln Pro Arg Gly Val
305                 310                 315                 320

Pro Leu Arg Glu Lys Lys Ala Thr Gln Met Val Ala Ile Val Leu Gly
                325                 330                 335

Ala Phe Ile Val Cys Trp Leu Pro Phe Phe Leu Thr His Val Leu Asn
```

```
                    340                 345                 350
Thr His Cys Gln Thr Cys His Val Ser Pro Glu Leu Tyr Ser Ala Thr
                355                 360                 365
Thr Trp Leu Gly Tyr Val Asn Ser Ala Leu Asn Pro Val Ile Tyr Thr
            370                 375                 380
Thr Phe Asn Ile Glu Phe Arg Lys Ala Phe Leu Lys Ile Leu Ser Cys
385                 390                 395                 400
```

<210> SEQ ID NO 30
<211> LENGTH: 400
<212> TYPE: PRT
<213> ORGANISM: Homo sapiens

<400> SEQUENCE: 30

```
Met Ala Ser Leu Ser Gln Leu Ser Ser His Leu Asn Tyr Thr Cys Gly
1               5                   10                  15
Ala Glu Asn Ser Thr Gly Ala Ser Gln Ala Arg Pro His Ala Tyr Tyr
            20                  25                  30
Ala Leu Ser Tyr Cys Ala Leu Ile Leu Ala Ile Val Phe Gly Asn Gly
        35                  40                  45
Leu Leu Cys Met Ala Val Leu Lys Glu Arg Ala Leu Gln Thr Thr Thr
50                  55                  60
Asn Tyr Leu Val Val Ser Leu Ala Val Ala Asp Leu Leu Val Ala Thr
65                  70                  75                  80
Leu Val Met Pro Trp Val Val Tyr Leu Glu Val Thr Gly Gly Val Trp
                85                  90                  95
Asn Phe Ser Arg Ile Cys Cys Asp Val Phe Val Thr Leu Asp Val Met
            100                 105                 110
Met Cys Thr Ala Ser Ile Leu Asn Leu Cys Ala Ile Ser Ile Asp Arg
        115                 120                 125
Tyr Thr Ala Val Val Met Pro Val His Tyr Gln His Gly Thr Gly Gln
130                 135                 140
Ser Ser Cys Arg Arg Val Ala Leu Met Ile Thr Ala Val Trp Val Leu
145                 150                 155                 160
Ala Phe Ala Val Ser Cys Pro Leu Leu Phe Gly Phe Asn Thr Thr Gly
                165                 170                 175
Asp Pro Thr Val Cys Ser Ile Ser Asn Pro Asp Phe Val Ile Tyr Ser
            180                 185                 190
Ser Val Val Ser Phe Tyr Leu Pro Phe Gly Val Thr Val Leu Val Tyr
        195                 200                 205
Ala Arg Ile Tyr Val Val Leu Lys Gln Arg Arg Arg Lys Arg Ile Leu
210                 215                 220
Thr Arg Gln Asn Ser Gln Cys Asn Ser Val Arg Pro Gly Phe Pro Gln
225                 230                 235                 240
Gln Thr Leu Ser Pro Asp Pro Ala His Leu Glu Leu Lys Arg Tyr Tyr
                245                 250                 255
Ser Ile Cys Gln Asp Thr Ala Leu Gly Gly Pro Gly Phe Gln Glu Arg
            260                 265                 270
Gly Gly Glu Leu Lys Arg Glu Glu Lys Thr Arg Asn Ser Leu Ser Pro
        275                 280                 285
Thr Ile Ala Pro Lys Leu Ser Leu Glu Val Arg Lys Leu Ser Asn Gly
            290                 295                 300
Arg Leu Ser Thr Ser Leu Lys Leu Gly Pro Leu Gln Pro Arg Gly Val
305                 310                 315                 320
```

```
Pro Leu Arg Glu Lys Lys Ala Thr Gln Met Val Ala Ile Val Leu Gly
            325                 330                 335

Ala Phe Ile Val Cys Trp Leu Pro Phe Phe Leu Thr His Val Leu Asn
        340                 345                 350

Thr His Cys Gln Thr Cys His Val Ser Pro Glu Leu Tyr Ser Ala Thr
    355                 360                 365

Thr Trp Leu Gly Tyr Val Asn Ser Ala Leu Asn Pro Val Ile Tyr Thr
370                 375                 380

Thr Phe Asn Ile Glu Phe Arg Lys Ala Phe Leu Lys Ile Leu Ser Cys
385                 390                 395                 400

<210> SEQ ID NO 31
<211> LENGTH: 5855
<212> TYPE: DNA
<213> ORGANISM: Homo sapiens

<400> SEQUENCE: 31
gagctcatca ttttttatgg ctgcatagta ttccatggtg tatatgtgcc acattttctt      60
atccagtcta tcattgttgg acagttgggt tggttccaag tctttgctac tgtgaatagt     120
gcctcaataa acatatgtgt gcatgtgtct ttatagcagc aagatttata gtcctttggg     180 tatatacccca gtaatgggat ggctgggtca aatggtattt ctagttctac atccctgagg    240
aatcgccaca ccgacttcca caatggttga actagtttac agtcccacca aaagtgtaaa    300
aatgttccta tttctccact tcctctccag catctgttgt ttcctgactt tttaatgatt    360
gctattctaa ctggtgtgag atggtatctc attgtggttt tgatttgcat ttctctgatg    420
gccagtgatg gtgagcattt tttcatgtgt ttttggatg cataaatgtc ttcttttgag    480
aagtgtctgt tcatgtcctt cgcccacttt tgatgggga tgttttttc ttgtaaattt      540 gtttgagttc attgtagatt ctggatatta gcccttttgc agatgagtag gttgtgaaaa   600
ttttctccca ttttgtaggt tgcctgttca ctctgatggt agtttctttt gctgtgcaga    660
aaatctttag tttaattaga tcccatttgt caattttggc ttttgttgcc attgtttttg    720
gtgttttaga catgaagtcc ttgcccatgc ctatgtcctg aatggtaatg cctaggattt    780
cttctggggg tttatggtt ttaggtctaa tgtttaagtc tttaatccat cttgaattaa    840 ttttttgtata aggtgtaagg aagggatcca gtttcagctt tctacatatg gctagccagt    900
tttcccagca cttttttatta aatagagaat ccttttcccca ttgcttttct caggtttgtc    960
aaagatcaga tagttgtaga tatgcaatgc tatttctgag ggctctgttc tgttccattg    1020
atctatatct ctgttttggt accagtacca tgctgttttg gttactgtgg ccttgtagta   1080
tagtttgaag tcaggtagca tgatgcctcc agctttgttc ttttggctta ggattgactt    1140
ggcgatgtgg gctcttttg gttccatatg aactttaaag tagttttttc caattctgtg    1200
aagaaagtca ttggtagctt gatggggatg gcattgaatc tatcaattac cttgggcagt    1260
atggccattt tcaagatatt gattcttcct acccatgagc atggaatgtt cttccatttg    1320
tttgtatcct cttttattc cttgagcagt ggtttgtagt tctcctcgaa gaggtccttc   1380
acatcccttg taagttggat tcctaggtat tttattctct ttgaagcaat tgtgaatggg    1440
agttcactca tgatttggct ctctgttttgt ctgttattgg tgtattagaa tgcttgtgat   1500
ttttgtacat tgattttgta tcctgagact ttgctgaagt tgcttatcag cttaaggaga   1560 tttgggctg agacaatggg gttttctaga tatacaatca tgtcatctgc aaacagggac    1620
aatttgactt cctctttttcc taattgagta ccctttattt ccttctcctg cctaattgcc    1680
```

```
ctggccagaa cttccaacac tatgttgaat aggagtggtg agagagggca tccctgtctt    1740
gtgccagttt tcaaagggaa tgcttgcagt ttttgcccat tcagtatgat actggctgtg    1800
ggtttgtcat agatagctct tattattttg agatacgtcc catgaatacc taatttattg    1860
agagttttta gcatgaaggg ttgttgaatt ttgtcaaagg ccttttctgc atctattgag    1920
ataatcatgt ggttttttgtc tttggttctg tttacatgct ggattacatt tattgatttg    1980
catatattga accagccttg catcccaggg atgaagtcca cttgatcacc cccaacagca    2040
tacaactcca gtctgatgaa catcatgcta ctaagtggcc actcatcacc caagtctctg    2100
accttacttt ttctctcttt tctcccaggg agtgagccat aactggcggc tgctcttgcg    2160
ccaatgagcc tccccaattc ctcctgcctc ttagaagaca agatgtgtga gggcaacaag    2220
accactatgg ccagccccca gctgatgccc ctggtggtgg tcctgagcac tatctgcttg    2280
gtcacagtag ggctcaacct gctggtgctg tatgccgtac ggagtgagcg aagctccac    2340 actgtgggga acctgtacat cgtcagcctc tcggtggcgg acttgatcgt gggtgccgtc    2400
gtcatgccta tgaacatcct ctacctgctc atgtccaagt ggtcactggg ccgtcctctc    2460
tgcctctttt ggctttccat ggactatgtg gccagcacag cgtccatttt cagtgtcttc    2520
atcctgtgca ttgatcgcta ccgctctgtc cagcagcccc tcaggtacct taagtatcgt    2580
accaagaccc gagcctcggc caccattctg ggggcctggt ttctctcttt tctgtgggtt    2640
attcccattc taggctggaa tcacttcatg cagcagacct cggtgcgccg agaggacaag    2700
tgtgagacag acttctatga tgtcacctgg ttcaaggtca tgactgccat catcaacttc    2760
tacctgccca ccttgctcat gctctggttc tatgccaaga tctacaaggc cgtacgacaa    2820
cactgccagc accgggagct catcaatagg tccctccctt ccttctcaga aattaagctg    2880
aggccagaga ccccaagggg ggatgccaag aaaccaggga aggagtctcc ctgggaggtt    2940
ctgaaaagga agccaaaaga tgctggtggt ggatctgtct gaagtcacc atcccaaacc    3000 cccaaggaga tgaaatcccc agttgtcttc agccaagagg atgatagaga agtagacaaa    3060
ctctactgct ttccacttga tattgtgcac atgcaggctg cggcagaggg gagtagcagg    3120
gactatgtag ccgtcaaccg gagccatggc cagctcaaga cagatgagca gggcctgaac    3180
acacatgggg ccagcgagat atcagaggat cagatgttag gtgatagcca atccttctct    3240
cgaacggact cagataccac cacagagaca gcaccaggca aaggcaaatt gaggagtggg    3300
tctaacacag gcctggatta catcaagttt acttggaaga ggctccgctc gcattcaaga    3360
cagtatgtat ctgggttgca catgaaccgc gaaaggaagg ccgccaaaca gttgggtttt    3420
atcatggcag ccttcatcct ctgctggatc ccttatttca tcttcttcat ggtcattgcc    3480
ttctgcaaga actgttgcaa tgaacatttg cacatgttca ccatctggct gggctacatc    3540
aactccacac tgaaccccct catctacccc ttgtgcaatg agaacttcaa gaagacattc    3600
aagagaattc tgcatattcg ctcctaaggg aggctctgag gggatgcaac aaaatgatcc    3660
ttatgatgtc caacaaggaa atagaggacg aaggcctgtg tgttgccagg caggcacctg    3720
ggctttctgg aatccaaacc acagtcttag gggcttggta gtttgaaag ttcttaggca    3780 ccatagaaga acagcagatg gcggtgatca gcagagagat tgaactttga ggaggaagca    3840
gaatctttgc aagaaagtca gacctgtttc ttgtaactgg gttcaaaaag aaaaaaataa    3900
taaaaataaa agagagagag aatcagacct gggtggaact ctcctgctcc tcaggaacta    3960
tgggagcctc agactcattg taattcaagc tttccgagtc aagtgattga caactgaaga    4020
gacacgtggc tagggttcca ctggagaatt gaaaaggact cttgagccct cctggaatgg    4080
```

```
agctgtataa ctgtgcagag actttatcca tgccaatagt tgctgtcccc ttccaggggt    4140
caccttgaga ggcatgacag ctgttccaca ggggctatcc cttctcagaa aacttctctt    4200
ctgagcctct ttaacagctt tctccagaac cagtgtctga accaccctgg aaattctgcc    4260
ttattatttc ttactcaaac atgtttagag tggatagaaa attatgcagc ttgcacaccc    4320
atcatcttta accccaaatt tcctttggct attaaaaaag tggtggcaaa aggcatcctc    4380
aaaagaaaga gaaatgaaat attttgaat ggttgcacgt taaaaattaa agaaggaat     4440 gggggcagaa tgccatattt ttgagggctg tactaggttt atctcattta agccccacaa    4500
caccccacag gagggtaatt ttctaactct agtttgcaga ggagcaaatt gaggttcagc    4560
aaggtgagag aggtacccaa ggtcacatag ctagttatgt gagaaagtta gagtacagat    4620
cctctggggt ttcagcttat tgtagcatat tttctccgaa aggcaaaaat gtgccctttt    4680
ggccgggcat ggtagctcaa gcctataatc ccagcatgtt gagaggctga ggtgggcaga    4740
tcatttgagg ccaggagttc aagaccagtc tggccaatat ggagaaacct tgtctctact    4800
aaaaacacaa aaattatctg ggcatggtgg ggcatgcctg tagtcccact tacttgggag    4860
gccgaggcac gagaatcgct tgaacccggg aggtggaggt tgccgtgagc caagatcacg    4920
ccactgcact ccagcctggg caacagagca agactctgtc tcaaaaaaaa aaatacaata    4980
ttttaacaat gtgccctctt aagtgtgcac agatacacat acacggtatt cccaagagtg    5040
gtggcagctc aaaatgatat gtttgagtag acgaacagct gacatggagt tcccgtgcac    5100
ctacggaagg ggacgctttg aaggaaccaa gtgcattttt atctgtgagt tctgttgtgt    5160
ttgtcaaaaa gtcattgtaa tcttttcatag ccatacctgg taagcaaaaa ctagtaaaga    5220
cataggaaca tgtagtttta cttggtgttt atgttgcaat ctggttgtga tttatatttt    5280
aaagcttggt gctaaaccac aatatgtata gcacatggag tgcctgtaca agctgatgtt    5340
ttgtattttg tgttcctctt tgcatgatct gtcaaagtga gatattttta cctgcctaaa    5400
atatgatgtt taaaagcata ctctatgtga tttatttatt tctaccttc tgagtctctt    5460 ggactaagaa gatgttttga aatgtaccat caaatgttaa cagagtttga tatgggcttt    5520
ctctttggtt tctcatcaca tttgtaaatg tcttttcaaa aggatttact ttttgtaaaa    5580
agcttcattc tcactctgct ttgcatcccc caaacttctt gttcaaaacg ggggagttt    5640 aggagacttt aatcccggtt tcagaagctg cagctggtct gtttccaggt cagaaaccat    5700
tgttcagaag acctccctgt gagagagttg ctcctcaggg tccctcagga ccaaagaaca    5760
ctcgaaaaga gcacttcaca cagacaagtg gctaagtgtc cattatttac cttgaacaat    5820
caaggcaact agtggagaga actgattgtg agctc                                5855
```

<210> SEQ ID NO 32
<211> LENGTH: 5855
<212> TYPE: DNA
<213> ORGANISM: Homo sapiens

<400> SEQUENCE: 32

```
gagctcatca ttttttatgg ctgcatagta ttccatggtg tatatgtgcc acattttctt      60
atccagtcta tcattgttgg acagttgggt tggttccaag tctttgctac tgtgaatagt     120
gcctcaataa acatatgtgt gcatgtgtct ttatagcagc aagatttata gtcctttggg     180 tatatacca gtaatgggat ggctgggtca aatggtattt ctagttctac atccctgagg     240
aatcgccaca ccgacttcca caatggttga actagtttac agtcccacca aaagtgtaaa    300
```

| | |
|---|---|
| aatgttccta tttctccact tcctctccag catctgttgt ttcctgactt tttaatgatt | 360 |
| gctattctaa ctggtgtgag atggtatctc attgtggttt tgatttgcat ttctctgatg | 420 |
| gccagtgatg gtgagcattt tttcatgtgt tttttggatg cataaatgtc ttcttttgag | 480 |
| aagtgtctgt tcatgtcctt cgcccacttt ttgatgggga tgttttttc ttgtaaattt | 540 |
| gtttgagttc attgtagatt ctggatatta gcccttgtc agatgagtag gttgtgaaaa | 600 |
| ttttctccca ttttgtaggt tgcctgttca ctctgatggt agtttctttt gctgtgcaga | 660 |
| aaatctttag tttaattaga tcccattgt caattttggc ttttgttgcc attgttttg | 720 |
| gtgttttaga catgaagtcc ttgcccatgc ctatgtcctg aatggtaatg cctaggattt | 780 |
| cttctggggg ttttatggtt ttaggtctaa tgtttaagtc tttaatccat cttgaattaa | 840 |
| ttttgtata aggtgtaagg aagggatcca gtttcagctt tctacatatg gctagccagt | 900 |
| tttcccagca ctttttatta aatagagaat ccttcccca ttgcttttct caggtttgtc | 960 |
| aaagatcaga tagttgtaga tatgcaatgc tatttctgag ggctctgttc tgttccattg | 1020 |
| atctatatct ctgttttggt accagtacca tgctgttttg gttactgtgg ccttgtagta | 1080 |
| tagtttgaag tcaggtagca tgatgcctcc agctttgttc ttttggctta ggattgactt | 1140 |
| ggcgatgtgg gctcttttg gttccatatg aactttaaag tagttttttc caattctgtg | 1200 |
| aagaaagtca ttggtagctt gatggggatg gcattgaatc tatcaattac cttgggcagt | 1260 |
| atggccattt tcaagatatt gattcttcct acccatgagc atggaatgtt cttccatttg | 1320 |
| tttgtatcct cttttatttc cttgagcagt ggtttgtagt tctcctcgaa gaggtccttc | 1380 |
| acatcccttg taagttggat tcctaggtat tttattctct ttgaagcaat tgtgaatggg | 1440 |
| agttcactca tgatttggct ctctgttgt ctgttattgg tgtattagaa tgcttgtgat | 1500 |
| ttttgtacat tgatttgta tcctgagact ttgctgaagt tgcttatcag cttaaggaga | 1560 |
| ttttgggctg agacaatggg gttttctaga tatacaatca tgtcatctgc aaacagggac | 1620 |
| aatttgactt cctcttttcc taattgagta ccctttattt ccttctcctg cctaattgcc | 1680 |
| ctggccagaa cttccaacac tatgttgaat aggagtggtg agagagggca tccctgtctt | 1740 |
| gtgccagttt tcaaagggaa tgcttgcagt ttttgcccat tcagtatgat actggctgtg | 1800 |
| ggtttgtcat agatagctct tattattttg agatacgtcc catgaatacc taatttattg | 1860 |
| agagttttta gcatgaaggg ttgttgaatt ttgtcaaagg ccttttctgc atctattgag | 1920 |
| ataatcatgt ggttttttgtc tttggttctg tttacatgct ggattacatt tattgatttg | 1980 |
| catatattga accagccttg catcccaggg atgaagtcca cttgatcacc cccaacagca | 2040 |
| tacaactcca gtctgatgaa catcatgcta ctaagtggcc actcatcacc caagtctctg | 2100 |
| accttacttt ttctctcttt tctcccaggg agtgagccat aactggcggc tgctcttgcg | 2160 |
| ccaatgagcc tccccaattc ctcctgcctc ttagaagaca agatgtgtga gggcaacaag | 2220 |
| accactatgg ccagccccca gctgatgccc ctggtggtgg tcctgagcac tatctgcttg | 2280 |
| gtcacagtag ggctcaacct gctggtgctg tatgccgtac ggagtgagcg gaagctccac | 2340 |
| actgtgggga acctgtacat cgtcagcctc tcggtggcgg acttgatcgt gggtgccgtc | 2400 |
| gtcatgccta tgaacatcct ctacctgctc atgtccaagt ggtcactggg ccgtcctctc | 2460 |
| tgcctctttt ggctttccat ggactatgtg gccagcacag cgtccatttt cagtgtcttc | 2520 |
| atcctgtgca ttgatcgcta ccgctctgtc cagcagcccc tcaggtacct taagtatcgt | 2580 |
| accaagaccc gagcctcggc caccattctg ggggcctgga ttctctcttt tctgtgggtt | 2640 |
| attcccattc taggctggaa tcacttcatg cagcagacct cggtgcgccg agaggacaag | 2700 |

```
tgtgagacag acttctatga tgtcacctgg ttcaaggtca tgactgccat catcaacttc    2760
tacctgccca ccttgctcat gctctggttc tatgccaaga tctacaaggg cgtacgacaa    2820
cactgccagc accgggagct catcaatagg tccctccctt ccttctcaga aattaagctg    2880
aggccagaga accccaaggg ggatgccaag aaaccaggga aggagtctcc ctgggaggtt    2940
ctgaaaagga agccaaaaga tgctggtggt ggatctgtct tgaagtcacc atcccaaacc    3000
cccaaggaga tgaaatcccc agttgtcttc agccaagagg atgatagaga agtagacaaa    3060
ctctactgct ttccacttga tattgtgcac atgcaggctg cggcagaggg gagtagcagg    3120
gactatgtag ccgtcaaccg gagccatggc cagctcaaga cagatgagca gggcctgaac    3180
acacatgggg ccagcgagat atcagaggat cagatgttag gtgatagcca atccttctct    3240
cgaacggact cagataccac cacagagaca gcaccaggca aaggcaaatt gaggagtggg    3300
tctaacacag gcctggatta catcaagttt acttggaaga ggctccgctc gcattcaaga    3360
cagtatgtat ctgggttgca catgaaccgc gaaaggaagg ccgccaaaca gttgggtttt    3420
atcatggcag ccttcatcct ctgctggatc ccttatttca tcttcttcat ggtcattgcc    3480
ttctgcaaga actgttgcaa tgaacatttg cacatgttca ccatctggct gggctacatc    3540
aactccacac tgaaccccct catctacccc ttgtgcaatg agaacttcaa gaagacattc    3600
aagagaattc tgcatattcg ctcctaaggg aggctctgag gggatgcaac aaaatgatcc    3660
ttatgatgtc caacaaggaa atagaggacg aaggcctgtg tgttgccagg caggcacctg    3720
ggctttctgg aatccaaacc acagtcttag gggcttggta gtttgaaag ttcttaggca    3780 ccatagaaga acagcagatg gcggtgatca gcagagagat tgaactttga ggaggaagca    3840
gaatctttgc aagaaagtca gacctgtttc ttgtaactgg gttcaaaaag aaaaaaataa    3900
taaaaataaa agagagagag aatcagacct gggtggaact ctcctgctcc tcaggaacta    3960
tgggagcctc agactcattg taattcaagc tttccgagtc aagtgattga caactgaaga    4020
gacacgtggc tagggttcca ctggagaatt gaaaaggact cttgagccct cctggaatgg    4080
agctgtataa ctgtgcagag actttatcca tgccaatagt tgctgtcccc ttccaggggt    4140
caccttgaga ggcatgacag ctgttccaca ggggctatcc cttctcagaa aacttctctt    4200
ctgagcctct ttaacagctt tctccagaac cagtgtctga accaccctgg aaattctgcc    4260
ttattatttc ttactcaaac atgtttagag tggatagaaa attatgcagc ttgcacaccc    4320
atcatcttta accccaaatt tccttttggct attaaaaaag tggtggcaaa aggcatcctc    4380
aaaagaaaga gaaatgaaat attttttgaat ggttgcacgt taaaaattaa aagaaggaat    4440
gggggcagaa tgccatattt ttgagggctg tactaggttt atctcattta agccccacaa    4500
caccccacag gagggtaatt ttctaactct agtttgcaga ggagcaaatt gaggttcagc    4560
aaggtgagag aggtacccaa ggtcacatag ctagttatgt gagaaagtta gagtacagat    4620
cctctggggt ttcagcttat tgtagcatat tttctccgaa aggcaaaaat gtgccctttt    4680
ggccgggcat ggtagctcaa gcctataatc ccagcatgtt gagaggctga ggtgggcaga    4740
tcatttgagg ccaggagttc aagaccagtc tggccaatat ggagaaacct tgtctctact    4800
aaaaacacaa aaattatctg ggcatggtgg ggcatgcctg tagtcccact tacttgggag    4860
gccgaggcac gagaatcgct tgaacccggg aggtggaggt tgccgtgagc caagatcacg    4920
ccactgcact ccagcctggg caacagagca agactctgtc tcaaaaaaaa aaatacaata    4980
ttttaacaat gtgccctctt aagtgtgcac agatacacat acacggtatt cccaagagtg    5040
```

```
gtggcagctc aaaatgatat gtttgagtag acgaacagct gacatggagt tcccgtgcac    5100
ctacggaagg ggacgctttg aaggaaccaa gtgcattttt atctgtgagt tctgttgtgt    5160
ttgtcaaaaa gtcattgtaa tctttcatag ccatacctgg taagcaaaaa ctagtaaaga    5220
cataggaaca tgtagtttta cttggtgttt atgttgcaat ctggttgtga tttatatttt    5280
aaagcttggt gctaaaccac aatatgtata gcacatggag tgcctgtaca agctgatgtt    5340
ttgtattttg tgttcctctt tgcatgatct gtcaaagtga gatatttta cctgcctaaa     5400 atatgatgtt taaaagcata ctctatgtga tttatttatt tctacctttc tgagtctctt    5460
ggactaagaa gatgttttga aatgtaccat caaatgttaa cagagtttga tatgggcttt    5520
ctctttggtt tctcatcaca tttgtaaatg tcttttcaaa aggatttact ttttgtaaaa    5580
agcttcattc tcactctgct ttgcatcccc caaacttctt gttcaaaacg ggggagttt     5640 aggagacttt aatcccggtt tcagaagctg cagctggtct gtttccaggt cagaaaccat    5700
tgttcagaag acctccctgt gagagagttg ctcctcaggg tccctcagga ccaaagaaca    5760
ctcgaaaaga gcacttcaca cagacaagtg gctaagtgtc cattatttac cttgaacaat    5820
caaggcaact agtggagaga actgattgtg agctc                               5855
```

<210> SEQ ID NO 33
<211> LENGTH: 5855
<212> TYPE: DNA
<213> ORGANISM: Homo sapiens

<400> SEQUENCE: 33

```
gagctcatca ttttttatgg ctgcatagta ttccatggtg tatatgtgcc acattttctt      60
atccagtcta tcattgttgg acagttgggt tggttccaag tctttgctac tgtgaatagt     120
gcctcaataa acatatgtgt gcatgtgtct ttatagcagc aagatttata gtcctttggg     180
tatataccca gtaatgggat ggctgggtca aatggtattt ctagttctac atccctgagg    240
aatcgccaca ccgacttcca caatggttga actagtttac agtcccacca aaagtgtaaa    300
aatgttccta tttctccact tcctctccag catctgttgt ttcctgactt tttaatgatt    360
gctattctaa ctggtgtgag atggtatctc attgtggttt tgatttgcat ttctctgatg    420
gccagtgatg gtgagcattt tttcatgtgt tttttggatg cataaatgtc ttcttttgag    480
aagtgtctgt tcatgtcctt cgcccacttt ttgatgggga tgttttttc ttgtaaattt     540 gtttgagttc attgtagatt ctggatatta gccctttgtc agatgagtag gttgtgaaaa    600
ttttctccca ttttgtaggt tgcctgttca ctctgatggt agtttctttt gctgtgcaga    660
aaatctttag tttaattaga tcccattgt caatttggc ttttgttgcc attgtttttg      720
gtgttttaga catgaagtcc ttgcccatgc ctatgtcctg aatggtaatg cctaggattt    780
cttctggggg tttatggtt ttaggtctaa tgtttaagtc tttaatccat cttgaattaa      840
tttttgtata aggtgtaagg aagggatcca gtttcagctt tctacatatg ctagccagt     900 tttcccagca ctttttatta aatagagaat cctttcccca ttgcttttct caggtttgtc    960
aaagatcaga tagttgtaga tatgcaatgc tattctgag ggctctgttc tgttccattg      1020
atctatatct ctgttttggt accagtacca tgctgttttg ttactgtgg ccttgtagta     1080 tagtttgaag tcaggtagca tgatgcctcc agctttgttc ttttggctta ggattgactt    1140
ggcgatgtgg gctcttttg gttccatatg aactttaaag tagttttttc caattctgtg    1200
aagaaagtca ttggtagctt gatggggatg gcattgaatc tatcaattac cttgggcagt    1260
atggccattt tcaagatatt gattcttcct acccatgagc atggaatgtt cttccatttg    1320
```

```
tttgtatcct cttttatttc cttgagcagt ggtttgtagt tctcctcgaa gaggtccttc    1380
acatcccttg taagttggat tcctaggtat tttattctct ttgaagcaat tgtgaatggg    1440
agttcactca tgatttggct ctctgtttgt ctgttattgg tgtattagaa tgcttgtgat    1500
ttttgtacat tgattttgta tcctgagact ttgctgaagt tgcttatcag cttaaggaga    1560
ttttgggctg agacaatggg gttttctaga tatacaatca tgtcatctgc aaacagggac    1620
aatttgactt cctctttttcc taattgagta ccctttattt ccttctcctg cctaattgcc    1680
ctggccagaa cttccaacac tatgttgaat aggagtggtg agagagggca tccctgtctt    1740
gtgccagttt tcaaagggaa tgcttgcagt ttttgcccat tcagtatgat actggctgtg    1800
ggtttgtcat agatagctct tattattttg agatacgtcc catgaatacc taatttattg    1860 agagtttttta gcatgaaggg ttgttgaatt ttgtcaaagg ccttttctgc atctattgag    1920
ataatcatgt ggttttttgtc tttggttctg tttacatgct ggattacatt tattgatttg    1980
catatattga accagccttg catcccaggg atgaagtcca cttgatcacc cccaacagca    2040
tacaactcca gtctgatgaa catcatgcta ctaagtggcc actcatcacc caagtctctg    2100
accttacttt ttctctcttt tctcccaggg agtgagccat aactggcggc tgctcttgcg    2160
ccaatgagcc tccccaattc ctcctgcctc ttagaagaca agatgtgtga gggcaacaag    2220
accactatgg ccagccccca gctgatgccc ctggtggtgg tcctgagcac tatctgcttg    2280
gtcacagtag ggctcaacct gctggtgctg tatgccgtac ggagtgagcg aagctccac    2340 actgtgggga acctgtacat cgtcagcctc tcggtggcgg acttgatcgt gggtgccgtc    2400
gtcatgccta tgaacatcct ctacctgctc atgtccaagt ggtcactggg ccgtcctctc    2460
tgcctctttt ggctttccat ggactatgtg ccagcacag cgtccatttt cagtgtcttc    2520
atcctgtgca ttgatcgcta ccgctctgtc cagcagcccc tcaggtacct taagtatcgt    2580
accaagaccc gagcctcggc caccattctg ggggcctggt ttctctcttt tctgtgggtt    2640
attcccattc taggctggaa tcacttcatg cagcagacct cggtgcgccg agaggacaag    2700
tgtgagacag acttctatga tgtcacctgg ttcaaggtca tgactgccat catcaacttc    2760
tacctgccca ccttgctcat gctctggttc tatgccaaga tctacaaggc cgtacgacaa    2820
cactgccagc accgggagcc catcaatagg tccctccctt ccttctcaga aattaagctg    2880
aggccagaga accccaaggg ggatgccaag aaaccaggga aggagtctcc ctgggaggtt    2940
ctgaaaagga agccaaaaga tgctggtggt ggatctgtct tgaagtcacc atcccaaacc    3000
cccaaggaga tgaaatcccc agttgtcttc agccaagagg atgatagaga agtagacaaa    3060
ctctactgct ttccacttga tattgtgcac atgcaggctg cggcagaggg gagtagcagg    3120
gactatgtag ccgtcaaccg gagccatggc cagctcaaga cagatgagca gggcctgaac    3180
acacatgggg ccagcgagat atcagaggat cagatgttag gtgatagcca atccttctct    3240
cgaacggact cagataccac cacagagaca gcaccaggca aaggcaaatt gaggagtggg    3300
tctaacacag gcctggatta catcaagttt acttggaaga ggctccgctc gcattcaaga    3360
cagtatgtat ctgggttgca catgaaccgc gaaaggaagg ccgccaaaca gttgggtttt    3420
atcatggcag ccttcatcct ctgctggatc ccttatttca tcttcttcat ggtcattgcc    3480
ttctgcaaga actgttgcaa tgaacatttg cacatgttca ccatctggct gggctacatc    3540
aactccacac tgaacccccct catctacccc ttgtgcaatg agaacttcaa gaagacattc    3600
aagagaattc tgcatattcg ctcctaaggg aggctctgag gggatgcaac aaaatgatcc    3660
```

```
ttatgatgtc caacaaggaa atagaggacg aaggcctgtg tgttgccagg caggcacctg   3720
ggctttctgg aatccaaacc acagtcttag gggcttggta gtttggaaag ttcttaggca   3780
ccatagaaga acagcagatg gcggtgatca gcagagagat tgaactttga ggaggaagca   3840
gaatctttgc aagaaagtca gacctgtttc ttgtaactgg gttcaaaaag aaaaaaataa   3900
taaaaataaa agagagagag aatcagacct gggtggaact ctcctgctcc tcaggaacta   3960
tgggagcctc agactcattg taattcaagc tttccgagtc aagtgattga caactgaaga   4020
gacacgtggc tagggttcca ctggagaatt gaaaaggact cttgagccct cctggaatgg   4080
agctgtataa ctgtgcagag actttatcca tgccaatagt tgctgtcccc ttccaggggt   4140
caccttgaga ggcatgacag ctgttccaca ggggctatcc cttctcagaa aacttctctt   4200
ctgagcctct ttaacagctt tctccagaac cagtgtctga accaccctgg aaattctgcc   4260
ttattatttc ttactcaaac atgtttagag tggatagaaa attatgcagc ttgcacaccc   4320
atcatcttta accccaaatt tcctttggct attaaaaaag tggtggcaaa aggcatcctc   4380
aaaagaaaga gaaatgaaat attttttgaat ggttgcacgt taaaaattaa agaaggaat   4440
gggggcagaa tgccatattt ttgagggctg tactaggttt atctcattta agccccacaa   4500
caccccacag gagggtaatt ttctaactct agtttgcaga ggagcaaatt gaggttcagc   4560
aaggtgagag aggtacccaa ggtcacatag ctagttatgt gagaaagtta gagtacagat   4620
cctctggggt ttcagcttat tgtagcatat tttctccgaa aggcaaaaat gtgccctttt   4680
ggccgggcat ggtagctcaa gcctataatc ccagcatgtt gagaggctga ggtgggcaga   4740
tcatttgagg ccaggagttc aagaccagtc tggccaatat ggagaaacct tgtctctact   4800
aaaaacacaa aaattatctg gcatggtgg ggcatgcctg tagtcccact tacttgggag   4860
gccgaggcac gagaatcgct tgaacccggg aggtggaggt tgccgtgagc caagatcacg   4920
ccactgcact ccagcctggg caacagagca agactctgtc tcaaaaaaaa aaatacaata   4980
ttttaacaat gtgccctctt aagtgtgcac agatacacat acacggtatt cccaagagtg   5040
gtggcagctc aaaatgatat gtttgagtag acgaacagct gacatggagt tcccgtgcac   5100
ctacggaagg ggacgctttg aaggaaccaa gtgcatttt atctgtgagt tctgttgtgt   5160
ttgtcaaaaa gtcattgtaa tctttcatag ccataccggg taagcaaaaa ctagtaaaga   5220
cataggaaca tgtagtttta cttggtgttt atgttgcaat ctggttgtga tttatatttt   5280
aaagcttggt gctaaaccac aatatgtata gcacatggag tgcctgtaca agctgatgtt   5340
ttgtattttg tgttcctctt tgcatgatct gtcaaagtga gatattttta cctgcctaaa   5400
atatgatgtt taaaagcata ctctatgtga tttatttatt tctacctttc tgagtctctt   5460
ggactaagaa gatgttttga aatgtaccat caaatgttaa cagagtttga tatgggcttt   5520
ctctttggtt tctcatcaca tttgtaaatg tctttcaaa aggatttact ttttgtaaaa   5580
agcttcattc tcactctgct ttgcatcccc caaacttctt gttcaaaacg ggggagttt   5640
aggagacttt aatcccggtt tcagaagctg cagctggtct gtttccaggt cagaaaccat   5700
tgttcagaag acctccctgt gagagagttg ctcctcaggg tccctcagga ccaaagaaca   5760
ctcgaaaaga gcacttcaca cagacaagtg gctaagtgtc cattatttac cttgaacaat   5820
caaggcaact agtggagaga actgattgtg agctc                              5855
```

<210> SEQ ID NO 34
<211> LENGTH: 487
<212> TYPE: PRT
<213> ORGANISM: Homo sapiens

<400> SEQUENCE: 34

```
Met Ser Leu Pro Asn Ser Ser Cys Leu Leu Glu Asp Lys Met Cys Glu
 1               5                  10                  15
Gly Asn Lys Thr Thr Met Ala Ser Pro Gln Leu Met Pro Leu Val Val
             20                  25                  30
Val Leu Ser Thr Ile Cys Leu Val Thr Val Gly Leu Asn Leu Leu Val
         35                  40                  45
Leu Tyr Ala Val Arg Ser Glu Arg Lys Leu His Thr Val Gly Asn Leu
     50                  55                  60
Tyr Ile Val Ser Leu Ser Val Ala Asp Leu Ile Val Gly Ala Val Val
 65                  70                  75                  80
Met Pro Met Asn Ile Leu Tyr Leu Leu Met Ser Lys Trp Ser Leu Gly
                 85                  90                  95
Arg Pro Leu Cys Leu Phe Trp Leu Ser Met Asp Tyr Val Ala Ser Thr
            100                 105                 110
Ala Ser Ile Phe Ser Val Phe Ile Leu Cys Ile Asp Arg Tyr Arg Ser
        115                 120                 125
Val Gln Gln Pro Leu Arg Tyr Leu Lys Tyr Arg Thr Lys Thr Arg Ala
    130                 135                 140
Ser Ala Thr Ile Leu Gly Ala Trp Phe Leu Ser Phe Leu Trp Val Ile
145                 150                 155                 160
Pro Ile Leu Gly Trp Asn His Phe Met Gln Gln Thr Ser Val Arg Arg
                165                 170                 175
Glu Asp Lys Cys Glu Thr Asp Phe Tyr Asp Val Thr Trp Phe Lys Val
            180                 185                 190
Met Thr Ala Ile Ile Asn Phe Tyr Leu Pro Thr Leu Leu Met Leu Trp
        195                 200                 205
Phe Tyr Ala Lys Ile Tyr Lys Ala Val Arg Gln His Cys Gln His Arg
    210                 215                 220
Glu Leu Ile Asn Arg Ser Leu Pro Ser Phe Ser Glu Ile Lys Leu Arg
225                 230                 235                 240
Pro Glu Asn Pro Lys Gly Asp Ala Lys Lys Pro Gly Lys Glu Ser Pro
                245                 250                 255
Trp Glu Val Leu Lys Arg Lys Pro Lys Asp Ala Gly Gly Gly Ser Val
            260                 265                 270
Leu Lys Ser Pro Ser Gln Thr Pro Lys Glu Met Lys Ser Pro Val Val
        275                 280                 285
Phe Ser Gln Glu Asp Asp Arg Glu Val Asp Lys Leu Tyr Cys Phe Pro
    290                 295                 300
Leu Asp Ile Val His Met Gln Ala Ala Ala Glu Gly Ser Ser Arg Asp
305                 310                 315                 320
Tyr Val Ala Val Asn Arg Ser His Gly Gln Leu Lys Thr Asp Glu Gln
                325                 330                 335
Gly Leu Asn Thr His Gly Ala Ser Glu Ile Ser Glu Asp Gln Met Leu
            340                 345                 350
Gly Asp Ser Gln Ser Phe Ser Arg Thr Asp Ser Asp Thr Thr Thr Glu
        355                 360                 365
Thr Ala Pro Gly Lys Gly Lys Leu Arg Ser Gly Ser Asn Thr Gly Leu
    370                 375                 380
Asp Tyr Ile Lys Phe Thr Trp Lys Arg Leu Arg Ser His Ser Arg Gln
385                 390                 395                 400
Tyr Val Ser Gly Leu His Met Asn Arg Glu Arg Lys Ala Ala Lys Gln
```

-continued

```
                405                 410                 415
Leu Gly Phe Ile Met Ala Ala Phe Ile Leu Cys Trp Ile Pro Tyr Phe
            420                 425                 430

Ile Phe Phe Met Val Ile Ala Phe Cys Lys Asn Cys Cys Asn Glu His
            435                 440                 445

Leu His Met Phe Thr Ile Trp Leu Gly Tyr Ile Asn Ser Thr Leu Asn
            450                 455                 460

Pro Leu Ile Tyr Pro Leu Cys Asn Glu Asn Phe Lys Lys Thr Phe Lys
465                 470                 475                 480

Arg Ile Leu His Ile Arg Ser
                485

<210> SEQ ID NO 35
<211> LENGTH: 487
<212> TYPE: PRT
<213> ORGANISM: Homo sapiens

<400> SEQUENCE: 35

Met Ser Leu Pro Asn Ser Ser Cys Leu Leu Glu Asp Lys Met Cys Glu
1               5                   10                  15

Gly Asn Lys Thr Thr Met Ala Ser Pro Gln Leu Met Pro Leu Val Val
            20                  25                  30

Val Leu Ser Thr Ile Cys Leu Val Thr Val Gly Leu Asn Leu Leu Val
            35                  40                  45

Leu Tyr Ala Val Arg Ser Glu Arg Lys Leu His Thr Val Gly Asn Leu
        50                  55                  60

Tyr Ile Val Ser Leu Ser Val Ala Asp Leu Ile Val Gly Ala Val Val
65                  70                  75                  80

Met Pro Met Asn Ile Leu Tyr Leu Leu Met Ser Lys Trp Ser Leu Gly
                85                  90                  95

Arg Pro Leu Cys Leu Phe Trp Leu Ser Met Asp Tyr Val Ala Ser Thr
            100                 105                 110

Ala Ser Ile Phe Ser Val Phe Ile Leu Cys Ile Asp Arg Tyr Arg Ser
        115                 120                 125

Val Gln Gln Pro Leu Arg Tyr Leu Lys Tyr Arg Thr Lys Thr Arg Ala
130                 135                 140

Ser Ala Thr Ile Leu Gly Ala Trp Phe Leu Ser Phe Leu Trp Val Ile
145                 150                 155                 160

Pro Ile Leu Gly Trp Asn His Phe Met Gln Gln Thr Ser Val Arg Arg
                165                 170                 175

Glu Asp Lys Cys Glu Thr Asp Phe Tyr Asp Val Thr Trp Phe Lys Val
            180                 185                 190

Met Thr Ala Ile Ile Asn Phe Tyr Leu Pro Thr Leu Leu Met Leu Trp
        195                 200                 205

Phe Tyr Ala Lys Ile Tyr Lys Gly Val Arg Gln His Cys Gln His Arg
        210                 215                 220

Glu Leu Ile Asn Arg Ser Leu Pro Ser Phe Ser Glu Ile Lys Leu Arg
225                 230                 235                 240

Pro Glu Asn Pro Lys Gly Asp Ala Lys Lys Pro Gly Lys Glu Ser Pro
                245                 250                 255

Trp Glu Val Leu Lys Arg Lys Pro Lys Asp Ala Gly Gly Gly Ser Val
            260                 265                 270

Leu Lys Ser Pro Ser Gln Thr Pro Lys Glu Met Lys Ser Pro Val Val
        275                 280                 285
```

```
Phe Ser Gln Glu Asp Asp Arg Glu Val Asp Lys Leu Tyr Cys Phe Pro
    290                 295                 300

Leu Asp Ile Val His Met Gln Ala Ala Ala Glu Gly Ser Ser Arg Asp
305                 310                 315                 320

Tyr Val Ala Val Asn Arg Ser His Gly Gln Leu Lys Thr Asp Glu Gln
                325                 330                 335

Gly Leu Asn Thr His Gly Ala Ser Glu Ile Ser Glu Asp Gln Met Leu
                340                 345                 350

Gly Asp Ser Gln Ser Phe Ser Arg Thr Asp Ser Asp Thr Thr Thr Glu
            355                 360                 365

Thr Ala Pro Gly Lys Gly Lys Leu Arg Ser Gly Ser Asn Thr Gly Leu
370                 375                 380

Asp Tyr Ile Lys Phe Thr Trp Lys Arg Leu Arg Ser His Ser Arg Gln
385                 390                 395                 400

Tyr Val Ser Gly Leu His Met Asn Arg Glu Arg Lys Ala Ala Lys Gln
                405                 410                 415

Leu Gly Phe Ile Met Ala Ala Phe Ile Leu Cys Trp Ile Pro Tyr Phe
                420                 425                 430

Ile Phe Phe Met Val Ile Ala Phe Cys Lys Asn Cys Cys Asn Glu His
                435                 440                 445

Leu His Met Phe Thr Ile Trp Leu Gly Tyr Ile Asn Ser Thr Leu Asn
        450                 455                 460

Pro Leu Ile Tyr Pro Leu Cys Asn Glu Asn Phe Lys Lys Thr Phe Lys
465                 470                 475                 480

Arg Ile Leu His Ile Arg Ser
                485

<210> SEQ ID NO 36
<211> LENGTH: 486
<212> TYPE: PRT
<213> ORGANISM: Homo sapiens

<400> SEQUENCE: 36

Met Ser Leu Pro Asn Ser Ser Cys Leu Leu Glu Asp Lys Met Cys Glu
  1               5                  10                  15

Gly Asn Lys Thr Thr Met Ala Ser Pro Gln Leu Met Pro Leu Val Val
                20                  25                  30

Val Leu Ser Thr Ile Cys Leu Val Thr Val Gly Leu Asn Leu Leu Val
            35                  40                  45

Leu Tyr Ala Val Arg Ser Glu Arg Lys Leu His Thr Val Gly Asn Leu
    50                  55                  60

Tyr Ile Val Ser Leu Ser Val Ala Asp Leu Ile Val Gly Ala Val Val
65                  70                  75                  80

Met Pro Met Asn Ile Leu Tyr Leu Leu Met Ser Lys Trp Ser Leu Gly
                85                  90                  95

Arg Pro Leu Cys Leu Phe Trp Leu Ser Met Asp Tyr Val Ala Ser Thr
            100                 105                 110

Ala Ser Ile Phe Ser Val Phe Ile Leu Cys Ile Asp Arg Tyr Arg Ser
        115                 120                 125

Val Gln Gln Pro Leu Arg Tyr Leu Lys Tyr Arg Thr Lys Thr Arg Ala
    130                 135                 140

Ser Ala Thr Ile Leu Gly Ala Trp Phe Leu Ser Phe Leu Trp Val Ile
145                 150                 155                 160

Pro Ile Leu Gly Trp Asn His Phe Met Gln Gln Thr Ser Val Arg Arg
                165                 170                 175
```

Glu Asp Lys Cys Glu Thr Asp Phe Tyr Asp Val Thr Trp Phe Lys Val
            180                 185                 190

Met Thr Ala Ile Ile Asn Phe Tyr Leu Pro Thr Leu Met Leu Trp
        195                 200                 205

Phe Tyr Ala Lys Ile Tyr Lys Ala Val Arg Gln His Cys Gln His Arg
        210                 215                 220

Glu Ile Asn Arg Ser Leu Pro Ser Phe Ser Ile Lys Leu Arg Pro
225                 230                 235                 240

Glu Asn Pro Lys Gly Asp Ala Lys Lys Pro Gly Lys Glu Ser Pro Trp
                245                 250                 255

Glu Val Leu Lys Arg Lys Pro Lys Asp Ala Gly Gly Gly Ser Val Leu
            260                 265                 270

Lys Ser Pro Ser Gln Thr Pro Lys Glu Met Lys Ser Pro Val Val Phe
        275                 280                 285

Ser Gln Glu Asp Asp Arg Glu Val Asp Lys Leu Tyr Cys Phe Pro Leu
        290                 295                 300

Asp Ile Val His Met Gln Ala Ala Ala Glu Gly Ser Ser Arg Asp Tyr
305                 310                 315                 320

Val Ala Val Asn Arg Ser His Gly Gln Leu Lys Thr Asp Glu Gln Gly
                325                 330                 335

Leu Asn Thr His Gly Ala Ser Glu Ile Ser Glu Asp Gln Met Leu Gly
            340                 345                 350

Asp Ser Gln Ser Phe Ser Arg Thr Asp Ser Asp Thr Thr Thr Glu Thr
        355                 360                 365

Ala Pro Gly Lys Gly Lys Leu Arg Ser Gly Ser Asn Thr Gly Leu Asp
        370                 375                 380

Tyr Ile Lys Phe Thr Trp Lys Arg Leu Arg Ser His Ser Arg Gln Tyr
385                 390                 395                 400

Val Ser Gly Leu His Met Asn Arg Glu Arg Lys Ala Ala Lys Gln Leu
                405                 410                 415

Gly Phe Ile Met Ala Ala Phe Ile Leu Cys Trp Ile Pro Tyr Phe Ile
            420                 425                 430

Phe Phe Met Val Ile Ala Phe Cys Lys Asn Cys Cys Asn Glu His Leu
        435                 440                 445

His Met Phe Thr Ile Trp Leu Gly Tyr Ile Asn Ser Thr Leu Asn Pro
        450                 455                 460

Leu Ile Tyr Pro Leu Cys Asn Glu Asn Phe Lys Lys Thr Phe Lys Arg
465                 470                 475                 480

Ile Leu His Ile Arg Ser
                485

<210> SEQ ID NO 37
<211> LENGTH: 3095
<212> TYPE: DNA
<213> ORGANISM: Homo sapiens

<400> SEQUENCE: 37
caggagattg cctgctctct gaaaaaccag gaggagctgg tagggaagga ctggggcgtg     60
gaacagggcc tcagcttgtt tctcgccagt tggaatcata tacagccacc actgggaggg    120
agccttggag attacctagt gaccaggggc tcttatttaa tcaagaggca ttgcacatgc    180
agttacttta ttgacgtagt gtttgcacta cttcaatagt gcaaagggag gaagggagga    240
aggagaaacc accctaatgc ccgtgagagg gtgatgtggg gatgatagga taaacctatt    300

```
catggtgagc ctccccacag actgttatgc aaccattaga aggaatgagt gagttctgtc      360
cctgctgacc tggatgtggg atcacgtgtt ctgccaagta agaccagtaa gatttagaga      420
tgcgttcgga gcaggggtgg cgtggatgac aggtgacgaa ctgccgatta aatctggccc      480
tctgcctggc tttgtacagc ccgtggctaa gaatggtttt tacatttta aatttggaa       540
aaaaatcaaa aaaaggagat ttttatgaca cgtgaaaatg atatgaaatt tacatttcag      600
tgttcattac tgaagttttg ttggagtgca gccacgctct tctgtcggca cgtcatctgc      660
atagctgcat tcgcactgca aaggcagagc cgagccgtca caggctgtga ggcagaacgt      720
gtttattacc tgacccttt  ctgaaaaagt ttgtcggcca ccgccttaga gtatgatgac      780
attttgccaa acagcagcac cagatatggt tctcagcact tcagaggagt agattcatta      840
catttgttta ttcgttcatt cattttatcc tttattcgtc agatgcttac tgtctatctg      900
tggggccagg caccaggaac cagcagagaa caaacagatg caggccttct tcttgtggag      960
ctgaaagtct gtgtctagat ccttcttttc tcagtacaag cacttccagc ctttccaact     1020
ctttctcacg agtctcagtg tccagcccct tgcatcctgc ctcccttctg cctccccagt     1080
atgtatcctg attgcccaag tccctcccaa aaagaggtat ccaaactggt cccatacttc     1140
ctggggtctt gccaagaggt tgagatctag tagaaggaca catcttgaat tgggtcatgc     1200
tttctatctg gtttcaaggt gcttaacatc caacctttgc cttttcagct cctgccctcc     1260
actgactcca gagagggaga tccccagtac ttgactccat cacgcagatg ggagcaggca     1320
ccagctatgg agagggatac agctgcgtct ccacatgacc catcctgcat gacaccaaag     1380
ccaccgccag acagtgcctc ggattctatg caaaacctgg gaagcggaga cctacccag      1440
ccccgggagg aagctagctc ttcaggggac cgtctgagga ctggagtttg atccatgaac     1500
ctggcttcga ggccttgctt ttctctcttc ttcattcata ttcattccca acaccttaga     1560
aggtgttgct taatttattt ctagaaaagc agcccagagt cagtcattga agccttcccc     1620
acccctggc caaaaaaaaa aaaaaaaaa  aactggacac attttggatc tgttgggagc      1680
ttggagtcca gtggttggca tagttgtcac attgggagca gagaagaagc aaccaggggc     1740
cctgatcagg ggactgagcc gtagagtccc aggatggcac ccaatggcac agcctcttcc     1800
ttttgcctgg actctaccgc atgcaagatc accatcaccg tggtccttgc ggtcctcatc     1860
ctcatcaccg ttgctggcaa tgtggtcgtc tgtctggccg tgggcttgaa ccgccggctc     1920
cgcaacctga ccaattgttt catcgtgtcc ttggctatca ctgacctgct cctcggcctc     1980
ctggtgctgc ccttctctgc catctaccag ctgtcctgca agtggagctt tggcaaggtc     2040
ttctgcaata tctacaccag cctggatgtg atgctctgca cagcctccat tcttaacctc     2100
ttcatgatca gcctcgaccg gtactgcgct gtcatggacc cactgcggta ccctgtgctg     2160
gtcaccccag ttcgggtcgc catctctctg gtcttaattt gggtcatctc cattaccctg     2220
tcctttctgt ctatccacct ggggtggaac agcaggaacg agaccagcaa gggcaatcat     2280
accacctcta agtgcaaagt ccaggtcaat gaagtgtacg ggctggtgga tgggctggtc     2340
accttctacc tcccgctact gatcatgtgc atcacctact accgcatctt caaggtcgcc     2400
cgggatcagg ccaagaggat caatcacatt agctcctgga aggcagccac catcagggag     2460
cacaaagcca cagtgacact ggccgccgtc atggggcct  tcatcatctg ctggtttccc     2520
tacttcaccg cgtttgtgta ccgtgggctg agagggatg  atgccatcaa tgaggtgtta     2580
gaagccatcg ttctgtggct gggctatgcc aactcagccc tgaacccat  cctgtatgct     2640
gcgctgaaca gagacttccg caccgggtac caacagctct tctgctgcag gctggccaac     2700
```

-continued

| | |
|---|---|
| cgcaactccc acaaaacttc tctgaggtcc aacgcctctc agctgtccag gacccaaagc | 2760 |
| cgagaaccca ggcaacagga agagaaaccc ctgaagctcc aggtgtggag tgggacagaa | 2820 |
| gtcacggccc cccagggagc cacagacagg taatagccct agccattggt gcacaggatg | 2880 |
| ggggcaatgg gaggggatgc tactgatggg aatgattaag ggagctgctg tttaggtggt | 2940 |
| gctggtttat gttctaggaa ctcttcatga gcactttgta aacaccctct tgcttaatcc | 3000 |
| tcccaacggc ccccaaaggt agaacttagc tcccttttaa aaggagcaca ttaaaattct | 3060 |
| cagaggactt ggcaagggcc gcacagctgg ggcat | 3095 |

<210> SEQ ID NO 38
<211> LENGTH: 3095
<212> TYPE: DNA
<213> ORGANISM: Homo sapiens

<400> SEQUENCE: 38

| | |
|---|---|
| caggagattg cctgctctct gaaaaaccag gaggagctgg tagggaagga ctggggcgtg | 60 |
| gaacagggcc tcagcttgtt tctcgccagt tggaatcata tacagccacc actgggaggg | 120 |
| agccttggag attacctagt gaccaggggc tcttatttaa tcaagaggca ttgcacatgc | 180 |
| agttacttta ttgacgtagt gttgcacta cttcaatagt gcaaaggag aagggagga | 240 |
| aggagaaacc accctaatgc ccgtgagagg gtgatgtggg gatgatagga taaacctatt | 300 |
| catggtgagc ctccccacag actgttatgc aaccattaga aggaatgagt gagttctgtc | 360 |
| cctgctgacc tggatgtggg atcacgtgtt ctgccaagta agaccagtaa gatttagaga | 420 |
| tgcgttcgga gcaggggtgg cgtggatgac aggtgacgaa ctgccgatta aatctggccc | 480 |
| tctgcctggc tttgtacagc ccgtggctaa gaatggtttt tacatttta aattttggaa | 540 |
| aaaaatcaaa aaaggagat tttatgaca cgtgaaatg atatgaaatt tacatttcag | 600 |
| tgttcattac tgaagttttg ttggagtgca gccacgctct tctgtcggca cgtcatctgc | 660 |
| atagctgcat tcgcactgca aaggcagagc cgagccgtca caggctgtga ggcagaacgt | 720 |
| gtttattacc tgacccttt ctgaaaaagt ttgtcggcca ccgccttaga gtatgatgac | 780 |
| attttgccaa acagcagcac cagatatggt tctcagcact tcagaggagt agattcatta | 840 |
| catttgttta ttcgttcatt cattttatcc tttattcgtc agatgcttac tgtctatctg | 900 |
| tggggccagg caccaggaac cagcagagaa caaacagatg caggccttct tcttgtggag | 960 |
| ctgaaagtct gtgtctagat ccttcttttc tcagtacaag cacttccagc ctttccaact | 1020 |
| ctttctcacg agtctcagtg tccagcccct tgcatcctgc ctcccttctg cctccccagt | 1080 |
| atgtatcctg attgcccaag tccctcccaa aaagaggtat ccaaactggt cccatacttc | 1140 |
| ctggggtctt gccaagaggt tgagatctag tagaaggaca catcttgaat tgggtcatgc | 1200 |
| tttctatctg gtttcaaggt gcttaacatc caacctttgc cttttcagct cctgccctcc | 1260 |
| actgactcca gagagggaga tccccagtac ttgactccat cacgcagatg ggagcaggca | 1320 |
| ccagctatgg agagggatac agctgcgtct ccacatgacc catcctgcat gacaccaaag | 1380 |
| ccaccgccag acagtgcctc ggattctatg caaaacctgg gaagcggaga cctacccag | 1440 |
| ccccgggagg aagctagctc ttcaggggac cgtctgagga ctggagtttg atccatgaac | 1500 |
| ctggcttcga ggccttgctt ttctctcttc ttcattcata ttcattccca acaccttaga | 1560 |
| aggtgttgct taatttattt ctagaaaagc agcccagagt cagtcattga agccttcccc | 1620 |
| acccccctggc caaaaaaaaa aaaaaaaaaa aactggacac attttggatc tgttgggagc | 1680 |

-continued

| | |
|---|---|
| ttggagtcca gtggttggca tagttgtcac attgggagca gagaagaagc aaccaggggc | 1740 |
| cctgatcagg ggactgagcc gtagagtccc aggatggcac ccaatggcac agcctcttcc | 1800 |
| ttttgcctgg actctaccgc atgcaagatc accatcaccg tggtccttgc ggtcctcatc | 1860 |
| ctcatcaccg ttgctggcaa tgtggtcgtc tgtctggccg tgggcttgaa ccgccggctc | 1920 |
| cgcaacctga ccaattgttt catcgtgtcc ttggctatca ctgacctgct cctcggcctc | 1980 |
| ctggtgctgc ccttctctgc catctaccag ctgtcctgca gtggagctt tggcaaggtc | 2040 |
| ttctgcaata tctacaccag cctggatgtg atgctctgca cagcctccat tcttaacctc | 2100 |
| ttcatgatca gcctcgaccg gtactgcgct gtcatggacc cactgcgta ccctgtgctg | 2160 |
| gtcaccccag ttcgggtcgc catctctctg gtcttaattt gggtcatctc cattaccctg | 2220 |
| tcctttctgt ctatccacct ggggtggaac agcaggaacg agaccagcaa gggcaatcat | 2280 |
| accacctcta agtgcaatgt ccaggtcaat gaagtgtacg ggctggtgga tgggctggtc | 2340 |
| accttctacc tcccgctact gatcatgtgc atcacctact accgcatctt caaggtcgcc | 2400 |
| cgggatcagg ccaagaggat caatcacatt agctcctgga aggcagccac catcagggag | 2460 |
| cacaaagcca cagtgacact ggccgccgtc atggggcct tcatcatctg ctggtttccc | 2520 |
| tacttcaccg cgtttgtgta ccgtgggctg agaggggatg atgccatcaa tgaggtgtta | 2580 |
| gaagccatcg ttctgtggct gggctatgcc aactcagccc tgaacccat cctgtatgct | 2640 |
| gcgctgaaca gagacttccg caccgggtac caacagctct ctgctgcag gctggccaac | 2700 |
| cgcaactccc acaaaacttc tctgaggtcc aacgcctctc agctgtccag acccaaagc | 2760 |
| cgagaaccca ggcaacagga agagaaaccc ctgaagctcc aggtgtggag tgggacagaa | 2820 |
| gtcacggccc cccagggagc cacagacagg taatagccct agccattggt gcacaggatg | 2880 |
| ggggcaatgg gaggggatgc tactgatggg aatgattaag ggagctgctg tttaggtggt | 2940 |
| gctggtttat gttctaggaa ctcttcatga gcactttgta aacaccctct tgcttaatcc | 3000 |
| tcccaacggc ccccaaaggt agaacttagc tcccttttaa aaggagcaca ttaaaattct | 3060 |
| cagaggactt ggcaagggcc gcacagctgg ggcat | 3095 |

<210> SEQ ID NO 39
<211> LENGTH: 3095
<212> TYPE: DNA
<213> ORGANISM: Homo sapiens

<400> SEQUENCE: 39

| | |
|---|---|
| caggagattg cctgctctct gaaaaaccag gaggagctgg tagggaagga ctgggcgtg | 60 |
| gaacagggcc tcagcttgtt tctcgccagt tggaatcata tacagccacc actgggaggg | 120 |
| agccttggag attacctagt gaccaggggc tcttatttaa tcaagaggca ttgcacatgc | 180 |
| agttacttta ttgacgtagt gtttgcacta cttcaatagt gcaaagggag gaagggagga | 240 |
| aggagaaacc accctaatgc ccgtgagagg gtgatgtggg gatgatagga taaacctatt | 300 |
| catggtgagc ctccccacag actgttatgc aaccattaga aggaatgagt gagttctgtc | 360 |
| cctgctgacc tggatgtggg atcacgtgtt ctgccaagta agaccagtaa gatttagaga | 420 |
| tgcgttcgga gcaggggtgg cgtggatgac aggtgacgaa ctgccgatta aatctggccc | 480 |
| tctgcctggc tttgtacagc ccgtggctaa gaatggtttt tacatttta aattttggaa | 540 |
| aaaaatcaaa aaaggagat ttttatgaca cgtgaaaatg atatgaaatt tacatttcag | 600 |
| tgttcattac tgaagttttg ttggagtgca gccacgctct tctgtcggca cgtcatctgc | 660 |
| atagctgcat tcgcactgca aaggcagagc cgagccgtca caggctgtga ggcagaacgt | 720 |

```
gtttattacc tgacccttttt ctgaaaaagt ttgtcggcca ccgccttaga gtatgatgac    780
attttgccaa acagcagcac cagatatggt tctcagcact tcagaggagt agattcatta    840
catttgttta ttcgttcatt cattttatcc tttattcgtc agatgcttac tgtctatctg    900
tggggccagg caccaggaac cagcagagaa caaacagatg caggccttct tcttgtggag    960
ctgaaagtct gtgtctagat ccttcttttc tcagtacaag cacttccagc cttttccaact  1020
cttctcacg agtctcagtg tccagcccct tgcatcctgc ctcccttctg cctccccagt    1080
atgtatcctg attgcccaag tccctcccaa aaagaggtat ccaaactggt cccatacttc    1140
ctggggtctt gccaagaggt tgagatctag tagaaggaca catcttgaat tgggtcatgc    1200
tttctatctg gtttcaaggt gcttaacatc caacctttgc cttttcagct cctgccctcc    1260
actgactcca gagagggaga tccccagtac ttgactccat cacgcagatg ggagcaggca    1320
ccagctatgg agagggatac agctgcgtct ccacatgacc catcctgcat gacaccaaag    1380
ccaccgccag acagtgcctc ggattctatg caaaacctgg gaagcggaga cctaccccag    1440
ccccgggagg aagctagctc ttcaggggac cgtctgagga ctggagtttg atccatgaac    1500
ctggcttcga ggccttgctt ttctctcttc ttcattcata ttcattccca acaccttaga    1560
aggtgttgct taatttattt ctagaaaagc agcccagagt cagtcattga agccttcccc    1620
accccctggc caaaaaaaaa aaaaaaaaaa aactggacac attttggatc tgttgggagc    1680
ttggagtcca gtggttggca tagttgtcac attgggagca gagaagaagc aaccaggggc    1740
cctgatcagg ggactgagcc gtagagtccc aggatggcac ccaatggcac agcctcttcc    1800
ttttgcctgg actctaccgc atgcaagatc accatcaccg tggtccttgc ggtcctcatc    1860
ctcatcaccg ttgctggcaa tgtggtcgtc tgtctggccg tgggcttgaa ccgccggctc    1920
cgcaacctga ccaattgttt catcgtgtcc ttggctatca ctgacctgct cctcggcctc    1980
ctggtgctgc ccttctctgc catctaccag ctgtcctgca gtggagcttg gcaaggtc     2040
ttctgcaata tctacaccag cctggatgtg atgctctgca cagcctccat tcttaacctc    2100
ttcatgatca gcctcgaccg gtactgcgct gtcatggacc cactgcggta ccctgtgctg    2160
gtcaccccag ttcgggtcgc catctctctg gtcttaattt gggtcatctc cattaccctg    2220
tcctttctgt ctatccacct ggggtggaac agcaggaacg agaccagcaa gggcaatcat    2280
accacctcta agtgcaaagt ccaggtcaat gaagtgtacg ggctggtgga tgggctggtc    2340
accttctacc tcccgctact gatcatgtgc atcacctact accgcatctt caaggtcgcc    2400
cgggatcagg ccaagggggat caatcacatt agctcctgga aggcagccac catcagggag    2460
cacaaagcca cagtgacact ggccgccgtc atggggcct tcatcatctg ctggtttccc    2520
tacttcaccg cgttttgtgta ccgtgggctg agaggggatg atgccatcaa tgaggtgtta    2580
gaagccatcg ttctgtggct gggctatgcc aactcagccc tgaacccat cctgtatgct    2640
gcgctgaaca gagacttccg caccgggtac caacagctct ctgctgcag gctggccaac    2700
cgcaactccc acaaaacttc tctgaggtcc aacgcctctc agctgtccag acccaaagc    2760
cgagaaccca ggcaacagga agagaaaccc ctgaagctcc aggtgtggag tgggacagaa    2820
gtcacggccc ccagggagc cacagacagg taatagccct agccattggt gcacaggatg    2880
ggggcaatgg gagggatgc tactgatggg aatgattaag ggagctgctg tttaggtggt    2940
gctggtttat gttctaggaa ctcttcatga gcactttgta aacaccctct tgcttaatcc    3000
tcccaacggc cccccaaggt agaacttagc tcccttttaa aaggagcaca ttaaaattct    3060
```
cagaggactt ggcaagggcc gcacagctgg ggcat          3095

<210> SEQ ID NO 40
<211> LENGTH: 3095
<212> TYPE: DNA
<213> ORGANISM: Homo sapiens

<400> SEQUENCE: 40

| | | | | | |
|---|---|---|---|---|---|
| caggagattg | cctgctctct | gaaaaaccag | gaggagctgg | tagggaagga | ctggggcgtg | 60 |
| gaacagggcc | tcagcttgtt | tctcgccagt | tggaatcata | tacagccacc | actgggaggg | 120 |
| agccttggag | attacctagt | gaccaggggc | tcttatttaa | tcaagaggca | ttgcacatgc | 180 |
| agttacttta | ttgacgtagt | gtttgcacta | cttcaatagt | gcaaagggag | gaagggagga | 240 |
| aggagaaacc | accctaatgc | ccgtgagagg | gtgatgtggg | gatgatagga | taaacctatt | 300 |
| catggtgagc | ctccccacag | actgttatgc | aaccattaga | aggaatgagt | gagttctgtc | 360 |
| cctgctgacc | tggatgtggg | atcacgtgtt | ctgccaagta | agaccagtaa | gatttagaga | 420 |
| tgcgttcgga | gcaggggtgg | cgtggatgac | aggtgacgaa | ctgccgatta | aatctggccc | 480 |
| tctgcctggc | tttgtacagc | ccgtggctaa | gaatggtttt | tacatttta | aattttggaa | 540 |
| aaaaatcaaa | aaaggagat | ttttatgaca | cgtgaaaatg | atatgaaatt | tacatttcag | 600 |
| tgttcattac | tgaagttttg | ttggagtgca | gccacgctct | tctgtcggca | cgtcatctgc | 660 |
| atagctgcat | tcgcactgca | aaggcagagc | cgagccgtca | caggctgtga | ggcagaacgt | 720 |
| gtttattacc | tgacccttt | ctgaaaaagt | ttgtcggcca | ccgccttaga | gtatgatgac | 780 |
| attttgccaa | acagcagcac | cagatatggt | tctcagcact | tcagaggagt | agattcatta | 840 |
| catttgttta | ttcgttcatt | cattttatcc | tttattcgtc | agatgcttac | tgtctatctg | 900 |
| tggggccagg | caccaggaac | cagcagagaa | caaacagatg | caggccttct | tcttgtggag | 960 |
| ctgaaagtct | gtgtctagat | ccttctttc | tcagtacaag | cacttccagc | ctttccaact | 1020 |
| ctttctcacg | agtctcagtg | tccagccct | tgcatcctgc | ctcccttctg | cctccccagt | 1080 |
| atgtatcctg | attgcccaag | tccctcccaa | aaagaggtat | ccaaactggt | cccatacttc | 1140 |
| ctggggtctt | gccaagaggt | tgagatctag | tagaaggaca | catcttgaat | tgggtcatgc | 1200 |
| tttctatctg | gtttcaaggt | gcttaacatc | caacctttgc | cttttcagct | cctgccctcc | 1260 |
| actgactcca | gagagggaga | tccccagtac | ttgactccat | cacgcagatg | ggagcaggca | 1320 |
| ccagctatgg | agagggatac | agctgcgtct | ccacatgacc | catcctgcat | gacaccaaag | 1380 |
| ccaccgccag | acagtgcctc | ggattctatg | caaaacctgg | gaagcggaga | cctacccag | 1440 |
| ccccgggagg | aagctagctc | ttcagggac | cgtctgagga | ctggagtttg | atccatgaac | 1500 |
| ctggcttcga | ggccttgctt | ttctctcttc | ttcattcata | ttcattccca | acaccttaga | 1560 |
| aggtgttgct | taatttattt | ctagaaaagc | agcccagagt | cagtcattga | agccttcccc | 1620 |
| accccctggc | caaaaaaaaa | aaaaaaaaa | aactggacac | attttggatc | tgttgggagc | 1680 |
| ttggagtcca | gtggttggca | tagttgtcac | attgggagca | gagaagaagc | aaccaggggc | 1740 |
| cctgatcagg | ggactgagcc | gtagagtccc | aggatgcac | ccaatggcac | agcctcttcc | 1800 |
| ttttgcctgg | actctaccgc | atgcaagatc | accatcaccg | tggtccttgc | ggtcctcatc | 1860 |
| ctcatcaccg | ttgctggcaa | tgtggtcgtc | tgtctggccg | tgggcttgaa | ccgccggctc | 1920 |
| cgcaacctga | ccaattgttt | catcgtgtcc | ttggctatca | ctgacctgct | cctcggcctc | 1980 |
| ctggtgctgc | ccttctctgc | catctaccag | ctgtcctgca | agtggagctt | ggcaaggtc | 2040 |
| ttctgcaata | tctacaccag | cctggatgtg | atgctctgca | cagcctccat | tcttaacctc | 2100 |

-continued

```
ttcatgatca gcctcgaccg gtactgcgct gtcatggacc cactgcggta ccctgtgctg    2160
gtcaccccag ttcgggtcgc catctctctg gtcttaattt gggtcatctc cattaccctg    2220
tcctttctgt ctatccacct ggggtggaac agcaggaacg agaccagcaa gggcaatcat    2280
accacctcta agtgcaaagt ccaggtcaat gaagtgtacg ggctggtgga tgggctggtc    2340
accttctacc tcccgctact gatcatgtgc atcacctact accgcatctt caaggtcgcc    2400
cgggatcagg ccaagaggat caatcacatt agctcctgga aggcagccac catcagggag    2460
cacagagcca cagtgacact ggccgccgtc atgggggcct tcatcatctg ctggtttccc    2520
tacttcaccg cgtttgtgta ccgtgggctg agaggggatg atgccatcaa tgaggtgtta    2580
gaagccatcg ttctgtggct gggctatgcc aactcagccc tgaacccccat cctgtatgct    2640 gcgctgaaca gagacttccg caccgggtac caacagctct tctgctgcag gctggccaac    2700
cgcaactccc acaaaacttc tctgaggtcc aacgcctctc agctgtccag gacccaaagc    2760
cgagaaccca ggcaacagga agagaaaccc ctgaagctcc aggtgtggag tgggacagaa    2820
gtcacggccc cccagggagc cacagacagg taatagcccct agccattggt gcacaggatg    2880
ggggcaatgg gaggggatgc tactgatggg aatgattaag ggagctgctg tttaggtggt    2940
gctggtttat gttctaggaa ctcttcatga gcactttgta aacaccctct tgcttaatcc    3000
tcccaacggc ccccaaaggt agaacttagc tccctttaa aaggagcaca ttaaaattct    3060
cagaggactt ggcaagggcc gcacagctgg ggcat                              3095
```

<210> SEQ ID NO 41
<211> LENGTH: 359
<212> TYPE: PRT
<213> ORGANISM: Homo sapiens

<400> SEQUENCE: 41

```
Met Ala Pro Asn Gly Thr Ala Ser Ser Phe Cys Leu Asp Ser Thr Ala
  1               5                  10                  15

Cys Lys Ile Thr Ile Thr Val Val Leu Ala Val Leu Ile Leu Ile Thr
                 20                  25                  30

Val Ala Gly Asn Val Val Val Cys Leu Ala Val Gly Leu Asn Arg Arg
             35                  40                  45

Leu Arg Asn Leu Thr Asn Cys Phe Ile Val Ser Leu Ala Ile Thr Asp
         50                  55                  60

Leu Leu Leu Gly Leu Leu Val Leu Pro Phe Ser Ala Ile Tyr Gln Leu
 65                  70                  75                  80

Ser Cys Lys Trp Ser Phe Gly Lys Val Phe Cys Asn Ile Tyr Thr Ser
                 85                  90                  95

Leu Asp Val Met Leu Cys Thr Ala Ser Ile Leu Asn Leu Phe Met Ile
                100                 105                 110

Ser Leu Asp Arg Tyr Cys Ala Val Met Asp Pro Leu Arg Tyr Pro Val
            115                 120                 125

Leu Val Thr Pro Val Arg Val Ala Ile Ser Leu Val Leu Ile Trp Val
        130                 135                 140

Ile Ser Ile Thr Leu Ser Phe Leu Ser Ile His Leu Gly Trp Asn Ser
145                 150                 155                 160

Arg Asn Glu Thr Ser Lys Gly Asn His Thr Thr Ser Lys Cys Lys Val
                165                 170                 175

Gln Val Asn Glu Val Tyr Gly Leu Val Asp Gly Leu Val Thr Phe Tyr
            180                 185                 190
```

```
Leu Pro Leu Leu Ile Met Cys Ile Thr Tyr Tyr Arg Ile Phe Lys Val
        195                 200                 205

Ala Arg Asp Gln Ala Lys Arg Ile Asn His Ile Ser Ser Trp Lys Ala
    210                 215                 220

Ala Thr Ile Arg Glu His Lys Ala Thr Val Thr Leu Ala Ala Val Met
225                 230                 235                 240

Gly Ala Phe Ile Ile Cys Trp Phe Pro Tyr Phe Thr Ala Phe Val Tyr
                245                 250                 255

Arg Gly Leu Arg Gly Asp Asp Ala Ile Asn Glu Val Leu Glu Ala Ile
            260                 265                 270

Val Leu Trp Leu Gly Tyr Ala Asn Ser Ala Leu Asn Pro Ile Leu Tyr
        275                 280                 285

Ala Ala Leu Asn Arg Asp Phe Arg Thr Gly Tyr Gln Gln Leu Phe Cys
    290                 295                 300

Cys Arg Leu Ala Asn Arg Asn Ser His Lys Thr Ser Leu Arg Ser Asn
305                 310                 315                 320

Ala Ser Gln Leu Ser Arg Thr Gln Ser Arg Glu Pro Arg Gln Gln Glu
                325                 330                 335

Glu Lys Pro Leu Lys Leu Gln Val Trp Ser Gly Thr Glu Val Thr Ala
            340                 345                 350

Pro Gln Gly Ala Thr Asp Arg
        355
```

<210> SEQ ID NO 42
<211> LENGTH: 359
<212> TYPE: PRT
<213> ORGANISM: Homo sapiens

<400> SEQUENCE: 42

```
Met Ala Pro Asn Gly Thr Ala Ser Ser Phe Cys Leu Asp Ser Thr Ala
1               5                   10                  15

Cys Lys Ile Thr Ile Thr Val Val Leu Ala Val Leu Ile Leu Ile Thr
                20                  25                  30

Val Ala Gly Asn Val Val Val Cys Leu Ala Val Gly Leu Asn Arg Arg
            35                  40                  45

Leu Arg Asn Leu Thr Asn Cys Phe Ile Val Ser Leu Ala Ile Thr Asp
    50                  55                  60

Leu Leu Leu Gly Leu Leu Val Leu Pro Phe Ser Ala Ile Tyr Gln Leu
65                  70                  75                  80

Ser Cys Lys Trp Ser Phe Gly Lys Val Phe Cys Asn Ile Tyr Thr Ser
                85                  90                  95

Leu Asp Val Met Leu Cys Thr Ala Ser Ile Leu Asn Leu Phe Met Ile
                100                 105                 110

Ser Leu Asp Arg Tyr Cys Ala Val Met Asp Pro Leu Arg Tyr Pro Val
            115                 120                 125

Leu Val Thr Pro Val Arg Val Ala Ile Ser Leu Val Leu Ile Trp Val
        130                 135                 140

Ile Ser Ile Thr Leu Ser Phe Leu Ser Ile His Leu Gly Trp Asn Ser
145                 150                 155                 160

Arg Asn Glu Thr Ser Lys Gly Asn His Thr Thr Ser Lys Cys Asn Val
                165                 170                 175

Gln Val Asn Glu Val Tyr Gly Leu Val Asp Gly Leu Val Thr Phe Tyr
            180                 185                 190

Leu Pro Leu Leu Ile Met Cys Ile Thr Tyr Tyr Arg Ile Phe Lys Val
        195                 200                 205
```

```
Ala Arg Asp Gln Ala Lys Arg Ile Asn His Ile Ser Ser Trp Lys Ala
    210                 215                 220

Ala Thr Ile Arg Glu His Lys Ala Thr Val Thr Leu Ala Ala Val Met
225                 230                 235                 240

Gly Ala Phe Ile Ile Cys Trp Phe Pro Tyr Phe Thr Ala Phe Val Tyr
                245                 250                 255

Arg Gly Leu Arg Gly Asp Asp Ala Ile Asn Glu Val Leu Glu Ala Ile
                260                 265                 270

Val Leu Trp Leu Gly Tyr Ala Asn Ser Ala Leu Asn Pro Ile Leu Tyr
            275                 280                 285

Ala Ala Leu Asn Arg Asp Phe Arg Thr Gly Tyr Gln Gln Leu Phe Cys
        290                 295                 300

Cys Arg Leu Ala Asn Arg Asn Ser His Lys Thr Ser Leu Arg Ser Asn
305                 310                 315                 320

Ala Ser Gln Leu Ser Arg Thr Gln Ser Arg Glu Pro Arg Gln Gln Glu
                325                 330                 335

Glu Lys Pro Leu Lys Leu Gln Val Trp Ser Gly Thr Glu Val Thr Ala
            340                 345                 350

Pro Gln Gly Ala Thr Asp Arg
        355
```

<210> SEQ ID NO 43
<211> LENGTH: 359
<212> TYPE: PRT
<213> ORGANISM: Homo sapiens

<400> SEQUENCE: 43

```
Met Ala Pro Asn Gly Thr Ala Ser Ser Phe Cys Leu Asp Ser Thr Ala
1               5                   10                  15

Cys Lys Ile Thr Ile Thr Val Val Leu Ala Val Leu Ile Leu Ile Thr
                20                  25                  30

Val Ala Gly Asn Val Val Val Cys Leu Ala Val Gly Leu Asn Arg Arg
            35                  40                  45

Leu Arg Asn Leu Thr Asn Cys Phe Ile Val Ser Leu Ala Ile Thr Asp
    50                  55                  60

Leu Leu Leu Gly Leu Leu Val Leu Pro Phe Ser Ala Ile Tyr Gln Leu
65                  70                  75                  80

Ser Cys Lys Trp Ser Phe Gly Lys Val Phe Cys Asn Ile Tyr Thr Ser
                85                  90                  95

Leu Asp Val Met Leu Cys Thr Ala Ser Ile Leu Asn Leu Phe Met Ile
                100                 105                 110

Ser Leu Asp Arg Tyr Cys Ala Val Met Asp Pro Leu Arg Tyr Pro Val
            115                 120                 125

Leu Val Thr Pro Val Arg Val Ala Ile Ser Leu Val Leu Ile Trp Val
    130                 135                 140

Ile Ser Ile Thr Leu Ser Phe Leu Ser Ile His Leu Gly Trp Asn Ser
145                 150                 155                 160

Arg Asn Glu Thr Ser Lys Gly Asn His Thr Thr Ser Lys Cys Lys Val
                165                 170                 175

Gln Val Asn Glu Val Tyr Gly Leu Val Asp Gly Leu Val Thr Phe Tyr
            180                 185                 190

Leu Pro Leu Leu Ile Met Cys Ile Thr Tyr Tyr Arg Ile Phe Lys Val
        195                 200                 205

Ala Arg Asp Gln Ala Lys Gly Ile Asn His Ile Ser Ser Trp Lys Ala
```

```
              210                 215                 220
Ala Thr Ile Arg Glu His Lys Ala Thr Val Thr Leu Ala Ala Val Met
225                 230                 235                 240

Gly Ala Phe Ile Ile Cys Trp Phe Pro Tyr Phe Thr Ala Phe Val Tyr
                245                 250                 255

Arg Gly Leu Arg Gly Asp Asp Ala Ile Asn Glu Val Leu Glu Ala Ile
                260                 265                 270

Val Leu Trp Leu Gly Tyr Ala Asn Ser Ala Leu Asn Pro Ile Leu Tyr
            275                 280                 285

Ala Ala Leu Asn Arg Asp Phe Arg Thr Gly Tyr Gln Gln Leu Phe Cys
        290                 295                 300

Cys Arg Leu Ala Asn Arg Asn Ser His Lys Thr Ser Leu Arg Ser Asn
305                 310                 315                 320

Ala Ser Gln Leu Ser Arg Thr Gln Ser Arg Glu Pro Arg Gln Gln Glu
                325                 330                 335

Glu Lys Pro Leu Lys Leu Gln Val Trp Ser Gly Thr Glu Val Thr Ala
                340                 345                 350

Pro Gln Gly Ala Thr Asp Arg
            355

<210> SEQ ID NO 44
<211> LENGTH: 359
<212> TYPE: PRT
<213> ORGANISM: Homo sapiens

<400> SEQUENCE: 44

Met Ala Pro Asn Gly Thr Ala Ser Ser Phe Cys Leu Asp Ser Thr Ala
 1               5                  10                  15

Cys Lys Ile Thr Ile Thr Val Val Leu Ala Val Leu Ile Leu Ile Thr
                20                  25                  30

Val Ala Gly Asn Val Val Val Cys Leu Ala Val Gly Leu Asn Arg Arg
            35                  40                  45

Leu Arg Asn Leu Thr Asn Cys Phe Ile Val Ser Leu Ala Ile Thr Asp
50                  55                  60

Leu Leu Leu Gly Leu Leu Val Leu Pro Phe Ser Ala Ile Tyr Gln Leu
65                  70                  75                  80

Ser Cys Lys Trp Ser Phe Gly Lys Val Phe Cys Asn Ile Tyr Thr Ser
                85                  90                  95

Leu Asp Val Met Leu Cys Thr Ala Ser Ile Leu Asn Leu Phe Met Ile
                100                 105                 110

Ser Leu Asp Arg Tyr Cys Ala Val Met Asp Pro Leu Arg Tyr Pro Val
            115                 120                 125

Leu Val Thr Pro Val Arg Val Ala Ile Ser Leu Val Leu Ile Trp Val
        130                 135                 140

Ile Ser Ile Thr Leu Ser Phe Leu Ser Ile His Leu Gly Trp Asn Ser
145                 150                 155                 160

Arg Asn Glu Thr Ser Lys Gly Asn His Thr Thr Ser Lys Cys Lys Val
                165                 170                 175

Gln Val Asn Glu Val Tyr Gly Leu Val Asp Gly Leu Val Thr Phe Tyr
                180                 185                 190

Leu Pro Leu Leu Ile Met Cys Ile Thr Tyr Tyr Arg Ile Phe Lys Val
            195                 200                 205

Ala Arg Asp Gln Ala Lys Arg Ile Asn His Ile Ser Ser Trp Lys Ala
        210                 215                 220
```

```
Ala Thr Ile Arg Glu His Arg Ala Thr Val Thr Leu Ala Ala Val Met
225                 230                 235                 240

Gly Ala Phe Ile Ile Cys Trp Phe Pro Tyr Phe Thr Ala Phe Val Tyr
            245                 250                 255

Arg Gly Leu Arg Gly Asp Asp Ala Ile Asn Glu Val Leu Glu Ala Ile
                260                 265                 270

Val Leu Trp Leu Gly Tyr Ala Asn Ser Ala Leu Asn Pro Ile Leu Tyr
            275                 280                 285

Ala Ala Leu Asn Arg Asp Phe Arg Thr Gly Tyr Gln Gln Leu Phe Cys
        290                 295                 300

Cys Arg Leu Ala Asn Arg Asn Ser His Lys Thr Ser Leu Arg Ser Asn
305                 310                 315                 320

Ala Ser Gln Leu Ser Arg Thr Gln Ser Arg Glu Pro Arg Gln Gln Glu
                325                 330                 335

Glu Lys Pro Leu Lys Leu Gln Val Trp Ser Gly Thr Glu Val Thr Ala
            340                 345                 350

Pro Gln Gly Ala Thr Asp Arg
        355
```

<210> SEQ ID NO 45
<211> LENGTH: 1938
<212> TYPE: DNA
<213> ORGANISM: Homo sapiens

<400> SEQUENCE: 45

| | | |
|---|---|---|
| tctagatatt tctgggattg gagactgttt gctagtgggg agactccagc tccggcagcc | 60 |
| agttcgggag cggcaaagta aaatggacag cgacagacag acgttccagc cacctctccg | 120 |
| ccgccggag atcctggagc tgctttcagg ccaactccag tttcccagct ggagcttctg | 180 |
| aacgcgctgg actgcgagag ccagggagcg cctgaaagct gctcctcgga gatacccttc | 240 |
| gccgaagcag taagaacttc ctgcttgggt ctctgcattc ccttcctccg aaacttccca | 300 |
| ggagaagggc ggaagacccc aggggaaggg gcgaggcgaa tcttcgcgct gcttttctt | 360 |
| ccctcccct tcccgcgccg ggcgcgcagg catggatgtg ctcagccctg gtcagggcaa | 420 |
| caacaccaca tcaccaccgg ctcccttga ccggcggc aacactactg gtatctccga | 480 |
| cgtgaccgtc agctaccaag tgatcacctc tctgctgctg ggcacgctca tcttctgcgc | 540 |
| ggtgctgggc aatgcgtgcg tggtggctgc catcgccttg gagcgctccc tgcagaacgt | 600 |
| ggccaattat cttattggct ctttggcggt caccgacctc atggtgtcgg tgttggtgct | 660 |
| gcccatggcc gcgctgtatc aggtgctcaa caagtggaca ctgggccagg taacctgcga | 720 |
| cctgttcatc gccctcgacg tgctgtgctg cacctcatcc atcttgcacc tgtgcgccat | 780 |
| cgcgctggac aggtactggg ccatcacgga ccccatcgac tacgtgaaca gaggacgcc | 840 |
| ccggcgcgcc gctgcgctca tctcgctcac ttggcttatt gcttcctca tctctatccc | 900 |
| gcccatgctg ggctggcgca ccccggaaga ccgctcggac ccgacgcat gcaccattag | 960 |
| caaggatcat ggctacacta tctattccac ctttggagct ttctacatcc cgctgctgct | 1020 |
| catgctggtt ctctatgggc gcatattccg agctgcgcgc ttccgcatcc gcaagacggt | 1080 |
| caaaaaggtg gagaagaccg gagcggacac ccgccatgga gcatctcccg ccccgcagcc | 1140 |
| caagaagagt gtgaatggag agtcggggag caggaactgg aggctgggcg tggagagcaa | 1200 |
| ggctgggggt gctctgtgcg ccaatggcgc ggtgaggcaa ggtgacgatg gcgccgccct | 1260 |
| ggaggtgatc gaggtgcacc gagtgggcaa ctccaaagag cacttgcctc tgcccagcga | 1320 |

| | |
|---|---|
| ggctggtcct accccttgtg cccccgcctc tttcgagagg aaaaatgagc gcaacgccga | 1380 |
| ggcgaagcgc aagatggccc tggcccgaga gaggaagaca gtgaagacgc tgggcatcat | 1440 |
| catgggcacc ttcatcctct gctggctgcc cttcttcatc gtggctcttg ttctgccctt | 1500 |
| ctgcgagagc agctgccaca tgcccaccct gttgggcgcc ataatcaatt ggctgggcta | 1560 |
| ctccaactct ctgcttaacc ccgtcattta cgcatacttc aacaaggact ttcaaaacgc | 1620 |
| gtttaagaag atcattaagt gtaagttctg ccgccagtga tgacggagga gtagccggcc | 1680 |
| agtcgaggct acaggatccg tcccattcac tatgcttccc ccaaccctag ggaatcaaca | 1740 |
| cttaagataa ttcgccactt ctcctctttc tctctgctcc gctcacggct tgcagacctg | 1800 |
| gtcccctccc cacttcctgc tccacggcag ggccctttgt gcaaaggaga cccagcggag | 1860 |
| gagcgttgag agcccaggaa attcagagag tttgtgagaa gcgacattgg ctcagacttc | 1920 |
| gcctgtatca tcagttttt | 1938 |

<210> SEQ ID NO 46
<211> LENGTH: 1938
<212> TYPE: DNA
<213> ORGANISM: Homo sapiens

<400> SEQUENCE: 46

| | |
|---|---|
| tctagatatt tctgggattg gagactgttt gctagtgggg agactccagc tccggcagcc | 60 |
| agttcgggag cggcaaagta aaatggacag cgacagacag acgttccagc cacctctccg | 120 |
| ccgccgggag atcctggagc tgcttcagg ccaactccag tttcccagct ggagcttctg | 180 |
| aacgcgctgg actgcgagag ccagggagcg cctgaaagct gctcctcgga gatacccttc | 240 |
| gccgaagcag taagaacttc ctgcttgggt ctctgcattc ccttcctccg aaacttccca | 300 |
| ggagaagggc ggaagacccc aggggaaggg gcgaggcgaa tcttcgcgct gcttttctt | 360 |
| ccctcccct tcccgcgccg ggcgcgcagg catggatgtg ctcagccctg gtcagggcaa | 420 |
| caacaccaca tcaccaccgg ctccctttga ccggcggc aacactactg gtatctccga | 480 |
| cgtgaccgtc agctaccaag tgatcacctc tctgctgctg ggcacgctca tcttctgcgt | 540 |
| ggtgctgggc aatgcgtgcg tggtggctgc catcgccttg gagcgctccc tgcagaacgt | 600 |
| ggccaattat cttattggct ctttggcggt caccgacctc atggtgtcgg tgttggtgct | 660 |
| gcccatggcc gcgctgtatc aggtgctcaa caagtggaca ctgggccagg taacctgcga | 720 |
| cctgttcatc gccctcgacg tgctgtgctg cacctcatcc atcttgcacc tgtgcgccat | 780 |
| cgcgctggac aggtactggg ccatcacgga ccccatcgac tacgtgaaca agaggacgcc | 840 |
| ccggcgcgcc gctgcgctca tctcgctcac ttggcttatt ggcttcctca tctctatccc | 900 |
| gcccatgctg ggctggcgca ccccggaaga ccgctcggac cccgacgcat gcaccattag | 960 |
| caaggatcat ggctacacta tctattccac cttttggagct ttctacatcc cgctgctgct | 1020 |
| catgctggtt ctctatgggc gcatattccg agctgcgcgc ttccgcatcc gcaagacggt | 1080 |
| caaaaaggtg gagaagaccg gagcggacac ccgccatgga gcatctcccg ccccgcagcc | 1140 |
| caagaagagt gtgaatggag agtcggggag caggaactgg aggctgggcg tggagagcaa | 1200 |
| ggctgggggt gctctgtgcg ccaatggcgc ggtgaggcaa ggtgacgatg gcgccgccct | 1260 |
| ggaggtgatc gaggtgcacc gagtgggcaa ctccaaagag cacttgcctc tgcccagcga | 1320 |
| ggctggtcct accccttgtg cccccgcctc tttcgagagg aaaaatgagc gcaacgccga | 1380 |
| ggcgaagcgc aagatggccc tggcccgaga gaggaagaca gtgaagacgc tgggcatcat | 1440 |
| catgggcacc ttcatcctct gctggctgcc cttcttcatc gtggctcttg ttctgccctt | 1500 |

```
ctgcgagagc agctgccaca tgcccaccct gttgggcgcc ataatcaatt ggctgggcta    1560
ctccaactct ctgcttaacc ccgtcattta cgcatacttc aacaaggact ttcaaaacgc    1620
gtttaagaag atcattaagt gtaagttctg ccgccagtga tgacggagga gtagccggcc    1680
agtcgaggct acaggatccg tcccattcac tatgcttccc ccaaccctag ggaatcaaca    1740
cttaagataa ttcgccactt ctcctctttc tctctgctcc gctcacggct gcagacctg     1800 gtcccctccc cacttcctgc tccacggcag ggccctttgt gcaaaggaga cccagcggag    1860
gagcgttgag agcccaggaa attcagagag tttgtgagaa gcgacattgg ctcagacttc    1920
gcctgtatca tcagtttt                                                  1938

<210> SEQ ID NO 47
<211> LENGTH: 1938
<212> TYPE: DNA
<213> ORGANISM: Homo sapiens

<400> SEQUENCE: 47
tctagatatt tctgggattg gagactgttt gctagtgggg agactccagc tccggcagcc     60
agttcgggag cggcaaagta aaatggacag cgacagacag acgttccagc cacctctccg    120
ccgccgggag atcctggagc tgctttcagg ccaactccag tttcccagct ggagcttctg    180
aacgcgctgg actgcgagag ccaggagcg cctgaaagct gctcctcgga gataccttc     240 gccgaagcag taagaacttc ctgcttgggt ctctgcattc ccttcctccg aaacttccca    300
ggagaagggc ggaagacccc aggggaaggg gcgaggcgaa tcttcgcgct gcttttctt     360 ccctccccct tcccgcgccg ggcgcgcagg catggatgtg ctcagccctg gtcagggcaa    420
caacaccaca tcaccaccgg ctcccttga accggcggc aacactactg gtatctccga      480
cgtgaccgtc agctaccaag tgatcacctc tctgctgctg ggcacgctca tcttctgcgc    540
ggtgctgggc aatgcgtgcg tggtggctgc catcgccttg agcgctccc tgcagaacgt     600 ggccaattat cttattggct ctttggcggt caccgacctc atggtgtcgg tgttggtgct    660
gcccatggcc gcgctgtatc aggtgctcaa caagtggaca ctgggccagg taacctgcga    720
cctgttcatc gccctcgacg tgctgtgctg cacctcatcc atcttgcacc tgtgcgccat    780
cgcgctggac aggtactggg ccatcacgga ccccatcgac tacgtgaaca agaggacgcc    840
ccggcgcgcc gctgcgctca tctcgctcac ttggcttatt ggcttcctca tctctatccc    900
gcccatcctg ggctggcgca ccccggaaga ccgctcggac cccgacgcat gcaccattag    960
caaggatcat ggctacacta tctattccac ctttggagct ttctacatcc cgctgctgct    1020
catgctggtt tctatgggc gcatattccg agctgcgcgc ttccgcatcc gcaagacggt    1080
caaaaaggtg gagaagaccg gagcggacac ccgccatgga gcatctcccg ccccgcagcc    1140
caagaagagt gtgaatggag agtcggggag caggaactgg aggctgggcg tggagagcaa    1200
ggctgggggt gctctgtgcg ccaatggcgc ggtgaggcaa ggtgacgatg gcgccgccct    1260
ggaggtgatc gaggtgcacc gagtgggcaa ctccaaagag cacttgcctc tgcccagcga    1320
ggctggtcct acccccttgtg cccccgcctc tttcgagagg aaaaatgagc gcaacgccga    1380
ggcgaagcgc aagatggccc tggcccgaga gaggaagaca gtgaagacgc tgggcatcat    1440
catgggcacc ttcatcctct gctggctgcc cttcttcatc gtggctcttg ttctgccctt    1500
ctgcgagagc agctgccaca tgcccaccct gttgggcgcc ataatcaatt ggctgggcta    1560
ctccaactct ctgcttaacc ccgtcattta cgcatacttc aacaaggact ttcaaaacgc    1620
```

-continued

| | |
|---|---|
| gtttaagaag atcattaagt gtaagttctg ccgccagtga tgacggagga gtagccggcc | 1680 |
| agtcgaggct acaggatccg tcccattcac tatgcttccc ccaaccctag ggaatcaaca | 1740 |
| cttaagataa ttcgccactt ctcctctttc tctctgctcc gctcacggct tgcagacctg | 1800 |
| gtcccctccc cacttcctgc tccacggcag ggccctttgt gcaaaggaga cccagcggag | 1860 |
| gagcgttgag agcccaggaa attcagagag tttgtgagaa gcgacattgg ctcagacttc | 1920 |
| gcctgtatca tcagtttt | 1938 |

<210> SEQ ID NO 48
<211> LENGTH: 1938
<212> TYPE: DNA
<213> ORGANISM: Homo sapiens

<400> SEQUENCE: 48

| | |
|---|---|
| tctagatatt tctgggattg gagactgttt gctagtgggg agactccagc tccggcagcc | 60 |
| agttcgggag cggcaaagta aaatggacag cgacagacag acgttccagc cacctctccg | 120 |
| ccgccgggag atcctggagc tgctttcagg ccaactccag tttcccagct ggagcttctg | 180 |
| aacgcgctgg actgcgagag ccagggagcg cctgaaagct gctcctcgga gataccctc | 240 |
| gccgaagcag taagaacttc ctgcttgggt ctctgcattc ccttcctccg aaacttccca | 300 |
| ggagaagggc ggaagacccc aggggaaggg gcgaggcgaa tcttcgcgct gcttttctt | 360 |
| ccctccccct tcccgcgccg ggcgcgcagg catggatgtg ctcagccctg tcagggcaa | 420 |
| caacaccaca tcaccaccgg ctcccttga accggcggc aacactactg gtatctccga | 480 |
| cgtgaccgtc agctaccaag tgatcacctc tctgctgctg ggcacgctca tcttctgcgc | 540 |
| ggtgctgggc aatgcgtgcg tggtggctgc catcgcttg gagcgctccc tgcagaacgt | 600 |
| ggccaattat cttattggct ctttggcggt caccgacctc atggtgtcgg tgttggtgct | 660 |
| gcccatggcc gcgctgtatc aggtgctcaa caagtggaca ctgggccagg taacctgcga | 720 |
| cctgttcatc gccctcgacg tgctgtgctg cacctcatcc atcttgcacc tgtgcgccat | 780 |
| cgcgctggac aggtactggg ccatcacgga ccccatcgac tacgtgaaca agaggacgcc | 840 |
| ccggcgcgcc gctgcgctca tctcgctcac ttggcttatt ggcttcctca tctctatccc | 900 |
| gcccatgctg ggctggcgca ccccggaaga ccgtcggac cccgacgcat gcaccattag | 960 |
| caaggatcat ggctacacta tctattccac ctttggagct ttctacatcc cgctgctgct | 1020 |
| catgctggtt ctctatgggc gcatattccg agctgcgcgc ttccgcatcc gcaagacggt | 1080 |
| caaaaaggtg gagaagaccg gagcggacac ccgccatgga gcatctcccg ccccgcagcc | 1140 |
| caagaagagt gtgaatggag agtcggggag caggaactgg aggctgggcg tggagagcaa | 1200 |
| ggctgggggt gctctgtgcg ccaatggcgc ggtgaggcaa ggtgacgatg gcgccgccct | 1260 |
| ggaggtgatc gaggtgcacc gagtgggcaa ctccaaagag cacttgcctc tgcccagcga | 1320 |
| ggctggtcct acccccttgtg ccccgcctc tttcgagagg aaaaatgagc gcaacgccga | 1380 |
| ggcgaagcgc aagatggccc tggcccgaga gaggaagaca gtgaagacgc tgggcatcat | 1440 |
| catgggcacc ttcatcctct gctggctgcc cttcttcatc gtggctcttg ttctgcctt | 1500 |
| ctgcgagagc agctgccaca tgcccaccct gttcggcgcc ataatcaatt ggctgggcta | 1560 |
| ctccaactct ctgcttaacc ccgtcattta cgcatacttc aacaaggact ttcaaaacgc | 1620 |
| gtttaagaag atcattaagt gtaagttctg ccgccagtga tgacggagga gtagccggcc | 1680 |
| agtcgaggct acaggatccg tcccattcac tatgcttccc ccaaccctag ggaatcaaca | 1740 |
| cttaagataa ttcgccactt ctcctctttc tctctgctcc gctcacggct tgcagacctg | 1800 |

```
gtcccctccc cacttcctgc tccacggcag ggcccttgt gcaaaggaga cccagcggag   1860
gagcgttgag agcccaggaa attcagagag tttgtgagaa gcgacattgg ctcagacttc   1920
gcctgtatca tcagtttt                                                  1938
```

<210> SEQ ID NO 49
<211> LENGTH: 422
<212> TYPE: PRT
<213> ORGANISM: Homo sapiens

<400> SEQUENCE: 49

```
Met Asp Val Leu Ser Pro Gly Gln Gly Asn Asn Thr Thr Ser Pro Pro
 1               5                  10                  15

Ala Pro Phe Glu Thr Gly Gly Asn Thr Thr Gly Ile Ser Asp Val Thr
             20                  25                  30

Val Ser Tyr Gln Val Ile Thr Ser Leu Leu Leu Gly Thr Leu Ile Phe
         35                  40                  45

Cys Ala Val Leu Gly Asn Ala Cys Val Val Ala Ala Ile Ala Leu Glu
     50                  55                  60

Arg Ser Leu Gln Asn Val Ala Asn Tyr Leu Ile Gly Ser Leu Ala Val
 65                  70                  75                  80

Thr Asp Leu Met Val Ser Val Leu Val Leu Pro Met Ala Ala Leu Tyr
                 85                  90                  95

Gln Val Leu Asn Lys Trp Thr Leu Gly Gln Val Thr Cys Asp Leu Phe
            100                 105                 110

Ile Ala Leu Asp Val Leu Cys Cys Thr Ser Ser Ile Leu His Leu Cys
        115                 120                 125

Ala Ile Ala Leu Asp Arg Tyr Trp Ala Ile Thr Asp Pro Ile Asp Tyr
    130                 135                 140

Val Asn Lys Arg Thr Pro Arg Arg Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
        195                 200                 205

Leu Leu Met Leu Val Leu Tyr Gly Arg Ile Phe Arg Ala Ala Arg Phe
    210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
    290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
                325                 330                 335

Leu Ala Arg Glu Arg Lys Thr Val Lys Thr Leu Gly Ile Ile Met Gly
```

-continued

```
                340                 345                 350
Thr Phe Ile Leu Cys Trp Leu Pro Phe Phe Ile Val Ala Leu Val Leu
                355                 360                 365

Pro Phe Cys Glu Ser Ser Cys His Met Pro Thr Leu Leu Gly Ala Ile
    370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
                405                 410                 415

Cys Lys Phe Cys Arg Gln
            420

<210> SEQ ID NO 50
<211> LENGTH: 422
<212> TYPE: PRT
<213> ORGANISM: Homo sapiens

<400> SEQUENCE: 50

Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
                20                  25                  30

Val Ser Tyr Gln Val Ile Thr Ser Leu Leu Leu Gly Thr Leu Ile Phe
                35                  40                  45

Cys Val Val Leu Gly Asn Ala Cys Val Val Ala Ala Ile Ala Leu Glu
            50                  55                  60

Arg Ser Leu Gln Asn Val Ala Asn Tyr Leu Ile Gly Ser Leu Ala Val
65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
                100                 105                 110

Ile Ala Leu Asp Val Leu Cys Cys Thr Ser Ser Ile Leu His Leu Cys
            115                 120                 125

Ala Ile Ala Leu Asp Arg Tyr Trp Ala Ile Thr Asp Pro Ile Asp Tyr
        130                 135                 140

Val Asn Lys Arg Thr Pro Arg Arg Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
        195                 200                 205

Leu Leu Met Leu Val Leu Tyr Gly Arg Ile Phe Arg Ala Ala Arg Phe
    210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285
```

```
Ala Leu Glu Val Ile Glu Val His Arg Val Gly Asn Ser Lys Glu His
    290             295                 300
Leu Pro Leu Pro Ser Glu Ala Gly Pro Thr Pro Cys Ala Pro Ala Ser
305             310                 315                 320
Phe Glu Arg Lys Asn Glu Arg Asn Ala Glu Ala Lys Arg Lys Met Ala
                325                 330                 335
Leu Ala Arg Glu Arg Lys Thr Val Lys Thr Leu Gly Ile Ile Met Gly
            340                 345                 350
Thr Phe Ile Leu Cys Trp Leu Pro Phe Phe Ile Val Ala Leu Val Leu
        355                 360                 365
Pro Phe Cys Glu Ser Ser Cys His Met Pro Thr Leu Leu Gly Ala Ile
    370                 375                 380
Ile Asn Trp Leu Gly Tyr Ser Asn Ser Leu Leu Asn Pro Val Ile Tyr
385                 390                 395                 400
Ala Tyr Phe Asn Lys Asp Phe Gln Asn Ala Phe Lys Lys Ile Ile Lys
                405                 410                 415
Cys Lys Phe Cys Arg Gln
                420

<210> SEQ ID NO 51
<211> LENGTH: 422
<212> TYPE: PRT
<213> ORGANISM: Homo sapiens

<400> SEQUENCE: 51

Met Asp Val Leu Ser Pro Gly Gln Gly Asn Asn Thr Thr Ser Pro Pro
1               5                   10                  15
Ala Pro Phe Glu Thr Gly Gly Asn Thr Thr Gly Ile Ser Asp Val Thr
                20                  25                  30
Val Ser Tyr Gln Val Ile Thr Ser Leu Leu Leu Gly Thr Leu Ile Phe
            35                  40                  45
Cys Ala Val Leu Gly Asn Ala Cys Val Val Ala Ala Ile Ala Leu Glu
        50                  55                  60
Arg Ser Leu Gln Asn Val Ala Asn Tyr Leu Ile Gly Ser Leu Ala Val
65                  70                  75                  80
Thr Asp Leu Met Val Ser Val Leu Val Leu Pro Met Ala Ala Leu Tyr
                85                  90                  95
Gln Val Leu Asn Lys Trp Thr Leu Gly Gln Val Thr Cys Asp Leu Phe
                100                 105                 110
Ile Ala Leu Asp Val Leu Cys Cys Thr Ser Ser Ile Leu His Leu Cys
            115                 120                 125
Ala Ile Ala Leu Asp Arg Tyr Trp Ala Ile Thr Asp Pro Ile Asp Tyr
        130                 135                 140
Val Asn Lys Arg Thr Pro Arg Arg Ala Ala Leu Ile Ser Leu Thr
145                 150                 155                 160
Trp Leu Ile Gly Phe Leu Ile Ser Ile Pro Pro Ile Leu Gly Trp Arg
                165                 170                 175
Thr Pro Glu Asp Arg Ser Asp Pro Asp Ala Cys Thr Ile Ser Lys Asp
                180                 185                 190
His Gly Tyr Thr Ile Tyr Ser Thr Phe Gly Ala Phe Tyr Ile Pro Leu
            195                 200                 205
Leu Leu Met Leu Val Leu Tyr Gly Arg Ile Phe Arg Ala Ala Arg Phe
        210                 215                 220
Arg Ile Arg Lys Thr Val Lys Lys Val Glu Lys Thr Gly Ala Asp Thr
225                 230                 235                 240
```

-continued

```
Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
    290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
                325                 330                 335

Leu Ala Arg Glu Arg Lys Thr Val Lys Thr Leu Gly Ile Ile Met Gly
            340                 345                 350

Thr Phe Ile Leu Cys Trp Leu Pro Phe Phe Ile Val Ala Leu Val Leu
        355                 360                 365

Pro Phe Cys Glu Ser Ser Cys His Met Pro Thr Leu Leu Gly Ala Ile
    370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
                405                 410                 415

Cys Lys Phe Cys Arg Gln
            420

<210> SEQ ID NO 52
<211> LENGTH: 422
<212> TYPE: PRT
<213> ORGANISM: Homo sapiens

<400> SEQUENCE: 52

Met Asp Val Leu Ser Pro Gly Gln Gly Asn Asn Thr Thr Ser Pro Pro
  1               5                  10                  15

Ala Pro Phe Glu Thr Gly Gly Asn Thr Thr Gly Ile Ser Asp Val Thr
                20                  25                  30

Val Ser Tyr Gln Val Ile Thr Ser Leu Leu Leu Gly Thr Leu Ile Phe
            35                  40                  45

Cys Ala Val Leu Gly Asn Ala Cys Val Val Ala Ala Ile Ala Leu Glu
        50                  55                  60

Arg Ser Leu Gln Asn Val Ala Asn Tyr Leu Ile Gly Ser Leu Ala Val
 65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
                100                 105                 110

Ile Ala Leu Asp Val Leu Cys Cys Thr Ser Ser Ile Leu His Leu Cys
            115                 120                 125

Ala Ile Ala Leu Asp Arg Tyr Trp Ala Ile Thr Asp Pro Ile Asp Tyr
        130                 135                 140

Val Asn Lys Arg Thr Pro Arg Arg Ala Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
```

```
                180             185             190
His Gly Tyr Thr Ile Tyr Ser Thr Phe Gly Ala Phe Tyr Ile Pro Leu
            195                 200                 205
Leu Leu Met Leu Val Leu Tyr Gly Arg Ile Phe Arg Ala Ala Arg Phe
    210                 215                 220
Arg Ile Arg Lys Thr Val Lys Val Glu Lys Thr Gly Ala Asp Thr
225                 230                 235                 240
Arg His Gly Ala Ser Pro Ala Pro Gln Pro Lys Lys Ser Val Asn Gly
                245                 250                 255
Glu Ser Gly Ser Arg Asn Trp Arg Leu Gly Val Glu Ser Lys Ala Gly
            260                 265                 270
Gly Ala Leu Cys Ala Asn Gly Ala Val Arg Gln Gly Asp Asp Gly Ala
        275                 280                 285
Ala Leu Glu Val Ile Glu Val His Arg Val Gly Asn Ser Lys Glu His
    290                 295                 300
Leu Pro Leu Pro Ser Glu Ala Gly Pro Thr Pro Cys Ala Pro Ala Ser
305                 310                 315                 320
Phe Glu Arg Lys Asn Glu Arg Asn Ala Glu Ala Lys Arg Lys Met Ala
                325                 330                 335
Leu Ala Arg Glu Arg Lys Thr Val Lys Thr Leu Gly Ile Ile Met Gly
            340                 345                 350
Thr Phe Ile Leu Cys Trp Leu Pro Phe Phe Ile Val Ala Leu Val Leu
        355                 360                 365
Pro Phe Cys Glu Ser Ser Cys His Met Pro Thr Leu Phe Gly Ala Ile
    370                 375                 380
Ile Asn Trp Leu Gly Tyr Ser Asn Ser Leu Leu Asn Pro Val Ile Tyr
385                 390                 395                 400
Ala Tyr Phe Asn Lys Asp Phe Gln Asn Ala Phe Lys Lys Ile Ile Lys
                405                 410                 415
Cys Lys Phe Cys Arg Gln
            420

<210> SEQ ID NO 53
<211> LENGTH: 2287
<212> TYPE: DNA
<213> ORGANISM: Homo sapiens

<400> SEQUENCE: 53
ccattggtca aagccttctc ctcaagcagt acttcaccct cctgcactag acgcctccag      60
ggagctggag cggagcaggg ctcggtgggc cagctcttag caacccaggt ctaagacccg     120
gtgtggagag gaacaaccac agacgcggcg gcttagctag gcgctctgga agtgcagggg     180
aggcgcccgc ctgccttgcg tgccgcaccc atgacctcta gtttcagctg tgaacctggg     240
cggaggaata ttgaggaac tcacggaact atcaactggg gacaaacctg cgatcgccac      300
ggtccttccg ccctctcctt cgtccgctcc atgcccaaga gctgcgctcc ggagctgggg     360
cgaggagagc catggaggaa ccgggtgctc agtgcgctcc accgccgccc gcgggctccg     420
agacctgggt tcctcaagcc aacttatcct ctgctccctc ccaaaactgc agcgccaagg     480
actacattta ccaggactct atctccctac cctggaaagt actgctggtt atgctattgg     540
cgctcatcac cttggccacc acgctctcca atgcctttgt gattgccaca gtgtaccgga     600
cccggaaact gcacacccccg gctaactacc tgatcgcctc tctggcggtc accgacctgc     660
ttgtgtccat cctggtgatg cccatcagca ccatgtacac tgtcaccggc cgctggacac     720
```

```
tgggccaggt ggtctgtgac ttctggctgt cgtcggacat cacttgttgc actgcctcca      780
tcctgcacct ctgtgtcatc gccctggacc gctactgggc catcacggac gccgtggagt      840
actcagctaa aaggactccc aagagggcgg cggtcatgat cgcgctggtg tgggtcttct      900
ccatctctat ctcgctgccg cccttcttct ggcgtcaggc taaggccgaa gaggaggtgt      960
cggaatgcgt ggtgaacacc gaccacatcc tctacacggt ctactccacg gtgggtgctt     1020
tctacttccc caccctgctc ctcatcgccc tctatggccg catctacgta aagcccgct      1080
cccggatttt gaaacagacg cccaacagga ccggcaagcg cttgacccga gcccagctga     1140
taaccgactc ccccgggtcc acgtcctcgg tcacctctat taactcgcgg gttcccgacg     1200
tgcccagcga atccggatct cctgtgtatg tcaaccaagt caaagtgcga gtctccgacg     1260
ccctgctgga aaagaagaaa ctcatggccg ctagggagcg caaagccacc aagaccctag     1320
ggatcatttt gggagccttt attgtgtgtt ggctacccct cttcatcatc tccctagtga     1380
tgcctatctg caaagatgcc tgctggttcc acctagccat ctttgacttc ttcacatggc     1440
tgggctatct caactccctc atcaaccccca taatctatac catgtccaat gaggacttta     1500
aacaagcatt ccataaactg atacgtttta agtgcacaag ttgacttgcc atttgcagtg     1560
gggtcgccta agcgaccttt ggggaccaag ttgtgtctgg ttccacaggt aggtcgaatc     1620
ttctttcgcg gtttctgggt cccagcgagg ctctctctcc tgggcaaggg caatggatcc     1680
tgagaagcca aatagtcct gagagagagc tctgaaagga gaagtgttga aactaaatgt     1740
agagcttccc tgcccaggag gaggctcact tcctcccctc aagccccggg ctcagcactg     1800
accctgcggc agccaatcca aaggggttgc aacttttaaa aattgataat ggaagggaat     1860
ccctgccctg ctttggtatc gtggataatg cccactagaa gcagtgtact tgtaattgtt     1920
gtctgaagcc tgtctgagac agatctacat acagcctggc agtacttgaa ctagacgctt     1980
aatgccctgt gttttgggg ggagaacttt gtgttacagc ttaatttaag aacagttact     2040
ttggcatcat tcagtcttca cttttgtct atttaaactt ggttggagaa acttgtggat     2100
tggtgcttc aaaccctatg tgtggcttgg atggcgcaga gaaaccttga agagttaaca     2160
gcaaaattct gatgctgaga tctctatttt tattatactt gaaactatat ggggtgggt     2220
gggtgggaat gggagatgag gagtgttaaa ctgagaatca acacctatga ttgtttgttt     2280
tctgcag                                                                2287
```

<210> SEQ ID NO 54
<211> LENGTH: 2287
<212> TYPE: DNA
<213> ORGANISM: Homo sapiens

<400> SEQUENCE: 54

```
ccattggtca aagccttctc ctcaagcagt acttcaccct cctgcactag acgcctccag       60
ggagctggag cggagcaggg ctcggtgggc cagctcttag caacccaggt ctaagacccg      120
gtgtggagag gaacaaccac agacgcggcg gcttagctag cgctctggaa agtgcagggg      180
aggcgcccgc ctgccttgcg tgccgcaccc atgacctcta gtttcagctg tgaacctggg      240
cggaggaata attgaggaac tcacggaact atcaactggg gacaaacctg cgatcgccac      300
ggtccttccg ccctctcctt cgtccgctcc atgcccaaga gctgcgctcc ggagctgggg      360
cgaggagagc catggaggaa ccgggtgctc agtgcgctcc accgccgccc gcgggctccg      420
agacctgggt tcctcaagcc aacttatcct ctgctccctc ccaaaactgc agcgccaagg      480
actacatttta ccaggactct atctccctac cctggaaagt actgctggtt atgctattgg      540
```

-continued

```
cgctcatcac cttggccacc acgtctccca atgcctttgt gattgccaca gtgtaccgga      600
cccggaaact gcacaccccg gctaactacc tgatcgcctc tctggcggtc accgacctgc      660
ttgtgtccat cctggtgatg cccatcagca ccatgtacac tgtcaccggc cgctggacac      720
tgggccaggt ggtctgtgac ttctggctgt cgtcggacat cacttgttgc actgcctcca      780
tcctgcacct ctgtgtcatc gccctggacc gctactgggc catcacggac gccgtggagt      840
actcagctaa aaggactccc aagagggcgg cggtcatgat cgcgctggtg tgggtcttct      900
ccatctctat ctcgctgccg cccttcttct ggcgtcaggc taaggccgaa gaggaggtgt      960
cggaatgcgt ggtgaacacc gaccacatcc tctacacggt ctactccacg gtgggtgctt     1020
tctacttccc caacctgctc ctcatcgccc tctatggccg catctacgta gaagcccgct     1080
cccggatttt gaaacagacg cccaacagga ccggcaagcg cttgacccga gcccagctga     1140
taaccgactc ccccgggtcc acgtcctcgg tcacctctat taactcgcgg gttcccgacg     1200
tgcccagcga atccggatct cctgtgtatg tcaaccaagt caaagtgcga gtctccgacg     1260
ccctgctgga aaagaagaaa ctcatggccg ctagggagcg caaagccacc aagaccctag     1320
ggatcatttt gggagccttt attgtgtgtt ggctacccct cttcatcatc tccctagtga     1380
tgcctatctg caaagatgcc tgctggttcc acctagccat cttttgacttc ttcacatggc     1440 tgggctatct caactccctc atcaaccccca taatctatac catgtccaat gaggacttta     1500
aacaagcatt ccataaactg atacgtttta agtgcacaag ttgacttgcc atttgcagtg     1560
gggtcgccta agcgaccttt ggggaccaag ttgtgtctgg ttccacaggt aggtcgaatc     1620
ttctttcgcg gtttctgggt cccagcgagg ctctctctcc tgggcaaggg caatggatcc     1680
tgagaagcca gaatagtcct gagagagagc tctgaaagga gaagtgttga aactaaatgt     1740
agagcttccc tgcccaggag gaggctcact tcctcccctc aagccccggg ctcagcactg     1800
accctgcggc agccaatcca aaggggttgc aacttttaaa aattgataat ggaagggaat     1860
ccctgccctg ctttggtatc gtggataatg cccactagaa gcagtgtact tgtaattgtt     1920
gtctgaagcc tgtctgagac agatctacat acagcctggc agtacttgaa ctagacgctt     1980
aatgccctgt gttttgggg ggagaacttt gtgttacagc ttaatttaag aacagttact     2040
ttggcatcat tcagtcttca cttttttgtct atttaaactt ggttggagaa acttgtggat     2100
ttggtgcttc aaaccctatg tgtggcttgg atggcgcaga gaaaccttga agagttaaca     2160
gcaaaattct gatgctgaga tctctatttt tattatactt gaaactatat gggggtgggt     2220
gggtgggaat gggagatgag gagtgttaaa ctgagaatca acacctatga ttgtttgttt     2280
tctgcag                                                              2287
```

<210> SEQ ID NO 55
<211> LENGTH: 390
<212> TYPE: PRT
<213> ORGANISM: Homo sapiens

<400> SEQUENCE: 55

```
Met Glu Glu Pro Gly Ala Gln Cys Ala Pro Pro Pro Ala Gly Ser
 1               5                  10                  15

Glu Thr Trp Val Pro Gln Ala Asn Leu Ser Ser Ala Pro Ser Gln Asn
                20                  25                  30

Cys Ser Ala Lys Asp Tyr Ile Tyr Gln Asp Ser Ile Ser Leu Pro Trp
            35                  40                  45

Lys Val Leu Leu Val Met Leu Leu Ala Leu Ile Thr Leu Ala Thr Thr
```

```
               50                  55                  60
Leu Ser Asn Ala Phe Val Ile Ala Thr Val Tyr Arg Thr Arg Lys Leu
 65                  70                  75                  80

His Thr Pro Ala Asn Tyr Leu Ile Ala Ser Leu Ala Val Thr Asp Leu
                 85                  90                  95

Leu Val Ser Ile Leu Val Met Pro Ile Ser Thr Met Tyr Thr Val Thr
                100                 105                 110

Gly Arg Trp Thr Leu Gly Gln Val Val Cys Asp Phe Trp Leu Ser Ser
                115                 120                 125

Asp Ile Thr Cys Cys Thr Ala Ser Ile Leu His Leu Cys Val Ile Ala
                130                 135                 140

Leu Asp Arg Tyr Trp Ala Ile Thr Asp Ala Val Glu Tyr Ser Ala Lys
145                 150                 155                 160

Arg Thr Pro Lys Arg Ala Ala Val Met Ile Ala Leu Val Trp Val Phe
                165                 170                 175

Ser Ile Ser Ile Ser Leu Pro Pro Phe Phe Trp Arg Gln Ala Lys Ala
                180                 185                 190

Glu Glu Glu Val Ser Glu Cys Val Val Asn Thr Asp His Ile Leu Tyr
                195                 200                 205

Thr Val Tyr Ser Thr Val Gly Ala Phe Tyr Phe Pro Thr Leu Leu Leu
                210                 215                 220

Ile Ala Leu Tyr Gly Arg Ile Tyr Val Glu Ala Arg Ser Arg Ile Leu
225                 230                 235                 240

Lys Gln Thr Pro Asn Arg Thr Gly Lys Arg Leu Thr Arg Ala Gln Leu
                245                 250                 255

Ile Thr Asp Ser Pro Gly Ser Thr Ser Ser Val Thr Ser Ile Asn Ser
                260                 265                 270

Arg Val Pro Asp Val Pro Ser Glu Ser Gly Ser Pro Val Tyr Val Asn
                275                 280                 285

Gln Val Lys Val Arg Val Ser Asp Ala Leu Leu Glu Lys Lys Lys Leu
                290                 295                 300

Met Ala Ala Arg Glu Arg Lys Ala Thr Lys Thr Leu Gly Ile Ile Leu
305                 310                 315                 320

Gly Ala Phe Ile Val Cys Trp Leu Pro Phe Phe Ile Ile Ser Leu Val
                325                 330                 335

Met Pro Ile Cys Lys Asp Ala Cys Trp Phe His Leu Ala Ile Phe Asp
                340                 345                 350

Phe Phe Thr Trp Leu Gly Tyr Leu Asn Ser Leu Ile Asn Pro Ile Ile
                355                 360                 365

Tyr Thr Met Ser Asn Glu Asp Phe Lys Gln Ala Phe His Lys Leu Ile
                370                 375                 380

Arg Phe Lys Cys Thr Ser
385                 390

<210> SEQ ID NO 56
<211> LENGTH: 390
<212> TYPE: PRT
<213> ORGANISM: Homo sapiens

<400> SEQUENCE: 56

Met Glu Glu Pro Gly Ala Gln Cys Ala Pro Pro Pro Ala Gly Ser
 1               5                  10                  15

Glu Thr Trp Val Pro Gln Ala Asn Leu Ser Ser Ala Pro Ser Gln Asn
                 20                  25                  30
```

```
Cys Ser Ala Lys Asp Tyr Ile Tyr Gln Asp Ser Ile Ser Leu Pro Trp
         35                  40                  45
Lys Val Leu Leu Val Met Leu Leu Ala Leu Ile Thr Leu Ala Thr Thr
 50                  55                  60
Leu Ser Asn Ala Phe Val Ile Ala Thr Val Tyr Arg Thr Arg Lys Leu
 65                  70                  75                  80
His Thr Pro Ala Asn Tyr Leu Ile Ala Ser Leu Ala Val Thr Asp Leu
                 85                  90                  95
Leu Val Ser Ile Leu Val Met Pro Ile Ser Thr Met Tyr Thr Val Thr
                100                 105                 110
Gly Arg Trp Thr Leu Gly Gln Val Val Cys Asp Phe Trp Leu Ser Ser
                115                 120                 125
Asp Ile Thr Cys Cys Thr Ala Ser Ile Leu His Leu Cys Val Ile Ala
            130                 135                 140
Leu Asp Arg Tyr Trp Ala Ile Thr Asp Ala Val Glu Tyr Ser Ala Lys
145                 150                 155                 160
Arg Thr Pro Lys Arg Ala Ala Val Met Ile Ala Leu Val Trp Val Phe
                165                 170                 175
Ser Ile Ser Ile Ser Leu Pro Pro Phe Phe Trp Arg Gln Ala Lys Ala
                180                 185                 190
Glu Glu Glu Val Ser Glu Cys Val Val Asn Thr Asp His Ile Leu Tyr
                195                 200                 205
Thr Val Tyr Ser Thr Val Gly Ala Phe Tyr Phe Pro Asn Leu Leu Leu
                210                 215                 220
Ile Ala Leu Tyr Gly Arg Ile Tyr Val Glu Ala Arg Ser Arg Ile Leu
225                 230                 235                 240
Lys Gln Thr Pro Asn Arg Thr Gly Lys Arg Leu Thr Arg Ala Gln Leu
                245                 250                 255
Ile Thr Asp Ser Pro Gly Ser Thr Ser Ser Val Thr Ser Ile Asn Ser
                260                 265                 270
Arg Val Pro Asp Val Pro Ser Glu Ser Gly Ser Pro Val Tyr Val Asn
                275                 280                 285
Gln Val Lys Val Arg Val Ser Asp Ala Leu Leu Glu Lys Lys Lys Leu
                290                 295                 300
Met Ala Ala Arg Glu Arg Lys Ala Thr Lys Thr Leu Gly Ile Ile Leu
305                 310                 315                 320
Gly Ala Phe Ile Val Cys Trp Leu Pro Phe Phe Ile Ile Ser Leu Val
                325                 330                 335
Met Pro Ile Cys Lys Asp Ala Cys Trp Phe His Leu Ala Ile Phe Asp
                340                 345                 350
Phe Phe Thr Trp Leu Gly Tyr Leu Asn Ser Leu Ile Asn Pro Ile Ile
                355                 360                 365
Tyr Thr Met Ser Asn Glu Asp Phe Lys Gln Ala Phe His Lys Leu Ile
                370                 375                 380
Arg Phe Lys Cys Thr Ser
385                 390

<210> SEQ ID NO 57
<211> LENGTH: 1506
<212> TYPE: DNA
<213> ORGANISM: Homo sapiens

<400> SEQUENCE: 57
agaccttaac taccagctgg tagttgtctc agcattcttc aaatagtccg gtcttgttta      60
```

-continued

```
atattattat tattattgtt atttaatttt attttattgc aactgtactt agagaatagt      120
ctggttcttg agacctttc actgtggtct gttctggtgt acggctccca ccagtgtgaa       180
gcagaaggat gactttgctc tgttgtcagg acaaccttga aggaaggagc caaatgtgtg      240
gaggtctgtg ggaagagaga gccacctagc atgtccccac tgaaccagtc agcagaaggc     300
cttccccagg aggcctccaa cagatccctg aatgccacag aaacctcaga ggcttgggat     360
cccaggaccc tccaggcgct caagatctcc cttgccgtgg tcctttccgt catcacactg    420
gccacagtcc tctccaatgc ctttgtactc accaccatct tactcaccag gaagctccac    480 accctgcca actacctgat tggctccctg gccaccaccg acctcttggt ttccatcttg      540
gtaatgccca tcagcatcgc ctataccatc acccacacct ggaactttgg ccaaatcttg     600
tgtgacatct ggctgtcctc tgacatcacg tgctgcacag cctccatcct gcatctctgt    660
gtcattgctc tggacaggta ctgggcaatc acagatgccc tggaatacag taaacgcagg     720
acggctggcc acgcggccac catgatcgcc attgtctggg ccatctccat ctgcatctcc    780 atccccgc tcttctggcg gcaggccaag gcccaggagg agatgtcgga ctgtctggtg       840
aacacctctc agatctccta caccatctac tccacctgtg gggccttcta cattccctcg    900
gtgttgctca tcatcctata tggccggatc taccgggctg cccggaaccg catcctgaat    960
ccaccctcac tctatgggaa gcgcttcacc acggcccacc tcatcacagg ctctgccggg   1020
tcctcgctct gctcgctcaa ctccagcctc catgaggggc actcgcactc ggctggctcc   1080
cctctctttt tcaaccacgt gaaaatcaag cttgctgaca gtgccctgga acgcaagagg   1140
atttctgctg ctcgagaaag gaaagccact aaaatcctgg gcatcattct gggggccttt   1200
atcatctgct ggctgcccct tcttcgtggtg tctctggtcc tccccatctg ccgggactcc   1260
tgctggatcc acccggcgct ctttgacttc ttcacctggc taggctattt aaactccctc   1320
atcaatccaa taatctacac tgtgtttaat gaagagtttc ggcaagcttt tcagaaaatt   1380 gtcccttttcc ggaaggcctc ctagtcttat tcggtgatga ctcttgttat cttttgtgtc   1440
ctgtaacctc atcgggattg tcttttttttt tttaattat tttctgagac ttggattaat   1500
tcatgg                                                                 1506
```

<210> SEQ ID NO 58
<211> LENGTH: 1506
<212> TYPE: DNA
<213> ORGANISM: Homo sapiens

<400> SEQUENCE: 58

```
agaccttaac taccagctgg tagttgtctc agcattcttc aaatagtccg gtcttgttta       60
atattattat tattattgtt atttaatttt attttattgc aactgtactt agagaatagt      120
ctggttcttg agacctttc actgtggtct gttctggtgt acggctccca ccagtgtgaa       180
gcagaaggat gactttgctc tgttgtcagg acaaccttga aggaaggagc caaatgtgtg      240
gaggtctgtg ggaagagaga gccacctagc atgtccccac tgaaccagtc agcagaaggc     300
cttccccagg aggcctccaa cagatccctg aatgccacag aaacctcaga ggcttgggat     360
cccaggaccc tccaggcgct caagatctcc cttgccgtgg tcctttccgt catcacactg    420
gccacactcc tctccaatgc ctttgtactc accaccatct tactcaccag gaagctccac    480 accctgcca actacctgat tggctccctg gccaccaccg acctcttggt ttccatcttg      540
gtaatgccca tcagcatcgc ctataccatc acccacacct ggaactttgg ccaaatcttg     600
tgtgacatct ggctgtcctc tgacatcacg tgctgcacag cctccatcct gcatctctgt    660
```

```
gtcattgctc tggacaggta ctgggcaatc acagatgccc tggaatacag taaacgcagg    720
acggctggcc acgcggccac catgatcgcc attgtctggg ccatctccat ctgcatctcc    780
atccccccgc tcttctggcg gcaggccaag gcccaggagg agatgtcgga ctgtctggtg    840
aacacctctc agatctccta caccatctac tccacctgtg gggccttcta cattccctcg    900
gtgttgctca tcatcctata tggccggatc taccgggctg cccggaaccg catcctgaat    960
ccaccctcac tctatgggaa gcgcttcacc acggcccacc tcatcacagg ctctgccggg   1020
tcctcgctct gctcgctcaa ctccagcctc catgaggggc actcgcactc ggctggctcc   1080
cctctctttt tcaaccacgt gaaaatcaag cttgctgaca gtgccctgga acgcaagagg   1140
atttctgctg ctcgagaaag gaaagccact aaaatcctgg gcatcattct ggggccttt   1200 atcatctgct ggctgcccctt cttcgtggtg tctctggtcc tccccatctg ccgggactcc   1260
tgctggatcc acccgcgct cttgacttc ttcacctggc taggctattt aaactccctc   1320
atcaatccaa taatctacac tgtgtttaat gaagagttc ggcaagcttt tcagaaaatt   1380 gtcccttttcc ggaaggcctc ctagtcttat tcggtgatga ctcttgttat cttttgtgtc   1440
ctgtaacctc atcgggattg tctttttttt ttttaattat tttctgagac ttggattaat   1500
tcatgg                                                               1506

<210> SEQ ID NO 59
<211> LENGTH: 1506
<212> TYPE: DNA
<213> ORGANISM: Homo sapiens

<400> SEQUENCE: 59
agaccttaac taccagctgg tagttgtctc agcattcttc aaatagtccg gtcttgttta     60
atattattat tattattgtt atttaatttt attttattgc aactgtactt agagaatagt    120
ctggttcttg agacctttc actgtggtct gttctggtgt acggctccca ccagtgtgaa    180
gcagaaggat gactttgctc tgttgtcagg acaaccttga aggaaggagc caaatgtgtg    240
gaggtctgtg ggaagagaga gccacctagc atgtccccac tgaaccagtc agcagaaggc    300
cttccccagg aggcctccaa cagatccctg aatgccacag aaacctcaga ggcttgggat    360
cccaggaccc tccaggcgct caagatctcc cttgccgtgg tcctttccgt catcacactg    420
gccacagtcc tctccaatgc ctttgtactc accaccatct tactcaccag gaagctccac    480 accccctgcca actacctgat tggctccctg gccaccaccg acctcttggt tccatcttg    540 gtaatgccca tcagcatcgc ctataccatc acccacacct ggaactttgg ccaaatcttg    600
tgtgacatct ggctgtcctc tgacatcacg tgctgcacag cctccatcct gcatctctgt    660
gtcattgctc tggacaggta ctgggcaatc acagatgccc tggaatacag taaacgcagg    720
acggctggcc acgcggccac catgatcgcc attgtctggg ccatctccat ctgcatctcc    780
atccccccgc tcttctggcg gcaggccaag gcccaggagg agatgtcgga ctgtctggtg    840
aacacctctc agatctccta caccatctac tccacctgtg gggccttcta cattccctcg    900
gtgttgctca tcatcctata tggccggatc taccgggctg cccggaaccg catcctgaat    960
ccaccctcac tctatgggaa gcgcttcacc acggcccacc tcatcacagg ctctgccggg   1020
tcctcgctct gctcgctcaa ctccagcctc catgaggggc actcgcactc ggctggctcc   1080
cctctctttt tcaaccacgt gaaaatcaag cttgctgaca gtgccctgga acgcaagagg   1140
atttctgctg ctcgagaaag gaaagccact aaaatcctgg gcatcattct ggggccttt   1200
```

```
atcatctgct ggctgcccctt cttcgtggtg tctctggtcc tccccatctg ccgggactcc    1260
tgctggatcc acccggcgct ctttgacttc ttcacctggc taggctattt aaactccctc    1320
atcaatccaa taatctacac tgtgtttaat gaagagtttc ggcaaggttt tcagaaaatt    1380
gtccctttcc ggaaggcctc ctagtcttat tcggtgatga ctcttgttat cttttgtgtc    1440
ctgtaacctc atcgggattg tcttttttt ttttaattat tttctgagac ttggattaat    1500
tcatgg                                                                1506

<210> SEQ ID NO 60
<211> LENGTH: 377
<212> TYPE: PRT
<213> ORGANISM: Homo sapiens

<400> SEQUENCE: 60
```

Met Ser Pro Leu Asn Gln Ser Ala Glu Gly Leu Pro Gln Glu Ala Ser
1               5                   10                  15

Asn Arg Ser Leu Asn Ala Thr Glu Thr Ser Glu Ala Trp Asp Pro Arg
            20                  25                  30

Thr Leu Gln Ala Leu Lys Ile Ser Leu Ala Val Val Leu Ser Val Ile
        35                  40                  45

Thr Leu Ala Thr Val Leu Ser Asn Ala Phe Val Leu Thr Thr Ile Leu
    50                  55                  60

Leu Thr Arg Lys Leu His Thr Pro Ala Asn Tyr Leu Ile Gly Ser Leu
65                  70                  75                  80

Ala Thr Thr Asp Leu Leu Val Ser Ile Leu Val Met Pro Ile Ser Ile
                85                  90                  95

Ala Tyr Thr Ile Thr His Thr Trp Asn Phe Gly Gln Ile Leu Cys Asp
            100                 105                 110

Ile Trp Leu Ser Ser Asp Ile Thr Cys Cys Thr Ala Ser Ile Leu His
        115                 120                 125

Leu Cys Val Ile Ala Leu Asp Arg Tyr Trp Ala Ile Thr Asp Ala Leu
    130                 135                 140

Glu Tyr Ser Lys Arg Arg Thr Ala Gly His Ala Ala Thr Met Ile Ala
145                 150                 155                 160

Ile Val Trp Ala Ile Ser Ile Cys Ile Ser Ile Pro Pro Leu Phe Trp
                165                 170                 175

Arg Gln Ala Lys Ala Gln Glu Glu Met Ser Asp Cys Leu Val Asn Thr
            180                 185                 190

Ser Gln Ile Ser Tyr Thr Ile Tyr Ser Thr Cys Gly Ala Phe Tyr Ile
        195                 200                 205

Pro Ser Val Leu Leu Ile Ile Leu Tyr Gly Arg Ile Tyr Arg Ala Ala
    210                 215                 220

Arg Asn Arg Ile Leu Asn Pro Pro Ser Leu Tyr Gly Lys Arg Phe Thr
225                 230                 235                 240

Thr Ala His Leu Ile Thr Gly Ser Ala Gly Ser Ser Leu Cys Ser Leu
                245                 250                 255

Asn Ser Ser Leu His Glu Gly His Ser His Ser Ala Gly Ser Pro Leu
            260                 265                 270

Phe Phe Asn His Val Lys Ile Lys Leu Ala Asp Ser Ala Leu Glu Arg
        275                 280                 285

Lys Arg Ile Ser Ala Ala Arg Glu Arg Lys Ala Thr Lys Ile Leu Gly
    290                 295                 300

Ile Ile Leu Gly Ala Phe Ile Ile Cys Trp Leu Pro Phe Phe Val Val
305                 310                 315                 320

```
Ser Leu Val Leu Pro Ile Cys Arg Asp Ser Cys Trp Ile His Pro Ala
            325                 330                 335

Leu Phe Asp Phe Phe Thr Trp Leu Gly Tyr Leu Asn Ser Leu Ile Asn
            340                 345                 350

Pro Ile Ile Tyr Thr Val Phe Asn Glu Glu Phe Arg Gln Ala Phe Gln
            355                 360                 365

Lys Ile Val Pro Phe Arg Lys Ala Ser
            370                 375

<210> SEQ ID NO 61
<211> LENGTH: 377
<212> TYPE: PRT
<213> ORGANISM: Homo sapiens

<400> SEQUENCE: 61

Met Ser Pro Leu Asn Gln Ser Ala Glu Gly Leu Pro Gln Glu Ala Ser
  1               5                  10                  15

Asn Arg Ser Leu Asn Ala Thr Glu Thr Ser Glu Ala Trp Asp Pro Arg
            20                  25                  30

Thr Leu Gln Ala Leu Lys Ile Ser Leu Ala Val Val Leu Ser Val Ile
        35                  40                  45

Thr Leu Ala Thr Leu Leu Ser Asn Ala Phe Val Leu Thr Thr Ile Leu
    50                  55                  60

Leu Thr Arg Lys Leu His Thr Pro Ala Asn Tyr Leu Ile Gly Ser Leu
65                  70                  75                  80

Ala Thr Thr Asp Leu Leu Val Ser Ile Leu Val Met Pro Ile Ser Ile
                85                  90                  95

Ala Tyr Thr Ile Thr His Thr Trp Asn Phe Gly Gln Ile Leu Cys Asp
            100                 105                 110

Ile Trp Leu Ser Ser Asp Ile Thr Cys Cys Thr Ala Ser Ile Leu His
            115                 120                 125

Leu Cys Val Ile Ala Leu Asp Arg Tyr Trp Ala Ile Thr Asp Ala Leu
        130                 135                 140

Glu Tyr Ser Lys Arg Arg Thr Ala Gly His Ala Ala Thr Met Ile Ala
145                 150                 155                 160

Ile Val Trp Ala Ile Ser Ile Cys Ile Ser Ile Pro Pro Leu Phe Trp
                165                 170                 175

Arg Gln Ala Lys Ala Gln Glu Glu Met Ser Asp Cys Leu Val Asn Thr
            180                 185                 190

Ser Gln Ile Ser Tyr Thr Ile Tyr Ser Thr Cys Gly Ala Phe Tyr Ile
        195                 200                 205

Pro Ser Val Leu Leu Ile Ile Leu Tyr Gly Arg Ile Tyr Arg Ala Ala
    210                 215                 220

Arg Asn Arg Ile Leu Asn Pro Pro Ser Leu Tyr Gly Lys Arg Phe Thr
225                 230                 235                 240

Thr Ala His Leu Ile Thr Gly Ser Ala Gly Ser Ser Leu Cys Ser Leu
                245                 250                 255

Asn Ser Ser Leu His Glu Gly His Ser His Ser Ala Gly Ser Pro Leu
            260                 265                 270

Phe Phe Asn His Val Lys Ile Lys Leu Ala Asp Ser Ala Leu Glu Arg
        275                 280                 285

Lys Arg Ile Ser Ala Ala Arg Glu Arg Lys Ala Thr Lys Ile Leu Gly
    290                 295                 300

Ile Ile Leu Gly Ala Phe Ile Ile Cys Trp Leu Pro Phe Phe Val Val
```

-continued

```
                305                 310                 315                 320
Ser Leu Val Leu Pro Ile Cys Arg Asp Ser Cys Trp Ile His Pro Ala
                    325                 330                 335

Leu Phe Asp Phe Phe Thr Trp Leu Gly Tyr Leu Asn Ser Leu Ile Asn
                    340                 345                 350

Pro Ile Ile Tyr Thr Val Phe Asn Glu Glu Phe Arg Gln Ala Phe Gln
                    355                 360                 365

Lys Ile Val Pro Phe Arg Lys Ala Ser
        370                 375

<210> SEQ ID NO 62
<211> LENGTH: 377
<212> TYPE: PRT
<213> ORGANISM: Homo sapiens

<400> SEQUENCE: 62

Met Ser Pro Leu Asn Gln Ser Ala Glu Gly Leu Pro Gln Glu Ala Ser
  1               5                  10                  15

Asn Arg Ser Leu Asn Ala Thr Glu Thr Ser Glu Ala Trp Asp Pro Arg
                20                  25                  30

Thr Leu Gln Ala Leu Lys Ile Ser Leu Ala Val Val Leu Ser Val Ile
            35                  40                  45

Thr Leu Ala Thr Val Leu Ser Asn Ala Phe Val Leu Thr Thr Ile Leu
        50                  55                  60

Leu Thr Arg Lys Leu His Thr Pro Ala Asn Tyr Leu Ile Gly Ser Leu
 65                  70                  75                  80

Ala Thr Thr Asp Leu Leu Val Ser Ile Leu Val Met Pro Ile Ser Ile
                85                  90                  95

Ala Tyr Thr Ile Thr His Thr Trp Asn Phe Gly Gln Ile Leu Cys Asp
                100                 105                 110

Ile Trp Leu Ser Ser Asp Ile Thr Cys Cys Thr Ala Ser Ile Leu His
            115                 120                 125

Leu Cys Val Ile Ala Leu Asp Arg Tyr Trp Ala Ile Thr Asp Ala Leu
        130                 135                 140

Glu Tyr Ser Lys Arg Arg Thr Ala Gly His Ala Ala Thr Met Ile Ala
145                 150                 155                 160

Ile Val Trp Ala Ile Ser Ile Cys Ile Ser Ile Pro Pro Leu Phe Trp
                165                 170                 175

Arg Gln Ala Lys Ala Gln Glu Glu Met Ser Asp Cys Leu Val Asn Thr
                180                 185                 190

Ser Gln Ile Ser Tyr Thr Ile Tyr Ser Thr Cys Gly Ala Phe Tyr Ile
            195                 200                 205

Pro Ser Val Leu Leu Ile Ile Leu Tyr Gly Arg Ile Tyr Arg Ala Ala
        210                 215                 220

Arg Asn Arg Ile Leu Asn Pro Pro Ser Leu Tyr Gly Lys Arg Phe Thr
225                 230                 235                 240

Thr Ala His Leu Ile Thr Gly Ser Ala Gly Ser Ser Leu Cys Ser Leu
                245                 250                 255

Asn Ser Ser Leu His Glu Gly His Ser His Ser Ala Gly Ser Pro Leu
                260                 265                 270

Phe Phe Asn His Val Lys Ile Lys Leu Ala Asp Ser Ala Leu Glu Arg
            275                 280                 285

Lys Arg Ile Ser Ala Ala Arg Glu Arg Lys Ala Thr Lys Ile Leu Gly
        290                 295                 300
```

```
Ile Ile Leu Gly Ala Phe Ile Ile Cys Trp Leu Pro Phe Phe Val Val
305                 310                 315                 320

Ser Leu Val Leu Pro Ile Cys Arg Asp Ser Cys Trp Ile His Pro Ala
                325                 330                 335

Leu Phe Asp Phe Phe Thr Trp Leu Gly Tyr Leu Asn Ser Leu Ile Asn
            340                 345                 350

Pro Ile Ile Tyr Thr Val Phe Asn Glu Glu Phe Arg Gln Gly Phe Gln
        355                 360                 365

Lys Ile Val Pro Phe Arg Lys Ala Ser
370                 375
```

<210> SEQ ID NO 63
<211> LENGTH: 1900
<212> TYPE: DNA
<213> ORGANISM: Homo sapiens

<400> SEQUENCE: 63

| | | |
|---|---|---|
| atcgaatgtt gagagaagca gtgctctgat ccagctcagg agaaaaagga gcgggttccg | 60 |
| agtgagactt ctggagccag ctggacgtgc cggtttgccc agtgcggcgc ggctgcacgc | 120 |
| accgtccaca agagtctcag tcgcccaggc tggagtgcag cagcacagtc tcacctcatt | 180 |
| gcaacctccg cctcccgggt tcgcgggttc tccgcctcag cttcctagta gctgggattg | 240 |
| caggcactca ccaccatgcc cggctaattt tttgaatttt tagtggagac gggatttcac | 300 |
| catgttggcc atgctggtct tgaaccccg acctcggatg attcgcccgc ctcggcctcc | 360 |
| caaagtgctg gaattacagg cgaaccttca ctcagaagaa atgctgtggc ccttcccttt | 420 |
| accaacagaa aatggaacac aagagaccac atagctgaac aaattatagc ctccttacaa | 480 |
| gtgagaaacc ttcgaggcta catagttttc agccaaagga aaataaccaa cagcttctcc | 540 |
| acagtgtaga ctgaaacaag gaaacatga acatcacaaa ctgtaccaca gaggccagca | 600 |
| tggctataag acccaagacc atcactgaga agatgctcat tgcatgact ctggtggtca | 660 |
| tcaccaccct caccacgttg ctgaacttgg ctgtgatcat ggctattggc accaccaaga | 720 |
| agctccacca gcctgccaac tacctaatct gttctctggc cgtgacggac ctcctggtgg | 780 |
| cagtgctcgt catgccctg agcatcatct acattgtcat ggatcgctgg aagcttgggt | 840 |
| acttcctctg tgaggtgtgg ctgagtgtgg acatgacctg ctgcacctgc tccatcctcc | 900 |
| acctctgtgt cattgccctg acaggtact gggccatcac caatgctatt gaatacgcca | 960 |
| ggaagaggac ggccaagagg gccgcgctga tgatccttac cgtctggacc atctccattt | 1020 |
| tcatctccat gccccctctg ttctggagaa gccaccgccg cctaagccct ccccctagtc | 1080 |
| agtgcaccat ccagcacgac catgttatct acaccattta ctccacgctg ggtgcgtttt | 1140 |
| atatcccctt gactttgata ctgattctct attaccggat ttaccacgcg gccaagagcc | 1200 |
| tttaccagaa aaggggatca agtcggcact taagcaacag aagcacagat agccagaatt | 1260 |
| cttttgcaag ttgtaaactt acacagactt tctgtgtgtc tgacttctcc acctcagacc | 1320 |
| ctaccacaga gtttgaaaag ttccatgcct ccatcaggat cccccccttc gacaatgatc | 1380 |
| tagatcaccc aggagaacgt cagcagatct ctagcaccag ggaacggaag gcagcacgca | 1440 |
| tcctgggct gattctgggt gcattcattt tatcctggct gccatttttc atcaaagagt | 1500 |
| tgattgtggg tctgagcatc tacaccgtgt cctcggaagt ggccgacttt ctgacgtggc | 1560 |
| tcggttatgt gaattctctg atcaaccctc tgctctatac gagttttaat gaagacttta | 1620 |
| agctggcttt taaaaagctc attagatgcc gagagcatac ttagactgta aaagctaaa | 1680 |

| | |
|---|---:|
| aggcacgact ttttccagag cctcatgagt ggatggggt aagggtgca acttattaat | 1740 |
| tcttgaacat acttggttca ggagagtttg taagtatgtg tggtcttgtt tccttgtttg | 1800 |
| tttgtttgtt ttgttctgtt ttgtttgagg attgttattt ggcgtgctgt tttctacctc | 1860 |
| tggtcttatc tgtgatacat aatttcaaat aaacattatc | 1900 |

<210> SEQ ID NO 64
<211> LENGTH: 1900
<212> TYPE: DNA
<213> ORGANISM: Homo sapiens

<400> SEQUENCE: 64

| | |
|---|---:|
| atcgaatgtt gagagaagca gtgctctgat ccagctcagg agaaaaagga gcgggttccg | 60 |
| agtgagactt ctggagccag ctggacgtgc cggtttgccc agtgcggcgc ggctgcacgc | 120 |
| accgtccaca agagtctcag tcgcccaggc tggagtgcag cagcacagtc tcacctcatt | 180 |
| gcaacctccg cctcccgggt tcgcgggttc tccgcctcag cttcctagta gctgggattg | 240 |
| caggcactca ccaccatgcc cggctaattt tttgaatttt tagtggagac gggatttcac | 300 |
| catgttggcc atgctggtct tgaacccccg acctcggatg attcgcccgc tcggcctcc | 360 |
| caaagtgctg gaattacagg cgaaccttca ctcagaagaa atgctgtggc ccttcccttt | 420 |
| accaacagaa aatggaacac aagagaccac atagctgaac aaattatagc ctccttacaa | 480 |
| gtgagaaacc ttcgaggcta catagttttc agccaaagga aaataaccaa cagcttctcc | 540 |
| acagtgtaga ctgaaacaag ggaaacatga acatcacaaa ctgtaccaca gaggccagca | 600 |
| tggctataag acccaagacc atcactgaga agatgctcat ttgcatgact ctggtggtca | 660 |
| tcaccaccct caccacgttg ctgaacttgg ctgtgaccat ggctattggc accaccaaga | 720 |
| agctccacca gcctgccaac tacctaatct gttctctggc cgtgacggac ctcctggtgg | 780 |
| cagtgctcgt catgccctg agcatcatct acattgtcat ggatcgctgg aagcttgggt | 840 |
| acttcctctg tgaggtgtgg ctgagtgtgg acatgacctg ctgcacctgc tccatcctcc | 900 |
| acctctgtgt cattgccctg acaggtact gggccatcac caatgctatt gaatacgcca | 960 |
| ggaagaggac ggccaagagg gccgcgctga tgatccttac cgtctggacc atctccattt | 1020 |
| tcatctccat gccccctctg ttctggagaa gccaccgccg cctaagccct ccccctagtc | 1080 |
| agtgcaccat ccagcacgac catgttatct acaccattta ctccacgctg ggtgcgtttt | 1140 |
| atatcccctt gactttgata ctgattctct attaccggat ttaccacgcg gccaagagcc | 1200 |
| tttaccagaa aaggggatca agtcggcact taagcaacag aagcacagat agccagaatt | 1260 |
| cttttgcaag ttgtaaactt acacagactt tctgtgtgtc tgacttctcc acctcagacc | 1320 |
| ctaccacaga gtttgaaaag ttccatgcct ccatcaggat cccccccttc gacaatgatc | 1380 |
| tagatcaccc aggagaacgt cagcagatct ctagcaccag ggaacggaag gcagcacgca | 1440 |
| tcctggggct gattctgggt gcattcattt tatcctggct gccattttc atcaaagagt | 1500 |
| tgattgtggg tctgagcatc tacaccgtgt cctcggaagt ggccgacttt ctgacgtggc | 1560 |
| tcggttatgt gaattctctg atcaaccctc tgctctatac gagttttaat gaagacttta | 1620 |
| agctggcttt taaaaagctc attagatgcc gagagcatac ttagactgta aaaagctaaa | 1680 |
| aggcacgact ttttccagag cctcatgagt ggatggggt aagggtgca acttattaat | 1740 |
| tcttgaacat acttggttca ggagagtttg taagtatgtg tggtcttgtt tccttgtttg | 1800 |
| tttgtttgtt ttgttctgtt ttgtttgagg attgttattt ggcgtgctgt tttctacctc | 1860 |
| tggtcttatc tgtgatacat aatttcaaat aaacattatc | 1900 |

<210> SEQ ID NO 65
<211> LENGTH: 1900
<212> TYPE: DNA
<213> ORGANISM: Homo sapiens

<400> SEQUENCE: 65

```
atcgaatgtt gagagaagca gtgctctgat ccagctcagg agaaaaagga gcgggttccg      60
agtgagactt ctggagccag ctggacgtgc cggtttgccc agtgcggcgc ggctgcacgc     120
accgtccaca agagtctcag tcgcccaggc tggagtgcag cagcacagtc tcacctcatt     180
gcaacctccg cctcccgggt tcgcgggttc tccgcctcag cttcctagta gctgggattg     240
caggcactca ccaccatgcc cggctaattt tttgaatttt tagtggagac gggatttcac     300
catgttggcc atgctggtct tgaaccccg acctcggatg attcgcccgc ctcggcctcc      360
caaagtgctg gaattacagg cgaaccttca ctcagaagaa atgctgtggc cttcccttt      420
accaacagaa aatggaacac aagagaccac atagctgaac aaattatagc ctccttacaa     480
gtgagaaacc ttcgaggcta catagttttc agccaaagga aataaccaa cagcttctcc      540
acagtgtaga ctgaaacaag ggaaacatga acatcacaaa ctgtaccaca gaggccagca     600
tggctataag acccaagacc atcactgaga agatgctcat ttgcatgact ctggtggtca     660
tcaccaccct caccacgttg ctgaacttgg ctgtgatcat ggctattggc accaccaaga     720
agctccacca gcctgccaac tacctaatct gttctctggc cgtgacggac ctcctggtgg     780
cagtgctcgt catgccctg agcatcatct acattgtcat ggatcgctgg aagcttgggt      840
acttcctctg tgaggtgtgg ctgagtgtgg acatgaccctg ctgcacctgc tccatcctcc     900
acctctgtgt cattgccctg acaggtact gggccatcac caatgctatt gaatacgcca      960
ggaagaggac ggccaagagg gccgcgctga tgatccttac cgtctggacc atctccattt    1020
tcatctccat gccccctctg ttctggagaa gccaccgccg cctaagccct ccccctagtc    1080
agtgcaccat ccagcacgac catgttatct acaccattta ctccacgctg ggtgcgtttt    1140
atatcccctt gactttgata ctgattctct attaccggat ttaccacgcg gccaagagcc    1200
tttaccagaa aaggggatca agtcggcact taagcaacag aagcacagat agccagaatt    1260
ctttttgcaag ttgtaaactt acacagactt tctgtgtgtc tgacttctcc acctcagacc    1320
ctaccacaga gttttgaaaag ttccatgcct tcatcaggat cccccccttc gacaatgatc    1380
tagatcaccc aggagaacgt cagcagatct ctagcaccag ggaacggaag gcagcacgca    1440
tcctggggct gattctgggt gcattcattt tatcctggct gccattttc atcaaagagt    1500
tgattgtggg tctgagcatc tacaccgtgt cctcggaagt ggccgacttt ctgacgtggc    1560
tcggttatgt gaattctctg atcaaccctc tgctctatac gagtttttaat gaagactta     1620
agctggcttt taaaaagctc attagatgcc gagagcatac ttagactgta aaagctaaa     1680
aggcacgact ttttccagag cctcatgagt ggatgggggt aagggtgca acttattaat     1740
tcttgaacat acttggttca ggagagtttg taagtatgtg tggtcttgtt tccttgtttg    1800
tttgtttgtt ttgttctgtt ttgtttgagg attgttattt ggcgtgctgt tttctacctc    1860
tggtcttatc tgtgatacat aatttcaaat aaacattatc                          1900
```

<210> SEQ ID NO 66
<211> LENGTH: 365
<212> TYPE: PRT
<213> ORGANISM: Homo sapiens

<400> SEQUENCE: 66

```
Met Asn Ile Thr Asn Cys Thr Thr Glu Ala Ser Met Ala Ile Arg Pro
1               5                   10                  15
Lys Thr Ile Thr Glu Lys Met Leu Ile Cys Met Thr Leu Val Val Ile
            20                  25                  30
Thr Thr Leu Thr Thr Leu Leu Asn Leu Ala Val Ile Met Ala Ile Gly
        35                  40                  45
Thr Thr Lys Lys Leu His Gln Pro Ala Asn Tyr Leu Ile Cys Ser Leu
    50                  55                  60
Ala Val Thr Asp Leu Leu Val Ala Val Leu Val Met Pro Leu Ser Ile
65                  70                  75                  80
Ile Tyr Ile Val Met Asp Arg Trp Lys Leu Gly Tyr Phe Leu Cys Glu
                85                  90                  95
Val Trp Leu Ser Val Asp Met Thr Cys Cys Thr Cys Ser Ile Leu His
            100                 105                 110
Leu Cys Val Ile Ala Leu Asp Arg Tyr Trp Ala Ile Thr Asn Ala Ile
        115                 120                 125
Glu Tyr Ala Arg Lys Arg Thr Ala Lys Arg Ala Ala Leu Met Ile Leu
    130                 135                 140
Thr Val Trp Thr Ile Ser Ile Phe Ile Ser Met Pro Pro Leu Phe Trp
145                 150                 155                 160
Arg Ser His Arg Arg Leu Ser Pro Pro Ser Gln Cys Thr Ile Gln
                165                 170                 175
His Asp His Val Ile Tyr Thr Ile Tyr Ser Thr Leu Gly Ala Phe Tyr
            180                 185                 190
Ile Pro Leu Thr Leu Ile Leu Ile Leu Tyr Tyr Arg Ile Tyr His Ala
        195                 200                 205
Ala Lys Ser Leu Tyr Gln Lys Arg Gly Ser Ser Arg His Leu Ser Asn
    210                 215                 220
Arg Ser Thr Asp Ser Gln Asn Ser Phe Ala Ser Cys Lys Leu Thr Gln
225                 230                 235                 240
Thr Phe Cys Val Ser Asp Phe Ser Thr Ser Asp Pro Thr Thr Glu Phe
                245                 250                 255
Glu Lys Phe His Ala Ser Ile Arg Ile Pro Pro Phe Asp Asn Asp Leu
            260                 265                 270
Asp His Pro Gly Glu Arg Gln Gln Ile Ser Ser Thr Arg Glu Arg Lys
        275                 280                 285
Ala Ala Arg Ile Leu Gly Leu Ile Leu Gly Ala Phe Ile Leu Ser Trp
    290                 295                 300
Leu Pro Phe Phe Ile Lys Glu Leu Ile Val Gly Leu Ser Ile Tyr Thr
305                 310                 315                 320
Val Ser Ser Glu Val Ala Asp Phe Leu Thr Trp Leu Gly Tyr Val Asn
                325                 330                 335
Ser Leu Ile Asn Pro Leu Leu Tyr Thr Ser Phe Asn Glu Asp Phe Lys
            340                 345                 350
Leu Ala Phe Lys Lys Leu Ile Arg Cys Arg Glu His Thr
        355                 360                 365
```

<210> SEQ ID NO 67
<211> LENGTH: 365
<212> TYPE: PRT
<213> ORGANISM: Homo sapiens

<400> SEQUENCE: 67

```
Met Asn Ile Thr Asn Cys Thr Thr Glu Ala Ser Met Ala Ile Arg Pro
 1               5                  10                  15

Lys Thr Ile Thr Glu Lys Met Leu Ile Cys Met Thr Leu Val Val Ile
             20                  25                  30

Thr Thr Leu Thr Thr Leu Leu Asn Leu Ala Val Thr Met Ala Ile Gly
             35                  40                  45

Thr Thr Lys Lys Leu His Gln Pro Ala Asn Tyr Leu Ile Cys Ser Leu
 50                  55                  60

Ala Val Thr Asp Leu Leu Val Ala Val Leu Val Met Pro Leu Ser Ile
 65              70                  75                  80

Ile Tyr Ile Val Met Asp Arg Trp Lys Leu Gly Tyr Phe Leu Cys Glu
                 85                  90                  95

Val Trp Leu Ser Val Asp Met Thr Cys Cys Thr Cys Ser Ile Leu His
             100                 105                 110

Leu Cys Val Ile Ala Leu Asp Arg Tyr Trp Ala Ile Thr Asn Ala Ile
             115                 120                 125

Glu Tyr Ala Arg Lys Arg Thr Ala Lys Arg Ala Ala Leu Met Ile Leu
             130                 135                 140

Thr Val Trp Thr Ile Ser Ile Phe Ile Ser Met Pro Pro Leu Phe Trp
145                 150                 155                 160

Arg Ser His Arg Arg Leu Ser Pro Pro Ser Gln Cys Thr Ile Gln
                 165                 170                 175

His Asp His Val Ile Tyr Thr Ile Tyr Ser Thr Leu Gly Ala Phe Tyr
             180                 185                 190

Ile Pro Leu Thr Leu Ile Leu Ile Leu Tyr Tyr Arg Ile Tyr His Ala
             195                 200                 205

Ala Lys Ser Leu Tyr Gln Lys Arg Gly Ser Ser Arg His Leu Ser Asn
             210                 215                 220

Arg Ser Thr Asp Ser Gln Asn Ser Phe Ala Ser Cys Lys Leu Thr Gln
225                 230                 235                 240

Thr Phe Cys Val Ser Asp Phe Ser Thr Ser Asp Pro Thr Thr Glu Phe
                 245                 250                 255

Glu Lys Phe His Ala Ser Ile Arg Ile Pro Pro Phe Asp Asn Asp Leu
             260                 265                 270

Asp His Pro Gly Glu Arg Gln Gln Ile Ser Ser Thr Arg Glu Arg Lys
             275                 280                 285

Ala Ala Arg Ile Leu Gly Leu Ile Leu Gly Ala Phe Ile Leu Ser Trp
290                 295                 300

Leu Pro Phe Phe Ile Lys Glu Leu Ile Val Gly Leu Ser Ile Tyr Thr
305                 310                 315                 320

Val Ser Ser Glu Val Ala Asp Phe Leu Thr Trp Leu Gly Tyr Val Asn
                 325                 330                 335

Ser Leu Ile Asn Pro Leu Leu Tyr Thr Ser Phe Asn Glu Asp Phe Lys
             340                 345                 350

Leu Ala Phe Lys Lys Leu Ile Arg Cys Arg Glu His Thr
             355                 360                 365
```

<210> SEQ ID NO 68
<211> LENGTH: 365
<212> TYPE: PRT
<213> ORGANISM: Homo sapiens

<400> SEQUENCE: 68

```
Met Asn Ile Thr Asn Cys Thr Thr Glu Ala Ser Met Ala Ile Arg Pro
 1               5                  10                  15
```

| | | | | | | | | | | | | |
|---|---|---|---|---|---|---|---|---|---|---|---|---|
|Lys|Thr|Ile|Thr|Glu|Lys|Met|Leu|Ile|Cys|Met|Thr|Leu|Val|Val|Ile|
| | |20| | | |25| | | |30| | |
|Thr|Thr|Leu|Thr|Thr|Leu|Leu|Asn|Leu|Ala|Val|Ile|Met|Ala|Ile|Gly|
| |35| | | | |40| | | | |45| | |

Lys Thr Ile Thr Glu Lys Met Leu Ile Cys Met Thr Leu Val Val Ile
            20                  25                  30

Thr Thr Leu Thr Thr Leu Leu Asn Leu Ala Val Ile Met Ala Ile Gly
        35                  40                      45

Thr Thr Lys Lys Leu His Gln Pro Ala Asn Tyr Leu Ile Cys Ser Leu
        50                  55                      60

Ala Val Thr Asp Leu Leu Val Ala Val Leu Val Met Pro Leu Ser Ile
65                  70                      75                  80

Ile Tyr Ile Val Met Asp Arg Trp Lys Leu Gly Tyr Phe Leu Cys Glu
                    85                  90                  95

Val Trp Leu Ser Val Asp Met Thr Cys Cys Thr Cys Ser Ile Leu His
                100                 105                 110

Leu Cys Val Ile Ala Leu Asp Arg Tyr Trp Ala Ile Thr Asn Ala Ile
            115                 120                 125

Glu Tyr Ala Arg Lys Arg Thr Ala Lys Arg Ala Ala Leu Met Ile Leu
        130                 135                 140

Thr Val Trp Thr Ile Ser Ile Phe Ile Ser Met Pro Pro Leu Phe Trp
145                 150                 155                 160

Arg Ser His Arg Arg Leu Ser Pro Pro Ser Gln Cys Thr Ile Gln
                165                 170                 175

His Asp His Val Ile Tyr Thr Ile Tyr Ser Thr Leu Gly Ala Phe Tyr
            180                 185                 190

Ile Pro Leu Thr Leu Ile Leu Ile Leu Tyr Tyr Arg Ile Tyr His Ala
        195                 200                 205

Ala Lys Ser Leu Tyr Gln Lys Arg Gly Ser Ser Arg His Leu Ser Asn
    210                 215                 220

Arg Ser Thr Asp Ser Gln Asn Ser Phe Ala Ser Cys Lys Leu Thr Gln
225                 230                 235                 240

Thr Phe Cys Val Ser Asp Phe Ser Thr Ser Asp Pro Thr Thr Glu Phe
                245                 250                 255

Glu Lys Phe His Ala Phe Ile Arg Ile Pro Pro Phe Asp Asn Asp Leu
            260                 265                 270

Asp His Pro Gly Glu Arg Gln Gln Ile Ser Ser Thr Arg Glu Arg Lys
    275                 280                 285

Ala Ala Arg Ile Leu Gly Leu Ile Leu Gly Ala Phe Ile Leu Ser Trp
        290                 295                 300

Leu Pro Phe Phe Ile Lys Glu Leu Ile Val Gly Leu Ser Ile Tyr Thr
305                 310                 315                 320

Val Ser Ser Glu Val Ala Asp Phe Leu Thr Trp Leu Gly Tyr Val Asn
                325                 330                 335

Ser Leu Ile Asn Pro Leu Leu Tyr Thr Ser Phe Asn Glu Asp Phe Lys
            340                 345                 350

Leu Ala Phe Lys Lys Leu Ile Arg Cys Arg Glu His Thr
        355                 360                 365

<210> SEQ ID NO 69
<211> LENGTH: 1790
<212> TYPE: DNA
<213> ORGANISM: Homo sapiens

<400> SEQUENCE: 69
tactaaccat gctgaccact gttcggaacg ggattgaatc acagaaaaac agcaaatggc      60
tctctcttac agagtgtctg aacttcaaag cacaattcct gagcacattt tgcagagcac     120

```
ctttgttcac gttatctctt ctaactggtc tggattacag acagaatcaa taccagagga      180
aatgaaacag attgttgagg aacagggaaa taaactgcac tgggcagctc ttctgatact      240
catggtgata atacccacaa ttggtggaaa taccccttgtt attctggctg tttcactgga     300
gaagaagctg cagtatgcta ctaattactt tctaatgtcc ttggcggtgg ctgatttgct      360
ggttggattg tttgtgatgc caattgccct cttgacaata atgtttgagg ctatgtggcc      420
cctcccactt gttctatgtc ctgcctggtt atttcttgac gttctctttt caaccgcatc      480
catcatgcat ctctgtgcca tttcagtgga tcgttacata gccatcaaaa agccaatcca      540
ggccaatcaa tataactcac gggctacagc attcatcaag attacagtgg tgtggttaat      600
ttcaataggc attgccattc cagtccctat taagggata gagactgatg tggacaaccc       660
aaacaatatc acttgtgtgc tgacaaagga acgttttggc gatttcatgc tctttggctc      720
actggctgcc ttcttcacac ctcttgcaat tatgattgtc acctactttc tcactatcca      780
tgctttacag aagaaggctt acttagtcaa aaacaagcca cctcaacgcc taacatggtt      840
gactgtgtct acagttttcc aaagggatga acaccttgc tcgtcaccgg aaaaggtggc       900
aatgctggat ggttctcgaa aggacaaggc tctgcccaac tcaggtgatg aaacacttat      960
gcgaagaaca tccacaattg ggaaaaagtc agtgcagacc atttccaacg aacagagagc     1020
ctcaaaggtc ctagggattg tgttttttcct cttttttgctt atgtggtgtc ccttctttat   1080
tacaaatata actttagttt tatgtgattc ctgtaaccaa actactctcc aaatgctcct     1140
ggagatattt gtgtggatag ctatgtttc tcaggagtg aatcctttgg tctacaccct       1200
cttcaataag acatttcggg atgcatttgg ccgatatatc acctgcaatt accgggccac     1260
aaagtcagta aaaactctca gaaaacgctc cagtaagatc tacttccgga atccaatggc    1320
agagaactct aagttttca gaaacatgg aattcgaaat gggattaacc ctgccatgta     1380
ccagagtcca atgaggctcc gaagttcaac cattcagtct tcatcaatca ttctactaga     1440
tacgcttctc ctcactgaaa atgaaggtga caaaactgaa gagcaagtta gttatgtata     1500
gcagaactgg cagttgtcat caaacataat gatgagtaag atgatgaatg agatgtaaat    1560
gtgcccagaa tatattatat aaagaatttt atgtcatata tcaaatcatc tctttaaccct   1620 aagatgtaag tattaagaat atctaatttt cctaatttgg acaagattat tccatgagga     1680
aaataatttt atatagctac aaatgaaaac aatccagcac tctggttaaa ttttaaggta     1740
ttcgaatgaa ataaagtcaa atcaataaat ttcaggcttt aaaaaaaaaa                 1790
```

<210> SEQ ID NO 70
<211> LENGTH: 1790
<212> TYPE: DNA
<213> ORGANISM: Homo sapiens

<400> SEQUENCE: 70

```
tactaaccat gctgaccact gttcggaacg ggattgaatc acagaaaaac agcaaatggc       60
tctctcttac agagtgtctg aacttcaaag cacaattcct gagcacattt tgcagagcac      120
ctttgttcac gttatctctt ctaactggtc tggattacag acagaatcaa taccagagga      180
aatgaaacag attgttgagg aacagggaaa taaactgcac tgggcagctc ttctgatact      240
catggtgata atacccacaa ttggtggaaa taccccttgtt attctggctg tttcactgga    300
gaagaagctg cagtatgcta ctaattactt tctaatgtcc ttggcggtgg ctgatttgct      360
ggttggattg tttgtgatgc caattgccct cttgacaata atgtttgagg ctatgtggcc      420
cctcccactt gttctatgtc ctgcctggtt atttcttgac gttctctttt caaccgcatc      480
```

-continued

```
catcatgcat ctctgtgcca tttcagtgga tcgttacata gccatcaaaa agccaatcca    540
ggccaatcaa tataactcac gggctacagc attcatcaag attacagtgg tgtggttaat    600
ttcaataggc attgccattc cagtccctat taaagggata gagactgatg tggacaaccc    660
aaacaatatc acttgtgtgc tgacaaagga acgttttggc gatttcatgc tctttggctc    720
actggctgcc ttcttcacac tcttgcaat tatgattgtc acctactttc tcactatcca     780
tgctttacag aagaaggctt acttagtcaa aaacaagcca cctcaacgcc taacatggtt    840
gactgtgtct acagttttcc aaagggatga acaccttgc tcgtcaccgg aaaaggtggc     900
aatgctggat ggttctcgaa aggacaaggc tctgcccaac tcaggtgatg aaacacttat    960
gcgaagaaca tccacaattg ggaaaaagtc agtgcagacc atttccaacg aacagagagc   1020
ctcaaaggtc ctagggattg tgttttttcct cttttttgctt atgtggtgtc ccttctttat  1080
tacaaatata actttagttt tatgtgattc ctgtaaccaa actactctcc aaatgctcct   1140
ggagatattt gtgtggatag ctatgtttc ctcaggagtg aatcctttgg tctacaccct    1200
cttcaataag acattttggg atgcatttgg ccgatatatc acctgcaatt accgggccac   1260
aaagtcagta aaaactctca gaaaacgctc cagtaagatc tacttccgga atccaatggc   1320
agagaactct aagttttca agaaacatgg aattcgaaat gggattaacc ctgccatgta    1380
ccagagtcca atgaggctcc gaagttcaac cattcagtct tcatcaatca ttctactaga   1440
tacgcttctc ctcactgaaa atgaaggtga caaaactgaa gagcaagtta gttatgtata   1500
gcagaactgg cagttgtcat caaacataat gatgagtaag atgatgaatg agatgtaaat   1560
gtgcccagaa tatattatat aaagaatttt atgtcatata tcaaatcatc tctttaacct   1620
aagatgtaag tattaagaat atctaatttt cctaatttgg acaagattat tccatgagga   1680
aaataatttt atatagctac aaatgaaaac aatccagcac tctggttaaa ttttaaggta   1740
ttcgaatgaa ataagtcaa atcaataaat ttcaggcttt aaaaaaaaaa                1790
```

<210> SEQ ID NO 71
<211> LENGTH: 481
<212> TYPE: PRT
<213> ORGANISM: Homo sapiens

<400> SEQUENCE: 71

```
Met Ala Leu Ser Tyr Arg Val Ser Glu Leu Gln Ser Thr Ile Pro Glu
  1               5                  10                  15

His Ile Leu Gln Ser Thr Phe Val His Val Ile Ser Ser Asn Trp Ser
             20                  25                  30

Gly Leu Gln Thr Glu Ser Ile Pro Glu Glu Met Lys Gln Ile Val Glu
         35                  40                  45

Glu Gln Gly Asn Lys Leu His Trp Ala Ala Leu Leu Ile Leu Met Val
     50                  55                  60

Ile Ile Pro Thr Ile Gly Gly Asn Thr Leu Val Ile Leu Ala Val Ser
 65                  70                  75                  80

Leu Glu Lys Lys Leu Gln Tyr Ala Thr Asn Tyr Phe Leu Met Ser Leu
                 85                  90                  95

Ala Val Ala Asp Leu Leu Val Gly Leu Phe Val Met Pro Ile Ala Leu
            100                 105                 110

Leu Thr Ile Met Phe Glu Ala Met Trp Pro Leu Pro Leu Val Leu Cys
        115                 120                 125

Pro Ala Trp Leu Phe Leu Asp Val Leu Phe Ser Thr Ala Ser Ile Met
    130                 135                 140
```

```
His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                165                 170                 175

Thr Val Val Trp Leu Ile Ser Ile Gly Ile Ala Ile Pro Val Pro Ile
            180                 185                 190

Lys Gly Ile Glu Thr Asp Val Asp Asn Pro Asn Asn Ile Thr Cys Val
        195                 200                 205

Leu Thr Lys Glu Arg Phe Gly Asp Phe Met Leu Phe Gly Ser Leu Ala
    210                 215                 220

Ala Phe Phe Thr Pro Leu Ala Ile Met Ile Val Thr Tyr Phe Leu Thr
225                 230                 235                 240

Ile His Ala Leu Gln Lys Lys Ala Tyr Leu Val Lys Asn Lys Pro Pro
                245                 250                 255

Gln Arg Leu Thr Trp Leu Thr Val Ser Thr Val Phe Gln Arg Asp Glu
                260                 265                 270

Thr Pro Cys Ser Ser Pro Glu Lys Val Ala Met Leu Asp Gly Ser Arg
275                 280                 285

Lys Asp Lys Ala Leu Pro Asn Ser Gly Asp Glu Thr Leu Met Arg Arg
    290                 295                 300

Thr Ser Thr Ile Gly Lys Lys Ser Val Gln Thr Ile Ser Asn Glu Gln
305                 310                 315                 320

Arg Ala Ser Lys Val Leu Gly Ile Val Phe Phe Leu Phe Leu Leu Met
                325                 330                 335

Trp Cys Pro Phe Phe Ile Thr Asn Ile Thr Leu Val Leu Cys Asp Ser
                340                 345                 350

Cys Asn Gln Thr Thr Leu Gln Met Leu Leu Glu Ile Phe Val Trp Ile
            355                 360                 365

Gly Tyr Val Ser Ser Gly Val Asn Pro Leu Val Tyr Thr Leu Phe Asn
        370                 375                 380

Lys Thr Phe Arg Asp Ala Phe Gly Arg Tyr Ile Thr Cys Asn Tyr Arg
385                 390                 395                 400

Ala Thr Lys Ser Val Lys Thr Leu Arg Lys Arg Ser Ser Lys Ile Tyr
                405                 410                 415

Phe Arg Asn Pro Met Ala Glu Asn Ser Lys Phe Phe Lys Lys His Gly
                420                 425                 430

Ile Arg Asn Gly Ile Asn Pro Ala Met Tyr Gln Ser Pro Met Arg Leu
            435                 440                 445

Arg Ser Ser Thr Ile Gln Ser Ser Ile Ile Leu Leu Asp Thr Leu
    450                 455                 460

Leu Leu Thr Glu Asn Glu Gly Asp Lys Thr Glu Gln Val Ser Tyr
465                 470                 475                 480

Val

<210> SEQ ID NO 72
<211> LENGTH: 481
<212> TYPE: PRT
<213> ORGANISM: Homo sapiens

<400> SEQUENCE: 72

Met Ala Leu Ser Tyr Arg Val Ser Glu Leu Gln Ser Thr Ile Pro Glu
1               5                   10                  15

His Ile Leu Gln Ser Thr Phe Val His Val Ile Ser Ser Asn Trp Ser
            20                  25                  30
```

-continued

Gly Leu Gln Thr Glu Ser Ile Pro Glu Glu Met Lys Gln Ile Val Glu
             35                  40                  45

Glu Gln Gly Asn Lys Leu His Trp Ala Ala Leu Leu Ile Leu Met Val
     50                  55                  60

Ile Ile Pro Thr Ile Gly Gly Asn Thr Leu Val Ile Leu Ala Val Ser
 65                  70                  75                  80

Leu Glu Lys Lys Leu Gln Tyr Ala Thr Asn Tyr Phe Leu Met Ser Leu
                 85                  90                  95

Ala Val Ala Asp Leu Leu Val Gly Leu Phe Val Met Pro Ile Ala Leu
             100                 105                 110

Leu Thr Ile Met Phe Glu Ala Met Trp Pro Leu Pro Leu Val Leu Cys
         115                 120                 125

Pro Ala Trp Leu Phe Leu Asp Val Leu Phe Ser Thr Ala Ser Ile Met
     130                 135                 140

His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                 165                 170                 175

Thr Val Val Trp Leu Ile Ser Ile Gly Ile Ala Ile Pro Val Pro Ile
             180                 185                 190

Lys Gly Ile Glu Thr Asp Val Asp Asn Pro Asn Asn Ile Thr Cys Val
         195                 200                 205

Leu Thr Lys Glu Arg Phe Gly Asp Phe Met Leu Phe Gly Ser Leu Ala
     210                 215                 220

Ala Phe Phe Thr Pro Leu Ala Ile Met Ile Val Thr Tyr Phe Leu Thr
225                 230                 235                 240

Ile His Ala Leu Gln Lys Lys Ala Tyr Leu Val Lys Asn Lys Pro Pro
                 245                 250                 255

Gln Arg Leu Thr Trp Leu Thr Val Ser Thr Val Phe Gln Arg Asp Glu
             260                 265                 270

Thr Pro Cys Ser Ser Pro Glu Lys Val Ala Met Leu Asp Gly Ser Arg
         275                 280                 285

Lys Asp Lys Ala Leu Pro Asn Ser Gly Asp Glu Thr Leu Met Arg Arg
     290                 295                 300

Thr Ser Thr Ile Gly Lys Lys Ser Val Gln Thr Ile Ser Asn Glu Gln
305                 310                 315                 320

Arg Ala Ser Lys Val Leu Gly Ile Val Phe Phe Leu Phe Leu Leu Met
                 325                 330                 335

Trp Cys Pro Phe Phe Ile Thr Asn Ile Thr Leu Val Leu Cys Asp Ser
             340                 345                 350

Cys Asn Gln Thr Thr Leu Gln Met Leu Leu Glu Ile Phe Val Trp Ile
         355                 360                 365

Gly Tyr Val Ser Ser Gly Val Asn Pro Leu Val Tyr Thr Leu Phe Asn
     370                 375                 380

Lys Thr Phe Trp Asp Ala Phe Gly Arg Tyr Ile Thr Cys Asn Tyr Arg
385                 390                 395                 400

Ala Thr Lys Ser Val Lys Thr Leu Arg Lys Arg Ser Ser Lys Ile Tyr
                 405                 410                 415

Phe Arg Asn Pro Met Ala Glu Asn Ser Lys Phe Phe Lys Lys His Gly
             420                 425                 430

Ile Arg Asn Gly Ile Asn Pro Ala Met Tyr Gln Ser Pro Met Arg Leu
         435                 440                 445

```
Arg Ser Ser Thr Ile Gln Ser Ser Ile Ile Leu Leu Asp Thr Leu
    450                 455                 460

Leu Leu Thr Glu Asn Glu Gly Asp Lys Thr Glu Glu Gln Val Ser Tyr
465                 470                 475                 480

Val

<210> SEQ ID NO 73
<211> LENGTH: 1518
<212> TYPE: DNA
<213> ORGANISM: Homo sapiens

<400> SEQUENCE: 73
ccatgggcag cggcacacgg cggcgcgatg atggacgtta acagcagcgg ccgcccggac      60
ctctacgggc acctccgctc tttccttctg ccagaagtgg ggcgcgggct gcccgacttg     120
agccccgacg gtggcgccga cccggtcgcg ggctcctggg cgccgcacct gctgagcgag     180
gtgacagcca gccggcgcc cacctgggac gcgcccccgg acaatgcctc cggctgtggg     240
gaacagatca actacggcag agtcgagaaa gttgtgatcg gctccatcct gacgctcatc     300
acgctgctga cgatcgcggg caactgcctg gtggtgatct ccgtgtgctt cgtcaagaag     360
ctccgccagc cctccaacta cctgatcgtg tccctggcgc tggccgacct ctcggtggct     420
gtggcggtca tgcccttcgt cagcgtcacc gacctcatcg ggggcaagtg gatctttgga     480
cactttttct gtaatgtctt catcgccatg gacgtcatgt gctgcacggc ctcgatcatg     540
accctgtgcg tgatcagcat tgacaggtac cttgggatca caaggccct cacatacct      600 gtgaggcaga atgggaaatg catggcgaag atgattctct ccgtctggct tctctccgcc     660
tccatcacct acctccact ctttggatgg gctcagaatg taaatgatga taaggtgtgc     720
ttgatcagcc aggactttgg ctatacgatt tactctaccg cagtggcatt ttatatcccc     780
atgtccgtca tgcttttcat gtactaccag atttacaagg ctgccaggaa gagtgctgcc     840
aaacacaagt tcctggctt ccctcgagtg gagccagaca gcgtcatcgc cctgaatggc     900
atagtgaagc tccagaagga ggtggaagag tgtgcaaacc tttcgagact cctcaagcat     960
gaaaggaaaa acatctccat ctttaagcga gaacagaaag cagccaccac cctggggatc    1020
atcgtcgggg cctttaccgt gtgctggctg ccatttttcc tcctctcgac agccagaccc    1080
ttcatctgtg gcacttcctg cagctgcatc ccactgtggg tggagaggac atttctgtgg    1140
ctaggctatg caaactctct cattaaccct tttatatatg ccttcttcaa ccggacctg    1200 aggaccacct atcgcagcct gctccagtgc cagtaccgga atatcaaccg gaagctctca    1260
gctgcaggca tgcatgaagc cctgaagctt gctgagaggc cagagagacc tgagtttgtg    1320
ctgagggcct gcacaaggag ggtgctgttt agaccagaaa agaggccacc ggtatctgtg    1380
tgggtgctac aatctccaga ccatcacaat tggttagcag acaaaatgct gactactgta    1440
gaaaaaaagg tcatgattca tgattgaaag cagaacaatg gagatgaaat aaacaaggca    1500
aaatagaggt ggaaacag                                                  1518

<210> SEQ ID NO 74
<211> LENGTH: 1518
<212> TYPE: DNA
<213> ORGANISM: Homo sapiens

<400> SEQUENCE: 74
ccatgggcag cggcacacgg cggcgcgatg atggacgtta acagcagcgg ccgcccggac      60
ctctacgggc acctccgctc tttccttctg ccagaagtgg ggcgcgggct gcccgacttg     120
```

```
agccccgacg gtggcgccga cccggtcgcg ggctcctggg cgccgcacct gctgagcgag      180
gtgacagcca gcccggcgcc cacctgggac gcgcccccgg acaatgcctc cggctgtggg      240
gaacagatca actacggcag agtcgagaaa gttgtgatcg gctccatcct gacgctcatc      300
aggctgctga cgatcgcggg caactgcctg gtggtgatct ccgtgtgctt cgtcaagaag      360
ctccgccagc cctccaacta cctgatcgtg tccctggcgc tggccgacct ctcggtggct      420
gtggcggtca tgcccttcgt cagcgtcacc gacctcatcg ggggcaagtg gatctttgga      480 cacttttttct gtaatgtctt catcgccatg gacgtcatgt gctgcacggc ctcgatcatg      540
accctgtgcg tgatcagcat tgacaggtac cttgggatca caaggccccct cacatacccct      600 gtgaggcaga atgggaaatg catggcgaag atgattctct ccgtctggct tctctccgcc      660
tccatcacct acctccact ctttggatgg gctcagaatg taaatgatga taggtgtgc      720 ttgatcagcc aggactttgg ctatacgatt tactctaccg cagtggcatt ttatatcccc      780
atgtccgtca tgcttttcat gtactaccag atttacaagg ctgccaggaa gagtgctgcc      840
aaacacaagt ttcctggctt ccctcgagtg gagccagaca gcgtcatcgc cctgaatggc      900
atagtgaagc tccagaagga ggtggaagag tgtgcaaacc tttcgagact cctcaagcat      960
gaaaggaaaa acatctccat ctttaagcga gaacagaaag cagccaccac cctgggatc      1020 atcgtcgggg cctttaccgt gtgctggctg ccattttcc tcctctcgac agccagaccc      1080
ttcatctgtg gcacttcctg cagctgcatc ccactgtggg tggagaggac atttctgtgg      1140
ctaggctatg caaactctct cattaaccct tttatatatg ccttcttcaa ccgggaccctg      1200 aggaccacct atcgcagcct gctccagtgc cagtaccgga atatcaaccg gaagctctca      1260
gctgcaggca tgcatgaagc cctgaagctt gctgagaggc cagagagacc tgagtttgtg      1320
ctgagggcct gcacaaggag ggtgctgttg agaccagaaa agaggccacc ggtatctgtg      1380
tgggtgctac aatctccaga ccatcacaat tggttagcag acaaaatgct gactactgta      1440
gaaaaaaagg tcatgattca tgattgaaag cagaacaatg gagatgaaat aaacaaggca      1500
aaatagaggt ggaaacag                                                    1518

<210> SEQ ID NO 75
<211> LENGTH: 1518
<212> TYPE: DNA
<213> ORGANISM: Homo sapiens

<400> SEQUENCE: 75
ccatgggcag cggcacacgg cggcgcgatg atggacgtta acagcagcgg ccgcccggac       60
ctctacgggc acctccgctc tttccttctg ccagaagtgg ggcgcgggct gcccgacttg      120
agccccgacg gtggcgccga cccggtcgcg ggctcctggg cgccgcacct gctgagcgag      180
gtgacagcca gcccggcgcc cacctgggac gcgcccccgg acaatgcctc cggctgtggg      240
gaacagatca actacggcag agtcgagaaa gttgtgatcg gctccatcct gacgctcatc      300
acgctgctga cgatcgcggg caactgcctg gtggtgatct ccgtgtgctt cgtcaagaag      360
ctccgccagc cctccaacta cctgatcgtg tccctggcgc tggccgacct ctcggtggct      420
gtggcggtca tgcccttcgt cagcgtcacc gacctcatcg ggggcaagtg gatctttgga      480 cacttttttct gtaatgtctt catcgccatg gacgtcatgt gctgcacggc ctcgatcatg      540
accctgtgcg tgatcagcat tgacaggtac cttgggatca caaggccccct cacatacccct      600 gtgaggcaga atgggaaatg catggcgaag atgattctct ccgtctggct tctctccgcc      660
```

```
tccatcacct tacctccact ctttggatgg gctcagaatg taaatgatga taaggtgtgc    720
ttgatcagcc aggactttgg ctatacgatt tactctaccg cagtggcatt ttatatcccc    780
atgtccgtca tgcttttcat gtactaccag atttacaagg ctgccaggaa gagtgctgcc    840
aaacacaagt ttcctggctt ccctcgagtg gagccagaca gcgtcatcgc cctgaatggc    900
atagtgaagc tccagaagga ggtggaagag tgtgcaaacc tttcgagact cctcaagcat    960
gaaaggaaaa acatctccat ctttaagcga aacagaaag cagccaccac cctggggatc   1020
atcgtcgggg cctttaccgt gtgctggctg ccattttttcc tcctctcgac agccagaccc   1080
ttcatctgtg gcacttcctg cagctgcatc ccactgtggg tggagaggac atttctgtgg   1140
ctaggctatg caaactctct cattaaccct tttatatatg ccttcttcaa ccgggacctg   1200
aggaccacct atcgcagcct gctccagtgc cagtaccgga atatcaaccg gaagctctca   1260
gctgcaggca tgcatgaagc cctgaagcct gctgagaggc cagagagacc tgagtttgtg   1320
ctgagggcct gcacaaggag ggtgctgttg agaccagaaa agaggccacc ggtatctgtg   1380
tgggtgctac aatctccaga ccatcacaat tggttagcag acaaaatgct gactactgta   1440
gaaaaaaagg tcatgattca tgattgaaag cagaacaatg gagatgaaat aaacaaggca   1500
aaatagaggt ggaaacag                                                 1518

<210> SEQ ID NO 76
<211> LENGTH: 478
<212> TYPE: PRT
<213> ORGANISM: Homo sapiens

<400> SEQUENCE: 76

Met Asp Val Asn Ser Ser Gly Arg Pro Asp Leu Tyr Gly His Leu Arg
  1               5                  10                  15

Ser Phe Leu Leu Pro Glu Val Gly Arg Gly Leu Pro Asp Leu Ser Pro
                 20                  25                  30

Asp Gly Gly Ala Asp Pro Val Ala Gly Ser Trp Ala Pro His Leu Leu
             35                  40                  45

Ser Glu Val Thr Ala Ser Pro Ala Pro Thr Trp Asp Ala Pro Pro Asp
         50                  55                  60

Asn Ala Ser Gly Cys Gly Glu Gln Ile Asn Tyr Gly Arg Val Glu Lys
 65                  70                  75                  80

Val Val Ile Gly Ser Ile Leu Thr Leu Ile Thr Leu Leu Thr Ile Ala
                 85                  90                  95

Gly Asn Cys Leu Val Val Ile Ser Val Cys Phe Val Lys Lys Leu Arg
            100                 105                 110

Gln Pro Ser Asn Tyr Leu Ile Val Ser Leu Ala Leu Ala Asp Leu Ser
        115                 120                 125

Val Ala Val Ala Val Met Pro Phe Val Ser Val Thr Asp Leu Ile Gly
    130                 135                 140

Gly Lys Trp Ile Phe Gly His Phe Phe Cys Asn Val Phe Ile Ala Met
145                 150                 155                 160

Asp Val Met Cys Cys Thr Ala Ser Ile Met Thr Leu Cys Val Ile Ser
                165                 170                 175

Ile Asp Arg Tyr Leu Gly Ile Thr Arg Pro Leu Thr Tyr Pro Val Arg
            180                 185                 190

Gln Asn Gly Lys Cys Met Ala Lys Met Ile Leu Ser Val Trp Leu Leu
        195                 200                 205

Ser Ala Ser Ile Thr Leu Pro Pro Leu Phe Gly Trp Ala Gln Asn Val
    210                 215                 220
```

```
Asn Asp Asp Lys Val Cys Leu Ile Ser Gln Asp Phe Gly Tyr Thr Ile
225                 230                 235                 240

Tyr Ser Thr Ala Val Ala Phe Tyr Ile Pro Met Ser Val Met Leu Phe
            245                 250                 255

Met Tyr Tyr Gln Ile Tyr Lys Ala Ala Arg Lys Ser Ala Ala Lys His
                260                 265                 270

Lys Phe Pro Gly Phe Pro Arg Val Glu Pro Asp Ser Val Ile Ala Leu
            275                 280                 285

Asn Gly Ile Val Lys Leu Gln Lys Glu Val Glu Glu Cys Ala Asn Leu
            290                 295                 300

Ser Arg Leu Leu Lys His Glu Arg Lys Asn Ile Ser Ile Phe Lys Arg
305                 310                 315                 320

Glu Gln Lys Ala Ala Thr Thr Leu Gly Ile Ile Val Gly Ala Phe Thr
                325                 330                 335

Val Cys Trp Leu Pro Phe Phe Leu Leu Ser Thr Ala Arg Pro Phe Ile
            340                 345                 350

Cys Gly Thr Ser Cys Ser Cys Ile Pro Leu Trp Val Glu Arg Thr Phe
            355                 360                 365

Leu Trp Leu Gly Tyr Ala Asn Ser Leu Ile Asn Pro Phe Ile Tyr Ala
370                 375                 380

Phe Phe Asn Arg Asp Leu Arg Thr Thr Tyr Arg Ser Leu Leu Gln Cys
385                 390                 395                 400

Gln Tyr Arg Asn Ile Asn Arg Lys Leu Ser Ala Ala Gly Met His Glu
                405                 410                 415

Ala Leu Lys Leu Ala Glu Arg Pro Glu Arg Pro Glu Phe Val Leu Arg
            420                 425                 430

Ala Cys Thr Arg Arg Val Leu Leu Arg Pro Glu Lys Arg Pro Pro Val
            435                 440                 445

Ser Val Trp Val Leu Gln Ser Pro Asp His His Asn Trp Leu Ala Asp
            450                 455                 460

Lys Met Leu Thr Thr Val Glu Lys Lys Val Met Ile His Asp
465                 470                 475

<210> SEQ ID NO 77
<211> LENGTH: 478
<212> TYPE: PRT
<213> ORGANISM: Homo sapiens

<400> SEQUENCE: 77

Met Asp Val Asn Ser Ser Gly Arg Pro Asp Leu Tyr Gly His Leu Arg
1               5                   10                  15

Ser Phe Leu Leu Pro Glu Val Gly Arg Gly Leu Pro Asp Leu Ser Pro
            20                  25                  30

Asp Gly Gly Ala Asp Pro Val Ala Gly Ser Trp Ala Pro His Leu Leu
            35                  40                  45

Ser Glu Val Thr Ala Ser Pro Ala Pro Thr Trp Asp Ala Pro Pro Asp
50                  55                  60

Asn Ala Ser Gly Cys Gly Glu Gln Ile Asn Tyr Gly Arg Val Glu Lys
65                  70                  75                  80

Val Val Ile Gly Ser Ile Leu Thr Leu Ile Lys Leu Leu Thr Ile Ala
            85                  90                  95

Gly Asn Cys Leu Val Val Ile Ser Val Cys Phe Val Lys Lys Leu Arg
            100                 105                 110

Gln Pro Ser Asn Tyr Leu Ile Val Ser Leu Ala Leu Ala Asp Leu Ser
```

```
            115                 120                 125
Val Ala Val Ala Val Met Pro Phe Val Ser Val Thr Asp Leu Ile Gly
130                 135                 140

Gly Lys Trp Ile Phe Gly His Phe Phe Cys Asn Val Phe Ile Ala Met
145                 150                 155                 160

Asp Val Met Cys Cys Thr Ala Ser Ile Met Thr Leu Cys Val Ile Ser
                165                 170                 175

Ile Asp Arg Tyr Leu Gly Ile Thr Arg Pro Leu Thr Tyr Pro Val Arg
            180                 185                 190

Gln Asn Gly Lys Cys Met Ala Lys Met Ile Leu Ser Val Trp Leu Leu
            195                 200                 205

Ser Ala Ser Ile Thr Leu Pro Pro Leu Phe Gly Trp Ala Gln Asn Val
210                 215                 220

Asn Asp Asp Lys Val Cys Leu Ile Ser Gln Asp Phe Gly Tyr Thr Ile
225                 230                 235                 240

Tyr Ser Thr Ala Val Ala Phe Tyr Ile Pro Met Ser Val Met Leu Phe
                245                 250                 255

Met Tyr Tyr Gln Ile Tyr Lys Ala Ala Arg Lys Ser Ala Ala Lys His
            260                 265                 270

Lys Phe Pro Gly Phe Pro Arg Val Glu Pro Asp Ser Val Ile Ala Leu
            275                 280                 285

Asn Gly Ile Val Lys Leu Gln Lys Glu Val Glu Glu Cys Ala Asn Leu
            290                 295                 300

Ser Arg Leu Leu Lys His Glu Arg Lys Asn Ile Ser Ile Phe Lys Arg
305                 310                 315                 320

Glu Gln Lys Ala Ala Thr Thr Leu Gly Ile Ile Val Gly Ala Phe Thr
                325                 330                 335

Val Cys Trp Leu Pro Phe Phe Leu Leu Ser Thr Ala Arg Pro Phe Ile
            340                 345                 350

Cys Gly Thr Ser Cys Ser Cys Ile Pro Leu Trp Val Glu Arg Thr Phe
            355                 360                 365

Leu Trp Leu Gly Tyr Ala Asn Ser Leu Ile Asn Pro Phe Ile Tyr Ala
            370                 375                 380

Phe Phe Asn Arg Asp Leu Arg Thr Thr Tyr Arg Ser Leu Leu Gln Cys
385                 390                 395                 400

Gln Tyr Arg Asn Ile Asn Arg Lys Leu Ser Ala Ala Gly Met His Glu
                405                 410                 415

Ala Leu Lys Leu Ala Glu Arg Pro Glu Arg Pro Glu Phe Val Leu Arg
            420                 425                 430

Ala Cys Thr Arg Arg Val Leu Leu Arg Pro Glu Lys Arg Pro Pro Val
            435                 440                 445

Ser Val Trp Val Leu Gln Ser Pro Asp His His Asn Trp Leu Ala Asp
450                 455                 460

Lys Met Leu Thr Thr Val Glu Lys Lys Val Met Ile His Asp
465                 470                 475

<210> SEQ ID NO 78
<211> LENGTH: 478
<212> TYPE: PRT
<213> ORGANISM: Homo sapiens

<400> SEQUENCE: 78

Met Asp Val Asn Ser Ser Gly Arg Pro Asp Leu Tyr Gly His Leu Arg
  1               5                  10                  15
```

-continued

```
Ser Phe Leu Leu Pro Glu Val Gly Arg Gly Leu Pro Asp Leu Ser Pro
             20                  25                  30

Asp Gly Gly Ala Asp Pro Val Ala Gly Ser Trp Ala Pro His Leu Leu
         35                  40                  45

Ser Glu Val Thr Ala Ser Pro Ala Pro Thr Trp Asp Ala Pro Pro Asp
 50                  55                  60

Asn Ala Ser Gly Cys Gly Glu Gln Ile Asn Tyr Gly Arg Val Glu Lys
 65                  70                  75                  80

Val Val Ile Gly Ser Ile Leu Thr Leu Ile Thr Leu Thr Ile Ala
                 85                  90                  95

Gly Asn Cys Leu Val Val Ile Ser Val Cys Phe Val Lys Lys Leu Arg
                100                 105                 110

Gln Pro Ser Asn Tyr Leu Ile Val Ser Leu Ala Leu Ala Asp Leu Ser
            115                 120                 125

Val Ala Val Ala Val Met Pro Phe Val Ser Val Thr Asp Leu Ile Gly
130                 135                 140

Gly Lys Trp Ile Phe Gly His Phe Phe Cys Asn Val Phe Ile Ala Met
145                 150                 155                 160

Asp Val Met Cys Cys Thr Ala Ser Ile Met Thr Leu Cys Val Ile Ser
                165                 170                 175

Ile Asp Arg Tyr Leu Gly Ile Thr Arg Pro Leu Thr Tyr Pro Val Arg
            180                 185                 190

Gln Asn Gly Lys Cys Met Ala Lys Met Ile Leu Ser Val Trp Leu Leu
        195                 200                 205

Ser Ala Ser Ile Thr Leu Pro Pro Leu Phe Gly Trp Ala Gln Asn Val
    210                 215                 220

Asn Asp Asp Lys Val Cys Leu Ile Ser Gln Asp Phe Gly Tyr Thr Ile
225                 230                 235                 240

Tyr Ser Thr Ala Val Ala Phe Tyr Ile Pro Met Ser Val Met Leu Phe
                245                 250                 255

Met Tyr Tyr Gln Ile Tyr Lys Ala Ala Arg Lys Ser Ala Ala Lys His
            260                 265                 270

Lys Phe Pro Gly Phe Pro Arg Val Glu Pro Asp Ser Val Ile Ala Leu
        275                 280                 285

Asn Gly Ile Val Lys Leu Gln Lys Glu Val Glu Glu Cys Ala Asn Leu
    290                 295                 300

Ser Arg Leu Leu Lys His Glu Arg Lys Asn Ile Ser Ile Phe Lys Arg
305                 310                 315                 320

Glu Gln Lys Ala Ala Thr Thr Leu Gly Ile Ile Val Gly Ala Phe Thr
                325                 330                 335

Val Cys Trp Leu Pro Phe Phe Leu Leu Ser Thr Ala Arg Pro Phe Ile
            340                 345                 350

Cys Gly Thr Ser Cys Ser Cys Ile Pro Leu Trp Val Glu Arg Thr Phe
        355                 360                 365

Leu Trp Leu Gly Tyr Ala Asn Ser Leu Ile Asn Pro Phe Ile Tyr Ala
    370                 375                 380

Phe Phe Asn Arg Asp Leu Arg Thr Thr Tyr Arg Ser Leu Leu Gln Cys
385                 390                 395                 400

Gln Tyr Arg Asn Ile Asn Arg Lys Leu Ser Ala Ala Gly Met His Glu
                405                 410                 415

Ala Leu Lys Pro Ala Glu Arg Pro Glu Arg Pro Glu Phe Val Leu Arg
            420                 425                 430

Ala Cys Thr Arg Arg Val Leu Leu Arg Pro Glu Lys Arg Pro Pro Val
```

```
                435                 440                 445
    Ser Val Trp Val Leu Gln Ser Pro Asp His His Asn Trp Leu Ala Asp
        450                 455                 460

Lys Met Leu Thr Thr Val Glu Lys Lys Val Met Ile His Asp
465                 470                 475

<210> SEQ ID NO 79
<211> LENGTH: 2173
<212> TYPE: DNA
<213> ORGANISM: Homo sapiens

<400> SEQUENCE: 79
agggcatgcc attgcaagag aatgctcagc catgttcatc tggggacctg ctcctggtag      60
agcaatagga tctgtgtgcc cagcaccact gcccacctag ctgtcctggc ctgtgcccaa     120
tgctgacctt cacctcagag tgtggctgta ccacattcgg tgtatttgat atagtgtttg     180
caacaaattc gacccaggtg atcaaaatga ttctcaactc ttctactgaa gatggtatta     240
aaagaatcca agatgattgt cccaaagctg gaaggcataa ttacatattt gtcatgattc     300
ctactttata cagtatcatc tttgtggtgg gaatatttgg aaacagcttg gtggtgatag     360
ttcatttact tttatatgaa gctgaagact gtggccagtg ttttttcttt gaatttagca     420
ctggctgact tatgcttttt actgactttg ccactatggg ctgtctacac agctatggaa     480
taccgctggc cctttggcaa ttacctatgt aagattgctt cagccagcgt cagtttcaac     540
ctgtacgcta gtgtgtttct actcacgtgt ctcagcattg atcgatacct ggctattgtt     600
cacccaatga agtcccgcct tcgacgcaca atgcttgtag ccaaagtcac ctgcatcatc     660
atttggctgc tggcaggctt ggccagtttg ccagctataa tccatcgaaa tgtatttttc     720
attgagaaca ccaatattac agtttgtgct ttccattatg agtcccaaaa ttcaaccctc     780
ccgatagggc tgggcctgac caaaaatata ctgggtttcc tgtttccttt tctgatcatt     840
cttacaagtt atactcttat ttggaaggcc ctaaagaagg cttatgaaat tcagaagaac     900
aaaccaagaa atgatgatat ttttaagata attatggcaa ttgtgctttt cttttctttt     960
tcctggattc cccaccaaat attcactttt ctggatgtat tgattcaact aggcatcata    1020
cgtgactgta gaattgcaga tattgtggac acggccatgc ctatcaccat ttgtatagct    1080
tattttaaca attgcctgaa tcctctttt tatggctttc tggggaaaaa atttaaagaa    1140
tattttctcc agcttctaaa atatattccc ccaaaagcca aatcccactc aaacctttca    1200
acaaaaatga gcacgctttc ctaccgcccc tcagataatg taagctcatc caccaagaag    1260
cctgcaccat gttttgaggt tgagtgacat gttcgaaacc tgtccataaa gtaattttgt    1320
gaaagaagga gcaagagaac attcctctgc agcacttcac taccaaatga gcattagcta    1380
cttttcagaa ttgaaggaga aaatgcatta tgtggactga accgactttt ctaaagctct    1440
gaacaaaagc ttttctttcc ttttgcaaca agacaaagca aagccacatt ttgcattaga    1500
cagatgacgg ctgctcgaag aacaatgtca gaaactcgat gaatgtgttg atttgagaaa    1560
ttttactgac agaaatgcaa tctccctagc ctgcttttgt cctgttattt tttatttcca    1620
cataaaggta tttagaatat attaaatcgt tagaggagca acaggagatg agagttccag    1680
attgttctgt ccagtttcca aagggcagta agtttcgt gccggttttc agctattagc    1740
aactgtgcta cacttgcacc tggtactgca cattttgtac aaagatatgc taagcagtag    1800
tcgtcaagtt gcagatcttt ttgtgaaatt caacctgtgt cttataggtt tccactgcca    1860
aaacaatgcc cgtaagatgg cttatttgta taatggtgtt actaaagtca catataaaag    1920
```

```
ttaaactact tgtaaaggtg ctgcactggt cccaagtagt agtgtcttcc tagtatatta      1980
gtttgattta atatctgaga agtgtatata gtttgtggta aaagattat atatcataaa       2040 gtatgccttc ctgtttaaaa aaagtatata ttctacacat atatgtatat gtatatctat     2100
atctctaaac tgctgttaat tgattaaaat ctggcaaagt tatatttact ttaaaataaa     2160
ataattttat tgc                                                        2173

<210> SEQ ID NO 80
<211> LENGTH: 2173
<212> TYPE: DNA
<213> ORGANISM: Homo sapiens

<400> SEQUENCE: 80
agggcatgcc attgcaagag aatgctcagc catgttcatc tggggacctg ctcctggtag      60
agcaatagga tctgtgtgcc cagcaccact gcccacctag ctgtcctggc ctgtgcccaa     120
tgctgacctt cacctcagag tgtggctgta ccacattcgg tgtatttgat atagtgtttg     180
caacaaattc gacccaggtg atcaaaatga ttctcaactc ttctactgaa gatggtatta     240
aaagaatcca agatgattgt cccaaagctg gaaggcataa ttacatattt gtcatgattc     300
ctactttata cagtatcatc tttgtggtgg gaatatttag aaacagcttg gtggtgataq     360 ttcatttact tttatatgaa gctgaagact gtggccagtg tttttctttt gaatttagca     420
ctggctgact tatgcttttt actgactttg ccactatggg ctgtctacac agctatggaa     480
taccgctggc cctttggcaa ttacctatgt aagattgctt cagccagcgt cagtttcaac     540
ctgtacgcta gtgtgtttct actcacgtgt ctcagcattg atcgatacct ggctattgtt     600
cacccaatga agtcccgcct tcgacgcaca atgcttgtag ccaaagtcac ctgcatcatc     660
atttggctgc tggcaggctt ggccagtttg ccagctataa tccatcgaaa tgtatttttc     720
attgagaaca ccaatattac agtttgtgct ttccattatg agtcccaaaa ttcaaccctc     780
ccgatagggc tgggcctgac caaaaatata ctgggtttcc tgtttccttt tctgatcatt     840
cttacaagtt atactcttat ttggaaggcc ctaaagaagg cttatgaaat tcagaagaac     900
aaaccaagaa atgatgatat ttttaagata attatggcaa ttgtgctttt cttttctttt     960
tcctggattc ccaccaaat attcactttt ctggatgtat tgattcaact aggcatcata    1020
cgtgactgta gaattgcaga tattgtggac acggccatgc ctatcaccat ttgtatagct    1080
tattttaaca attgcctgaa tcctcttttt tatggctttc tggggaaaaa atttaaagaa   1140
tattttctcc agcttctaaa atatattccc ccaaaagcca atcccactc aaacctttca    1200 acaaaaatga gcacgctttc ctaccgcccc tcagataatg taagctcatc caccaagaag   1260
cctgcaccat gttttgaggt tgagtgacat gttcgaaacc tgtccataaa gtaattttgt   1320
gaaagaagga gcaagagaac attcctctgc agcacttcac taccaaatga gcattagcta   1380
cttttcagaa ttgaaggaga aaatgcatta tgtggactga accgactttt ctaaagctct   1440
gaacaaaagc ttttctttcc ttttgcaaca agacaaagca aagccacatt ttgcattaga   1500
cagatgacgg ctgctcgaag aacaatgtca gaaactcgat gaatgtgttg atttgagaaa   1560
ttttactgac agaaatgcaa tctccctagc ctgcttttgt cctgttattt tttatttcca   1620
cataaaggta tttagaatat attaaatcgt tagaggagca acaggagatg agagttccag   1680
attgttctgt ccagtttcca aagggcagta agtttcgt gccggttttc agctattagc     1740
aactgtgcta cacttgcacc tggtactgca cattttgtac aaagatatgc taagcagtag   1800
```

-continued

| | |
|---|---|
| tcgtcaagtt gcagatcttt ttgtgaaatt caacctgtgt cttataggtt tccactgcca | 1860 |
| aaacaatgcc cgtaagatgg cttatttgta taatggtgtt actaaagtca catataaaag | 1920 |
| ttaaactact tgtaaaggtg ctgcactggt cccaagtagt agtgtcttcc tagtatatta | 1980 |
| gtttgattta atatctgaga agtgtatata gtttgtggta aaaagattat atatcataaa | 2040 |
| gtatgccttc ctgtttaaaa aaagtatata ttctacacat atatgtatat gtatatctat | 2100 |
| atctctaaac tgctgttaat tgattaaaat ctggcaaagt tatatttact ttaaaataaa | 2160 |
| ataattttat tgc | 2173 |

<210> SEQ ID NO 81
<211> LENGTH: 2173
<212> TYPE: DNA
<213> ORGANISM: Homo sapiens

<400> SEQUENCE: 81

| | |
|---|---|
| agggcatgcc attgcaagag aatgctcagc catgttcatc tggggacctg ctcctggtag | 60 |
| agcaatagga tctgtgtgcc cagcaccact gcccacctag ctgtcctggc ctgtgcccaa | 120 |
| tgctgacctt cacctcagag tgtggctgta ccacattcgg tgtatttgat atagtgtttg | 180 |
| caacaaattc gacccaggtg atcaaaatga ttctcaactc ttctactgaa gatggtatta | 240 |
| aaagaatcca agatgattgt cccaaagctg gaaggcataa ttacatattt gtcatgattc | 300 |
| ctactttata cagtatcatc tttgtggtgg gaatatttgg aaacagcttg gtggtgatag | 360 |
| ttcatttact tttatatgaa gctgaagact gtggccagtg ttttctcttt gaatttagca | 420 |
| ctggctgact tatgcttttt actgactttg ccactatggg ctgtctacac agctatggaa | 480 |
| taccgctggc cctttggcaa ttacctatgt aagattgctt cagccagcgt cagtttcaac | 540 |
| ctgtacgcta gtgtgtttct actcacgtgt ctcagcattg atcgatacct ggctattgtt | 600 |
| cacccaatga agtcccgcct tcgacgcaca atgcttgtag ccaaagtcac ctgcatcatc | 660 |
| atttggctgc tggcaggctt ggccagtttg ccagctataa tccatcgaaa tgtatttttc | 720 |
| attgagaaca ccaatattac agtttgtgct ttccattatg agtcccaaaa ttcaaccctc | 780 |
| ccgatagggc tgggcctgac caaaaatata ctgggttccc tgtttccttt tctgatcatt | 840 |
| cttacaagtt atactcttat ttggaaggcc ctaaagaagg cttatgaaat tcagaagaac | 900 |
| aaaccaagaa atgatgatat ttttaagata attatggcaa ttgtgctttt cttttctttt | 960 |
| tcctggattc cccaccaaat attcactttt ctggatgtat tgattcaact aggcatcata | 1020 |
| cgtgactgta gaattgcaga tattgtggac acggccatgc ctatcaccat ttgtatagct | 1080 |
| tattttaaca attgcctgaa tcctctttttt tatggctttc tggggaaaaa atttaaaaga | 1140 |
| tattttctcc agcttctaaa atatattccc ccaaaagcca aatcccactc aaaccttttca | 1200 |
| acaaaaatga gcacgctttc ctaccgcccc tcagataatg taagctcatc caccaagaag | 1260 |
| cctgcaccat gttttgaggt tgagtgacat gttcgaaacc tgtccataaa gtaattttgt | 1320 |
| gaaagaagga gcaagagaac attcctctgc agcacttcac taccaaatga gcattagcta | 1380 |
| cttttcagaa ttgaaggaga aaatgcatta tgtggactga accgactttt ctaaagctct | 1440 |
| gaacaaaagc ttttctttcc ttttgcaaca agacaaagca aagccacatt tgcattaga | 1500 |
| cagatgacgg ctgctcgaag aacaatgtca gaaactcgat gaatgtgttg atttgagaaa | 1560 |
| ttttactgac agaaatgcaa tctccctagc ctgcttttgt cctgttattt tttatttcca | 1620 |
| cataaaggta tttagaatat attaaatcgt tagaggagca acaggagatg agagttccag | 1680 |
| attgttctgt ccagtttcca aagggcagta aagttttcgt gccggttttc agctattagc | 1740 |

-continued

| | | | | |
|---|---|---|---|---|
| aactgtgcta | cacttgcacc | tggtactgca | cattttgtac | aaagatatgc taagcagtag | 1800 |
| tcgtcaagtt | gcagatcttt | ttgtgaaatt | caacctgtgt | cttataggtt tccactgcca | 1860 |
| aaacaatgcc | cgtaagatgg | cttatttgta | taatggtgtt | actaaagtca catataaaag | 1920 |
| ttaaactact | tgtaaaggtg | ctgcactggt | cccaagtagt | agtgtcttcc tagtatatta | 1980 |
| gtttgattta | atatctgaga | agtgtatata | gtttgtggta | aaaagattat atatcataaa | 2040 |
| gtatgccttc | ctgttttaaaa | aaagtatata | ttctacacat | atatgtatat gtatatctat | 2100 |
| atctctaaac | tgctgttaat | tgattaaaat | ctggcaaagt | tatatttact ttaaaataaa | 2160 |
| ataattttat | tgc | | | | 2173 |

<210> SEQ ID NO 82
<211> LENGTH: 2173
<212> TYPE: DNA
<213> ORGANISM: Homo sapiens

<400> SEQUENCE: 82

| | | | | |
|---|---|---|---|---|
| agggcatgcc | attgcaagag | aatgctcagc | catgttcatc | tggggacctg ctcctggtag | 60 |
| agcaatagga | tctgtgtgcc | cagcaccact | gcccacctag | ctgtcctggc ctgtgcccaa | 120 |
| tgctgacctt | cacctcagag | tgtggctgta | ccacattcgg | tgtatttgat atagtgtttg | 180 |
| caacaaattc | gacccaggtg | atcaaaatga | ttctcaactc | ttctactgaa gatggtatta | 240 |
| aaagaatcca | agatgattgt | cccaaagctg | gaaggcataa | ttacatattt gtcatgattc | 300 |
| ctactttata | cagtatcatc | tttgtggtgg | gaatatttgg | aaacagcttg gtggtgatag | 360 |
| ttcatttact | tttatatgaa | gctgaagact | gtggccagtg | ttttctcttt gaatttagca | 420 |
| ctggctgact | tatgcttttt | actgactttg | ccactatggg | ctgtctacac agctatggaa | 480 |
| taccgctggc | cctttggcaa | ttacctatgt | aagattgctt | cagccagcgt cagtttcaac | 540 |
| ctgtacgcta | gtgtgtttct | actcacgtgt | ctcagcattg | atcgatacct ggctattgtt | 600 |
| cacccaatga | agtcccgcct | tcgacgcaca | atgcttgtag | ccaaagtcac ctgcatcatc | 660 |
| atttggctgc | tggcaggctt | ggccagtttg | ccagctataa | tccatcgaaa tgtatttttc | 720 |
| attgagaaca | ccaatattac | agtttgtgct | ttccattatg | agtcccaaaa ttcaaccctc | 780 |
| ccgatagggc | tgggcctgac | caaaaatata | ctgggtttcc | tgtttccttt tctgatcatt | 840 |
| cttacaagtt | atactcttat | ttggaaggcc | ctaaagaagg | cttatgaaat tcagaagaac | 900 |
| aaaccaagaa | atgatgatat | ttttaagata | attatggcaa | ttgtgctttt cttttttcttt | 960 |
| tcctggattc | cccaccaaat | attcactttt | ctggatgtat | tgattcaact aggcatcata | 1020 |
| cgtgactgta | gaattgcaga | tattgtggac | acggccatgc | ctatcaccat ttggatagct | 1080 |
| tattttaaca | attgcctgaa | tcctctttttt | tatggctttc | tggggaaaaa atttaaaaga | 1140 |
| tattttctcc | agcttctaaa | atatattccc | ccaaaagcca | aatcccactc aaaccttca | 1200 |
| acaaaaatga | gcacgctttc | ctaccgcccc | tcagataatg | taagctcatc caccaagaag | 1260 |
| cctgcaccat | gttttgaggt | tgagtgacat | gttcgaaacc | tgtccataaa gtaattttgt | 1320 |
| gaaagaagga | gcaagagaac | attcctctgc | agcacttcac | taccaaatga gcattagcta | 1380 |
| cttttcagaa | ttgaaggaga | aaatgcatta | tgtggactga | accgacttt ctaaagctct | 1440 |
| gaacaaaagc | ttttctttcc | ttttgcaaca | agacaaagca | aagccacatt tgcattaga | 1500 |
| cagatgacgg | ctgctcgaag | aacaatgtca | gaaactcgat | gaatgtgttg atttgagaaa | 1560 |
| ttttactgac | agaaatgcaa | tctccctagc | ctgctttttgt | cctgttattt tttatttcca | 1620 |

```
cataaaggta tttagaatat attaaatcgt tagaggagca acaggagatg agagttccag    1680
attgttctgt ccagtttcca aagggcagta aagttttcgt gccggttttc agctattagc    1740
aactgtgcta cacttgcacc tggtactgca cattttgtac aaagatatgc taagcagtag    1800
tcgtcaagtt gcagatcttt ttgtgaaatt caacctgtgt cttataggtt tccactgcca    1860
aaacaatgcc cgtaagatgg cttatttgta taatggtgtt actaaagtca catataaaag    1920
ttaaactact tgtaaaggtg ctgcactggt cccaagtagt agtgtcttcc tagtatatta    1980
gtttgattta atatctgaga agtgtatata gtttgtggta aaagattat atatcataaa    2040 gtatgccttc ctgtttaaaa aaagtatata ttctacacat atatgtatat gtatatctat    2100
atctctaaac tgctgttaat tgattaaaat ctggcaaagt tatatttact ttaaaataaa    2160
ataattttat tgc                                                      2173

<210> SEQ ID NO 83
<211> LENGTH: 359
<212> TYPE: PRT
<213> ORGANISM: Homo sapiens

<400> SEQUENCE: 83

Met Ile Leu Asn Ser Ser Thr Glu Asp Gly Ile Lys Arg Ile Gln Asp
  1               5                  10                  15

Asp Cys Pro Lys Ala Gly Arg His Asn Tyr Ile Phe Val Met Ile Pro
             20                  25                  30

Thr Leu Tyr Ser Ile Ile Phe Val Val Gly Ile Phe Gly Asn Ser Leu
         35                  40                  45

Val Val Ile Val Ile Tyr Phe Tyr Met Lys Leu Lys Thr Val Ala Ser
     50                  55                  60

Val Phe Leu Leu Asn Leu Ala Leu Ala Asp Leu Cys Phe Leu Leu Thr
 65                  70                  75                  80

Leu Pro Leu Trp Ala Val Tyr Thr Ala Met Glu Tyr Arg Trp Pro Phe
                 85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
    130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
    210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Phe Ser Trp Ile Pro His
                245                 250                 255

Gln Ile Phe Thr Phe Leu Asp Val Leu Ile Gln Leu Gly Ile Ile Arg
            260                 265                 270
```

-continued

```
Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
        290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Ser Thr Lys Lys Pro
                340                 345                 350

Ala Pro Cys Phe Glu Val Glu
        355
```

<210> SEQ ID NO 84
<211> LENGTH: 359
<212> TYPE: PRT
<213> ORGANISM: Homo sapiens

<400> SEQUENCE: 84

```
Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
                20                  25                  30

Thr Leu Tyr Ser Ile Ile Phe Val Gly Ile Phe Arg Asn Ser Leu
            35                  40                  45

Val Val Ile Val Ile Tyr Phe Tyr Met Lys Leu Lys Thr Val Ala Ser
    50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
                100                 105                 110

Tyr Ala Ser Val Phe Leu Leu Thr Cys Leu Ser Ile Asp Arg Tyr Leu
            115                 120                 125

Ala Ile Val His Pro Met Lys Ser Arg Leu Arg Arg Thr Met Leu Val
130                 135                 140

Ala Lys Val Thr Cys Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Ser Trp Ile Pro His
            245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285
```

```
Cys Ile Ala Tyr Phe Asn Asn Cys Leu Asn Pro Leu Phe Tyr Gly Phe
    290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Ser Thr Lys Lys Pro
            340                 345                 350

Ala Pro Cys Phe Glu Val Glu
        355

<210> SEQ ID NO 85
<211> LENGTH: 358
<212> TYPE: PRT
<213> ORGANISM: Homo sapiens

<400> SEQUENCE: 85

Met Ile Leu Asn Ser Ser Thr Glu Asp Gly Ile Lys Arg Ile Gln Asp
  1               5                  10                  15

Asp Cys Pro Lys Ala Gly Arg His Asn Tyr Ile Phe Val Met Ile Pro
             20                  25                  30

Thr Leu Tyr Ser Ile Ile Phe Val Val Gly Ile Phe Gly Asn Ser Leu
         35                  40                  45

Val Val Ile Val Ile Tyr Phe Tyr Met Lys Leu Lys Thr Val Ala Ser
     50                  55                  60

Val Phe Leu Leu Asn Leu Ala Leu Ala Asp Leu Cys Phe Leu Leu Thr
 65                  70                  75                  80

Leu Pro Leu Trp Ala Val Tyr Thr Ala Met Glu Tyr Arg Trp Pro Phe
                 85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Leu Phe Pro Phe Leu
        195                 200                 205

Ile Ile Leu Thr Ser Tyr Thr Leu Ile Trp Lys Ala Leu Lys Lys Ala
    210                 215                 220

Tyr Glu Ile Gln Lys Asn Lys Pro Arg Asn Asp Asp Ile Phe Lys Ile
225                 230                 235                 240

Ile Met Ala Ile Val Leu Phe Phe Phe Ser Trp Ile Pro His Gln
                245                 250                 255

Ile Phe Thr Phe Leu Asp Val Leu Ile Gln Leu Gly Ile Ile Arg Asp
                260                 265                 270

Cys Arg Ile Ala Asp Ile Val Asp Thr Ala Met Pro Ile Thr Ile Cys
            275                 280                 285

Ile Ala Tyr Phe Asn Asn Cys Leu Asn Pro Leu Phe Tyr Gly Phe Leu
```

```
                    290                 295                 300
Gly Lys Lys Phe Lys Arg Tyr Phe Leu Gln Leu Leu Lys Tyr Ile Pro
305                 310                 315                 320

Pro Lys Ala Lys Ser His Ser Asn Leu Ser Thr Lys Met Ser Thr Leu
                325                 330                 335

Ser Tyr Arg Pro Ser Asp Asn Val Ser Ser Thr Lys Lys Pro Ala
                340                 345                 350

Pro Cys Phe Glu Val Glu
        355

<210> SEQ ID NO 86
<211> LENGTH: 359
<212> TYPE: PRT
<213> ORGANISM: Homo sapiens

<400> SEQUENCE: 86

Met Ile Leu Asn Ser Ser Thr Glu Asp Gly Ile Lys Arg Ile Gln Asp
  1               5                  10                  15

Asp Cys Pro Lys Ala Gly Arg His Asn Tyr Ile Phe Val Met Ile Pro
                 20                  25                  30

Thr Leu Tyr Ser Ile Ile Phe Val Gly Ile Phe Gly Asn Ser Leu
             35                  40                  45

Val Val Ile Val Ile Tyr Phe Tyr Met Lys Leu Lys Thr Val Ala Ser
 50                  55                  60

Val Phe Leu Leu Asn Leu Ala Leu Ala Asp Leu Cys Phe Leu Leu Thr
 65                  70                  75                  80

Leu Pro Leu Trp Ala Val Tyr Thr Ala Met Glu Tyr Arg Trp Pro Phe
                 85                  90                  95

Gly Asn Tyr Leu Cys Lys Ile Ala Ser Ala Ser Val Ser Phe Asn Leu
                100                 105                 110

Tyr Ala Ser Val Phe Leu Leu Thr Cys Leu Ser Ile Asp Arg Tyr Leu
                115                 120                 125

Ala Ile Val His Pro Met Lys Ser Arg Leu Arg Arg Thr Met Leu Val
130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
                180                 185                 190

Ile Gly Leu Gly Leu Thr Lys Asn Ile Leu Gly Phe Leu Phe Pro Phe
                195                 200                 205

Leu Ile Ile Leu Thr Ser Tyr Thr Leu Ile Trp Lys Ala Leu Lys Lys
210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
                260                 265                 270

Asp Cys Arg Ile Ala Asp Ile Val Asp Thr Ala Met Pro Ile Thr Ile
                275                 280                 285

Trp Ile Ala Tyr Phe Asn Asn Cys Leu Asn Pro Leu Phe Tyr Gly Phe
                290                 295                 300
```

```
Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Thr Lys Lys Pro
            340                 345                 350

Ala Pro Cys Phe Glu Val Glu
        355

<210> SEQ ID NO 87
<211> LENGTH: 1755
<212> TYPE: DNA
<213> ORGANISM: Homo sapiens

<400> SEQUENCE: 87
ggggactacg gagagctctg cagggagccg aggcccccgc ccgggccaag ggagcttctg      60
tcccgaggac caggggatgc gaagggattg cccctgtgg gtcactttct cagtcatttt     120
gagctcagcc taatcaaaga ctgaggttat gaagtcgatc ctagatggcc ttgcagatac     180
caccttccgc accatcacca ctgacctcct gtacgtgggc tcaaatgaca ttcagtacga     240
agacatcaaa ggtgacatgg catccaaatt agggtacttc ccacagaaat tccctttaac     300
ttcctttagg ggaagtccct tccaagagaa gatgactgcg ggagacaacc cccagctagt     360
cccagcagac caggtgaaca ttacagaatt ttacaacaag tctctctcgt ccttcaagga     420
gaatgaggag aacatccagt gtggggagaa cttcatggac atagagtgtt tcatggtcct     480
gaaccccagc cagcagctgg ccattgcagt cctgtccctc acgctgggca ccttcacggt     540
cctggagaac ctcctggtgc tgtgcgtcat cctccactcc cgcagcctcc gctgcaggcc     600
ttcctaccac ttcatcggca gcctggcggt ggcagacctc ctggggagtg tcattttgt      660
ctacagcttc attgacttcc acgtgttcca ccgcaaagat agccgcaacg tgtttctgtt     720
caaactgggt ggggtcacgg cctccttcac tgcctccgtg ggcagcctgt tcctcacagc     780
catcgacagg tacatatcca ttcacaggcc cctggcctat aagaggattg tcaccaggcc     840
caaggccgtg gtggcgtttt gcctgatgtg gaccatagcc attgtgatcg ccgtgctgcc     900
tctcctgggc tggaactgcg agaaactgca atctgtttgc tcagacattt tcccacacat     960
tgatgaaacc tacctgatgt tctggatcgg ggtcaccagc gtactgcttc tgttcatcgt    1020
gtatgcgtac atgtatattc tctggaaggc tcacagccac gccgtccgca tgattcagcg    1080
tggcacccag aagagcatca tcatccacac gtctgaggat gggaaggtac aggtgacccg    1140
gccagaccaa gcccgcatgg acattaggtt agccaagacc ctggtcctga tcctggtggt    1200
gttgatcatc tgctggggcc ctctgcttgc aatcatggtg tatgatgtct ttgggaagat    1260
gaacaagctc attaagacgg tgtttgcatt ctgcagtatg ctctgcctgc tgaactccac    1320
cgtgaacccc atcatctatg ctctgaggag taaggacctg cgacacgctt ccggagcat     1380
gtttccctct tgtgaaggca ctgcgcagcc tctggataac agcatggggg actcggactg    1440
cctgcacaaa cacgcaaaca atgcagccag tgttcacagg gccgcagaaa gctgcatcaa    1500
gagcacggtc aagattgcca aggtaaccat gtctgtgtcc acagacacgt ctgccgaggc    1560
tctgtgagcc tgatgcctcc ctggcagcac aggaaaagaa ttttttttt taagctcaaa      1620
atctagaaga gtctattgtc tccttggtta tattttttta actttaccat gctcaatgaa    1680
aaggtgattg ccacatgtca cttatttgct tagtttccgt ttgggctaat cttccggggt    1740
tcgtaggaaa cctt                                                      1755
```

<210> SEQ ID NO 88
<211> LENGTH: 1755
<212> TYPE: DNA
<213> ORGANISM: Homo sapiens

<400> SEQUENCE: 88

```
ggggactacg agagctctg cagggagccg aggcccccgc ccgggccaag ggagcttctg      60
tcccgaggac caggggatgc gaagggattg cccctgtgg gtcactttct cagtcatttt     120
gagctcagcc taatcaaaga ctgaggttat gaagtcgatc ctagatggcc ttgcagatac    180
caccttccgc accatcacca ctgacctcct gtacgtgggc tcaaatgaca ttcagtacga    240
agacatcaaa ggtgacatgg catccaaatt agggtacttc ccacagaaat ccctttaac    300
ttcctttagg ggaagtccct ccaagagaaa gatgactgcg ggagacaacc cccagctagt    360
cccagcagac caggtgaaca ttacagaatt ttacaacaag tctctctcgt ccttcaagga    420
gaatgaggag aacatccagt gtggggagaa cttcatggac atagagtgtt tcatggtcct    480
gaaccccagc cagcagctgg ccattgcagt cctgtccctc acgctgggca ccttcacggt    540
cctggagaac ctcctggtgc tgtgcgtcat cctccactcc cgcagcctcc gctgcaggcc    600
ttcctaccac ttcatcggca gcctggcggt ggcagacctc ctggggagtg tcattttgt    660
ctacagcttc attgacttcc acgtgttcca ccgcaaagat agccgcaacg tgtttctgtt    720
caaactgggt ggggtcacgg cctccctcac tgcctccgtg ggcagcctgt tcctcacagc    780
catcgacagg tacatatcca ttcacaggcc cctggcctat aagaggattg tcaccaggcc    840
caaggccgtg gtggcgtttt gcctgatgtg gaccatagcc attgtgatcg ccgtgctgcc    900
tctcctgggc tggaactgcg agaaactgca atctgtttgc tcagacattt tcccacacat    960
tgatgaaacc tacctgatgt tctggatcgg ggtcaccagc gtactgcttc tgttcatcgt   1020
gtatgcgtac atgtatattc tctggaaggc tcacagccac gccgtccgca tgattcagcg   1080
tggcacccag aagagcatca tcatccacac gtctgaggat gggaaggtac aggtgacccg   1140
gccagaccaa gcccgcatgg acattaggtt agccaagacc ctggtcctga tcctggtggt   1200
gttgatcatc tgctggggcc ctctgcttgc aatcatggtg tatgatgtct ttgggaagat   1260
gaacaagctc attaagacgg tgtttgcatt ctgcagtatg ctctgcctgc tgaactccac   1320
cgtgaacccc atcatctatg ctctgaggag taaggacctg cgacacgctt ccggagcat    1380
gtttccctct tgtgaaggca ctgcgcagcc tctggataac agcatggggg actcggactg   1440
cctgcacaaa cacgcaaaca atgcagccag tgttcacagg gccgcagaaa gctgcatcaa   1500
gagcacggtc aagattgcca aggtaaccat gtctgtgtcc acagacacgt ctgccgaggc   1560
tctgtgagcc tgatgcctcc ctggcagcac aggaaaagaa tttttttttt taagctcaaa   1620
atctagaaga gtctattgtc tccttggtta tatttttta actttaccat gctcaatgaa   1680
aaggtgattg ccacatgtca cttatttgct tagtttccgt ttgggctaat cttccggggt   1740
tcgtaggaaa cctt                                                     1755
```

<210> SEQ ID NO 89
<211> LENGTH: 471
<212> TYPE: PRT
<213> ORGANISM: Homo sapiens

<400> SEQUENCE: 89

```
Met Lys Ser Ile Leu Asp Gly Leu Ala Asp Thr Thr Phe Arg Thr Ile
 1               5                  10                  15
```

```
Thr Thr Asp Leu Leu Tyr Val Gly Ser Asn Asp Ile Gln Tyr Glu Asp
            20                  25                  30

Ile Lys Gly Asp Met Ala Ser Lys Leu Gly Tyr Phe Pro Gln Lys Phe
        35                  40                  45

Pro Leu Thr Ser Phe Arg Gly Ser Pro Phe Gln Glu Lys Met Thr Ala
    50                  55                  60

Gly Asp Asn Pro Gln Leu Val Pro Ala Asp Gln Val Asn Ile Thr Glu
65                  70                  75                  80

Phe Tyr Asn Lys Ser Leu Ser Ser Phe Lys Glu Asn Glu Glu Asn Ile
                85                  90                  95

Gln Cys Gly Glu Asn Phe Met Asp Ile Glu Cys Phe Met Val Leu Asn
            100                 105                 110

Pro Ser Gln Gln Leu Ala Ile Ala Val Leu Ser Leu Thr Leu Gly Thr
            115                 120                 125

Phe Thr Val Leu Glu Asn Leu Leu Val Leu Cys Val Ile Leu His Ser
        130                 135                 140

Arg Ser Leu Arg Cys Arg Pro Ser Tyr His Phe Ile Gly Ser Leu Ala
145                 150                 155                 160

Val Ala Asp Leu Leu Gly Ser Val Ile Phe Val Tyr Ser Phe Ile Asp
                165                 170                 175

Phe His Val Phe His Arg Lys Asp Ser Arg Asn Val Phe Leu Phe Lys
            180                 185                 190

Leu Gly Gly Val Thr Ala Ser Phe Thr Ala Ser Val Gly Ser Leu Phe
                195                 200                 205

Leu Thr Ala Ile Asp Arg Tyr Ile Ser Ile His Arg Pro Leu Ala Tyr
    210                 215                 220

Lys Arg Ile Val Thr Arg Pro Lys Ala Val Val Ala Phe Cys Leu Met
225                 230                 235                 240

Trp Thr Ile Ala Ile Val Ile Ala Val Leu Pro Leu Leu Gly Trp Asn
            245                 250                 255

Cys Glu Lys Leu Gln Ser Val Cys Ser Asp Ile Phe Pro His Ile Asp
            260                 265                 270

Glu Thr Tyr Leu Met Phe Trp Ile Gly Val Thr Ser Val Leu Leu Leu
        275                 280                 285

Phe Ile Val Tyr Ala Tyr Met Tyr Ile Leu Trp Lys Ala His Ser His
    290                 295                 300

Ala Val Arg Met Ile Gln Arg Gly Thr Gln Lys Ser Ile Ile Ile His
305                 310                 315                 320

Thr Ser Glu Asp Gly Lys Val Gln Val Thr Arg Pro Asp Gln Ala Arg
                325                 330                 335

Met Asp Ile Arg Leu Ala Lys Thr Leu Val Leu Ile Leu Val Val Leu
            340                 345                 350

Ile Ile Cys Trp Gly Pro Leu Leu Ala Ile Met Val Tyr Asp Val Phe
            355                 360                 365

Gly Lys Met Asn Lys Leu Ile Lys Thr Val Phe Ala Phe Cys Ser Met
    370                 375                 380

Leu Cys Leu Leu Asn Ser Thr Val Asn Pro Ile Ile Tyr Ala Leu Arg
385                 390                 395                 400

Ser Lys Asp Leu Arg His Ala Phe Arg Ser Met Phe Pro Ser Cys Glu
                405                 410                 415

Gly Thr Ala Gln Pro Leu Asp Asn Ser Met Gly Asp Ser Asp Cys Leu
            420                 425                 430
```

```
His Lys His Ala Asn Asn Ala Ala Ser Val His Arg Ala Ala Glu Ser
        435                 440                 445

Cys Ile Lys Ser Thr Val Lys Ile Ala Lys Val Thr Met Ser Val Ser
        450                 455                 460

Thr Asp Thr Ser Ala Glu Ala
465                 470

<210> SEQ ID NO 90
<211> LENGTH: 471
<212> TYPE: PRT
<213> ORGANISM: Homo sapiens

<400> SEQUENCE: 90

Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp
                20                  25                  30

Ile Lys Gly Asp Met Ala Ser Lys Leu Gly Tyr Phe Pro Gln Lys Phe
            35                  40                  45

Pro Leu Thr Ser Phe Arg Gly Ser Pro Phe Gln Glu Lys Met Thr Ala
    50                  55                  60

Gly Asp Asn Pro Gln Leu Val Pro Ala Asp Gln Val Asn Ile Thr Glu
65                  70                  75                  80

Phe Tyr Asn Lys Ser Leu Ser Phe Lys Glu Asn Glu Glu Asn Ile
                85                  90                  95

Gln Cys Gly Glu Asn Phe Met Asp Ile Glu Cys Phe Met Val Leu Asn
            100                 105                 110

Pro Ser Gln Gln Leu Ala Ile Ala Val Leu Ser Leu Thr Leu Gly Thr
        115                 120                 125

Phe Thr Val Leu Glu Asn Leu Leu Val Leu Cys Val Ile Leu His Ser
    130                 135                 140

Arg Ser Leu Arg Cys Arg Pro Ser Tyr His Phe Ile Gly Ser Leu Ala
145                 150                 155                 160

Val Ala Asp Leu Leu Gly Ser Val Ile Phe Val Tyr Ser Phe Ile Asp
                165                 170                 175

Phe His Val Phe His Arg Lys Asp Ser Arg Asn Val Phe Leu Phe Lys
            180                 185                 190

Leu Gly Gly Val Thr Ala Ser Leu Thr Ala Ser Val Gly Ser Leu Phe
        195                 200                 205

Leu Thr Ala Ile Asp Arg Tyr Ile Ser Ile His Arg Pro Leu Ala Tyr
    210                 215                 220

Lys Arg Ile Val Thr Arg Pro Lys Ala Val Val Ala Phe Cys Leu Met
225                 230                 235                 240

Trp Thr Ile Ala Ile Val Ile Ala Val Leu Pro Leu Leu Gly Trp Asn
                245                 250                 255

Cys Glu Lys Leu Gln Ser Val Cys Ser Asp Ile Phe Pro His Ile Asp
            260                 265                 270

Glu Thr Tyr Leu Met Phe Trp Ile Gly Val Thr Ser Val Leu Leu Leu
        275                 280                 285

Phe Ile Val Tyr Ala Tyr Met Tyr Ile Leu Trp Lys Ala His Ser His
    290                 295                 300

Ala Val Arg Met Ile Gln Arg Gly Thr Gln Lys Ser Ile Ile Ile His
305                 310                 315                 320

Thr Ser Glu Asp Gly Lys Val Gln Val Thr Arg Pro Asp Gln Ala Arg
                325                 330                 335
```

```
Met Asp Ile Arg Leu Ala Lys Thr Leu Val Leu Ile Leu Val Val Leu
            340                 345                 350
Ile Ile Cys Trp Gly Pro Leu Leu Ala Ile Met Val Tyr Asp Val Phe
        355                 360                 365
Gly Lys Met Asn Lys Leu Ile Lys Thr Val Phe Ala Phe Cys Ser Met
    370                 375                 380
Leu Cys Leu Leu Asn Ser Thr Val Asn Pro Ile Ile Tyr Ala Leu Arg
385                 390                 395                 400
Ser Lys Asp Leu Arg His Ala Phe Arg Ser Met Phe Pro Ser Cys Glu
                405                 410                 415
Gly Thr Ala Gln Pro Leu Asp Asn Ser Met Gly Asp Ser Asp Cys Leu
            420                 425                 430
His Lys His Ala Asn Asn Ala Ala Ser Val His Arg Ala Ala Glu Ser
        435                 440                 445
Cys Ile Lys Ser Thr Val Lys Ile Ala Lys Val Thr Met Ser Val Ser
    450                 455                 460
Thr Asp Thr Ser Ala Glu Ala
465                 470

<210> SEQ ID NO 91
<211> LENGTH: 2152
<212> TYPE: DNA
<213> ORGANISM: Homo sapiens

<400> SEQUENCE: 91
ccaggcgggg cgagccgcgg gagagtggag ggcaggcgcc tgggctgggg gcggggacca        60
ggcggggcag ggggcaggga gaggagggcg gcgggagcct gagccggaat cgcagcgtga       120
gcaggtggag ccgcggtggg agccgccggg tcgagctgag taaggcggcg ggctcggcgg       180
gggccatgga gctgctaaag ctgaaccgga gcgtgcaggg aaccggaccc gggccggggg       240
cttccctgtg ccgcccgggg gcgcctctcc tcaacagcag cagtgtgggc aacctcagct       300
gcgagccccc tcgcattcgc ggagccggga cacgagaatt ggagctggcc attagaatca       360
ctctttacgc agtgatcttc ctgatgagcg ttggaggaaa tatgctcatc atcgtggtcc       420
tgggactgag ccgccgcctg aggactgtca ccaatgcctt cctcctctca ctggcagtca       480
gcgacctcct gctggctgtg gcttgcatgc ccttcaccct cctgcccaat ctcatgggca       540
cattcatctt tggcaccgtc atctgcaagg cggtttccta cctcatgggg gtgtctgtga       600
gtgtgtccac gctaagcctc gtggccatcg cactggagcg atatagcgcc atctgccgac       660
cactgcaggc acgagtgtgg cagacgcgct cccacgcggc tcgcgtgatt gtagccacgt       720
ggctgctgtc cggactactc atggtgccct accccgtgta cactgtcgtg caaccagtgg       780
ggcctcgtgt gctgcagtgc gtgcatcgct ggcccagtgc gcgggtccgc cagacctggt       840
ccgtactgct gcttctgctc ttgttcttca tcccaggtgt ggttatgccc gtggcctacg       900
gcttaatctc tcgcgagctc tacttagggc ttcgctttga cggcgacagt gacagcgaca       960
gccaaagcag ggtccgaaac caaggcgggc tgccaggggc tgttcaccag aacgggcgtt      1020
gccggcctga gactggcgcg gttggcaaag acagcgatgg ctgctacgtg caacttccac      1080
gttcccggcc tgccctggag ctgacggcgc tgacggctcc tgggccggga tccggctccc      1140
ggcccaccca ggcccagctg ctggctaaga gcgcgtggt gcgaatgttg ctggtgatcg      1200
ttgtgctttt ttttctgtgt tggttgccag tttatagtgc caacacgtgg cgcgcctttg      1260
atggcccggg tgcacaccga gcactctcgg gtgctcctat ctccttcatt cacttgctga      1320
```

```
gctacgcctc ggcctgtgtc aaccccctgg tctactgctt catgcaccgt cgctttcgcc    1380
aggcctgcct ggaaacttgc gctcgctgct gcccccggcc tccacgagct cgccccaggg    1440
ctcttcccga tgaggaccct cccactccct ccattgcttc gctgtccagg cttagctaca    1500
ccaccatcag cacactgggc cctggctgag gagtagaggg gccgtggggg ttgaggcagg    1560
gcaaatgaca tgcactgacc cttccagaca tagaaaacac aaaccacaac tgacacagga    1620
aaccaacacc caaagcatgg actaaccccca agcacaggaa aaggtagctt acctgactca    1680
gaggaataag aatggagcag tacatgggaa aggaggcatg cctctgatat gggactgagc    1740
ctggcccata gaaacatgac actgaccttg gagagacaca gcgtccctag cagtgaacta    1800
tttctacaca gtgggaactc tgacaagggc tgacctgcct ctcacacaca tagattaatg    1860
gcactgattg ttttagagac tatggagcct ggcacaggac tgactctggg atgctcctag    1920
ttgacctcac agtgaccttc ccaatcagtc actgaaaata ccgtcaggcc taatctcata    1980
cctctgacca acaggctgtt cgcactgaaa aggttcttca tcccttttcca gttaaggacc    2040 gtggccctgc cctctccttc cttacccaaa ctgttcaaga aataataaat tgtttggctt    2100
cctcctgaaa aaaaaaaaaa aaaaaaaaa aaaaaaaaa aaaaaaaaaa aa              2152

<210> SEQ ID NO 92
<211> LENGTH: 2152
<212> TYPE: DNA
<213> ORGANISM: Homo sapiens

<400> SEQUENCE: 92
ccaggcgggg cgagccgcgg gagagtggag ggcaggcgcc tgggctgggg gcggggacca      60
ggcggggcag ggggcaggga gaggagggcg gcggagcct gagccggaat cgcagcgtga     120
gcaggtggag ccgcggtggg agccgccggg tcgagctgag taaggcggcg ggctcggcgg     180
gggccatgga gctgctaaag ctgaaccgga gcgtgcaggg aaccggaccc gggccggggg     240
cttccctgtg ccgcccgggg gcgcctctcc tcaacagcag cagtgtgggc aacctcagct     300
gcgagccccc tcgcattcgc ggagccggga cacgagaatt ggagctggcc attagaatca     360
ctctttacgc agtgatcttc ctgatgagcg ttggaggaaa tatgctcatc atcgtggtcc     420
tgggactgag ccgccgcctg aggactgtca ccaatgcctt cctcctctca ctggcagtca     480
gcgacctcct gctggctgtg gcttgcatgc ccttcaccct cctgcccaat ctcatgggca     540
cattcatctt tggcaccgtc atctgcaagg cggtttccta cctcatgggg gtgtctgtga     600
gtgtgtccac gctaagcctc gtggccatcg cactggagcg atatagcgcc atctgccgac     660
cactgcaggc acgagtgtgg cagacgcgct cccacgcggc tcgcgtgatt gtagccacgt     720
ggctgctgtc cggactactc atggtgccct accccgtgta cactgtcgtg caaccagtgg     780
ggcctcgtgt gctgcagtgc gtgcatcgct ggcccagtgc gcgggtccgc cagacctggt     840
ccgtactgct gcttcagctc ttgttcttca tcccaggtgt ggttatggcc gtggcctacg     900
gcttaatctc tcgcgagctc tacttagggc ttcgctttga cggcgacagt gacagcgaca     960
gccaaagcag ggtccgaaac caaggcgggc tgccaggggc tgttcaccag aacgggcgtt    1020
gccgccctga gactggcgcg gttggcaaag acagcgatgg ctgctacgtg caacttccac    1080
gttcccggcc tgccctggag ctgacggcgc tgacggctcc tgggccggga tccggctccc    1140
ggcccaccca ggccaagctg ctggctaaga agcgcgtggt gcgaatgttg ctggtgatcg    1200
ttgtgctttt ttttctgtgt tggttgccag tttatagtgc caacacgtgg cgcgcctttg    1260
```

```
atggcccggg tgcacaccga gcactctcgg gtgctcctat ctccttcatt cacttgctga  1320
gctacgcctc ggcctgtgtc aaccccctgg tctactgctt catgcaccgt cgctttcgcc  1380
aggcctgcct ggaaacttgc gctcgctgct gccccggcc tccacgagct cgccccaggg  1440
ctcttcccga tgaggaccct cccactccct ccattgcttc gctgtccagg cttagctaca  1500
ccaccatcag cacactgggc cctggctgag gagtagaggg gccgtggggg ttgaggcagg  1560
gcaaatgaca tgcactgacc cttccagaca tagaaaacac aaaccacaac tgacacagga  1620
aaccaacacc caaagcatgg actaacccca agcacaggaa aaggtagctt acctgactca  1680
gaggaataag aatggagcag tacatgggaa aggaggcatg cctctgatat gggactgagc  1740
ctggcccata gaaacatgac actgaccttg gagagacaca gcgtccctag cagtgaacta  1800
tttctacaca gtgggaactc tgacaagggc tgacctgcct ctcacacaca tagattaatg  1860
gcactgattg tttttagagac tatggagcct ggcacaggac tgactctggg atgctcctag  1920
ttgacctcac agtgaccttc ccaatcagtc actgaaaata ccgtcaggcc taatctcata  1980
cctctgacca acaggctgtt cgcactgaaa aggttcttca tcccttttcca gttaaggacc  2040 gtggccctgc cctctccttc cttacccaaa ctgttcaaga ataataaat tgtttggctt  2100 cctcctgaaa aaaaaaaaaa aaaaaaaaaa aaaaaaaaaa aaaaaaaaaa aa  2152
```

<210> SEQ ID NO 93  
<211> LENGTH: 447  
<212> TYPE: PRT  
<213> ORGANISM: Homo sapiens

<400> SEQUENCE: 93

```
Met Glu Leu Leu Lys Leu Asn Arg Ser Val Gln Gly Thr Gly Pro Gly
 1               5                  10                  15

Pro Gly Ala Ser Leu Cys Arg Pro Gly Ala Pro Leu Leu Asn Ser Ser
            20                  25                  30

Ser Val Gly Asn Leu Ser Cys Glu Pro Pro Arg Ile Arg Gly Ala Gly
        35                  40                  45

Thr Arg Glu Leu Glu Leu Ala Ile Arg Ile Thr Leu Tyr Ala Val Ile
    50                  55                  60

Phe Leu Met Ser Val Gly Gly Asn Met Leu Ile Ile Val Val Leu Gly
65                  70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
        115                 120                 125

Ala Val Ser Tyr Leu Met Gly Val Ser Val Ser Val Ser Thr Leu Ser
    130                 135                 140

Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170                 175

Ala Thr Trp Leu Leu Ser Gly Leu Leu Met Val Pro Tyr Pro Val Tyr
            180                 185                 190

Thr Val Val Gln Pro Val Gly Pro Arg Val Leu Gln Cys Val His Arg
        195                 200                 205

Trp Pro Ser Ala Arg Val Arg Gln Thr Trp Ser Val Leu Leu Leu Leu
    210                 215                 220
```

```
Leu Leu Phe Phe Ile Pro Gly Val Val Met Ala Val Ala Tyr Gly Leu
225                 230                 235                 240

Ile Ser Arg Glu Leu Tyr Leu Gly Leu Arg Phe Asp Gly Asp Ser Asp
                245                 250                 255

Ser Asp Ser Gln Ser Arg Val Arg Asn Gln Gly Gly Leu Pro Gly Ala
            260                 265                 270

Val His Gln Asn Gly Arg Cys Arg Pro Glu Thr Gly Ala Val Gly Lys
        275                 280                 285

Asp Ser Asp Gly Cys Tyr Val Gln Leu Pro Arg Ser Arg Pro Ala Leu
    290                 295                 300

Glu Leu Thr Ala Leu Thr Ala Pro Gly Pro Gly Ser Gly Ser Arg Pro
305                 310                 315                 320

Thr Gln Ala Lys Leu Ala Lys Lys Arg Val Val Arg Met Leu Leu
                325                 330                 335

Val Ile Val Val Leu Phe Phe Leu Cys Trp Leu Pro Val Tyr Ser Ala
                340                 345                 350

Asn Thr Trp Arg Ala Phe Asp Gly Pro Gly Ala His Arg Ala Leu Ser
                355                 360                 365

Gly Ala Pro Ile Ser Phe Ile His Leu Leu Ser Tyr Ala Ser Ala Cys
            370                 375                 380

Val Asn Pro Leu Val Tyr Cys Phe Met His Arg Arg Phe Arg Gln Ala
385                 390                 395                 400

Cys Leu Glu Thr Cys Ala Arg Cys Cys Pro Arg Pro Pro Arg Ala Arg
                405                 410                 415

Pro Arg Ala Leu Pro Asp Glu Asp Pro Pro Thr Pro Ser Ile Ala Ser
                420                 425                 430

Leu Ser Arg Leu Ser Tyr Thr Thr Ile Ser Thr Leu Gly Pro Gly
                435                 440                 445

<210> SEQ ID NO 94
<211> LENGTH: 447
<212> TYPE: PRT
<213> ORGANISM: Homo sapiens

<400> SEQUENCE: 94

Met Glu Leu Leu Lys Leu Asn Arg Ser Val Gln Gly Thr Gly Pro Gly
1               5                   10                  15

Pro Gly Ala Ser Leu Cys Arg Pro Gly Ala Pro Leu Leu Asn Ser Ser
                20                  25                  30

Ser Val Gly Asn Leu Ser Cys Glu Pro Pro Arg Ile Arg Gly Ala Gly
            35                  40                  45

Thr Arg Glu Leu Glu Leu Ala Ile Arg Ile Thr Leu Tyr Ala Val Ile
    50                  55                  60

Phe Leu Met Ser Val Gly Gly Asn Met Leu Ile Ile Val Val Leu Gly
65              70                  75                  80

Leu Ser Arg Arg Leu Arg Thr Val Thr Asn Ala Phe Leu Leu Ser Leu
                85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
        115                 120                 125

Ala Val Ser Tyr Leu Met Gly Val Ser Val Ser Val Ser Thr Leu Ser
    130                 135                 140

Leu Val Ala Ile Ala Leu Glu Arg Tyr Ser Ala Ile Cys Arg Pro Leu
```

-continued

```
            145                 150                 155                 160
Gln Ala Arg Val Trp Gln Thr Arg Ser His Ala Ala Arg Val Ile Val
                165                 170                 175
Ala Thr Trp Leu Leu Ser Gly Leu Leu Met Val Pro Tyr Pro Val Tyr
            180                 185                 190
Thr Val Val Gln Pro Val Gly Pro Arg Val Leu Gln Cys Val His Arg
        195                 200                 205
Trp Pro Ser Ala Arg Val Arg Gln Thr Trp Ser Val Leu Leu Leu Gln
    210                 215                 220
Leu Leu Phe Phe Ile Pro Gly Val Val Met Ala Val Ala Tyr Gly Leu
225                 230                 235                 240
Ile Ser Arg Glu Leu Tyr Leu Gly Leu Arg Phe Asp Gly Asp Ser Asp
                245                 250                 255
Ser Asp Ser Gln Ser Arg Val Arg Asn Gln Gly Gly Leu Pro Gly Ala
            260                 265                 270
Val His Gln Asn Gly Arg Cys Arg Pro Glu Thr Gly Ala Val Gly Lys
        275                 280                 285
Asp Ser Asp Gly Cys Tyr Val Gln Leu Pro Arg Ser Arg Pro Ala Leu
    290                 295                 300
Glu Leu Thr Ala Leu Thr Ala Pro Gly Pro Gly Ser Gly Ser Arg Pro
305                 310                 315                 320
Thr Gln Ala Lys Leu Leu Ala Lys Lys Arg Val Val Arg Met Leu Leu
                325                 330                 335
Val Ile Val Val Leu Phe Phe Leu Cys Trp Leu Pro Val Tyr Ser Ala
            340                 345                 350
Asn Thr Trp Arg Ala Phe Asp Gly Pro Gly Ala His Arg Ala Leu Ser
        355                 360                 365
Gly Ala Pro Ile Ser Phe Ile His Leu Leu Ser Tyr Ala Ser Ala Cys
    370                 375                 380
Val Asn Pro Leu Val Tyr Cys Phe Met His Arg Arg Phe Arg Gln Ala
385                 390                 395                 400
Cys Leu Glu Thr Cys Ala Arg Cys Cys Pro Arg Pro Pro Arg Ala Arg
                405                 410                 415
Pro Arg Ala Leu Pro Asp Glu Asp Pro Pro Thr Pro Ser Ile Ala Ser
            420                 425                 430
Leu Ser Arg Leu Ser Tyr Thr Thr Ile Ser Thr Leu Gly Pro Gly
        435                 440                 445

<210> SEQ ID NO 95
<211> LENGTH: 4281
<212> TYPE: DNA
<213> ORGANISM: Homo sapiens

<400> SEQUENCE: 95
ttgaggcccg gggagagccg gggagccggg cccgcgcgcc gagatgttgc tgctgctgct      60
actggcgcca ctcttcctcc gcccccgggg cgcgggcggg gcgcagaccc ccaacgccac     120
ctcagaaggt tgccagatca tacacccgcc ctgggaaggg ggcatcaggt accgggcct     180 gactcgggac caggtgaagg ctatcaactt cctgccagtg gactatgaga ttgagtatgt     240
gtgccggggg gagcgcgagg tggtgggggcc caaggtccgc aagtgcctgg ccaacggctc     300
ctggacagat atggacacac ccagccgctg tgtccgaatc tgctccaagt cttatttgac     360
cctggaaaat gggaaggttt tcctgacggg tggggacctc ccagctctgg acggagcccg     420
ggtggatttc cggtgtgacc ccgacttcca tctggtgggc agctccccgga gcatctgtag     480
```

```
tcagggccag tggagcaccc ccaagcccca ctgccaggtg aatcgaacgc cacactcaga   540
acggcgcgca gtgtacatcg gggcactgtt tcccatgagc gggggctggc caggggggca   600
ggcctgccaa cccgcggtgg agatggcgct ggaggacgtg aatagccgca gggacatcct   660
gccggactat gagctcaagc tcatccacca cgacagcaag tgtgatccag gccaagccac   720
caagtaccta tatgagctgc tctacaacga ccctatcaag atcatcctta tgcctggctg   780
cagctctgtc tccacgctgg tggctgaggc tgctaggatg tggaacctca ttgtgctttc   840
ctatggctcc agctcaccag ccctgtcaaa ccggcagcgt ttccccactt tcttccgaac   900
gcacccatca gccacactcc acaaccctac ccgcgtgaaa ctctttgaaa agtggggctg   960
gaagaagatt gctaccatcc agcagaccac tgaggtcttc acttcgactc tggacgacct  1020
ggaggaacga gtgaaggagg ctggaattga gattactttc cgccagagtt tcttctcaga  1080
tccagctgtg cccgtcaaaa acctgaagcg ccaggatgcc cgaatcatcg tgggactttt  1140
ctatgagact gaagcccgga agttttttg tgaggtgtac aaggagcgtc tctttgggaa  1200
gaagtacgtc tggttcctca ttgggtggta tgctgacaat tggttcaaga tctacgaccc  1260
ttctatcaac tgcacagtgg atgagatgac tgaggcggtg gagggccaca tcacaactga  1320
gattgtcatg ctgaatcctg ccaatacccg cagcatttcc aacatgacat cccaggaatt  1380
tgtggagaaa ctaaccaagc gactgaaaag acaccctgag gagacaggag cttccagga   1440
ggcaccgctg gcctatgatg ccatctgggc cttggcactg gccctgaaca agacatctgg  1500
aggaggcggc cgttctggtg tgcgcctgga ggacttcaac tacaacaacc agaccattac  1560
cgaccaaatc taccgggcaa tgaactcttc gtcctttgag ggtgtctctg gccatgtggt  1620
gtttgatgcc agcggctctc ggatggcatg gacgcttatc gagcagcttc agggtggcag  1680
ctacaagaag attggctact atgacagcac caaggatgat cttcctggt ccaaaacaga   1740
taaatggatt ggagggtccc ccccagctga ccagaccctg gtcatcaaga cattccgctt  1800
cctgtcacag aaactcttta tctccgtctc agttctctcc agcctgggca ttgtcctagc  1860
tgttgtctgt ctgtccttta acatctacaa ctcacatgtc cgttatatcc agaactcaca  1920
gcccaacctg aacaacctga ctgctgtggg ctgctcactg gctttagctg ctgtcttccc  1980
cctgggctc gatggttacc acattgggag gaaccagttt cctttcgtct gccaggcccg  2040
cctctggctc ctgggcctgg gctttagtct gggctacggt tccatgttca ccaagatttg  2100
gtgggtccac acggtcttca caagaaggaa agaaaagaag gagtggagga agactctgga  2160
accctggaag ctgtatgcca cagtgggcct gctggtgggc atggatgtcc tcactctcgc  2220
catctggcag atcgtggacc ctctgcaccg gaccattgag acatttgcca aggaggaacc  2280
taaggaagat attgacgtct ctattctgcc ccagctggag cattgcagct ccaggaagat  2340
gaatacatgg cttggcattt tctatggtta caagggggctg ctgctgctgc tgggaatctt  2400
ccttgcttat gagaccaaga gtgtgtccac tgagaagatc aatgatcacc gggctgtggg  2460
catggctatc tacaatgtgg cagtcctgtg cctcatcact gctcctgtca ccatgattct  2520
gtccagccag caggatgcag cctttgcctt tgcctctctt gccatagttt tctcctccta  2580
tatcactctt gttgtgctct ttgtgcccaa gatgcgcagg ctgatcaccc gaggggaatg  2640
gcagtcggag gcgcaggaca ccatgaagac agggtcatcg accaacaaca acgaggagga  2700
gaagtcccgg ctgttggaga aggagaaccg tgaactggaa aagatcattg ctgagaaaga  2760
ggagcgtgtc tctgaactgc gccatcaact ccagtctcgg cagcagctcc gctcccggcg  2820
```

```
ccacccaccg acaccccccag aaccctctgg gggcctgccc aggggacccc ctgagccccc    2880
cgaccggctt agctgtgatg ggagtcgagt gcatttgctt tataagtgag ggtagggtga    2940
gggaggacag gccagtaggg ggagggaaag ggagagggga agggcagggg actcaggaag    3000
caggggtcc  ccatcccag  ctgggaagaa catgctatcc aatctcatct cttgtaaata    3060
catgtccccc tgtgagttct gggctgattt ggtctctca  tacctctggg aaacagacct    3120
ttttctctct tactgcttca tgtaattttg tatcacctct tcacaattta gttcgtacct    3180
ggcttgaagc tgctcactgc tcacacgctg cctcctcagc agcctcactg catctttctc    3240
ttcccatgca acaccctctt ctagttacca cggcaacccc tgcagctcct ctgcctttgt    3300
gctctgttcc tgtccagcag gggtctccca acaagtgctc tttccacccc aaagggggcct   3360
ctccttttct ccactgtcat aatctctttc catcttactt gcccttctat actttctcac    3420
atgtggctcc ccctgaattt tgcttccttt gggagctcat tcttttcgcc aaggctcaca    3480
tgctccttgc ctctgctctg tgcactcacg ctcagcacac atgcatcctc ccctctcctg    3540
cgtgtgccca ctgaacatgc tcatgtgtac acacgctttt cccgtatgct ttcttcatgt    3600
tcagtcacat gtgctctcgg gtgccctgca ttcacagcta cgtgtgcccc tctcatggtc    3660
atgggtctgc ccttgagcgt gtttgggtag gcatgtgcaa tttgtctagc atgctgagtc    3720
atgtctttcc tatttgcaca cgtccatgtt tatccatgta cttttccctgt gtaccctcca   3780
tgtaccttgt gtactttctt cccttaaatc atggtattct tctgacagag ccatatgtac    3840
cctaccctgc acattgttat gcacttttcc ccaattcatg tttggtgggg ccatccacac    3900
cctctccttg tcacagaatc tccatttctg ctcagattcc ccccatctcc attgcattca    3960
tgtactaccc tcagtctaca ctcacaatca tcttctccca agactgctcc cttttgtttt    4020
gtgttttttt gagggaatt  aaggaaaaat aagtggggc  aggtttggag agctgcttcc    4080
agtggatagt tgatgagaat cctgaccaaa ggaaggcacc cttgactgtt gggatagaca    4140
gatggaccta tggggtggga ggtggtgtcc cttcacact  gtggtgtctc ttggggaagg    4200
atctccccga atctcaataa accagtgaac agtgtgaaaa aaaaaaaaaa aaaaaaaaa     4260
aaaaaaaaaa aaaaaaaaa  a                                              4281
```

<210> SEQ ID NO 96
<211> LENGTH: 4281
<212> TYPE: DNA
<213> ORGANISM: Homo sapiens

<400> SEQUENCE: 96

```
ttgaggcccg gggagagccg gggagccggg cccgcgcgcc gagatgttgc tgctgctgct     60
actggcgcca ctcttcctcc gccccccggg cgcgggcggg gcgcagaccc ccaacgccac    120
ctcagaaggt tgccagatca tacacccgcc ctgggaaggg ggcatcaggt accggggcct    180
gactcgggac caggtgaagg ctatcaactt cctgccagtg gactatgaga ttgagtatgt    240
gtgccggggg gagcgcgagg tggtggggcc caaggtccgc aagtgcctgg ccaacggctc    300
ctggacagat atggacacac tcagccgctg tgtccgaatc tgctccaagt cttatttgac    360
cctggaaaat gggaaggttt tcctgacggg tggggacctc ccagctctgg acggagcccg    420
ggtggatttc cggtgtgacc ccgacttcca tctggtgggc agctcccgga gcatctgtag    480
tcagggccag tggagcaccc ccaagcccca ctgccaggtg aatcgaacgc cacactcaga    540
acggcgcgca gtgtacatcg gggcactgtt tccatgagc  ggggggctggc cagggggcca   600
ggcctgccag cccgcggtgg agatggcgct ggaggacgtg aatagccgca gggacatcct    660
```

```
gccggactat gagctcaagc tcatccacca cgacagcaag tgtgatccag gccaagccac    720
caagtaccta tatgagctgc tctacaacga ccctatcaag atcatcctta tgcctggctg    780
cagctctgtc tccacgctgg tggctgaggc tgctaggatg tggaacctca ttgtgctttc    840
ctatggctcc agctcaccag ccctgtcaaa ccggcagcgt ttccccactt tcttccgaac    900
gcacccatca gccacactcc acaaccctac ccgcgtgaaa ctcttgaaa agtggggctg     960
gaagaagatt gctaccatcc agcagaccac tgaggtcttc acttcgactc tggacgacct   1020
ggaggaacga gtgaaggagg ctggaattga gattactttc cgccagagtt tcttctcaga   1080
tccagctgtg cccgtcaaaa acctgaagcg ccaggatgcc cgaatcatcg tgggacttt    1140
ctatgagact gaagcccgga agttttttg tgaggtgtac aaggagcgtc tctttgggaa   1200
gaagtacgtc tggttcctca ttgggtggta tgctgacaat tggttcaaga tctacgaccc   1260
ttctatcaac tgcacagtgg atgagatgac tgaggcggtg gagggccaca tcacaactga   1320
gattgtcatg ctgaatcctg ccaatacccg cagcatttcc aacatgacat cccaggaatt   1380
tgtggagaaa ctaaccaagc gactgaaaag acaccctgag gagacaggag cttccagga    1440
ggcaccgctg gcctatgatg ccatctgggc cttggcactg gccctgaaca agacatctgg   1500
aggaggcggc cgttctggtg tgcgcctgga ggacttcaac tacaacaacc agaccattac   1560
cgaccaaatc taccgggcaa tgaactcttc gtcctttgag ggtgtctctg gccatgtggt   1620
gtttgatgcc agcggctctc ggatggcatg gacgcttatc gagcagcttc agggtggcag   1680
ctacaagaag attggctact atgacagcac caaggatgat ctttcctggt ccaaaacaga   1740
taaatggatt ggagggtccc cccagctgcc cagaccctg gtcatcaaga cattccgctt    1800
cctgtcacag aaactcttta tctccgtctc agttctctcc agcctgggca ttgtcctagc   1860
tgttgtctgt ctgtccttta acatctacaa ctcacatgtc cgttatatcc agaactcaca   1920
gcccaacctg aacaacctga ctgctgtggg ctgctcactg gctttagctg ctgtcttccc   1980
cctggggctc gatggttacc acattgggag gaaccagttt cctttcgtct gccaggcccg   2040
cctctggctc ctgggcctgg gctttagtct gggctacggt tccatgttca ccaagatttg   2100
gtgggtccac acggtcttca caaagaagga agaaaagaag gagtggagga agactctgga   2160
accctggaag ctgtatgcca cagtgggcct gctggtgggc atggatgtcc tcactctcgc   2220
catctggcag atcgtggacc ctctgcaccg gaccattgag acatttgcca aggaggaacc   2280
taaggaagat attgacgtct ctattctgcc ccagctggag cattgcagct ccaggaagat   2340
gaatacatgg cttggcattt tctatggtta caaggggctg ctgctgctgc tgggaatctt   2400
ccttgcttat gagaccaaga gtgtgtccac tgagaagatc aatgatcacc gggctgtggg   2460
catggctatc tacaatgtgg cagtcctgtg cctcatcact gctcctgtca ccatgattct   2520
gtccagccag caggatgcag cctttgcctt tgcctctctt gccatagttt tctcctccta   2580
tatcactctt gttgtgctct ttgtgcccaa gatgcgcagg ctgatcaccc gagggaatg    2640
gcagtcggag gcgcaggaca ccatgaagac agggtcatcg accaacaaca acgaggagga   2700
gaagtcccgg ctgttggaga aggagaaccg tgaactggaa aagatcattg ctgagaaaga   2760
ggagcgtgtc tctgaactgc gccatcaact ccagtctcgg cagcagctcc gctcccggcg   2820
ccacccaccg acacccccag aaccctctgg gggcctgccc aggggacccc ctgagccccc   2880
cgaccggctt agctgtgatg ggagtcgagt gcatttgctt tataagtgag gtagggtga    2940
gggaggacag gccagtaggg ggagggaaag ggagaggga agggcagggg actcaggaag   3000
```

-continued

```
caggggggtcc ccatccccag ctgggaagaa catgctatcc aatctcatct cttgtaaata   3060
catgtccccc tgtgagttct gggctgattt gggtctctca tacctctggg aaacagacct   3120
ttttctctct tactgcttca tgtaattttg tatcacctct tcacaattta gttcgtacct   3180
ggcttgaagc tgctcactgc tcacacgctg cctcctcagc agcctcactg catctttctc   3240
ttcccatgca acaccctctt ctagttacca cggcaacccc tgcagctcct ctgcctttgt   3300
gctctgttcc tgtccagcag gggtctccca acaagtgctc tttccacccc aaaggggcct   3360
ctccttttct ccactgtcat aatctctttc catcttactt gcccttctat actttctcac   3420
atgtggctcc ccctgaattt tgcttccttt gggagctcat tcttttcgcc aaggctcaca   3480
tgctccttgc ctctgctctg tgcactcacg ctcagcacac atgcatcctc ccctctcctg   3540
cgtgtgccca ctgaacatgc tcatgtgtac acacgctttt cccgtatgct ttcttcatgt   3600
tcagtcacat gtgctctcgg gtgccctgca ttcacagcta cgtgtgcccc tctcatggtc   3660
atgggtctgc ccttgagcgt gtttgggtag gcatgtgcaa tttgtctagc atgctgagtc   3720
atgtctttcc tatttgcaca cgtccatgtt tatccatgta ctttccctgt gtaccctcca   3780
tgtaccttgt gtactttctt cccttaaatc atggtattct tctgacagag ccatatgtac   3840
cctaccctgc acattgttat gcacttttcc ccaattcatg tttggtgggg ccatccacac   3900
cctctccttg tcacagaatc tccatttctg ctcagattcc ccccatctcc attgcattca   3960
tgtactaccc tcagtctaca ctcacaatca tcttctccca agactgctcc cttttgtttt   4020
gtgttttttt gaggggaatt aaggaaaaat aagtgggggc aggtttggag agctgcttcc   4080
agtggatagt tgatgagaat cctgaccaaa ggaaggcacc cttgactgtt gggatagaca   4140
gatggaccta tggggtggga ggtggtgtcc ctttcacact gtggtgtctc ttggggaagg   4200
atctccccga atctcaataa accagtgaac agtgtgaaaa aaaaaaaaaa aaaaaaaaaa   4260
aaaaaaaaaa aaaaaaaaaa a                                             4281
```

```

<210> SEQ ID NO 97
<211> LENGTH: 4281
<212> TYPE: DNA
<213> ORGANISM: Homo sapiens

<400> SEQUENCE: 97
ttgaggcccg gggagagccg gggagccggg cccgcgcgcc gagatgttgc tgctgctgct     60
actggcgcca ctcttcctcc gcccccgggg cgcgggcggg gcgcagaccc ccaacgccac    120
ctcagaaggt tgccagatca tacacccgcc ctgggaaggg ggcatcaggt accggggcct    180
gactcgggac caggtgaagg ctatcaactt cctgccagtg gactatgaga ttgagtatgt    240
gtgccggggg gagcgcgagg tggtggggcc caaggtccgc aagtgcctgg ccaacggctc    300
ctggacagat atggacacac ccagccgctg tgtccgaatc tgctccaagt cttatttgac    360
cctggaaaat gggaaggttt tcctgacggg tggggacctc ccagctctgg acggagcccg    420
ggtggatttc cggtgtgacc ccgacttcca tctggtgggc agctcccgga gcatctgtag    480
tcagggccag tggagcaccc ccaagcccca ctgccaggtg aatcgaacgc cacactcaga    540
acggcgcgca gtgtacatcg ggcactgtt tcccatgagc gggggctggc caggggggcca    600
ggcctgccag cccgcggtgg agatggcgct ggaggacgtg aatagccgca gggacatcct    660
gccggactat gagctcaagc tcatccacca cgacagcaag tgtgatccag gccaagccac    720
caagtaccta tatgagctgc tctacaacga ccctatcaag atcatcctta tgcctggctg    780
cagctctgtc tccacgctgg tggctgaggc tgctaggatg tggaacctca ttgtgctttc    840
```

-continued

```
ctatggctcc agctcaccag ccctgtcaaa ccggcagcgt ttccccactt tcttccgaac      900
gcacccatca gccacactcc acaaccctac ccgcgtgaaa ctctttgaaa agtggggctg      960
gaagaagatt gctaccatcc agcagaccac tgaggtcttc acttcgactc tggacgacct     1020
ggaggaacga gtgaaggagg ctggaattga gattactttc cgccagagtt tcttctcaga     1080
tccagctgtg cccgtcaaaa acctgaagcg ccaggatgcc cgaatcatcg tgggactttt     1140
ctatgagact gaagcccgga agttttttg tgaggtgtac aaggagcgtc tctttgggaa      1200
gaagtacgtc tggttcctca ttgggtggta tgctgacaat tggttcaaga tctacgaccc     1260
ttctatcaac tgcacagtgg atgagatgac tgaggcggtg gagggccaca tcacaactga     1320
gattgtcatg ctgaatcctg ccaatacccg cagcatttcc aacatgacat cccaggaatt     1380
tgtggagaaa ctaaccaagc gactgaaaag acaccctgag gagacaggag gcttccagga     1440
ggcaccgctg gcctatgatg ccatctgggc cttggcactg gccctgaaca agacatctgg     1500
aggaggcggc cgttctggtg tgcgcctgga ggacttcaac tacaacaacc agaccattac     1560
cgaccaaatc taccgggcaa tgaactcttc gtcctttgag ggtgtctctg gccatgtggt     1620
gtttgatgcc agcggctctc ggatggcatg gacgcttatc gagcagcctc agggtggcag     1680
ctacaagaag attggctact atgacagcac caaggatgat ctttcctggt ccaaaacaga     1740
taaatggatt ggagggtccc ccccagctga ccagaccctg gtcatcaaga cattccgctt     1800
cctgtcacag aaactcttta tctccgtctc agttctctcc agcctgggca ttgtcctagc     1860
tgttgtctgt ctgtcctta acatctacaa ctcacatgtc cgttatatcc agaactcaca      1920
gcccaacctg aacaacctga ctgctgtggg ctgctcactg gctttagctg ctgtcttccc     1980
cctggggctc gatggttacc acattgggag gaaccagttt cctttcgtct gccaggcccg     2040
cctctggctc ctgggcctgg gctttagtct gggctacggt tccatgttca ccaagatttg     2100
gtgggtccac acggtcttca caaagaagga agaaaagaag gagtggagga agactctgga     2160
accctggaag ctgtatgcca cagtgggcct gctggtgggc atggatgtcc tcactctcgc     2220
catctggcag atcgtggacc ctctgcaccg gaccattgag acatttgcca aggaggaacc     2280
taaggaagat attgacgtct ctattctgcc ccagctggag cattgcagct ccaggaagat     2340
gaatacatgg cttggcattt ctatggttta caaggggctg ctgctgctgc tgggaatctt     2400
ccttgcttat gagaccaaga gtgtgtccac tgagaagatc aatgatcacc gggctgtggg     2460
catggctatc tacaatgtgg cagtcctgtg cctcatcact gctcctgtca ccatgattct     2520
gtccagccag caggatgcag cctttgcctt tgcctctctt gccatagttt tctcctccta     2580
tatcactctt gttgtgctct ttgtgcccaa gatgcgcagg ctgatcaccc gaggggaatg     2640
gcagtcggag gcgcaggaca ccatgaagac agggtcatcg accaacaaca acgaggagga     2700
gaagtcccgc tgttggagag aggagaaccg tgaactggaa aagatcattg ctgagaaaga     2760
ggagcgtgtc tctgaactgc gccatcaact ccagtctcgg cagcagctcc gctcccggcg     2820
ccacccaccg acaccccag aaccctctgg gggcctgccc aggggacccc ctgagccccc      2880
cgaccggctt agctgtgatg ggagtcgagt gcatttgctt tataagtgag ggtagggtga     2940
gggaggacag gccagtaggg ggagggaaag ggagagggga agggcagggg actcaggaag     3000
cagggggtcc ccatccccag ctgggaagaa catgctatcc aatctcatct cttgtaaata     3060
catgtccccc tgtgagttct gggctgattt gggtctctca tacctctggg aaacagacct     3120
tttctctctct tactgcttca tgtaattttg tatcacctct tcacaattta gttcgtacct     3180
```

```
ggcttgaagc tgctcactgc tcacacgctg cctcctcagc agcctcactg catctttctc    3240
ttcccatgca acaccctctt ctagttacca cggcaacccc tgcagctcct ctgcctttgt    3300
gctctgttcc tgtccagcag gggtctccca acaagtgctc tttccacccc aaagggcct    3360
ctccttttct ccactgtcat aatctctttc catcttactt gcccttctat actttctcac    3420
atgtggctcc ccctgaattt tgcttccttt gggagctcat tcttttcgcc aaggctcaca    3480
tgctccttgc ctctgctctg tgcactcacg ctcagcacac atgcatcctc ccctctcctg    3540
cgtgtgccca ctgaacatgc tcatgtgtac acacgctttt cccgtatgct tcttcatgt    3600
tcagtcacat gtgctctcgg gtgccctgca ttcacagcta cgtgtgcccc tctcatggtc    3660
atgggtctgc ccttgagcgt gtttgggtag gcatgtgcaa tttgtctagc atgctgagtc    3720
atgtctttcc tatttgcaca cgtccatgtt tatccatgta ctttccctgt gtaccctcca    3780
tgtaccttgt gtactttctt cccttaaatc atggtattct tctgacagag ccatatgtac    3840
cctaccctgc acattgttat gcactttttcc ccaattcatg tttggtgggg ccatccacac    3900
cctctccttg tcacagaatc tccatttctg ctcagattcc ccccatctcc attgcattca    3960
tgtactaccc tcagtctaca ctcacaatca tcttctccca agactgctcc cttttgtttt    4020
gtgttttttt gagggaatt aaggaaaaat aagtgggggc aggtttggag agctgcttcc    4080
agtggatagt tgatgagaat cctgaccaaa ggaaggcacc cttgactgtt gggatagaca    4140
gatggaccta tggggtggga ggtggtgtcc ctttcacact gtggtgtctc ttggggaagg    4200
atctccccga atctcaataa accagtgaac agtgtgaaaa aaaaaaaaaa aaaaaaaaa    4260
aaaaaaaaaa aaaaaaaaaa a                                             4281
```

<210> SEQ ID NO 98
<211> LENGTH: 959
<212> TYPE: PRT
<213> ORGANISM: Homo sapiens

<400> SEQUENCE: 98

```
Met Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
    130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175
```

```
Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
            195                 200                 205

Tyr Glu Leu Lys Leu Ile His His Asp Ser Lys Cys Asp Pro Gly Gln
            210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
            245                 250                 255

Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Phe Arg Thr His Pro
            275                 280                 285

Ser Ala Thr Leu His Asn Pro Thr Arg Val Lys Leu Phe Glu Lys Trp
            290                 295                 300

Gly Trp Lys Lys Ile Ala Thr Ile Gln Gln Thr Thr Glu Val Phe Thr
305                 310                 315                 320

Ser Thr Leu Asp Asp Leu Glu Glu Arg Val Lys Glu Ala Gly Ile Glu
            325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
            355                 360                 365

Thr Glu Ala Arg Lys Val Phe Cys Glu Val Tyr Lys Glu Arg Leu Phe
            370                 375                 380

Gly Lys Lys Tyr Val Trp Phe Leu Ile Gly Trp Tyr Ala Asp Asn Trp
385                 390                 395                 400

Phe Lys Ile Tyr Asp Pro Ser Ile Asn Cys Thr Val Asp Glu Met Thr
            405                 410                 415

Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
            435                 440                 445

Lys Leu Thr Lys Arg Leu Lys Arg His Pro Glu Glu Thr Gly Gly Phe
450                 455                 460

Gln Glu Ala Pro Leu Ala Tyr Asp Ala Ile Trp Ala Leu Ala Leu Ala
465                 470                 475                 480

Leu Asn Lys Thr Ser Gly Gly Gly Arg Ser Gly Val Arg Leu Glu
            485                 490                 495

Asp Phe Asn Tyr Asn Asn Gln Thr Ile Thr Asp Gln Ile Tyr Arg Ala
            500                 505                 510

Met Asn Ser Ser Ser Phe Glu Gly Val Ser Gly His Val Val Phe Asp
            515                 520                 525

Ala Ser Gly Ser Arg Met Ala Trp Thr Leu Ile Glu Gln Leu Gln Gly
            530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Gly Gly Ser Pro Pro Ala Asp
            565                 570                 575

Gln Thr Leu Val Ile Lys Thr Phe Arg Phe Leu Ser Gln Lys Leu Phe
            580                 585                 590

Ile Ser Val Ser Val Leu Ser Ser Leu Gly Ile Val Leu Ala Val Val
```

```
                595                 600                 605
Cys Leu Ser Phe Asn Ile Tyr Asn Ser His Val Arg Tyr Ile Gln Asn
        610                 615                 620

Ser Gln Pro Asn Leu Asn Asn Leu Thr Ala Val Gly Cys Ser Leu Ala
625                 630                 635                 640

Leu Ala Ala Val Phe Pro Leu Gly Leu Asp Gly Tyr His Ile Gly Arg
                645                 650                 655

Asn Gln Phe Pro Phe Val Cys Gln Ala Arg Leu Trp Leu Leu Gly Leu
        660                 665                 670

Gly Phe Ser Leu Gly Tyr Gly Ser Met Phe Thr Lys Ile Trp Trp Val
            675                 680                 685

His Thr Val Phe Thr Lys Lys Glu Glu Lys Lys Glu Trp Arg Lys Thr
        690                 695                 700

Leu Glu Pro Trp Lys Leu Tyr Ala Thr Val Gly Leu Leu Val Gly Met
705                 710                 715                 720

Asp Val Leu Thr Leu Ala Ile Trp Gln Ile Val Asp Pro Leu His Arg
                725                 730                 735

Thr Ile Glu Thr Phe Ala Lys Glu Glu Pro Lys Glu Asp Ile Asp Val
        740                 745                 750

Ser Ile Leu Pro Gln Leu Glu His Cys Ser Ser Arg Lys Met Asn Thr
    755                 760                 765

Trp Leu Gly Ile Phe Tyr Gly Tyr Lys Gly Leu Leu Leu Leu Leu Gly
770                 775                 780

Ile Phe Leu Ala Tyr Glu Thr Lys Ser Val Ser Thr Glu Lys Ile Asn
785                 790                 795                 800

Asp His Arg Ala Val Gly Met Ala Ile Tyr Asn Val Ala Val Leu Cys
                805                 810                 815

Leu Ile Thr Ala Pro Val Thr Met Ile Leu Ser Ser Gln Gln Asp Ala
        820                 825                 830

Ala Phe Ala Phe Ala Ser Leu Ala Ile Val Phe Ser Ser Tyr Ile Thr
            835                 840                 845

Leu Val Val Leu Phe Val Pro Lys Met Arg Arg Leu Ile Thr Arg Gly
        850                 855                 860

Glu Trp Gln Ser Glu Ala Gln Asp Thr Met Lys Thr Gly Ser Ser Thr
865                 870                 875                 880

Asn Asn Asn Glu Glu Glu Lys Ser Arg Leu Leu Glu Lys Glu Asn Arg
                885                 890                 895

Glu Leu Glu Lys Ile Ile Ala Glu Lys Glu Glu Arg Val Ser Glu Leu
                900                 905                 910

Arg His Gln Leu Gln Ser Arg Gln Gln Leu Arg Ser Arg Arg His Pro
        915                 920                 925

Pro Thr Pro Pro Glu Pro Ser Gly Gly Leu Pro Arg Gly Pro Pro Glu
    930                 935                 940

Pro Pro Asp Arg Leu Ser Cys Asp Gly Ser Arg Val His Leu Leu
945                 950                 955

<210> SEQ ID NO 99
<211> LENGTH: 959
<212> TYPE: PRT
<213> ORGANISM: Homo sapiens

<400> SEQUENCE: 99

Met Leu Leu Leu Leu Leu Leu Ala Pro Leu Phe Leu Arg Pro Pro Gly
  1               5                  10                  15
```

-continued

```
Ala Gly Gly Ala Gln Thr Pro Asn Ala Thr Ser Glu Gly Cys Gln Ile
            20                  25                  30

Ile His Pro Pro Trp Glu Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Leu Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
    130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
        195                 200                 205

Tyr Glu Leu Lys Leu Ile His His Asp Ser Lys Cys Asp Pro Gly Gln
    210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
                245                 250                 255

Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Arg Thr His Pro
        275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305                 310                 315                 320

Ser Thr Leu Asp Asp Leu Glu Glu Arg Val Lys Glu Ala Gly Ile Glu
                325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
        355                 360                 365

Thr Glu Ala Arg Lys Val Phe Cys Glu Val Tyr Lys Glu Arg Leu Phe
    370                 375                 380

Gly Lys Lys Tyr Val Trp Phe Leu Ile Gly Trp Tyr Ala Asp Asn Trp
385                 390                 395                 400

Phe Lys Ile Tyr Asp Pro Ser Ile Asn Cys Thr Val Asp Glu Met Thr
                405                 410                 415

Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
```

-continued

```
            435                 440                 445
Lys Leu Thr Lys Arg Leu Lys Arg His Pro Glu Glu Thr Gly Gly Phe
    450                 455                 460
Gln Glu Ala Pro Leu Ala Tyr Asp Ala Ile Trp Ala Leu Ala Leu Ala
465                 470                 475                 480
Leu Asn Lys Thr Ser Gly Gly Gly Arg Ser Gly Val Arg Leu Glu
                485                 490                 495
Asp Phe Asn Tyr Asn Asn Gln Thr Ile Thr Asp Gln Ile Tyr Arg Ala
                500                 505                 510
Met Asn Ser Ser Ser Phe Glu Gly Val Ser Gly His Val Val Phe Asp
                515                 520                 525
Ala Ser Gly Ser Arg Met Ala Trp Thr Leu Ile Glu Gln Leu Gln Gly
            530                 535                 540
Gly Ser Tyr Lys Lys Ile Gly Tyr Tyr Asp Ser Thr Lys Asp Asp Leu
545                 550                 555                 560
Ser Trp Ser Lys Thr Asp Lys Trp Ile Gly Ser Pro Pro Ala Asp
                565                 570                 575
Gln Thr Leu Val Ile Lys Thr Phe Arg Phe Leu Ser Gln Lys Leu Phe
                580                 585                 590
Ile Ser Val Ser Val Leu Ser Ser Leu Gly Ile Val Leu Ala Val Val
                595                 600                 605
Cys Leu Ser Phe Asn Ile Tyr Asn Ser His Val Arg Tyr Ile Gln Asn
            610                 615                 620
Ser Gln Pro Asn Leu Asn Asn Leu Thr Ala Val Gly Cys Ser Leu Ala
625                 630                 635                 640
Leu Ala Ala Val Phe Pro Leu Gly Leu Asp Gly Tyr His Ile Gly Arg
                645                 650                 655
Asn Gln Phe Pro Phe Val Cys Gln Ala Arg Leu Trp Leu Leu Gly Leu
                660                 665                 670
Gly Phe Ser Leu Gly Tyr Gly Ser Met Phe Thr Lys Ile Trp Trp Val
            675                 680                 685
His Thr Val Phe Thr Lys Lys Glu Glu Lys Glu Trp Arg Lys Thr
            690                 695                 700
Leu Glu Pro Trp Lys Leu Tyr Ala Thr Val Gly Leu Leu Val Gly Met
705                 710                 715                 720
Asp Val Leu Thr Leu Ala Ile Trp Gln Ile Val Asp Pro Leu His Arg
                725                 730                 735
Thr Ile Glu Thr Phe Ala Lys Glu Pro Lys Glu Asp Ile Asp Val
                740                 745                 750
Ser Ile Leu Pro Gln Leu Glu His Cys Ser Ser Arg Lys Met Asn Thr
                755                 760                 765
Trp Leu Gly Ile Phe Tyr Gly Tyr Lys Gly Leu Leu Leu Leu Gly
            770                 775                 780
Ile Phe Leu Ala Tyr Glu Thr Lys Ser Val Ser Thr Glu Lys Ile Asn
785                 790                 795                 800
Asp His Arg Ala Val Gly Met Ala Ile Tyr Asn Val Ala Val Leu Cys
                805                 810                 815
Leu Ile Thr Ala Pro Val Thr Met Ile Leu Ser Ser Gln Gln Asp Ala
                820                 825                 830
Ala Phe Ala Phe Ala Ser Leu Ala Ile Val Phe Ser Ser Tyr Ile Thr
            835                 840                 845
Leu Val Val Leu Phe Val Pro Lys Met Arg Arg Leu Ile Thr Arg Gly
850                 855                 860
```

```
Glu Trp Gln Ser Glu Ala Gln Asp Thr Met Lys Thr Gly Ser Ser Thr
865                 870                 875                 880

Asn Asn Asn Glu Glu Glu Lys Ser Arg Leu Leu Glu Lys Glu Asn Arg
                885                 890                 895

Glu Leu Glu Lys Ile Ile Ala Glu Lys Glu Arg Val Ser Glu Leu
            900                 905                 910

Arg His Gln Leu Gln Ser Arg Gln Gln Leu Arg Ser Arg Arg His Pro
                915                 920                 925

Pro Thr Pro Pro Glu Pro Ser Gly Gly Leu Pro Arg Gly Pro Pro Glu
            930                 935                 940

Pro Pro Asp Arg Leu Ser Cys Asp Gly Ser Arg Val His Leu Leu
945                 950                 955

<210> SEQ ID NO 100
<211> LENGTH: 959
<212> TYPE: PRT
<213> ORGANISM: Homo sapiens

<400> SEQUENCE: 100

Met Leu Leu Leu Leu Leu Ala Pro Leu Phe Leu Arg Pro Pro Gly
1               5                   10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
        195                 200                 205

Tyr Glu Leu Lys Leu Ile His His Asp Ser Lys Cys Asp Pro Gly Gln
210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
                245                 250                 255

Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Phe Arg Thr His Pro
```

-continued

```
              275                 280                 285
Ser Ala Thr Leu His Asn Pro Thr Arg Val Lys Leu Phe Glu Lys Trp
    290                 295                 300
Gly Trp Lys Lys Ile Ala Thr Ile Gln Gln Thr Thr Glu Val Phe Thr
305                 310                 315                 320
Ser Thr Leu Asp Asp Leu Glu Glu Arg Val Lys Glu Ala Gly Ile Glu
                325                 330                 335
Ile Thr Phe Arg Gln Ser Phe Ser Asp Pro Ala Val Pro Val Lys
                340                 345                 350
Asn Leu Lys Arg Gln Asp Ala Arg Ile Ile Val Gly Leu Phe Tyr Glu
                355                 360                 365
Thr Glu Ala Arg Lys Val Phe Cys Glu Val Tyr Lys Glu Arg Leu Phe
    370                 375                 380
Gly Lys Lys Tyr Val Trp Phe Leu Ile Gly Trp Tyr Ala Asp Asn Trp
385                 390                 395                 400
Phe Lys Ile Tyr Asp Pro Ser Ile Asn Cys Thr Val Asp Glu Met Thr
                405                 410                 415
Glu Ala Val Glu Gly His Ile Thr Thr Glu Ile Val Met Leu Asn Pro
                420                 425                 430
Ala Asn Thr Arg Ser Ile Ser Asn Met Thr Ser Gln Glu Phe Val Glu
                435                 440                 445
Lys Leu Thr Lys Arg Leu Lys Arg His Pro Glu Glu Thr Gly Gly Phe
    450                 455                 460
Gln Glu Ala Pro Leu Ala Tyr Asp Ala Ile Trp Ala Leu Ala Leu Ala
465                 470                 475                 480
Leu Asn Lys Thr Ser Gly Gly Gly Arg Ser Gly Val Arg Leu Glu
                485                 490                 495
Asp Phe Asn Tyr Asn Asn Gln Thr Ile Thr Asp Gln Ile Tyr Arg Ala
                500                 505                 510
Met Asn Ser Ser Ser Phe Glu Gly Val Ser Gly His Val Val Phe Asp
                515                 520                 525
Ala Ser Gly Ser Arg Met Ala Trp Thr Leu Ile Glu Gln Pro Gln Gly
    530                 535                 540
Gly Ser Tyr Lys Lys Ile Gly Tyr Tyr Asp Ser Thr Lys Asp Asp Leu
545                 550                 555                 560
Ser Trp Ser Lys Thr Asp Lys Trp Ile Gly Gly Ser Pro Pro Ala Asp
                565                 570                 575
Gln Thr Leu Val Ile Lys Thr Phe Arg Phe Leu Ser Gln Lys Leu Phe
                580                 585                 590
Ile Ser Val Ser Val Leu Ser Ser Leu Gly Ile Val Leu Ala Val Val
                595                 600                 605
Cys Leu Ser Phe Asn Ile Tyr Asn Ser His Val Arg Tyr Ile Gln Asn
    610                 615                 620
Ser Gln Pro Asn Leu Asn Asn Leu Thr Ala Val Gly Cys Ser Leu Ala
625                 630                 635                 640
Leu Ala Ala Val Phe Pro Leu Gly Leu Asp Gly Tyr His Ile Gly Arg
                645                 650                 655
Asn Gln Phe Pro Phe Val Cys Gln Ala Arg Leu Trp Leu Leu Gly Leu
                660                 665                 670
Gly Phe Ser Leu Gly Tyr Gly Ser Met Phe Thr Lys Ile Trp Trp Val
                675                 680                 685
His Thr Val Phe Thr Lys Lys Glu Glu Lys Lys Glu Trp Arg Lys Thr
    690                 695                 700
```

```
Leu Glu Pro Trp Lys Leu Tyr Ala Thr Val Gly Leu Val Gly Met
705                 710                 715                 720

Asp Val Leu Thr Leu Ala Ile Trp Gln Ile Val Asp Pro Leu His Arg
            725                 730                 735

Thr Ile Glu Thr Phe Ala Lys Glu Glu Pro Lys Glu Asp Ile Asp Val
            740                 745                 750

Ser Ile Leu Pro Gln Leu Glu His Cys Ser Ser Arg Lys Met Asn Thr
            755                 760                 765

Trp Leu Gly Ile Phe Tyr Gly Tyr Lys Gly Leu Leu Leu Leu Gly
770                 775                 780

Ile Phe Leu Ala Tyr Glu Thr Lys Ser Val Ser Thr Glu Lys Ile Asn
785                 790                 795                 800

Asp His Arg Ala Val Gly Met Ala Ile Tyr Asn Val Ala Val Leu Cys
            805                 810                 815

Leu Ile Thr Ala Pro Val Thr Met Ile Leu Ser Ser Gln Gln Asp Ala
            820                 825                 830

Ala Phe Ala Phe Ala Ser Leu Ala Ile Val Phe Ser Ser Tyr Ile Thr
            835                 840                 845

Leu Val Val Leu Phe Val Pro Lys Met Arg Arg Leu Ile Thr Arg Gly
850                 855                 860

Glu Trp Gln Ser Glu Ala Gln Asp Thr Met Lys Thr Gly Ser Ser Thr
865                 870                 875                 880

Asn Asn Asn Glu Glu Glu Lys Ser Arg Leu Leu Glu Lys Glu Asn Arg
            885                 890                 895

Glu Leu Glu Lys Ile Ile Ala Glu Lys Glu Glu Arg Val Ser Glu Leu
            900                 905                 910

Arg His Gln Leu Gln Ser Arg Gln Gln Leu Arg Ser Arg His Pro
            915                 920                 925

Pro Thr Pro Pro Glu Pro Ser Gly Gly Leu Pro Arg Gly Pro Pro Glu
            930                 935                 940

Pro Pro Asp Arg Leu Ser Cys Asp Gly Ser Arg Val His Leu Leu
945                 950                 955

<210> SEQ ID NO 101
<211> LENGTH: 2932
<212> TYPE: DNA
<213> ORGANISM: Homo sapiens

<400> SEQUENCE: 101
gtaatgcaga gataataaaa cttcttaggt ccataggtct tataataatt taataaccta      60
aacatggtat acaaattcct ccaaacccaa taacataatt atagtttcaa aaagttcccc     120
aaactttcaa gttagatttt attgctttga tgagtggctt taaatatgaa aagtcttgcc     180
tgtgaagggc aatccttttc ccgtggactg ggatctatag aaatacagaa atgtgcccag     240
gggttcatct ccctaataac catcattcac atttctcaac ctccctaata accagccacc     300
atgtgagaag gatccacagt tactgtttat gactataatt aactagtacc tgggactggt     360
cagtggagtt ggttgcaacc tgatgctaag gatgtcaaag ttgtctcggc ctctgttccc     420
agccagtaag taattccctg gcctcgggcc atacccccta atcttggtca gctgattatg     480
acaggcagac agcacagtaa ataacactat atattaagaa aacccaaagc atatgtatca     540
atggtatata cccaacagca tcctaggaat ggagagtctg tagcaagggc ctccaatgtg     600
aaggtcaaca cagtcactgt gatgcgtgta tttccatttt gtaaagcatg atctctggtg     660
```

```
gtcattttta tcttcctaac ttattggaaa agtctcctgt tttgggggcc cgcccctggt    720
cacagccaga ctgactcagt ttccctggga ggtcccgctc gagcccgtcc ttcccctccc    780
tctgcccgcc cccagccctc gcccaccct cggcgcccgc acatctgcct gctcagctcc     840
agacggcgcc cggacccccg ggcgcgggat ccagccaggt gggagcccg cagatgaggt     900 ctctgaaggt gtgcctgaac cagtgccagc ctgccctgtc tgcagcatcg gcctgatggg    960
gtggtgactg atccctcagg gctccggagc catgtggccc aacggcagtt ccctggggcc   1020
ctgtttccgg cccacaaaca ttaccctgga ggagagacgg ctgatcgcct cgccctggtt   1080
cgccgcctcc ttctgcgtgg tgggcctggc ctccaacctg ctggccctga gcgtgctggc   1140
gggcgcgcgg caggggggtt cgcacacgcg ctcctccttc ctcaccttcc tctgcggcct   1200
cgtcctcacc gacttcctgg ggctgctggt gaccggtacc atcgtggtgt cccagcacgc   1260
cgcgctcttc gagtggcacg ccgtggaccc tggctgccgt ctctgtcgct tcatgggcgt   1320
cgtcatgatc ttcttcggcc tgtccccgct gctgctgggg gccgccatgg cctcagagcg   1380
ctacctgggt atcacccggc ccttctcgcg cccggcggtc gcctcgcagc gccgcgcctg   1440
ggccaccgtg gggctggtgt gggcggccg gctggcgctg gcctgctgc ccctgctggg    1500 cgtgggtcgc tacaccgtgc aatacccggg gtcctggtgc ttcctgacgc tgggcgccga   1560
gtccggggac gtgccttcg ggctgctctt ctccatgctg gcggcctct cggtcgggct     1620 gtccttcctg ctgaacacgg tcagcgtggc caccctgtgc cacgtctacc acgggcagga   1680
ggcggcccag cagcgtcccc gggactccga ggtggagatg atggctcagc tcctggggat   1740
catggtggtg gccagcgtgt gttggctgcc ccttctggtc ttcattgccc agacagtgct   1800
gcgaaacccg cctgccatga gccccgccgg gcagctgtcc cgcaccacgg agaaggagct   1860
gctcatctac ttgcgcgtgg ccacctggaa ccagatcctg gaccctgggg tgtatatcct   1920
gttccgccgc gccgtgctcc ggcgtctcca gcctcgcctc agcacccggc ccaggtcgct   1980
gtccctccag ccccagctca cgcagcgctc cgggctgcag taggaagtgg acagagcgcc   2040
cctcccgcgc ctttccgcgg agcccttggc ccctcggaca gcccatctgc ctgttctgag   2100
gattcagggg ctgggggtgc tggatggaca gtgggcatca gcagcaggt tttgggttga    2160 ccccaatcca acccggggac ccccaactcc tccctgatcc ttttaccaag cactctccct   2220
tcctcggccc cttttttccca tccagagctc ccaccccttc tctgcgtccc tcccaacccc   2280
aggaagggca tgcagacatt ggaagagggt cttgcattgc tattttttt tttagacgga   2340 gtcttgctct gtccccagg ctggagtgca gtggcgcaat ctcagctcac tgcaacctcc    2400
acctcccggg ttcaagcgat tctcctgcct cagcctcctg agtagctggg actataggcg   2460
cgcgccacca cgcccggcta ttttttgtat ttttagtaga cggggttt caccgtgttg     2520 gccaggctgg tcttgaactc ctgacctcag gtgattcacc agcctcagcc tcccaaagtg   2580
ctgggatcac aggcatgaac caccacacct ggcatttttt tttttttttt tagacggagt   2640
ctcactctgt ggcccagcct ggagtacagt ggcacgatct cggctcactg caacctccgc   2700
ctcccgggtt caagcgattc tcgtgcctca gcctccgag cagctgggat tacaggcgta    2760
agccactgcg cccggccttg catgctcttt gaccctgaat ttgacctact gctggggta    2820 cagttgcttc cttttgaacc tccaacaggg aaggctctgt ccagaaagga ttgaatgtga   2880
aacgggggca cccccttttc ttgccaaaat atatctctgc ctttggtttt at           2932
```

<210> SEQ ID NO 102
<211> LENGTH: 2932

```
<212> TYPE: DNA
<213> ORGANISM: Homo sapiens

<400> SEQUENCE: 102
gtaatgcaga gataataaaa cttcttaggt ccataggtct tataataatt taataaccta        60
aacatggtat acaaattcct ccaaacccaa taacataatt atagtttcaa aaagttcccc       120
aaactttcaa gttagatttt attgctttga tgagtggctt taaatatgaa aagtcttgcc       180
tgtgaagggc aatccttttc ccgtggactg ggatctatag aaatacagaa atgtgcccag       240
gggttcatct ccctaataac catcattcac atttctcaac ctccctaata accagccacc       300
atgtgagaag gatccacagt tactgtttat gactataatt aactagtacc tgggactggt       360
cagtggagtt ggttgcaacc tgatgctaag gatgtcaaag ttgtctcggc ctctgttccc       420
agccagtaag taattccctg gcctcgggcc ataccccta atcttggtca gctgattatg        480
acaggcagac agcacagtaa ataacactat atattaagaa acccaaagc atatgtatca        540
atggtatata cccaacagca tcctaggaat ggagagtctg tagcaagggc ctccaatgtg       600
aaggtcaaca cagtcactgt gatgcgtgta tttccatttt gtaaagcatg atctctggtg       660
gtcatttta tcttcctaac ttattggaaa agtctcctgt tttgggggcc cgcccctggt         720
cacagccaga ctgactcagt ttccctggga ggtcccgctc gagcccgtcc ttcccctccc       780
tctgcccgcc cccagccctc gccccaccct cggcgcccgc acatctgcct gctcagctcc       840
agacggcgcc cggaccccg ggcgcgggat ccagccaggt gggagccccg cagatgaggt        900
ctctgaaggt gtgcctgaac cagtgccagc ctgccctgtc tgcagcatcg gcctgatggg       960
gtggtgactg atccctcagg gctccggagc catgtggccc aacggcagtt ccctggggcc      1020
ctgtttccgg cccacaaaca ttaccctgga ggagagacgg ctgatcgcct cgccctggtt      1080
cgccgcctcc ttctgcgtgg tgggcctggc ctccaacctg ctggccctga gcgtgctggc      1140
gggcgcgcgg caggggggtt cgcacacgcg ctcctccttc ctcaccttcc tctgcggcct      1200
cgtcctcacc gacttcctgg ggctgctgga gaccggtacc atcgtggtgt cccagcacgc      1260
cgcgctcttc gagtggcacg ccgtggaccc tggctgccgt tctgtcgct tcatgggcgt       1320
cgtcatgatc ttcttcggcc tgtccccgct gctgctgggg gccgccatgg cctcagagcg      1380
ctacctgggt atcaccccggc ccttctcgcg cccggcggtc gcctcgcagc gccgcgcctg     1440
ggccaccgtg gggctggtgt gggcggccgc gctgcgctg ggcctgctgc ccctgctggg       1500
cgtgggtcgc tacaccgtgc aatacccggg gtcctggtgc ttcctgacgc tgggcgccga      1560
gtccggggac gtggccttcg ggctgctctt ctccatgctg gcggcctct cggtcgggct       1620
gtccttcctg ctgaacacgg tcagcgtggc caccctgtgc cacgtctacc acggcagga      1680
ggcggcccag cagcgtcccc gggactccga ggtggagatg atggctcagc tcctggggat      1740
catggtggtg ccagcgtgt gttggctgcc ccttctggtc ttcattgccc agacagtgct      1800
gcgaaacccg cctgccatga gccccgcgg gcagctgtcc cgcaccacgg agaaggagct      1860
gctcatctac ttgcgcgtgg ccacctggaa ccagatcctg gaccctgggg tgtatatcct      1920
gttccgccgc gccgtgctcc ggcgtctcca gcctcgcctc agcacccggc ccaggtcgct      1980
gtccctccag ccccagctca cgcagcgctc cgggctgcag taggaagtgg acagagcgcc      2040
cctcccgcgc cttccgcgg agcccttggc ccctcggaca gcccatctgc ctgttctgag      2100
gattcagggg ctgggggtgc tggatggaca gtgggcatca gcagcaggt tttgggttga      2160
ccccaatcca acccggggac ccccaactcc tccctgatcc ttttaccaag cactctccct      2220
```

| | |
|---|---|
| tcctcggccc cttttttccca tccagagctc ccacccctc tctgcgtccc tcccaacccc | 2280 |
| aggaagggca tgcagacatt ggaagagggt cttgcattgc tatttttttt tttagacgga | 2340 |
| gtcttgctct gtcccccagg ctggagtgca gtggcgcaat ctcagctcac tgcaacctcc | 2400 |
| acctcccggg ttcaagcgat tctcctgcct cagcctcctg agtagctggg actataggcg | 2460 |
| cgcgccacca cgcccggcta attttttgtat ttttagtaga cgggggttt caccgtgttg | 2520 |
| gccaggctgg tcttgaactc ctgacctcag gtgattcacc agcctcagcc tcccaaagtg | 2580 |
| ctgggatcac aggcatgaac caccacacct ggccatttttt tttttttttt tagacggagt | 2640 |
| ctcactctgt ggcccagcct ggagtacagt ggcacgatct cggctcactg caacctccgc | 2700 |
| ctcccgggtt caagcgattc tcgtgcctca gcctcccgag cagctgggat tacaggcgta | 2760 |
| agccactgcg cccggccttg catgctcttt gaccctgaat tgacctact tgctggggta | 2820 |
| cagttgcttc cttttgaacc tccaacaggg aaggctctgt ccagaaagga ttgaatgtga | 2880 |
| aacgggggca cccccttttc ttgccaaaat atatctctgc ctttggtttt at | 2932 |

<210> SEQ ID NO 103
<211> LENGTH: 2932
<212> TYPE: DNA
<213> ORGANISM: Homo sapiens

<400> SEQUENCE: 103

| | |
|---|---|
| gtaatgcaga gataataaaa cttcttaggt ccataggtct tataataatt taataaccta | 60 |
| aacatggtat acaaattcct ccaaacccaa taacataatt atagtttcaa aaagttcccc | 120 |
| aaactttcaa gttagatttt attgctttga tgagtggctt taaatatgaa aagtcttgcc | 180 |
| tgtgaagggc aatccttttc ccgtggactg ggatctatag aaatacagaa atgtgcccag | 240 |
| gggttcatct ccctaataac catcattcac atttctcaac ctccctaata accagccacc | 300 |
| atgtgagaag gatccacagt tactgtttat gactataatt aactagtacc tgggactggt | 360 |
| cagtggagtt ggttgcaacc tgatgctaag gatgtcaaag ttgtctcggc ctctgttccc | 420 |
| agccagtaag taattccctg gcctcgggcc tacccccta atcttggtca gctgattatg | 480 |
| acaggcagac agcacagtaa ataacactat atattaagaa aacccaaagc atatgtatca | 540 |
| atggtatata cccaacagca tcctaggaat ggagagtctg tagcaagggc ctccaatgtg | 600 |
| aaggtcaaca cagtcactgt gatgcgtgta tttccattttt gtaaagcatg atctctggtg | 660 |
| gtcatttttta tcttcctaac ttattggaaa agtctcctgt tttggggggcc cgcccctggt | 720 |
| cacagccaga ctgactcagt ttccctggga ggtcccgctc gagcccgtcc ttcccctccc | 780 |
| tctgcccgcc cccagccctc gccccaccct cggcgcccgc acatctgcct gctcagctcc | 840 |
| agacggcgcc cggaccccg ggcgcgggat ccagccaggt gggagcccg cagatgaggt | 900 |
| ctctgaaggt gtgcctgaac cagtgccagc ctgccctgtc tgcagcatcg gcctgatggg | 960 |
| gtggtgactg atccctcagg gctccggagc catgtggccc aacggcagtt ccctggggcc | 1020 |
| ctgtttccgg cccacaaaca ttaccctgga ggagagacgg ctgatcgcct cgccctggtt | 1080 |
| cgccgcctcc ttctgcgtgg tgggcctggc ctccaacctg ctggccctga gcgtgctggc | 1140 |
| gggcgcgcgg cagggggggtt cgcacacgcg ctcctccttc ctcaccttcc tctgcggcct | 1200 |
| cgtcctcacc gacttcctgg ggctgctggt gaccggtacc atcgtggtgt cccagcacgc | 1260 |
| cgcgctcttc gtgtggcacg ccgtggaccc tggctgccgt ctctgtcgct tcatgggcgt | 1320 |
| cgtcatgatc ttcttcggcc tgtccccgct gctgctgggg gccgcatgg cctcagagcg | 1380 |
| ctacctgggt atcacccggc ccttctcgcg cccggcggtc gcctcgcagc gccgcgcctg | 1440 |

```
ggccaccgtg gggctggtgt gggcggccgc gctggcgctg ggcctgctgc ccctgctggg   1500
cgtgggtcgc tacaccgtgc aatacccggg gtcctggtgc ttcctgacgc tgggcgccga   1560
gtccggggac gtggccttcg ggctgctctt ctccatgctg gcggcctct cggtcgggct    1620 gtccttcctg ctgaacacgg tcagcgtggc caccctgtgc cacgtctacc acgggcagga   1680
ggcggcccag cagcgtcccc gggactccga ggtggagatg atggctcagc tcctggggat   1740
catggtggtg gccagcgtgt gttggctgcc ccttctggtc ttcattgccc agacagtgct   1800
gcgaaacccg cctgccatga gccccgccgg gcagctgtcc cgcaccacgg agaaggagct   1860
gctcatctac ttgcgcgtgg ccacctggaa ccagatcctg gaccctgggg tgtatatcct   1920
gttccgccgc gccgtgctcc ggcgtctcca gcctcgcctc agcacccggc ccaggtcgct   1980
gtccctccag ccccagctca cgcagcgctc cgggctgcag taggaagtgg acagagcgcc   2040
cctcccgcgc ctttccgcgg agcccttggc ccctcggaca gcccatctgc ctgttctgag   2100
gattcagggg ctggggtgc tggatggaca gtgggcatca gcagcagggt tttgggttga    2160
ccccaatcca acccggggac ccccaactcc tccctgatcc ttttaccaag cactctccct   2220
tcctcggccc cttttttccca tccagagctc ccacccttc tctgcgtccc tcccaacccc   2280
aggaagggca tgcagacatt ggaagagggt cttgcattgc tattttttttt tttagacgga   2340 gtcttgctct gtcccccagg ctggagtgca gtggcgcaat ctcagctcac tgcaacctcc   2400
acctcccggg ttcaagcgat tctcctgcct cagcctcctg agtagctggg actataggcg   2460
cgcgccacca cgcccggcta ttttttgtat ttttagtaga cggggttt caccgtgttg      2520 gccaggctgg tcttgaactc ctgacctcag gtgattcacc agcctcagcc tcccaaagtg   2580
ctgggatcac aggcatgaac caccacacct ggccattttt ttttttttttt tagacggagt  2640 ctcactctgt ggcccagcct ggagtacagt ggcacgatct cggctcactg caacctccgc   2700
ctcccgggtt caagcgattc tcgtgcctca gcctccgag cagctgggat acaggcgta     2760 agccactgcg cccggccttg catgctcttt gaccctgaat ttgacctact tgctggggta   2820
cagttgcttc cttttgaacc tccaacaggg aaggctctgt ccagaaagga ttgaatgtga   2880
aacgggggca cccccttttc ttgccaaaat atatctctgc ctttggtttt at           2932

<210> SEQ ID NO 104
<211> LENGTH: 2932
<212> TYPE: DNA
<213> ORGANISM: Homo sapiens

<400> SEQUENCE: 104
gtaatgcaga gataataaaa cttcttaggt ccataggtct tataataatt taataaccta     60
aacatggtat acaaattcct ccaaacccaa taacataatt atagtttcaa aaagttcccc   120
aaactttcaa gttagatttt attgctttga tgagtggctt taaatatgaa aagtcttgcc   180
tgtgaagggc aatcctttc ccgtggactg ggatctatag aaatacagaa atgtgcccag    240
gggttcatct ccctaataac catcattcac atttctcaac ctccctaata accagccacc   300
atgtgagaag gatccacagt tactgtttat gactataatt aactagtacc tgggactggt   360
cagtggagtt ggttgcaacc tgatgctaag gatgtcaaag ttgtctcggc ctctgttccc   420
agccagtaag taattccctg gcctcgggcc atacccccta atcttggtca gctgattatg   480
acaggcagac agcacagtaa ataacactat atattaagaa aacccaaagc atatgtatca   540
atggtatata cccaacagca tcctaggaat ggagagtctg tagcaagggc ctccaatgtg   600
```

```
aaggtcaaca cagtcactgt gatgcgtgta tttccatttt gtaaagcatg atctctggtg        660
gtcattttta tcttcctaac ttattggaaa agtctcctgt tttgggggcc cgcccctggt        720
cacagccaga ctgactcagt ttccctggga ggtcccgctc gagcccgtcc ttcccctccc        780
tctgcccgcc cccagccctc gccccaccct cggcgcccgc acatctgcct gctcagctcc        840
agacggcgcc cggacccccg ggcgcgggat ccagccaggt gggagccccg cagatgaggt        900
ctctgaaggt gtgcctgaac cagtgccagc ctgccctgtc tgcagcatcg gcctgatggg        960
gtggtgactg atccctcagg gctccggagc catgtggccc aacggcagtt ccctggggcc       1020
ctgtttccgg cccacaaaca ttaccctgga ggagagacgg ctgatcgcct cgccctggtt       1080
cgccgcctcc ttctgcgtgg tgggcctggc ctccaacctg ctggccctga gcgtgctggc       1140 gggcgcgcg caggggggtt cgcacacgcg ctcctccttc ctcaccttcc tctgcgcct        1200 cgtcctcacc gacttcctgg ggctgctggt gaccggtacc atcgtggtgt cccagcacgc       1260
cgcgctcttc gagtggcacg ccgtggaccc tggctgccgt tctgtcgct tcatgggcgt       1320 cgtcatgatc ttcttcggcc tgtccccgct gctgctgggg gccgccatgg cctcagagcg       1380
ctacctgggt atcaccccgg ccttctcgcg cccggcggtc gcctcgcagc gccgcgcctg       1440
ggccaccgtg gggctggtgt gggcggccgc gctggcgctg ggcctgctgc ccctgctggg       1500
cgtgggtcgc tacaccgagc aataccccggg gtcctggtgc ttcctgacgc tgggcgccga       1560
gtccggggac gtggccttcg ggctgctctt ctccatgctg ggcggcctct cggtcgggct       1620
gtccttcctg ctgaacacgg tcagcgtggc caccctgtgc cacgtctacc acgggcagga       1680
ggcggcccag cagcgtcccc gggactccga ggtggagatg atggctcagc tcctggggat       1740
catggtggtg gccagcgtgt gttggctgcc ccttctggtc ttcattgccc agacagtgct       1800
gcgaaacccg cctgccatga gccccgccgg gcagctgtcc cgcaccacgg agaaggagct       1860
gctcatctac ttgcgcgtgg ccacctggaa ccagatcctg gacccctggg tgtatatcct       1920
gttccgccgc gccgtgctcc ggcgtctcca gcctcgcctc agcacccggc ccaggtcgct       1980
gtccctccag ccccagctca cgcagcgctc cgggctgcag taggaagtgg acagagcgcc       2040
cctcccgcgc ctttccgcgg agcccttggc ccctcggaca gcccatctgc ctgttctgag       2100
gattcagggg ctggggtgc tggatggaca gtgggcatca gcagcaggt tttgggttga       2160 ccccaatcca acccggggac ccccaactcc tccctgatcc ttttaccaag cactctccct       2220
tcctcggccc cttttcccca tccagagctc ccacccctc tctgcgtccc tcccaacccc       2280
aggaagggca tgcagacatt ggaagagggt cttgcattgc tattttttt tttagacgga       2340 gtcttgctct gtcccccagg ctggagtgca gtggcgcaat ctcagctcac tgcaacctcc       2400
acctcccggg ttcaagcgat tctcctgcct cagcctcctg agtagctggg actataggcg       2460
cgcgccacca cgcccggcta atttttgtat ttttagtaga cggggttt caccgtgttg       2520 gccaggctgt tcttgaactc ctgacctcag gtgattcacc agcctcagcc tcccaaagtg       2580
ctgggatcac aggcatgaac caccacacct ggccattttt ttttttttt tagacggagt       2640 ctcactctgt ggcccagcct ggagtacagt ggcacgatct cggctcactg caacctccgc       2700 ctcccggtt caagcgattc tcgtgcctca gcctcccgag cagctgggat acaggcgta       2760 agccactgcg cccggccttg catgctcttt gaccctgaat tgacctact tgctgggta       2820 cagttgcttc cttttgaacc tccaacaggg aaggctctgt ccagaaagga ttgaatgtga       2880
aacgggggca ccccctttc ttgccaaaat atatctctgc ctttggtttt at             2932
```

```
<210> SEQ ID NO 105
<211> LENGTH: 343
<212> TYPE: PRT
<213> ORGANISM: Homo sapiens

<400> SEQUENCE: 105

Met Trp Pro Asn Gly Ser Ser Leu Gly Pro Cys Phe Arg Pro Thr Asn
1               5                   10                  15

Ile Thr Leu Glu Glu Arg Arg Leu Ile Ala Ser Pro Trp Phe Ala Ala
            20                  25                  30

Ser Phe Cys Val Val Gly Leu Ala Ser Asn Leu Leu Ala Leu Ser Val
        35                  40                  45

Leu Ala Gly Ala Arg Gln Gly Gly Ser His Thr Arg Ser Ser Phe Leu
    50                  55                  60

Thr Phe Leu Cys Gly Leu Val Leu Thr Asp Phe Leu Gly Leu Leu Val
65                  70                  75                  80

Thr Gly Thr Ile Val Val Ser Gln His Ala Ala Leu Phe Glu Trp His
                85                  90                  95

Ala Val Asp Pro Gly Cys Arg Leu Cys Arg Phe Met Gly Val Val Met
            100                 105                 110

Ile Phe Phe Gly Leu Ser Pro Leu Leu Leu Gly Ala Ala Met Ala Ser
        115                 120                 125

Glu Arg Tyr Leu Gly Ile Thr Arg Pro Phe Ser Arg Pro Ala Val Ala
    130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
        195                 200                 205

Gly Leu Ser Phe Leu Leu Asn Thr Val Ser Val Ala Thr Leu Cys His
    210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                245                 250                 255

Cys Trp Leu Pro Leu Leu Val Phe Ile Ala Gln Thr Val Leu Arg Asn
            260                 265                 270

Pro Pro Ala Met Ser Pro Ala Gly Gln Leu Ser Arg Thr Thr Glu Lys
        275                 280                 285

Glu Leu Leu Ile Tyr Leu Arg Val Ala Thr Trp Asn Gln Ile Leu Asp
    290                 295                 300

Pro Trp Val Tyr Ile Leu Phe Arg Arg Ala Val Leu Arg Arg Leu Gln
305                 310                 315                 320

Pro Arg Leu Ser Thr Arg Pro Arg Ser Leu Ser Leu Gln Pro Gln Leu
                325                 330                 335

Thr Gln Arg Ser Gly Leu Gln
            340

<210> SEQ ID NO 106
<211> LENGTH: 343
<212> TYPE: PRT
<213> ORGANISM: Homo sapiens
```

<400> SEQUENCE: 106

```
Met Trp Pro Asn Gly Ser Ser Leu Gly Pro Cys Phe Arg Pro Thr Asn
 1               5                  10                  15

Ile Thr Leu Glu Glu Arg Arg Leu Ile Ala Ser Pro Trp Phe Ala Ala
             20                  25                  30

Ser Phe Cys Val Val Gly Leu Ala Ser Asn Leu Leu Ala Leu Ser Val
             35                  40                  45

Leu Ala Gly Ala Arg Gln Gly Ser His Thr Arg Ser Ser Phe Leu
         50                  55                  60

Thr Phe Leu Cys Gly Leu Val Leu Thr Asp Phe Leu Gly Leu Leu Glu
 65                  70                  75                  80

Thr Gly Thr Ile Val Val Ser Gln His Ala Ala Leu Phe Glu Trp His
                 85                  90                  95

Ala Val Asp Pro Gly Cys Arg Leu Cys Arg Phe Met Gly Val Val Met
             100                 105                 110

Ile Phe Phe Gly Leu Ser Pro Leu Leu Leu Gly Ala Ala Met Ala Ser
             115                 120                 125

Glu Arg Tyr Leu Gly Ile Thr Arg Pro Phe Ser Arg Pro Ala Val Ala
130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                 165                 170                 175

Gln Tyr Pro Gly Ser Trp Cys Phe Leu Thr Leu Gly Ala Glu Ser Gly
             180                 185                 190

Asp Val Ala Phe Gly Leu Leu Phe Ser Met Leu Gly Gly Leu Ser Val
             195                 200                 205

Gly Leu Ser Phe Leu Leu Asn Thr Val Ser Val Ala Thr Leu Cys His
210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                 245                 250                 255

Cys Trp Leu Pro Leu Leu Val Phe Ile Ala Gln Thr Val Leu Arg Asn
             260                 265                 270

Pro Pro Ala Met Ser Pro Ala Gly Gln Leu Ser Arg Thr Thr Glu Lys
             275                 280                 285

Glu Leu Leu Ile Tyr Leu Arg Val Ala Thr Trp Asn Gln Ile Leu Asp
             290                 295                 300

Pro Trp Val Tyr Ile Leu Phe Arg Arg Ala Val Leu Arg Arg Leu Gln
305                 310                 315                 320

Pro Arg Leu Ser Thr Arg Pro Arg Ser Leu Ser Leu Gln Pro Gln Leu
                 325                 330                 335

Thr Gln Arg Ser Gly Leu Gln
            340
```

<210> SEQ ID NO 107
<211> LENGTH: 343
<212> TYPE: PRT
<213> ORGANISM: Homo sapiens

<400> SEQUENCE: 107

```
Met Trp Pro Asn Gly Ser Ser Leu Gly Pro Cys Phe Arg Pro Thr Asn
 1               5                  10                  15
```

```
Ile Thr Leu Glu Glu Arg Arg Leu Ile Ala Ser Pro Trp Phe Ala Ala
             20                  25                  30

Ser Phe Cys Val Val Gly Leu Ala Ser Asn Leu Leu Ala Leu Ser Val
         35                  40                  45

Leu Ala Gly Ala Arg Gln Gly Gly Ser His Thr Arg Ser Ser Phe Leu
     50                  55                  60

Thr Phe Leu Cys Gly Leu Val Leu Thr Asp Phe Leu Gly Leu Leu Val
 65                  70                  75                  80

Thr Gly Thr Ile Val Val Ser Gln His Ala Ala Leu Phe Val Trp His
                 85                  90                  95

Ala Val Asp Pro Gly Cys Arg Leu Cys Arg Phe Met Gly Val Val Met
            100                 105                 110

Ile Phe Phe Gly Leu Ser Pro Leu Leu Leu Gly Ala Ala Met Ala Ser
            115                 120                 125

Glu Arg Tyr Leu Gly Ile Thr Arg Pro Phe Ser Arg Pro Ala Val Ala
        130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
        195                 200                 205

Gly Leu Ser Phe Leu Leu Asn Thr Val Ser Val Ala Thr Leu Cys His
    210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                245                 250                 255

Cys Trp Leu Pro Leu Leu Val Phe Ile Ala Gln Thr Val Leu Arg Asn
            260                 265                 270

Pro Pro Ala Met Ser Pro Ala Gly Gln Leu Ser Arg Thr Thr Glu Lys
        275                 280                 285

Glu Leu Leu Ile Tyr Leu Arg Val Ala Thr Trp Asn Gln Ile Leu Asp
    290                 295                 300

Pro Trp Val Tyr Ile Leu Phe Arg Arg Ala Val Leu Arg Arg Leu Gln
305                 310                 315                 320

Pro Arg Leu Ser Thr Arg Pro Arg Ser Leu Ser Leu Gln Pro Gln Leu
                325                 330                 335

Thr Gln Arg Ser Gly Leu Gln
            340

<210> SEQ ID NO 108
<211> LENGTH: 343
<212> TYPE: PRT
<213> ORGANISM: Homo sapiens

<400> SEQUENCE: 108

Met Trp Pro Asn Gly Ser Ser Leu Gly Pro Cys Phe Arg Pro Thr Asn
 1               5                  10                  15

Ile Thr Leu Glu Glu Arg Arg Leu Ile Ala Ser Pro Trp Phe Ala Ala
             20                  25                  30

Ser Phe Cys Val Val Gly Leu Ala Ser Asn Leu Leu Ala Leu Ser Val
         35                  40                  45
```

```
Leu Ala Gly Ala Arg Gln Gly Gly Ser His Thr Arg Ser Ser Phe Leu
 50                  55                  60
Thr Phe Leu Cys Gly Leu Val Leu Thr Asp Phe Leu Gly Leu Leu Val
 65                  70                  75                  80
Thr Gly Thr Ile Val Val Ser Gln His Ala Ala Leu Phe Glu Trp His
                 85                  90                  95
Ala Val Asp Pro Gly Cys Arg Leu Cys Arg Phe Met Gly Val Val Met
            100                 105                 110
Ile Phe Phe Gly Leu Ser Pro Leu Leu Leu Gly Ala Ala Met Ala Ser
        115                 120                 125
Glu Arg Tyr Leu Gly Ile Thr Arg Pro Phe Ser Arg Pro Ala Val Ala
130                 135                 140
Ser Gln Arg Arg Ala Trp Ala Thr Val Gly Leu Val Trp Ala Ala Ala
145                 150                 155                 160
Leu Ala Leu Gly Leu Leu Pro Leu Leu Gly Val Gly Arg Tyr Thr Glu
                165                 170                 175
Gln Tyr Pro Gly Ser Trp Cys Phe Leu Thr Leu Gly Ala Glu Ser Gly
            180                 185                 190
Asp Val Ala Phe Gly Leu Leu Phe Ser Met Leu Gly Gly Leu Ser Val
        195                 200                 205
Gly Leu Ser Phe Leu Leu Asn Thr Val Ser Val Ala Thr Leu Cys His
210                 215                 220
Val Tyr His Gly Gln Glu Ala Ala Gln Gln Arg Pro Arg Asp Ser Glu
225                 230                 235                 240
Val Glu Met Met Ala Gln Leu Leu Gly Ile Met Val Val Ala Ser Val
                245                 250                 255
Cys Trp Leu Pro Leu Leu Val Phe Ile Ala Gln Thr Val Leu Arg Asn
            260                 265                 270
Pro Pro Ala Met Ser Pro Ala Gly Gln Leu Ser Arg Thr Thr Glu Lys
        275                 280                 285
Glu Leu Leu Ile Tyr Leu Arg Val Ala Thr Trp Asn Gln Ile Leu Asp
290                 295                 300
Pro Trp Val Tyr Ile Leu Phe Arg Arg Ala Val Leu Arg Arg Leu Gln
305                 310                 315                 320
Pro Arg Leu Ser Thr Arg Pro Arg Ser Leu Ser Leu Gln Pro Gln Leu
                325                 330                 335
Thr Gln Arg Ser Gly Leu Gln
            340

<210> SEQ ID NO 109
<211> LENGTH: 2624
<212> TYPE: DNA
<213> ORGANISM: Homo sapiens
<220> FEATURE:
<221> NAME/KEY: misc_feature
<222> LOCATION: 1622, 1623, 1624
<223> OTHER INFORMATION: n = A,T,C or G

<400> SEQUENCE: 109
attgttcagt tcaagggaat gaagaattca gaataatttt ggtaaatgga ttccaatatc     60
gggaataaga ataagctgaa cagttgacct gctttgaaga acatactgt ccatttgtct    120 aaaataatct ataacaacca aaccaatcaa aatgaattca acattatttt cccaggttga    180
aaatcattca gtccactcta atttctcaga gaagaatgcc cagcttctgg cttttgaaaa    240
tgatgattgt catctgccct tggccatgat atttacctta gctcttgctt atggagctgt    300
```

-continued

```
gatcattctt ggtgtctctg gaaacctggc cttgatcata atcatcttga aacaaaagga    360
gatgagaaat gttaccaaca tcctgattgt gaacctttcc ttctcagact tgcttgttgc    420
catcatgtgt ctcccctta catttgtcta cacattaatg gaccactggg tctttggtga     480
ggcgatgtgt aagttgaatc cttttgtgca atgtgtttca atcactgtgt ccattttctc    540
tctggttctc attgctgtgg aacgacatca gctgataatc aaccctcgag ggtgagacc     600
aaataataga catgcttatg taggtattgc tgtgatttgg gtccttgctg tggcttcttc    660
tttgccttc ctgatctacc aagtaatgac tgatgagccg ttccaaaatg taacacttga     720
tgcgtacaaa gacaaatacg tgtgctttga tcaatttcca tcggactctc ataggttgtc    780
ttataccact ctcctcttgg tgctgcagta ttttggtcca ctttgttta tatttatttg     840
ctacttcaag atatatatac gcctaaaaag gagaaacaac atgatggaca agatgagaga    900
caataagtac aggtccagtg aaaccaaaag aatcaatatc atgctgctct ccattgtggt    960
agcatttgca gtctgctggc tccctcttac catctttaac actgtgtttg attggaatca   1020
tcagatcatt gctacctgca accacaatct gttattcctg ctctgccacc tcacagcaat   1080
gatatccact tgtgtcaacc ccatatttta tgggttcctg aacaaaaact tccagagaga   1140
cttgcagttc ttcttcaact tttgtgattt ccggtctcgg gatgatgatt atgaaacaat   1200
agccatgtcc acgatgcaca cagatgtttc caaaacttct ttgaagcaag caagcccagt   1260
cgcatttaaa aaaatcaaca caatgatga taatgaaaaa atctgaaact acttatagcc    1320
tatggtcccg gatgacatct gtttaaaaac aagcacaacc tgcaacatac tttgattacc   1380
tgttctccca aggaatgggg ttgaaatcat ttgaaaatga ctaagatttt cttgtcttgc   1440
ttttttactg cttttgttgt agtgtcataa ttacatttgg aacaaaaggt gtgggctttg   1500
gggtcttctg gaaatagttt tgaccagaca tctttgaagt gcttttgtg aatttatgca    1560
tataatataa agacttttat actgtactta ttggaatgaa atttctttaa agtattcga    1620
tnnnctgact tcagaagtac ctgccatcca atacggtcat tagattgggt catcttgatt   1680
agattagatt agattagatt gtcaacagat tgggccatcc ttactttatg ataggcatca   1740
ttttagtgtg ttacaatagt aacagtatgc aaaagcagca ttcaggagcc gaaagatagt   1800
cttgaagtca ttcagaagtg gtttgaggtt tctgttttt ggtggttttt gtttgttttt    1860
tttttttc accttaaggg aggctttcat ttcctcccga ctgattgtca cttaaatcaa     1920
aatttaaaaa tgaataaaaa gacatacttc tcagctgcaa atattatgga gaattgggca   1980
cccacaggaa tgaagagaga aagcagctcc ccaacttcaa aaccattttg gtacctgaca   2040
acaagagcat tttagagtaa ttaatttaat aaagtaaatt agtattgctg caaatagcta   2100
aattatattt atttgaattg atggtcaaga gattttccat tttttttaca gactgttcag   2160
tgtttgtcaa gcttctggtc taatatgtac tcgaaagact ttccgcttac aatttgtaga   2220
aacacaaata tcgtttttcca tacagcagtg cctatatagt gactgatttt aactttcaat   2280
gtccatcttt caaaggaagt aacaccaagg tacaatgtta aaggaatatt cactttacct   2340
agcagggaaa aatacacaaa aactgcagat acttcatata gcccatttta acttgtataa   2400
actgtgtgac ttgtggcgtc ttataaataa tgcactgtaa agattactga atagttgtgt   2460
catgttaatg tgcctaattt catgtatctt gtaatcatga ttgagcctca gaatcatttg   2520
gagaaactat attttaaaga acaagacata cttcaatgta ttatacagat aaagtattac   2580
atgtgtttga tttaaaaagg gcggacattt tattaaaatc aagg                    2624
```

<210> SEQ ID NO 110
<211> LENGTH: 2624
<212> TYPE: DNA
<213> ORGANISM: Homo sapiens
<220> FEATURE:
<221> NAME/KEY: misc_feature
<222> LOCATION: 1622, 1623, 1624
<223> OTHER INFORMATION: n = A,T,C or G

<400> SEQUENCE: 110

| | | | | | |
|---|---|---|---|---|---|
| attgttcagt | tcaagggaat | gaagaattca | gaataatttt | ggtaaatgga | ttccaatatc | 60 |
| gggaataaga | ataagctgaa | cagttgacct | gctttgaaga | aacatactgt | ccatttgtct | 120 |
| aaaataatct | ataacaacca | aaccaatcaa | aatgaattca | acattatttt | cccaggttga | 180 |
| aaatcattca | gtccactcta | atttctcaga | gaagaatgcc | cagcttctgg | cttttgaaaa | 240 |
| tgatgattgt | catctgccct | tggccatgat | atttacctta | gctcttgctt | atggagctgt | 300 |
| gatcattctt | ggtgtctctg | gaaacctggc | cttgatcata | atcatcttga | aacaaaagga | 360 |
| gatgagaaat | gttaccaaca | tcctgattgt | gaacctttcc | ttctcagact | tgcttgttgc | 420 |
| catcatgtgt | ctccccttta | catttgtcta | cacattaatg | gaccactggg | tctttggtga | 480 |
| ggcgatgtgt | aagttgaatc | cttttgtgca | atgtgtttca | atcactgtgt | ccatttttctc | 540 |
| tctggttctc | attgctgtgg | aacgacatca | gctgataatc | aaccctcgag | ggtgagacc | 600 |
| aaataataga | catgcttatg | taggtattgc | tgtgatttgg | gtccttgctg | tggcttcttc | 660 |
| tttgcctttc | ctgatctacc | aagtaatgac | tgatgagccg | ttccaaaatg | taacacttga | 720 |
| tgcgtacaaa | gacaaatacg | tgtgctttga | tcaatttcca | tcggactctc | ataggttgtc | 780 |
| ttataccact | ctcctcttgg | tgctgcagta | ttttggtcca | cttgttttta | tatttatttg | 840 |
| ctacttcaag | atatatatac | gcctaaaaag | gagaaacaac | atgatggaca | agatgagaga | 900 |
| caataagtac | aggtccagtg | aaaccaaaag | aatcaatatc | atgctgctct | ccattgtggt | 960 |
| agcatttgca | gtctgctggc | tccctcttac | catctttaac | actgtgtttg | attggaatca | 1020 |
| tcagatcatt | gctacctgca | accacaatct | gttattcctg | ctctgccccc | tcacagcaat | 1080 |
| gatatccact | tgtgtcaacc | ccatatttta | tgggttcctg | aacaaaaact | tccagagaga | 1140 |
| cttgcagttc | ttcttcaact | tttgtgattt | ccggtctcgg | gatgatgatt | atgaaacaat | 1200 |
| agccatgtcc | acgatgcaca | cagatgtttc | caaaacttct | ttgaagcaag | caagcccagt | 1260 |
| cgcatttaaa | aaaatcaaca | acaatgatga | taatgaaaaa | atctgaaact | acttatagcc | 1320 |
| tatggtcccg | gatgacatct | gtttaaaaac | aagcacaacc | tgcaacatac | tttgattacc | 1380 |
| tgttctccca | aggaatgggg | ttgaaatcat | ttgaaaatga | ctaagatttt | cttgtcttgc | 1440 |
| ttttttactg | cttttgttgt | agtgtcataa | ttacatttgg | aacaaaggt | gtgggctttg | 1500 |
| gggtcttctg | gaaatagttt | tgaccagaca | tctttgaagt | gcttttttgtg | aatttatgca | 1560 |
| tataatataa | agacttttat | actgtactta | ttggaatgaa | atttctttaa | agtattacga | 1620 |
| tnnnctgact | tcagaagtac | ctgccatcca | atacggtcat | tagattgggt | catcttgatt | 1680 |
| agattagatt | agattagatt | gtcaacagat | tgggccatcc | ttactttatg | ataggcatca | 1740 |
| ttttagtgtg | ttacaatagt | aacagtatgc | aaaagcagca | ttcaggagcc | gaaagatagt | 1800 |
| cttgaagtca | ttcagaagtg | gtttgaggtt | tctgttttttt | ggtggttttt | gtttgttttt | 1860 |
| tttttttttc | accttaaggg | aggctttcat | ttcctcccga | ctgattgtca | cttaaatcaa | 1920 |
| aatttaaaaa | tgaataaaaa | gacatacttc | tcagctgcaa | atattatgga | gaattgggca | 1980 |
| cccacaggaa | tgaagagaga | aagcagctcc | ccaacttcaa | aaccatttg | gtacctgaca | 2040 |

-continued

```
acaagagcat tttagagtaa ttaatttaat aaagtaaatt agtattgctg caaatagcta    2100
aattatattt atttgaattg atggtcaaga gattttccat ttttttttaca gactgttcag   2160 tgtttgtcaa gcttctggtc taatatgtac tcgaaagact ttccgcttac aatttgtaga   2220
aacacaaata tcgttttcca tacagcagtg cctatatagt gactgatttt aactttcaat   2280
gtccatcttt caaggaagt aacaccaagg tacaatgtta aaggaatatt cactttacct    2340
agcagggaaa atacacaaa aactgcagat acttcatata gcccatttta acttgtataa    2400
actgtgtgac ttgtggcgtc ttataaataa tgcactgtaa agattactga atagttgtgt   2460
catgttaatg tgcctaattt catgtatctt gtaatcatga ttgagcctca gaatcatttg   2520
gagaaactat attttaaaga acaagacata cttcaatgta ttatacagat aaagtattac   2580
atgtgtttga ttttaaaagg gcggacattt tattaaaatc aagg                   2624
```

<210> SEQ ID NO 111
<211> LENGTH: 383
<212> TYPE: PRT
<213> ORGANISM: Homo sapiens

<400> SEQUENCE: 111

```
Met Asn Ser Thr Leu Phe Ser Gln Val Glu Asn His Ser Val His Ser
 1               5                   10                  15

Asn Phe Ser Glu Lys Asn Ala Gln Leu Leu Ala Phe Glu Asn Asp Asp
                20                  25                  30

Cys His Leu Pro Leu Ala Met Ile Phe Thr Leu Ala Leu Ala Tyr Gly
            35                  40                  45

Ala Val Ile Ile Leu Gly Val Ser Gly Asn Leu Ala Leu Ile Ile Ile
        50                  55                  60

Ile Leu Lys Gln Lys Glu Met Arg Asn Val Thr Asn Ile Leu Ile Val
 65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270
```

```
Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
        290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Asn
                325                 330                 335

Phe Cys Asp Phe Arg Ser Arg Asp Asp Tyr Glu Thr Ile Ala Met
                340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asn Asp Asp Asn Glu Lys
        370                 375                 380

<210> SEQ ID NO 112
<211> LENGTH: 383
<212> TYPE: PRT
<213> ORGANISM: Homo sapiens

<400> SEQUENCE: 112

Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
                20                  25                  30

Cys His Leu Pro Leu Ala Met Ile Phe Thr Leu Ala Leu Ala Tyr Gly
            35                  40                  45

Ala Val Ile Ile Leu Gly Val Ser Gly Asn Leu Ala Leu Ile Ile Ile
        50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
        210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270
```

-continued

```
Ala Val Cys Trp Leu Pro Leu Thr Ile Phe Asn Thr Val Phe Asp Trp
        275             280             285

Asn His Gln Ile Ile Ala Thr Cys Asn Pro Asn Leu Leu Phe Leu Leu
    290             295             300

Cys His Leu Thr Ala Met Ile Ser Thr Cys Val Asn Pro Ile Phe Tyr
305             310             315                     320

Gly Phe Leu Asn Lys Asn Phe Gln Arg Asp Leu Gln Phe Phe Phe Asn
            325             330                     335

Phe Cys Asp Phe Arg Ser Arg Asp Asp Tyr Glu Thr Ile Ala Met
            340             345             350

Ser Thr Met His Thr Asp Val Ser Lys Thr Ser Leu Lys Gln Ala Ser
        355             360             365

Pro Val Ala Phe Lys Lys Ile Asn Asn Asn Asp Asp Asn Glu Lys
    370             375             380
```

CLINICAL INDICATIONS FOR GENOTYPING POLYMORPHIC VARIANTS OF G-PROTEIN COUPLED RECEPTORS

RELATED APPLICATIONS

This application claims the benefit of priority of application Ser. Nos. 60/308,037, filed Jul. 25, 2001; 60/323,206, filed Sep. 12, 2001; 60/347,053, filed Jan. 8, 2002; 60/348,633, filed Jan. 14, 2002; and 60/372,703, filed Apr. 15, 2002.

FIELD OF THE INVENTION

The invention relates to G-protein coupled receptor (GPCR) genes. More particularly, the invention relates to the discovery of physiologically relevant functional differences between genetic variants of G-protein coupled receptor (GPCR) genes.

BACKGROUND OF THE INVENTION

When physicians treat patients with a drug, significant clinical variability is often observed. This variability is manifested in both the frequency of response to treatment, as well as the frequency and nature of possible adverse "side effects." Because of this well documented heterogeneity in clinical responses to drug treatment, physicians often must empirically adjust clinical dosages of the therapeutic agents used, or discontinue the use of a drug and switch to an alternative treatment to successfully treat a given medical indication. This variability in response to pharmacotherapy results in significantly increased health care costs, and delays in successful treatment. Clearly, there exists a need to identify patients who will respond positively to a particular medication, as well as those who are more prone to adverse side effects.

Similarly, the susceptibility to a given disease, as well as the rate of a disease's clinical progression varies across human populations. This is particularly true for human diseases where a complex interaction of genetics and environment are necessary for disease manifestation. In some individuals the clinical course of disease may be very benign, abrogating the need for intensive treatment that may expose that individual to adverse side effects. Conversely, the clinical course may be very severe, emphasizing the risk benefit ratio for aggressive and early intervention in disease treatment. Consequently, it is important to identify patients who exhibit increased risk of disease, or to identify individuals who will display either a severe or benign clinical course, as this will provide valuable information to clinicians to help tailor therapeutic decisions, and optimize the diagnosis and treatment of human disease.

Variability in clinical response to therapeutic drugs is determined in large part by genetic heterogeneity across human populations. For any given therapeutic drug, inter-individual variation in factors such as absorption, distribution, drug/target interactions, and elimination can all create variability in treatment response. Processes such as absorption, distribution, and elimination can all be easily assessed in the clinical setting by determining serum levels of a given therapeutic drug. However, variability in drug/target molecules has yet to be routinely considered in the clinical variability of drug treatment responses.

Similarly, variability in disease progression and susceptibility is determined in large part by genetic heterogeneity across human populations. Particular genes may be directly pathophysiological in a particular disease state, or may serve a modulatory role, where alterations in gene function may be modifying factors in the clinical manifestation and course of an individual's illness. The knowledge that a particular genetic variant is functionally altered can enable that genetic variant to be a marker for disease susceptibility and progression, even in a setting where the precise role of that gene and gene product are currently not understood.

Drug target genes, specifically the large gene families of receptor proteins (GPCR's) that transduce information by coupling to guanine nucleotide binding proteins, not only mediate the physiological effects of exogenously administered pharmaceutical agents, they also sub-serve critical roles in a diverse set of physiological processes. As such, genetic variants of these genes, in particular those variants that alter receptor function, are candidates to not only determine clinical responses to therapeutic drugs, but to modify disease susceptibility and progression.

Most mammalian genes, including drug target genes, are highly polymorphic across human populations. The most common form of polymorphism is the single nucleotide polymorphism (SNP), where a single nucleotide of DNA differs between individuals in a population. SNPs occur within both intergenic sequences, as well as in regulatory, and both exonic and intronic regions of human genes. In addition, any given individual may harbor multiple SNPs within a given genomic region, resulting in a multitude of different possible combinations of SNPs termed a haplotype. Of those SNPs that occur within exonic regions of genes, some are termed synonymous, in that they do not change the amino acid sequence of the resulting protein, and are unlikely to affect protein function. However, some of these coding region SNP's are non-synonymous (nscSNP), in that the single base change in the DNA does change the amino acid at that corresponding position in the protein. Significantly, SNPs are surprisingly frequent across the human genome (current estimates suggest 10 million total SNPs), and although most of these SNPs will have little or no functional consequences, others may affect protein function. Therefore, the identification of SNPs that alter protein function provides the genetic basis of the biological and pharmacological differences between individuals with respect to pharmacological treatment outcomes and disease susceptibility and progression. In addition, identification of functionally altered polymorphic variants of a given drug target gene can be generalized to define the genetic haplotypes associated with altered clinical outcomes.

SUMMARY OF THE INVENTION

The present invention provides compositions and methods for screening individuals for GPCR variants as clinical indications. Such clinical indications include predicting clinical response to any drug whose actions are mediated in full or in part by GPCR activation or inactivation. Such clinical indications also include predicting susceptibility or resistance to adverse side effects to any drug whose actions are mediated in full or in part by GPCR activation or inactivation. Additionally, the invention compositions and methods are useful for screening individuals for disease related susceptibility or disease related progression factors that are mediated by GPCR activation or inactivation. The invention therefore provides methods for screening a subject for the presence of a variant GPCR. In one embodiment, a method includes providing a subject or sample from a subject; andassaying the subject or the sample from the subject for the presence of a GPCR variant selected from: alpha 1A/C adrenergic receptor having a cysteine residue at amino acid position 78 or a haplotype linked with a cysteine residue at amino acid position 78, or a serine residue at amino acid position 200 or a haplotype linked with a serine residue at amino acid position 200; beta 3 adrenergic receptor having a leucine residue at amino acid position 78 or a haplotype linked with a leucine residue at amino acid position 78; dopamine D1 receptor having a proline at amino acid position 37 or a haplotype linked with a proline at amino acid position 37, or an arginine at amino acid position 37 or a haplotype linked with an arginine at amino acid position 37, or a serine at amino acid position 79 or a haplotype linked with a serine at amino acid position 79, or an alanine at amino acid position 199 or a haplotype linked with an alanine at amino acid position 199; dopamine D2 receptor having an arginine at amino acid position 40 or a haplotype linked with an arginine at amino acid position 40, or a leucine at amino acid position 208 or a haplotype linked to a leucine at amino acid position 208; dopamine D3 receptor having a leucine at amino acid position 50 or a haplotype linked with a leucine at amino acid position 50; histamine H1 receptor having a glycine at amino acid position 216 or a haplotype linked to a glycine at amino acid position 216, or a proline at amino acid position 226 or a haplotype linked to a proline at amino acid position 226; histamine H2 receptor having an asparagine at amino acid 175 or a haplotype linked to an asparagine at amino acid 175, or a glycine at amino acid position 215 or a haplotype linked to a glycine at amino acid position 215, or an arginine at amino acid position 231 or a haplotype linked to an arginine at amino acid 231; serotonin 1A receptor having a valine at amino acid position 50 or a haplotype linked to a valine at amino acid position 50, or an isoleucine at amino acid position 172 or a haplotype linked to an isoleucine at amino acid position 172, or a phenylalanine at amino acid position 381 or a haplotype linked to a phenylalanine at amino acid position 381; serotonin 1B receptor having an asparagine at amino acid position 221 or a haplotype linked to an asparagine at amino acid position 221; serotonin 1D receptor having a leucine at amino acid position 53 or a haplotype linked to a leucine at amino acid position 53, or a glycine at amino acid position 366 or a haplotype linked to a glycine at amino acid position 366; serotonin 1E receptor having a threonine at amino acid position 44 or a haplotype linked to a threonine at amino acid position 44, or a phenylalanine at amino acid position 262 or a haplotype linked to a phenylalanine at amino acid position 262; serotonin 2B receptor having a tryptophan at amino acid position 388 or a haplotype linked to a tryptophan at amino acid position 388; serotonin 7 receptor having a lysine at amino acid position 92 or a haplotype linked to a lysine at amino acid position 92, or a proline at amino acid position 421 or a haplotype linked to a proline at amino acid position 421; angiotensin II type 1 receptor having an arginine at amino acid position 45 or a haplotype linked to an arginine at amino acid position 45, or a serine at amino acid position 204 or a haplotype linked to a serine at amino acid position 204, or a tryptophan at amino acid position 289 or a haplotype linked to a tryptophan at amino acid position 289; CB1 cannabinoid receptor having a leucine at amino acid position 200 or a haplotype linked to a leucine at amino acid position 200; cholecystokinin B receptor having a glutamine at amino acid position 224 or a haplotype linked to a glutamine at amino acid position 224; gamma-amino-butyric acid B receptor having a leucine at amino acid position 93 or a haplotype linked to a leucine at amino acid position 93, or a proline at amino acid position 452 or a haplotype linked to a proline at amino acid position 452; thromboxane A2 receptor having a glutamic acid at amino acid position 80 or a haplotype linked to a glutamic acid at amino acid position, 80, a valine at amino acid position 94 or a haplotype linked to a valine at amino acid position 94, or a glutamic acid at amino acid position 176 or a haplotype linked to a glutamic acid at amino acid position 176; or a neuropeptide Y1 receptor having a proline at amino acid position 298, or a haplotype linked to a proline at amino acid position 298. Detecting the presence of a GPCR variant indicates the presence of the GPCR variant in the subject.

The invention also provides methods for identifying a subject having a clinical indication associated with a variant GPCR. In one embodiment, a method includes providing a subject or sample from a subject; and assaying the subject or the sample from the subject for the presence of a GPCR variant selected from: alpha 1A/C adrenergic receptor having a cysteine residue at amino acid position 78 or a haplotype linked with a cysteine residue at amino acid position 78, or a serine residue at amino acid position 200 or a haplotype linked with a serine residue at amino acid position 200; beta 3 adrenergic receptor having a leucine residue at amino acid position 78 or a haplotype linked with a leucine residue at amino acid position 78; dopamine D1 receptor having a proline at amino acid position 37 or a haplotype linked with a proline at amino acid position 37, or an arginine at amino acid position 37 or a haplotype linked with an arginine at amino acid position 37, or a serine at amino acid position 79 or a haplotype linked with a serine at amino acid position 79, or an alanine at amino acid position 199 or a haplotype linked with an alanine at amino acid position 199; dopamine D2 receptor having an arginine at amino acid position 40 or a haplotype linked with an arginine at amino acid position 40, or a leucine at amino acid position 208 or a haplotype linked to a leucine at amino acid position 208; dopamine D3 receptor having a leucine at amino acid position 50 or a haplotype linked with a leucine at amino acid position 50; histamine H1 receptor having a glycine at amino acid position 216 or a haplotype linked to a glycine at amino acid position 216, or a proline at amino acid position 226 or a haplotype linked to a proline at amino acid position 226; histamine H2 receptor having an asparagine at amino acid 175 or a haplotype linked to an asparagine at amino acid 175, or a glycine at amino acid position 215 or a haplotype linked to a glycine at amino acid position 215, or an arginine at amino acid position 231 or a haplotype linked to an arginine at amino acid 231; serotonin 1A receptor having a valine at amino acid position 50 or a haplotype linked to a valine at amino acid position 50, or an isoleucine at amino acid position 172 or a haplotype linked to an isoleucine at amino acid position 172, or a phenylalanine at amino acid position 381 or a haplotype linked to a phenylalanine at amino acid position 381; serotonin 1B receptor having an asparagine at amino acid position 221 or a haplotype linked to an asparagine at amino acid position 221; serotonin 1D receptor having a leucine at amino acid position 53 or a haplotype linked to a leucine at amino acid position 53, or a glycine at amino acid position 366 or a haplotype linked to a glycine at amino acid position 366; serotonin 1E receptor having a threonine at amino acid position 44 or a haplotype linked to a threonine at amino acid position 44, or a phenylalanine at amino acid position 262 or a haplotype linked to a phenylalanine at amino acid position 262; serotonin 2B receptor having a tryptophan at amino acid position 388 or a haplotype linked to a tryptophan at amino acid position 388; serotonin 7 receptor having a lysine at amino acid position 92 or a haplotype linked to a lysine at amino acid position 92, or a proline at amino acid position 421 or a haplotype linked to a proline at amino acid position 421; angiotensin II type 1 receptor having an arginine at amino acid position 45 or a haplotype linked to an arginine at amino acid position 45, or a serine at amino acid position 204 or a haplotype linked to a serine at amino acid position 204, or a tryptophan at amino acid position 289 or a haplotype linked to a tryptophan at amino acid position 289; CB1 cannabinoid receptor having a leucine at amino acid position 200 or a haplotype linked to a leucine at amino acid position 200; cholecystokinin B receptor having a glutamine at amino acid position 224 or a haplotype linked to a glutamine at amino acid position 224; gamma-amino-butyric acid B receptor having a leucine at amino acid position 93 or a haplotype linked to a leucine at amino acid position 93, or a proline at amino acid position 452 or a haplotype linked to a proline at amino acid position 452; thromboxane A2 receptor having a glutamic acid at amino acid position 80 or a haplotype linked to a glutamic acid at amino acid position 80, a valine at amino acid position 94 or a haplotype linked to a valine at amino acid position 94, or a glutamic acid at amino acid position 176 or a haplotype linked to a glutamic acid at amino acid position 176; or a neuropeptide Y1 receptor having a proline at amino acid position 298, or a haplotype linked to a proline at amino acid position 298. Detecting the presence of a GPCR variant identifies the subject as having a clinical indication associated with the variant GPCR.

Clinical indications associated with the presence of the variant GPCR include, for example, increased or decreased sensitivity or insensitivity to a beneficial physiological effect of an agonist or antagonist of the GPCR variant; increased or decreased sensitivity or insensitivity to an adverse side effect of an agonist or antagonist of the GPCR variant; increased or decreased resistance or susceptibility to, or benign disease progression in, a pathophysiological state in which the GPCR receptor agonist or antagonist activity is therapeutically useful.

Subjects include human subjects and further include subjects that are being treated or are candidates for treatment with an agent that affects an activity of one or more of the GPCR variants. In particular aspects, the agent is selected from: dobutamine hydrochloride, ephedrine, ephedrine hydrochloride, ephedrine sulfate, epinephrine, epinephrine bitartrate, epinephrine hydrochloride, mephentermine sulfate, metaraminol bitartrate, methoxamine hydrochloride, midodrine hydrochloride, norepinephrine bitartrate, phenylephrine hydrochloride, psuedoephedrine hydrochloride, psuedoephedrine sulfate, dihydroergotamine mesylate, ergotamine tartrate, doxazosin mesylate, ergoloid mesylates, phenoxyb enz amine hydrochloride, phentolamine mesylate, labetalol hydrochloride, prazosin hydrochloride, terazosin hydrochloride, tolazoline hydrochloride, chlorpromazine, risperidone, amitriptyline, desipramine; albuterol, carvedilol, esmolol hydrochloride, isoproterenol hydrochloride, metoprolol succinate, metoprolol tartrate, pindolol, propranolol hydrochloride; L-748,328, L-742,791, L-748,337, fenoldopam, dopexamine, pergolide, bromocriptine, SCH23390, dopamine hydrochloride, bromocriptine mesylate, ergonovine maleate, methylergonovine maleate, trihexyphenidyl hydrochloride, pramipexole, ropinirole, haloperidol, thiothixene, clozapine, respiridone, olanzapine, quetiapine, amoxapine, buspirone, amitriptyline, nortriptyline, imipramine, prochlorperazine edisylate, prochlorperazine maleate, meclizine hydrochloride, thiethylperazine malate, thiethylperazine maleate, loperamide hydrochloride, histamine, lisuride, acrivastine, azatadine maleate, brompheniramine maleate, dexbrompheniramine maleate, carbinoxamine maleate, cetrizine hydrochloride, chlorpheniramine maleate, clemastine fumarate, cyproheptadine hydrochloride, diphenhydramine hydrochloride, doxylamine succinate, fexofenadine hydrochloride, loratadine, promethazine hydrochloride, tripelennamine hydrochloride, triprolidine hydrochloride, azelastine hydrochloride, emedastine hydrochloride, ketotifen fumarate, levoclabastine hydrochloride, olopatadine hydrochloride, dimenhydrinate, trimethobenzamide hydrochloride, cimetidine hydrochloride, famotidine, nizatidine ranitidine hydrochloride, buspirone hydrochloride, gepirone, ipsaperone, sumatriptan succinate, serotonin, oxymetazoline hydrochloride, rizatriptan benzoate, naratriptan hydrochloride, zolmitriptan, and eletriptan, perlapine, cis-flupenthixol, ocaperidone, tefludazine, triflouperazine hydrochloride, timolol maleate, methysergide maleate, desipramine hydrochloride, nortriptyline hydrochloride, fluoxetine hydrochloride, fluvoxamine maleate, mirtazepine, loxapine hydrochloride, loxapine succinate, mesioridazine besylate, serotonin hydrochloride, dihydroergotamine methanosulfate, dihydroergotamine mesylate, modafinil, protryptiline hydrochloride, amoxapine, trazodone hydrochloride, fluphenazine, fluspirilene, ziprasidone, chlorpromazine hydrochloride, angiotensin II, valsartan, irbesartan, candesartan, eprosartan, zolasartan, tasosartan, telmisartan, olmesartan, fonsartan, embusartan, saprisartan, losartan potassium, dronabinol, nabilone, sincalide, CCK-4, CCK-8, gastrin, C1988, L265260; baclofen, thromboxane A2, sulotroban, vapiprost, NPY and PYY.

The invention further provides polynucleotides that specifically hybridize to nucleic acid sequence encoding a variant GPCR, variant GPCR polypeptides and antibodies that specifically bind to the variant GPCR polypeptides. In one embodiment, a nucleic acid sequence encoding a variant GPCR is selected from: Alpha 1A/C adrenergic receptor having a cysteine residue at amino acid position 43 or a serine at amino acid position 200; Beta 3 adrenergic receptor having a leucine residue at amino acid position 78; D1 dopamine receptor having a proline at amino acid position 37 or an arginine at amino acid position 37 or a serine at amino acid position 79 or an alanine at amino acid position 199; D2 dopamine receptor having an arginine at amino acid position 40 or a leucine at amino acid position 208; D3 dopamine receptor having a leucine at amino acid position 50; H1 histamine receptor having a glycine at amino acid position 216 or a proline at amino acid 226; H2 histamine receptor having an asparagine at amino acid position 175 or a glycine at amino acid position 215 or an arginine at amino acid position 231; 1A serotonin receptor having a valine at amino acid position 50 or an isoleucine at amino acid position 172 or a phenylalanine at amino acid position 381; 1B serotonin receptor having an asparagine at amino acid position 221; 1D serotonin receptor having a leucine at amino acid position 53 or a glycine at amino acid position 366; 1E serotonin receptor having a threonine at amino acid position 44 or a phenylalanine at amino acid position 262; 2B serotonin receptor having a tryptophan at amino acid position 388; serotonin 7 receptor having a lysine at amino acid position 92 or a proline at amino acid position 421; angiotensin 2 type 1 receptor having an arginine at amino acid position 45 or a serine at amino acid position 204 or a tryptophan at amino acid position 289; cannabinoid CB1 receptor having a leucine at amino acid position 200; cholecystokinin B receptor having a glutamine at amino acid position 224; gamma-amino-butyric acid B receptor having a leucine at amino acid position 93 or a proline at amino acid position 452; thromboxane A2 receptor having a glutamic acid at amino acid position 80 or a valine at amino position 94 or a glutamic acid at amino acid position 176; or neuropeptide Y1 receptor having a proline at amino acid position 298; and a sequence encoding a portion of the above variant GPCR having at least 10 bases that includes the sequence that encodes the designated amino acid.

Polynucleotides of the invention can be of various lengths. In one embodiment, the polynucleotide is from about 10 to 50 bases in length. Polynucleotides of the invention can also have various amounts of complementarity or homology to the nucleic acid sequence encoding GPCR. In one embodiment, the polynucleotide has 90% or more complementarity or homology to a sequence that encodes the GPCR. In another embodiment, the polynucleotide specifically hybridizes to a GPCR variant nucleic acid sequence selected from any of (SEQ ID NOs:2, 3, 8, 12-15, 22, 23, 28, 32, 33, 38-40, 46-48, 54, 58, 59, 64, 65, 70, 74, 75, 80-82, 88, 92, 96, 97, 102-104, 110).

Polynucleotides of the invention include single and double strand, circular and linear and which specifically hybridize to a double strand sequence; a single strand sense sequence; a single strand antisense sequence; a cDNA sequence, a genomic sequence; or an RNA sequence, the sequence including that portion of the GPCR sequence that contains the nucleotide variant that encodes the variant amino acid residue.

The invention additionally provides detection substrates, which include a two-dimensional array of one or more of the invention compositions. In one embodiment, a detection substrate includes a polynucleotide that specifically hybridizes to nucleic acid sequence encoding a variant GPCR, attached to a substrate at defined positions. In additional embodiments, detection substrates include multiple GPCR variant sequences, or alternatively or in addition to, one or more nucleic acids distinct from a GPCR variant sequence. In various aspect, additional nucleic acids number from about 10 to 100, 100 to 500, 500 to 100, 1000 to 5000, 5000 to 10,000, 10,000 to 100,000, which optionally includes variant GPCRs, wild type GPCRs sequences (e.g., wild type in respect to a GPCR variant) distinct from GPCRs.

The invention moreover provides kits that includes one or more of the compositions of the invention. In one embodiment, a kit includes a polynucleotide that specifically hybridizes to nucleic acid sequence encoding a variant GPCR, and instructions for detecting the presence of the variant GPCR in a subject. In another embodiment, a kit includes a detection substrate with one or more polynucleotides that specifically hybridize to nucleic acid sequence encoding a variant GPCR, attached to a substrate at defined positions and, optionally, instructions for detecting the presence of the variant GPCR in a subject. In particular aspects, instructions for screening a subject for a clinical indication of a GPCR variant are included in the kit. In more particular aspects, the clinical indications are selected from: decreased or increased sensitivity to a beneficial physiological effect of an agonist or antagonist of the corresponding GPCR; identifying a subject requiring a higher or lower clinical dose of an agonist or antagonist of the corresponding GPCR; identifying a subject having decreased or increased sensitivity towards an adverse side effect of an agonist or antagonist of the corresponding GPCR; identifying a subject susceptible to, or at risk of malignant or benign disease progression in a pathophysiological state in which an agonist or antagonist of the corresponding GPCR is therapeutically useful; identifying a subject having lesser susceptibility to, or decreased risk of malignant or benign disease progression in a pathophysiological state in which an agonist or antagonist of the corresponding GPCR is therapeutically useful.

DETAILED DESCRIPTION

Figure 1:
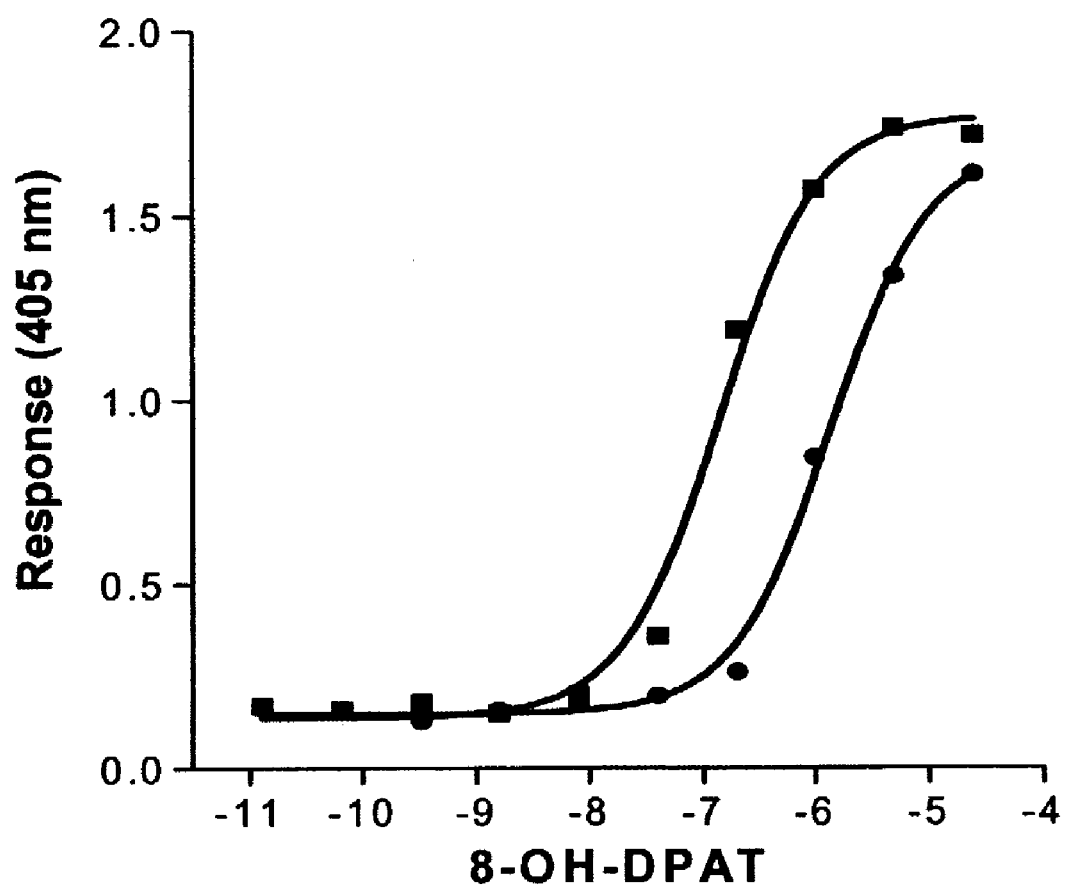
FIG. 1 shows the functional response of the "Wild Type" human 5HT1A receptor (Filled Squares), and the A50V 5HT1A receptor polymorphic variant (Filled Diamonds) to the 5HT1A receptor agonist 8-OH-DPAT as determined by the R-SAT assay. There is an approximately twenty-fold decrease in functional potency observed for this particular GPCR variant.
Figure 2:
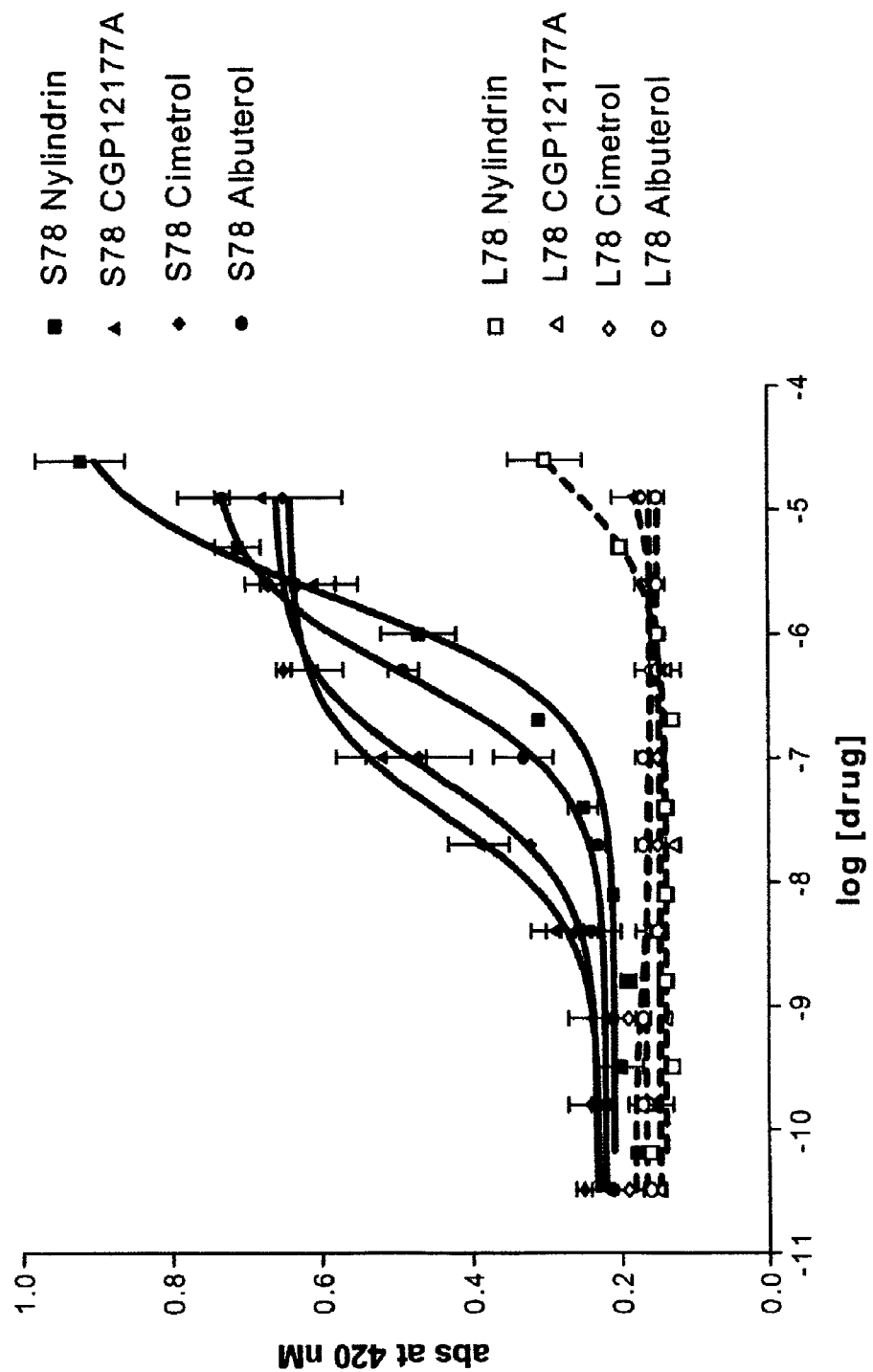
FIG. 2 shows that a S78L mutation in the beta 3 receptor protein renders the receptor unresponsive to the reference and clinical agonists tested.
Figure 3:
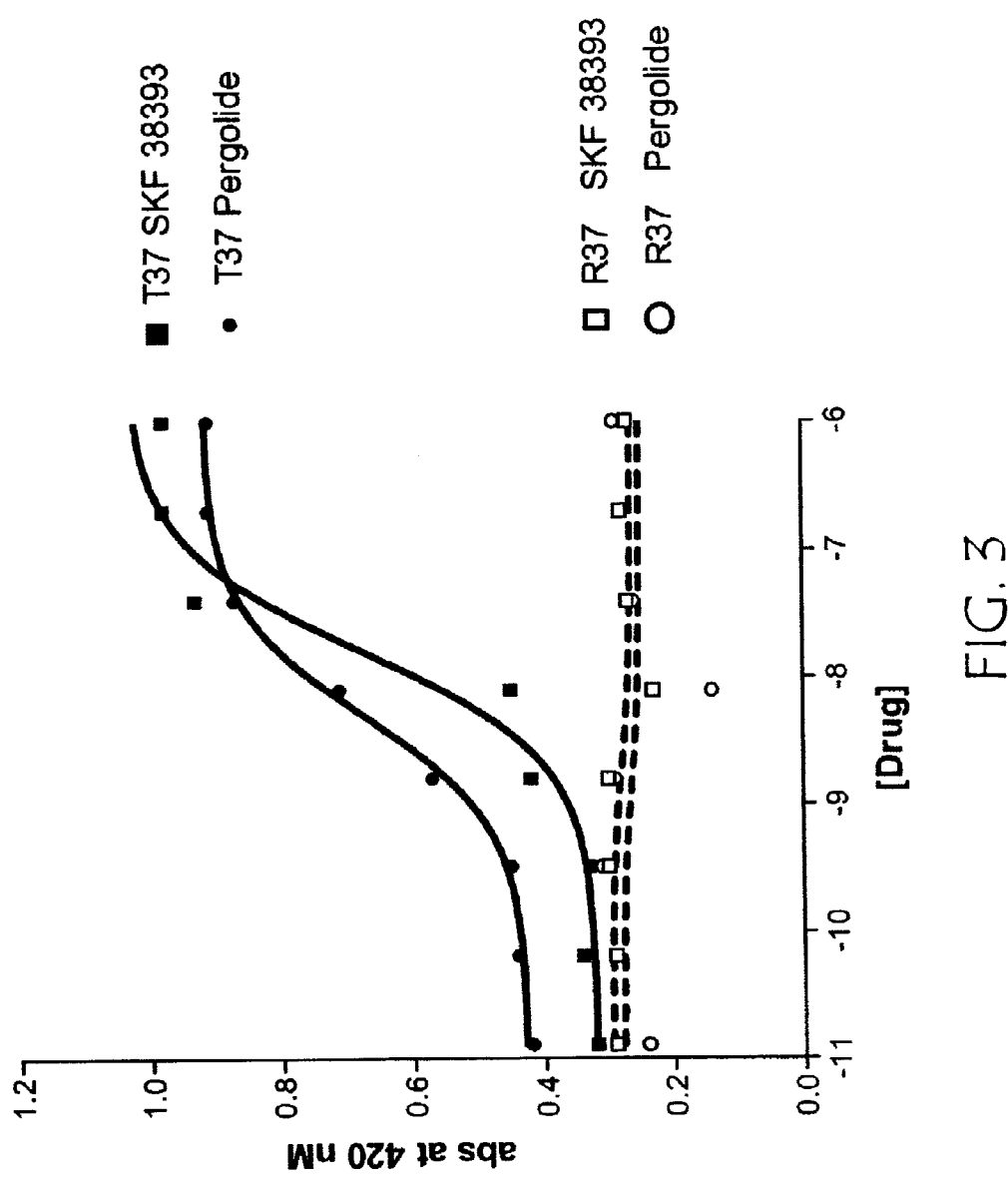
FIG. 3 shows that a T37R mutation in the dopamine D1 receptor protein renders the receptor unresponsive to the reference and clinical agonists tested.
Figure 4:
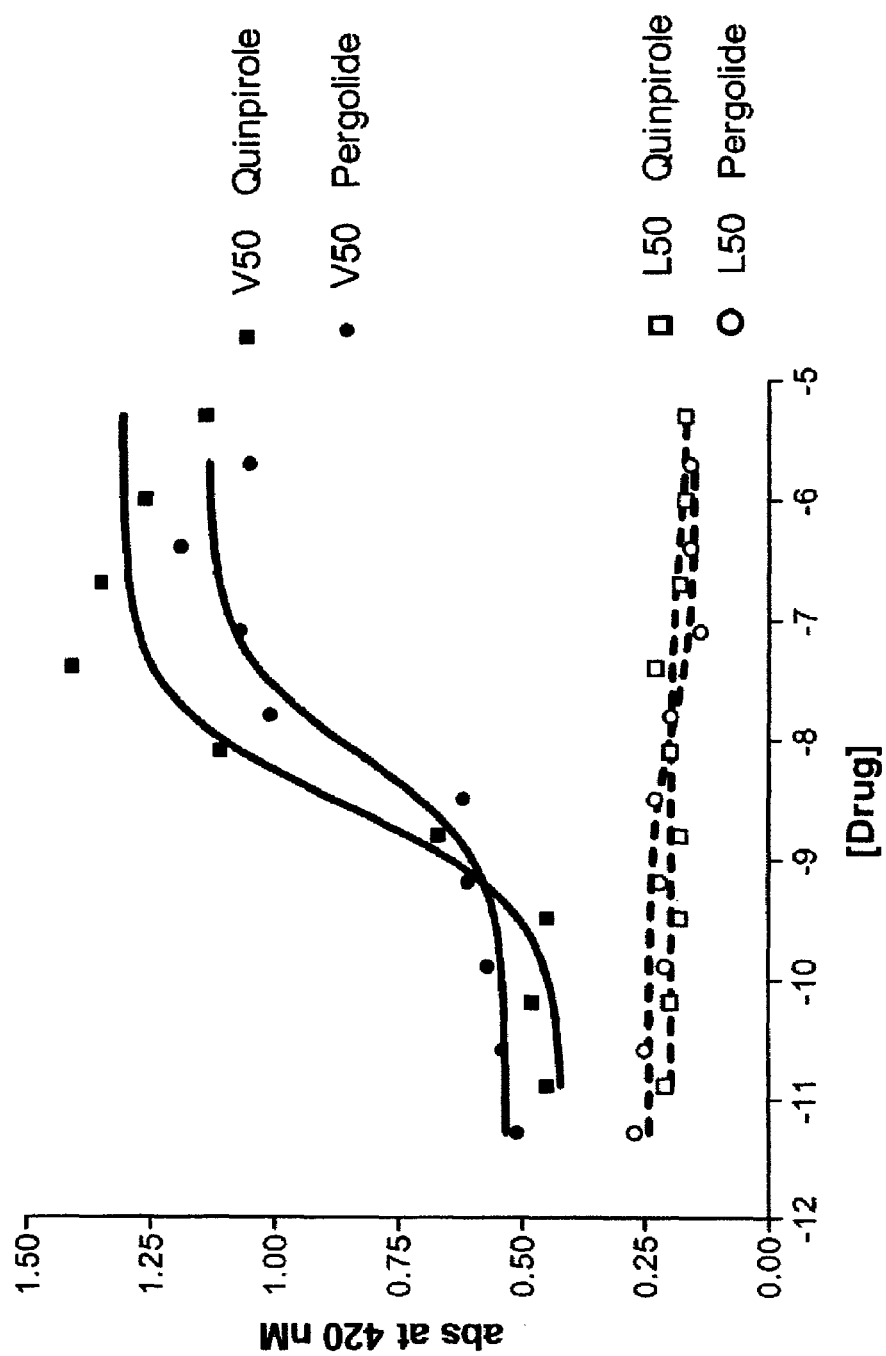
FIG. 4 shows that a V50L mutation in the dopamine D3 receptor protein renders the receptor unresponsive to the reference and clinical agonists tested.
Figure 5:
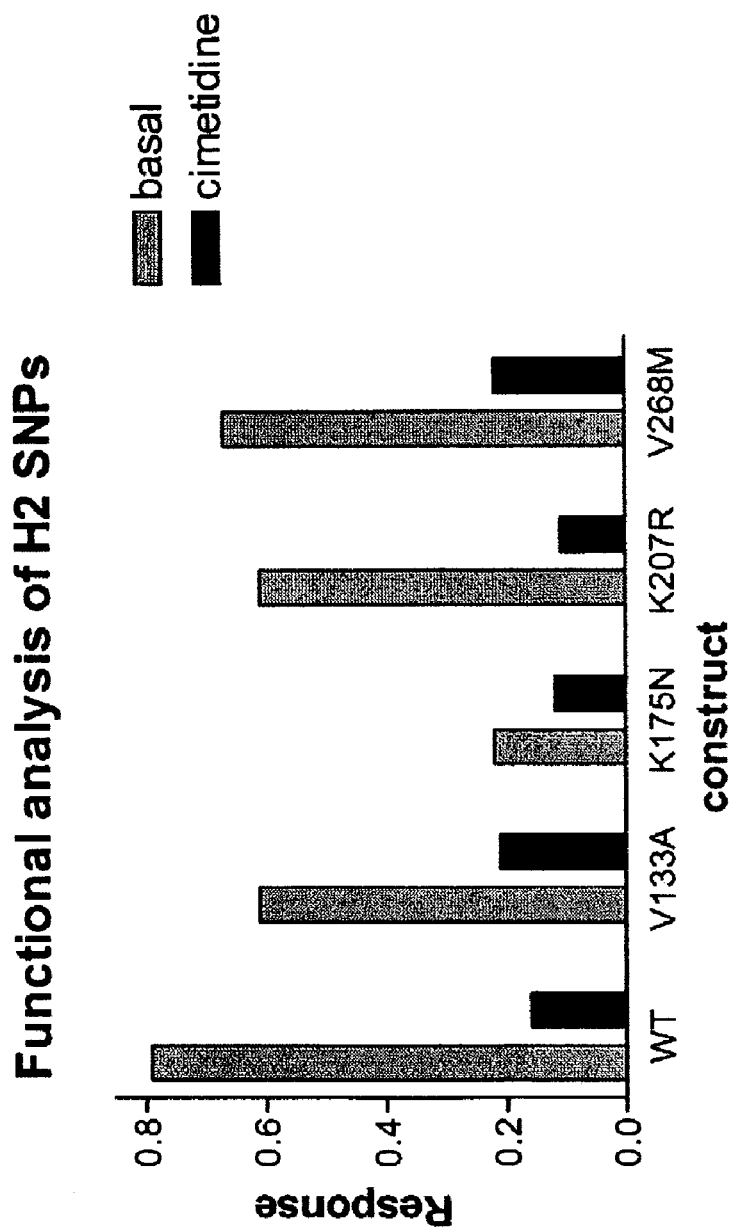
FIG. 5 shows that a K175N mutation in the histamine H2 receptor protein significantly diminishes constitutive receptor activity.
Figure 6:
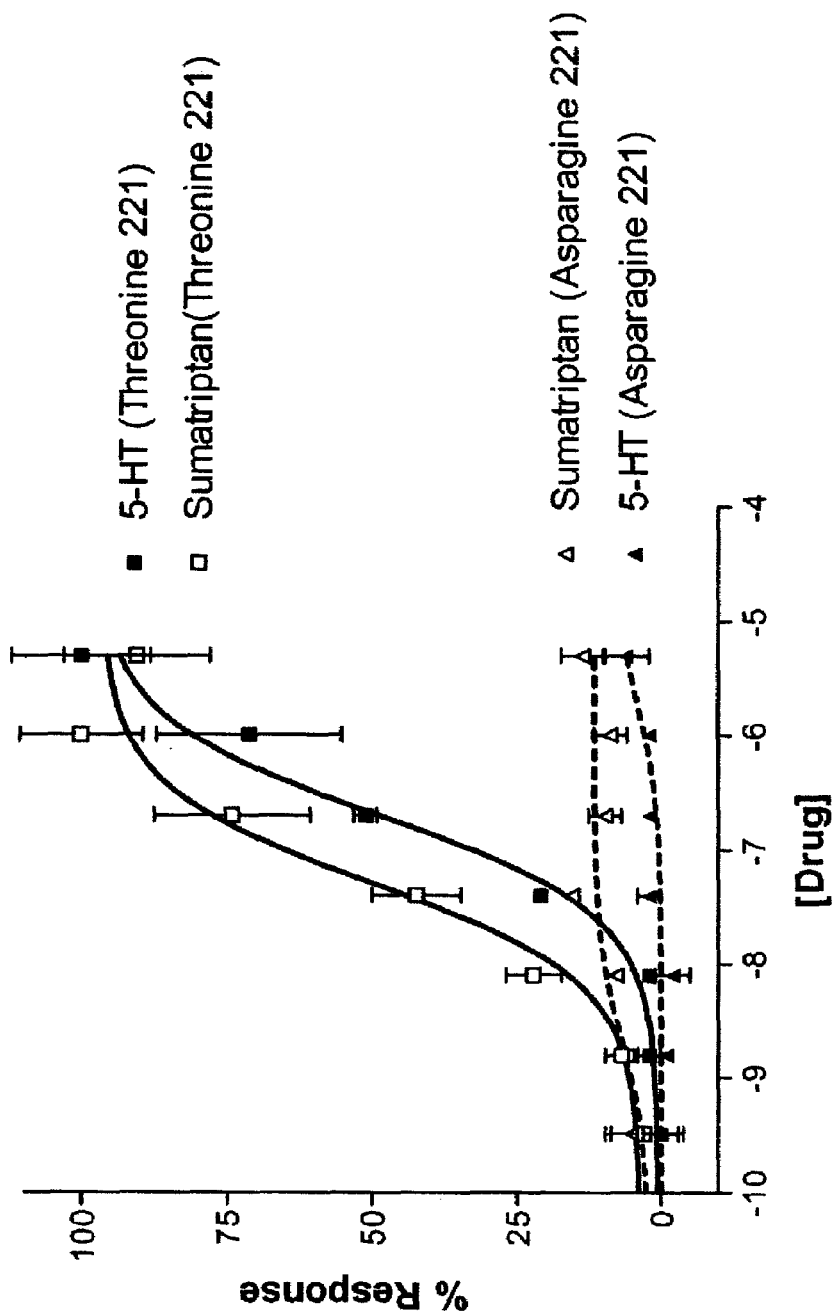
FIG. 6 shows that a T221N mutation in the serotonin 1B receptor protein renders the receptor protein non-functional.
Figure 7:
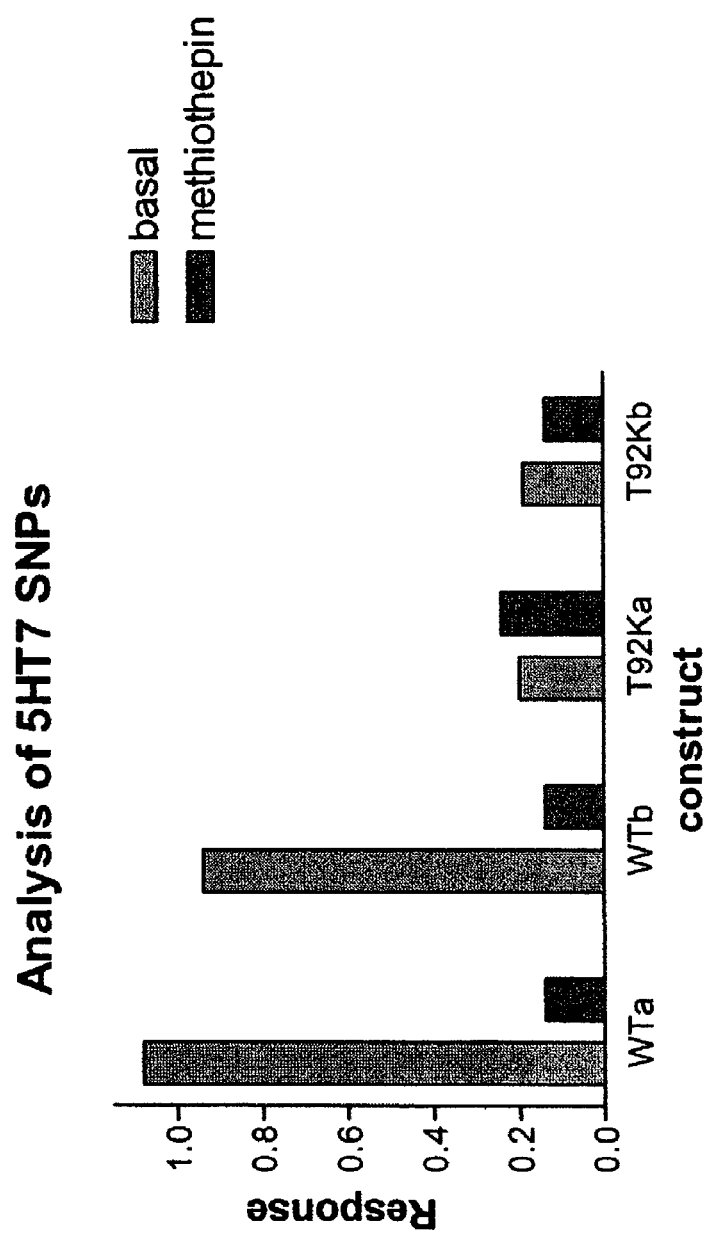
FIG. 7 shows that a T92K mutation in the serotonin 7 receptor protein significantly diminishes constitutive receptor activity.
Figure 8:
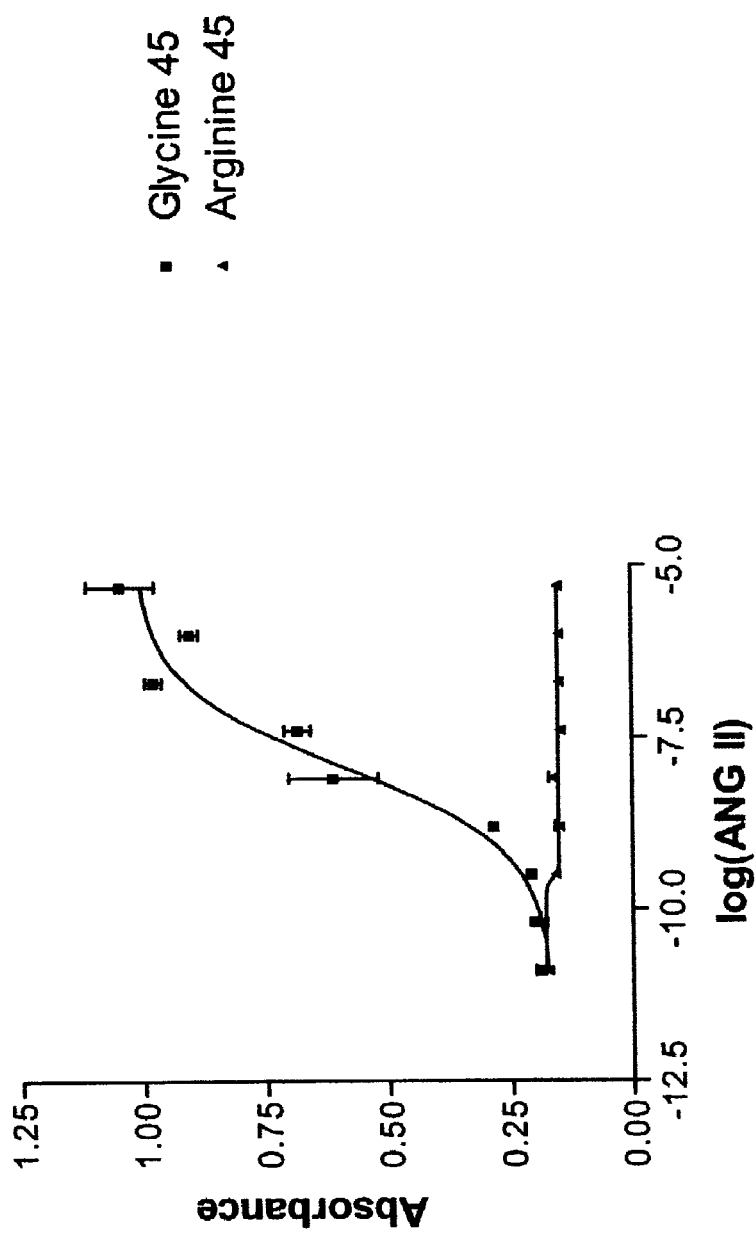
FIG. 8 shows that a G45W mutation in the angiotensin II Type 1 receptor protein renders the receptor protein non-functional.
Figure 9:
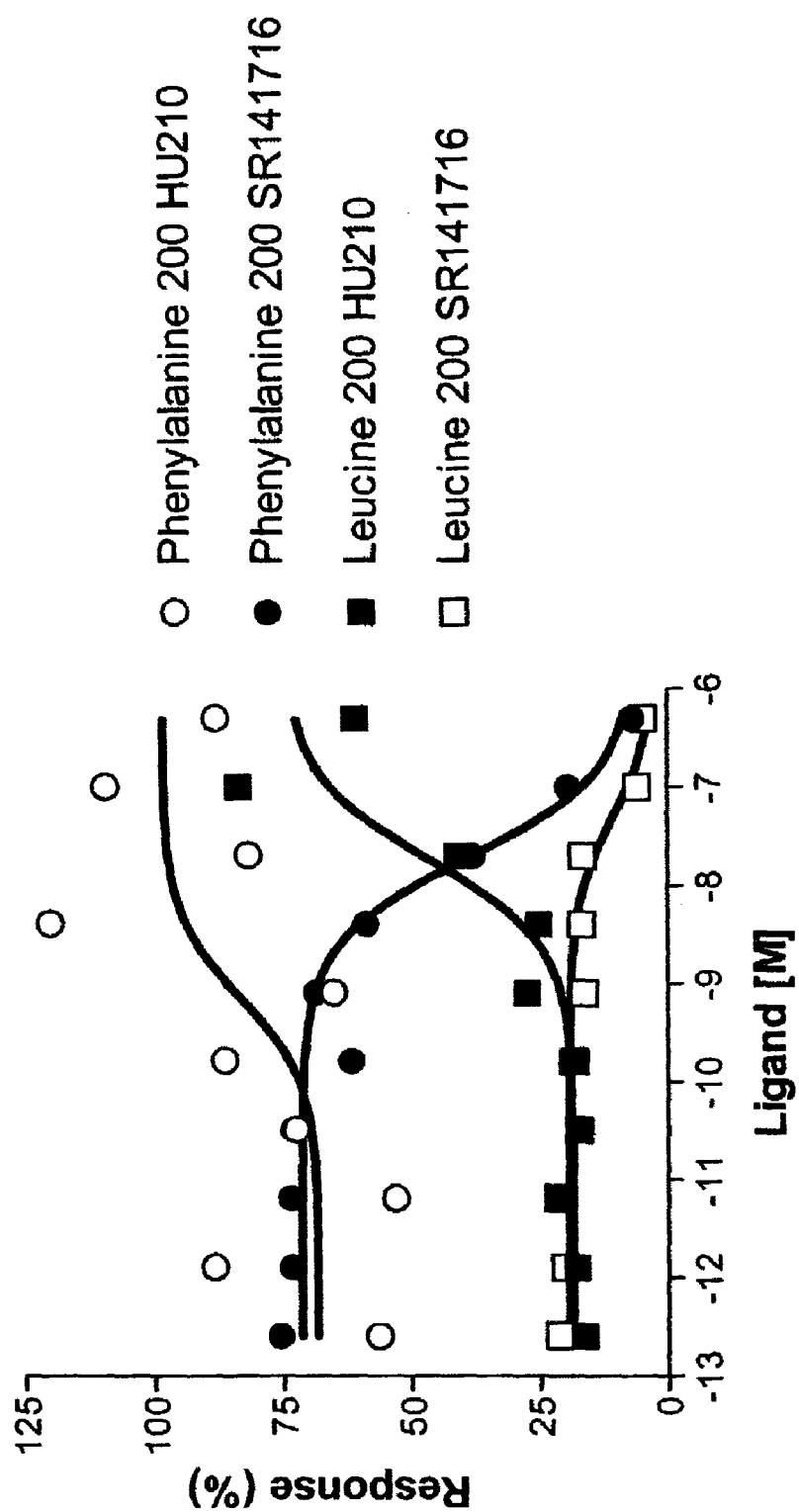
FIG. 9 shows that a F200L mutation in the cannabinoid 1 receptor decreases the basal biological activity of the receptor protein.
Figure 10:
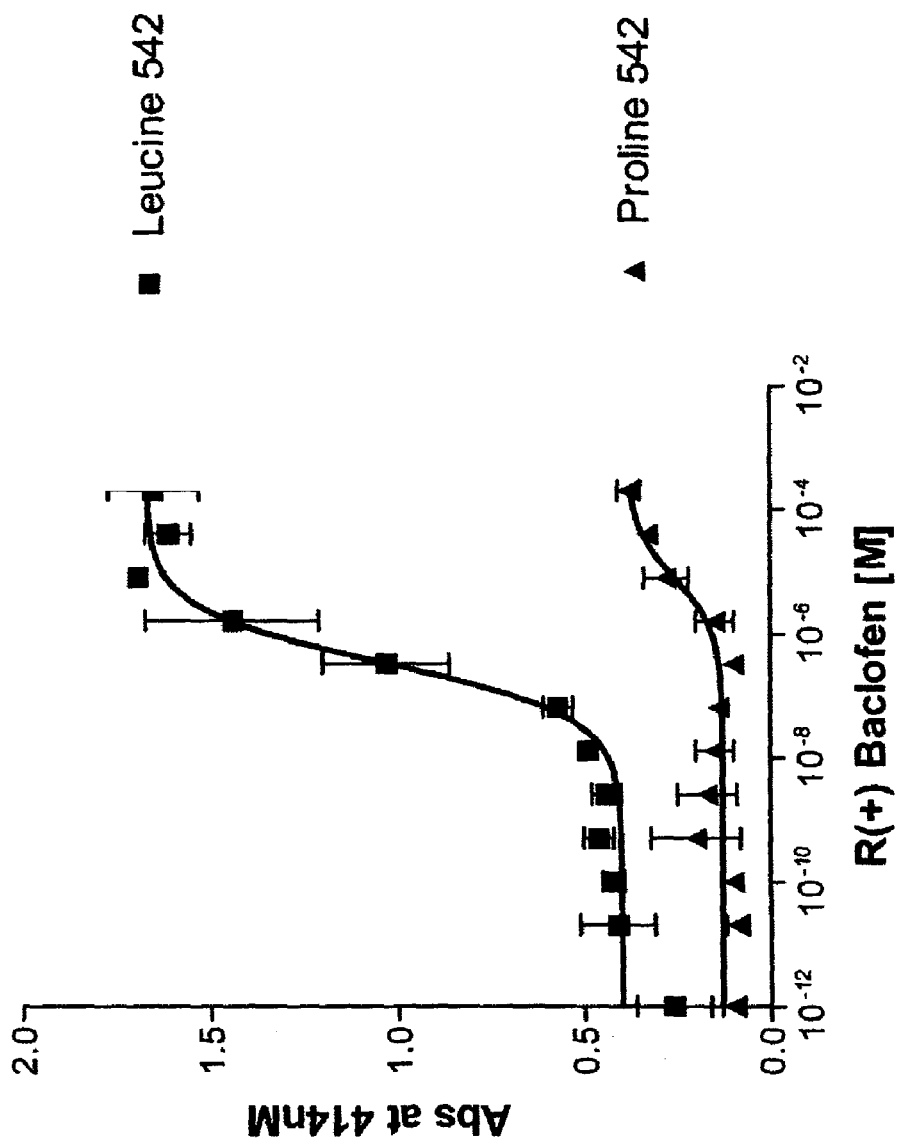
FIG. 10 shows that a L542P mutation in the GABA-BR1 receptor protein renders the receptor protein significantly less responsive.

The functional consequences of genetic variation in 19 G-protein coupled receptor genes are disclosed. For each receptor a number of reference agonists, and clinically useful therapeutic agents, were assayed for functional potency at the variants under study using the in-vitro, cell based, receptor selection and amplification technology (R-SAT) system (Example 1). The majority of polymorphic variants studied did not affect receptor function. However, 37 GPCR polymorphisms were found to have functional consequences. In particular, polymorphic variation altered the functional potencies observed for the various clinically used agents. Two phenotypes were observed: 1) Loss of function phenotypes were characterized by a statistically significant (two tailed student T-Test with $p<0.05$) decrease in functional potencies for the ligands tested, or a decrease in agonist independent, basal, constitutive receptor activity; and 2) Gain of function phenotypes were characterized by a statistically significant (two tailed student T-Test with $p<0.05$) increase in functional potencies for the ligands tested, or an increase in agonist independent, basal, constitutive receptor activity.

The altered function of 37 variants of G-protein coupled receptor genes include: two variants of the alpha 1A/C adrenergic receptor gene, a variant of the beta 3 adrenergic receptor gene, four variants in the dopamine D1 receptor gene, two variants of the dopamine D2 receptor, a variant of the dopamine D3 receptor, two variants of the H1 histamine receptor, three variants of the H2 histamine receptor, three variants of the serotonin 1A receptor, one variant of the serotonin 1B receptor, two variants of the serotonin 1D receptor, two variants of the serotonin 1E receptor, one variant of the serotonin 2B receptor, two variants of the serotonin 7 receptor, three variants of the angiotensin II, type 1 receptor, one variant of the CB1 cannabinoid receptor, one variant of the cholecystokinin B receptor, two variants of the gamma-amino-butyric acid type B receptor, and three variants of the TP prostanoid receptor, and one variant of the neuropeptide Y1 receptor.

The identification of the functional consequences of theses polymorphic variations enables predictions of the clinical consequences of drugs that target these proteins. For example, genotyping individuals for these variants allows an assessment of: 1) sensitivity towards, or resistance to, therapeutic or adverse side effects of a given drug whose actions are mediated in full, or in part, by GPCR activation or inactivation, and 2) susceptibility or predisposition towards, and/or benign or malignant progression of, a disease whose cause or clinical course is determined or modified GPCR activation or inactivation.

The genotyping of individuals for the presence of these genetic variants, or any genetic haplotype associated with these variants, can guide decisions regarding which patients to treat with a given drug, and which doses of a given drug will achieve a therapeutic response. In addition, such genotyping will guide decisions concerning disease diagnosis, disease predisposition, and decisions regarding aggressive or passive disease treatment options.

As used herein, the terms "variant" and "polymorphism" and grammatical variations thereof, are used interchangeably to refer to one or more nucleotide changes in a gene sequence that is different than that which is most commonly found at that nucleotide position in the population, e.g., different from a wild-type sequence. The nucleotide changes of the GPCR variants disclosed herein result in changes of single amino acid residues (point mutations) in the expressed GPCR protein, which in turn alters the functional potency of the variant GPCR relative to wild type GPCR.

As used herein, the term "functional potency," when used in reference to a receptor (e.g., a GPCR), means the response of the receptor to a ligand, such as a drug. A "shift" in functional potency means that the receptors' response to the given drug or class of drugs is different relative to a reference receptors' response. The shift may reflect an increased or decreased response of the receptor to a ligand relative to a reference receptors' response. For example, an isoleucine to serine transition at amino acid position 200 (I200S) of the alpha 1A/C receptor protein induces a 2 to 4 fold shift in functional potency for several drugs tested, which indicates that 2 to 4 fold more or less drug is required to activate the alpha 1A/C receptor protein when serine is substituted for isoleucine at position 200. In this example, the shift results in a decrease of biological function.

As used herein, the term "haplotype linked with," when used in reference to a polymorphic variant, means that there is a polymorphism elsewhere in the gene or the genomic sequence (e.g., introns, 5' or 3' upstream regions, etc.), which is associated with the presence of a particular variant. Thus, where the presence of a haplotype is linked with the presence of a particular polymorphic variant, detecting the presence of the haplotype that is associated with the variant allows one to detect the presence of the polymorphic variant.

As used herein, the term "EC50" means the concentration of drug required to produce 50% of the maximal biological or pharmacological response observed in an assay. Thus, in the case of GPCR's, the EC50 is the amount of ligand that provides 50% maximal activity as determined using an assay (see, e.g., Example 1, which describes an R-SAT assay for determining the amount of a given ligand needed for 50% maximal activity). The EC50 values displayed in the Tables are inverse log values such that a higher value denotes a lower concentration of agonist required to activate the receptor. Thus, a variant GPCR having a number greater than the wild type GPCR indicates that the variant exhibits a gain of function (requires less agonist to exhibit the same activity), whereas a variant GPCR having a number less than wild type GPCR indicates that the variant GPCR exhibits a loss of function (requires more agonist to exhibit the same activity).

As used herein, the terms "sensitivity" or "insensitivity" refers to the response of a receptor to a ligand (e.g., a drug) relative to a reference receptor. Thus, when the term is used with a modifier, such as "increase," "enhance," "stimulate" "promote," and the like, the receptor exhibits greater sensitivity or greater insensitivity to a ligand, such as a drug, relative to a reference receptor. When the term is used with a modifier, such as "decrease," "abrogate," "inhibit" "prevent," "block" and the like, the receptor exhibits lesser sensitivity or lesser insensitivity to a ligand, such as a drug, relative to a reference receptor.

As used herein, the term "susceptibility" refers to a relative likelihood of the phenomenon referred to occurring. Thus, when the term is used with a modifier, such as "increase," "enhance," "stimulate" "promote," and the like, there is a greater likelihood of the phenomenon occurring (e.g., clinical indication). When the term is used with a modifier, such as "decrease," "abrogate," "inhibit" "prevent," and the like, there is a greater likelihood of the phenomenon (e.g., clinical indication) occurring.

The following abbreviations are used for convenience:

| | |
|---|---|
| NR | no response |
| "n" | defines the number of experimental replicates |
| AVE | average |
| STD DEV | standard deviation |
| 8-OH-DPAT | (+/−)-2-DIPROPYLAMINO-8-HYDROXY-1,2,3,4-TETRAHYDRONAPHTHALENE HYDROBROMIDE |
| 5HT | 5-hydroxytryptamine |
| 5CT | 5-carboxytryptamine |
| DHE | dihydroergotamine |
| mCPP | 1-(3-CHLOROPHENYL)PIPERAZINE DIHYDROCHLORIDE |
| CCK | cholecystokinin |
| AMPA | 3-AminopropylMethylPhosphonic Acid |
| PYY | PEPTIDE YY (HUMAN) |
| BRL4443 | 3-(1-Methylpiperidin-4-yl)-1H-indole-5-ol maleate |
| CGP12177A | 4-[3-[(1,1-Dimethylethyl)amino]-2-hydroxypropoxy]-1,3-dihydro-2H-benzimidazol-2-one hydrochloride |
| SKF 38393 | (+/−)-1-Phenyl-2,3,4,5-tetrahydro-(1H)-3-benzazapine-7,8-diol hydrochloride |
| SKF 82957 | R(+)-6-Chloro-7,8-dihydroxy-3-methyl-1-phenyl-2,3,4,5-tetrahydro-1H-3-benzazapine hydrobromide |
| SKF 81297 | R(+)-6-Chloro-7,8-dihydroxy-1-phenyl-2,3,4,5-tetrahydro-1H-3-benzazapine hydrobromide |
| ANG II | Angiotensin 2 |
| HU210 | (6AR)-TRANS-3-(1,1-DIMETHYLHEPTYL)-6A,7,10,10A-TETRAHYDRO-1-HYDROXY-6,6-DIMETHYL-6H-DIBENZO[B,D]PYRAN-9-METHANOL |
| SR141716 | N-(PIPERIDIN-1-YL)-5-(4-CHLOROPHENYL)-4-METHYL-1H-PYRAZOLE-3-CARBOXAMIDE |

Alpha Adrenergic 1A/C Receptors (ADRA1A, Genbank #NM_000680)

A functional effect of polymorphic variation at amino acid position 43 was observed:

TABLE 1

| G43C Compound | Glycine 43 | | | Cysteine 43 | | | |
|---|---|---|---|---|---|---|---|
| | Ave -Log EC50 | STD DEV | "n" | Ave -Log EC50 | STD DEV | "n" | FOLD |
| Phenylephrine | 6.97 | 0.10 | 7 | 7.57 | 0.09 | 7 | −4.0 |
| Cirazoline | 7.37 | 0.08 | 5 | 7.84 | 0.13 | 5 | −3.0 |
| Oxymetazoline | 8.00 | 0.33 | 6 | 8.72 | 0.28 | 6 | −5.2 |

A glycine to cysteine transition at amino acid position 43 (G43C) in the alpha 1A/C receptor protein was found to induce 3 to 5 fold shifts in functional potency for the reference and clinical agonists tested. This variant displays a gain of biological function, and individuals that possess this variant will be particularly sensitive to the physiological effects of a therapeutic drug that activates the Alpha 1A/C receptor.

A functional effect of polymorphic variation at amino acid position 200 was observed:

TABLE 2

| I200S Compound | Isoleucine 200 | | | Serine 200 | | | |
|---|---|---|---|---|---|---|---|
| | Ave -Log EC50 | STD DEV | "n" | Ave -Log EC50 | STD DEV | "n" | FOLD |
| Phenylephrine | 7.05 | 0.10 | 7 | 6.61 | 0.14 | 7 | 2.8 |
| Dobutamine | 6.26 | 0.24 | 7 | 5.67 | 0.19 | 7 | 3.9 |
| Cirazoline | 7.81 | 0.17 | 7 | 7.32 | 0.27 | 7 | 3.1 |
| Oxymetazoline | 8.10 | 0.50 | 7 | 7.66 | 0.43 | 7 | 2.8 |

A isoleucine to serine transition at amino acid position 200 (I200S) in the alpha 1A/C receptor protein was found to induce 2 to 4 fold shifts in functional potency for the reference and clinical agonists tested. This variant displays a loss of biological function, and individuals that possess this variant will be particularly insensitive to the physiological effects of a therapeutic drug that activates the Alpha 1A/C receptor.

Alpha 1A/C receptors mediate some of the varied physiological effects of the endogenous catecholamines epinephrine and norepinephrine. Therapeutic drugs with alpha 1A/C receptor agonist activity are used clinically to treat hypotension, orthostatic hypotension, hypotension associated with shock and sepsis, vascular headache (migraine), nasal congestion, cardiac arrhythmias including paroxysmal supraventricular tachycardia, cardiopulmonary arrest, broncospasm, allergic reactions, deep venous thrombosis prophylaxis, and the behavioral aspects of chronic neurodegenerative diseases such as Alzheimer's disease. Therapeutic drugs with alpha 1A/C receptor antagonist activity are used clinically to treat hypertension, hypertensive crises, the hypertension associated with pheochromocytomas, congestive heart failure, cocaine overdoses, erectile dysfunction, and urinary retention often associated with benign prostatic hypertrophy.

GPCR Variants #1 and #2: Alpha 1A/C Receptor G43C and I200S Polymorphisms

The presence in an individual of the genetic variant in the alpha 1A/C receptor gene that introduces a cysteine residue at amino acid position 43 or a serine residue at amino acid position 200 will predispose that individual to one or more of the following clinical indications:

1) Particular sensitivity or insensitivity (variant #2) to the beneficial physiological effects of alpha 1A/C receptor agonists, including, yet not limited to; dobutamine hydrochloride, ephedrine, ephedrine hydrochloride, ephedrine sulfate, epinephrine, epinephrine bitartrate, epinephrine hydrochloride, mephentermine sulfate, metaraminol bitartrate, methoxamine hydrochloride, midodrine hydrochloride, norepinephrine bitartrate, phenylephrine hydrochloride, psuedoephedrine hydrochloride, psuedoephedrine sulfate, dihydroergotamine mesylate, ergotamine tartrate. Genotyping individuals for polymorphic variants, cysteine residue at amino acid position 43 or a serine residue at amino acid position 200 (variant #2), can identify those patients requiring lower or higher (variant #2), respectively, clinical doses of these agents.

2) Particular sensitivity or insensitivity (variant #2), respectively, to the adverse cardiovascular (including, yet not limited to; hypertension, hypotension, syncope, tachycardia, bradycardia, angina, myocardial infarction, severe vasospasm, heart valvulopathies, and arrhythmias), gastrointestinal (including, yet not limited to; nausea, vomiting, abdominal pain, hepatotoxicity, and diarrhea), neuropsychiatric (including, yet not limited to; anxiety, depression, irritability, headache, confusion, dizziness, parasthesias, blurred vision, miosis, drowsiness, fatigue, and stroke), and urologic (including, yet not limited to; urinary retention, priapism) side effects of alpha 1A/C receptor agonists including, dobutamine hydrochloride, ephedrine, ephedrine hydrochloride, ephedrine sulfate, epinephrine, epinephrine bitartrate, epinephrine hydrochloride, mephentermine sulfate, metaraminol bitartrate, methoxamine hydrochloride, midodrine hydrochloride, norepinephrine bitartrate, phenylephrine hydrochloride, psuedoephedrine hydrochloride, psuedoephedrine sulfate, dihydroergotamine mesylate, ergotamine tartrate. Genotyping individuals for polymorphic variants, cysteine residue at amino acid position 43 or a serine residue at amino acid position 200 (variant #2), can identify those patients that will exhibit increased sensitivity or insensitivity (variant #2), respectively, towards these side effects.

3) Particular resistance or susceptibility (variant #2) to, or benign disease progression in, pathophysiological states in which alpha 1A/C receptor agonist activity is a therapeutically useful intervention including, yet not limited to: hypotension orthostatic hypotension, hypotension associated with shock and sepsis, vascular (migraine) headache, cardiac arrhythmias including paroxysmal supraventricular tachycardia, broncospasm, allergic reactions, deep venous thrombosis, and the behavioral aspects of chronic neurodegenerative diseases such as Alzheimer's disease. Genotyping individuals for the polymorphic variants, cysteine residue at amino acid position 43 or a serine residue at amino acid position 200(variant #2), can identify those patients that will exhibit a lesser or greater (variant #2), respectively, susceptibility to, or benign progression of, these disease states.

4) Particular insensitivity or sensitivity (variant #2) to the beneficial physiological effects of alpha 1A/C receptor antagonists including, yet not limited to: doxazosin mesylate, ergoloid mesylates, phenoxybenzamine hydrochloride, phentolamine mesylate, labetalol hydrochloride, prazosin hydrochloride, terazosin hydrochloride, tolazoline hydrochloride, a variety of clinically useful antipsychotics including chlorpromazine and risperidone, and a variety of clinically useful antidepressants including amitriptyline and desipramine. Genotyping individuals for the polymorphic-variants, cysteine residue at amino acid position 43 or a serine residue at amino acid position 200 (variant #2), can identify those patients requiring higher or lower (variant #2), respectively, clinical doses of these agents.

Particular insensitivity or sensitivity (variant #2) to the adverse cardiovascular (including, yet not limited to; hypertension, hypotension, syncope, tachycardia, bradycardia, angina, myocardial infarction, severe vasospasm, and arrhythmias), gastrointestinal (including, yet not limited to; nausea, vomiting, abdominal pain, hepatotoxicity, and diarrhea), neuropsychiatric (including, yet not limited to; anxiety, depression, irritability, headache, confusion, dizziness, parasthesias, blurred vision, miosis, drowsiness, fatigue, and stroke), urologic (including, yet not limited to; urinary retention), and other (including, yet not limited to; muscle and joint pain, and rash) side effects of alpha 1A/C receptor antagonists including, yet not limited to: doxazosin mesylate, ergoloid mesylates, phenoxybenzamine hydrochloride, phentolamine mesylate, labetalol hydrochloride, prazosin hydrochloride, terazosin hydrochloride, tolazoline hydrochloride, a variety of clinically useful antipsychotics including chlorpromazine and risperidone, and a variety of clinically useful antidepressants including amitriptyline and desipramine. Genotyping individuals for the polymorphic variants, cysteine residue at amino acid position 43 or a serine residue at amino acid position 200 (variant #2), can identify those patients that will exhibit a lesser or greater (variant #2) propensity, respectively, towards these side effects.

6) Particular susceptibility or resistance (variant #2) to, or malignant disease progression, in pathophysiological states in which alpha 1A/C receptor antagonist activity is a therapeutically useful intervention including, yet not limited to: hypertension, congestive heart failure, cocaine addiction and overdose, erectile dysfunction, and benign prostatic hypertrophy. Genotyping individuals for the polymorphic variants, cysteine residue at amino acid position 43 or a serine residue at amino acid position 200 (variant #2), can identify those patients that will exhibit a greater or lesser (variant #2), respectively, susceptibility to, or malignant progression of, these disease states.

Beta 3 Adrenergic Receptors (ADRB3, Genbank # X72861)

A functional effect of polymorphic variation at amino acid position 78 was observed:

A serine to leucine transition at amino acid position 78 (S78L) in the beta 3 receptor protein was found render the receptor unresponsive to the reference and clinical agonists tested. This variant displays a loss of biological function, such that individuals that possess this variant will be particularly insensitive to the physiological effects of a therapeutic drug that activates the beta 3 receptor. Beta 3 receptors mediate some of the varied physiological effects of the endogenous catecholamines epinephrine and norepinephrine. Therapeutic drugs with beta 3 receptor agonist activity are used clinically to treat; hypertension, chronic obstructive airway disease, asthma, acute bronchospasm, as tocolytics, the hypotension associated with shock and sepsis, arrhythmias including paroxysmal supraventricular tachycardia, cardiopulmonary arrest, migraines, and as metabolism increasing agents for the control of obesity and body weight. Therapeutic drugs with beta 3 receptor antagonist activity are in development to treat anorexia nervosa, and to treat various neuropsychiatric diseases.

GPCR Variant #3: Beta 3 Receptor S78L Polymorphism

The presence in an individual of the genetic variant in the beta 3 receptor gene that introduces a leucine residue at amino acid position 78 will predispose the individual to one or more of the following clinical indications:

1) Particular insensitivity to the beneficial physiological effects of beta 3 receptor agonists, including, yet not limited to; albuterol, carvedilol, dihydro-ergotamine mesylate, ergotamine tartrate, epinephrine, epinephrine bitartrate, epinephrine hydrochloride, esmolol hydrochloride, isoproterenol hydrochloride, metoprolol succinate, metoprolol tartrate, norepinephrine bitartrate, phenylephrine hydrochloride, pindolol, and propranolol hydrochloride. Genotyping individuals for this polymorphic variant can identify those patients requiring higher clinical doses of these agents.

2) Particular insensitivity to the adverse cardiovascular (including, yet not limited to; hypertension, hypotension, syncope, tachycardia, bradycardia, angina, myocardial infarction, severe vasospasm, heart valvulopathies, peripheral ischemia, and arrhythmias), gastrointestinal (including, yet not limited to; nausea, vomiting, abdominal pain, hepatotoxicity, and diarrhea), neuropsychiatric (including, yet not limited to; anxiety, depression, irritability, headache, confusion, dizziness, parasthesias, blurred vision, miosis, drowsiness, fatigue, insomnia, hallucinations, and stroke), pulmonary, (including, yet not limited to; dyspnea, bronchoconstriction, and wheezing), metabolic (including, yet not limited to; hyperglycemia, and transaminitis), and urologic (including, yet not limited to; urinary retention, priapism) side effects of beta 3 receptor agonists including, albuterol, carvedilol, dihydro-ergotamine mesylate, ergotamine tartrate, epinephrine, epinephrine bitartrate, epinephrine hydrochloride, esmolol hydrochloride, isoproterenol hydrochloride, metoprolol succinate, metoprolol tartrate, norepinephrine bitartrate, phenylephrine hydrochloride, pindolol, and propranolol hydrochloride. Genotyping individuals for this polymorphic variant can identify those patients that will exhibit a lesser propensity towards these side effects.

3) Particular susceptibility to, or malignant disease progression in, pathophysiological states in which beta 3 receptor agonist activity is a therapeutically useful intervention including, yet not limited to: hypertension, chronic obstructive airway disease, asthma, acute bronchospasm, premature labor, the hypotension associated with shock and sepsis, arrhythmias including paroxysmal supraventricular tachycardia, cardiopulmonary arrest, migraines, and obesity. Genotyping individuals for this polymorphic variant can identify those patients that will exhibit a greater susceptibility to, or malignant progression of, these disease states.

4) Particular sensitivity to the beneficial physiological effects of beta 3 receptor antagonists including, yet not limited to: L-748,328, L-742,791, and L-748,337. Genotyping individuals for this polymorphic variant can identify those patients requiring lower clinical doses of these agents.

5) Particular sensitivity to the adverse effects of beta 3 receptor antagonists. Genotyping individuals for this polymorphic variant can identify those patients that will exhibit a heightened sensitivity towards these side effects.

6) Particular resistance to, or benign disease progression in, pathophysiological states in which beta 3 receptor antagonist activity is a therapeutically useful intervention including, yet not limited to anorexia nervosa, and various neuropsychiatric diseases. Genotyping individuals for this polymorphic variant can identify those patients that will exhibit a lesser susceptibility to, or benign progression of, these disease states.

Dopamine D1 Receptors (DRD1, Genbank # S58541)

A functional effect of polymorphic variation at amino acid position 37 was observed:

TABLE 3

| T37P Compound | Threonine 37 | | | Proline 37 | | | FOLD |
|---|---|---|---|---|---|---|---|
| | Ave −Log EC50 | STD DEV | "n" | Ave −Log EC50 | STD DEV | "n" | |
| SKF38393 | 7.46 | 0.21 | 7 | 5.24 | 0.44 | 7 | 166 |
| SKF82957 | 7.04 | 0.12 | 6 | 6.02 | 0.15 | 5 | 11 |
| SKF81297 | 7.87 | 0.21 | 7 | 5.95 | 0.36 | 7 | 83 |
| Pergolide | 8.02 | 0.33 | 6 | 5.78 | 0.45 | 6 | 173 |

A threonine to proline transition at amino acid position 37 (T37P) in the dopamine D1 receptor protein was found to induce 11-173 fold shifts in functional potency for the reference and clinical agonists tested. This variant displays a loss of biological function, such that individuals that possess this variant will be particularly insensitive to the physiological effects of a therapeutic drug that activates the dopamine D1 receptor.

A functional effect of polymorphic variation at amino acid position 37 was observed:

A threonine to arginine transition at amino acid position 37 (T37R) in the dopamine D1 receptor protein was found to render the receptor unresponsive to the reference and clinical agonists tested. This variant displays a loss of biological function, such that individuals that possess this variant will be particularly insensitive to the physiological effects of a therapeutic drug that activates the dopamine D1 receptor.

A functional effect of polymorphic variation at amino acid position 79 was observed:

TABLE 4

| P79S Compound | Proline 79 | | | Serine 79 | | | FOLD |
|---|---|---|---|---|---|---|---|
| | Ave −Log EC50 | STD DEV | "n" | Ave −Log EC50 | STD DEV | "n" | |
| SKF38393 | 7.67 | 0.17 | 6 | 6.61 | 0.07 | 6 | 12 |
| SKF82957 | 7.46 | 0.14 | 6 | 5.34 | 0.28 | 6 | 132 |
| SKF81297 | 8.02 | 0.28 | 6 | 6.79 | 0.08 | 6 | 17 |
| Pergolide | 8.45 | 0.37 | 5 | 7.05 | 0.25 | 6 | 25 |

A proline to serine transition at amino acid position 79 (P79S) in the dopamine D1 receptor protein was found to induce 12-178 fold decreases in functional potency for the reference and clinical agonists tested. This variant displays a loss of biological function, such that individuals that possess this variant will be particularly insensitive to the physiological effects of a therapeutic drug that activates the dopamine D1 receptor.

A functional effect of polymorphic variation at amino acid position 199 was observed:

TABLE 5

| S199A Compound | Serine 199 | | | Alanine 199 | | | FOLD |
|---|---|---|---|---|---|---|---|
| | Ave −Log EC50 | STD DEV | "n" | Ave −Log EC50 | STD DEV | "n" | |
| SKF38393 | 7.60 | 0.17 | 10 | 6.46 | 0.22 | 8 | 14 |
| SKF82957 | 7.04 | 0.13 | 8 | 6.02 | 0.09 | 7 | 11 |
| SKF81297 | 7.89 | 0.16 | 10 | 6.72 | 0.12 | 7 | 15 |
| Pergolide | 8.18 | 0.29 | 8 | 7.01 | 0.16 | 6 | 15 |

A serine to alanine transition at amino acid position 199 (S199A) in the dopamine D1 receptor protein was found to induce 11-15 fold shifts in functional potency for the reference and clinical agonists tested. This variant displays a loss of biological function, such that individuals that possess this variant will be particularly insensitive to the physiological effects of a therapeutic drug that activates the dopamine D1 receptor.

Dopamine D1 receptors mediate some of the varied physiological effects of the endogenous catecholamine dopamine. Therapeutic drugs with D1 receptor agonist activity are used clinically to treat shock, cardiopulmonary arrest, hepato-renal syndrome, and renal failure. Therapeutic drugs with dopamine D1 receptor antagonist activity are currently in clinical trials for the treatment of neuropsychiatric disease, including addiction and dependence behaviors.

GPCR Variants #4, #5, #6, and #7: Dopamine D1 Receptor T37P, T37R, P79S, and S199A Polymorphisms The presence in an individual of the genetic variant in the dopamine D1 receptor gene that introduces a proline residue at amino acid position 37, an arginine at amino acid position 37, a serine at amino acid position 79, or an alanine at amino acid position 199 will predispose the individual to one or more of the following clinical indications:

1) Particular insensitivity to the beneficial physiological effects of dopamine D1 receptor agonists including, yet not limited to; dopamine hydrochloride, fenoldopam, dopexamine, and pergolide. Genotyping individuals for these polymorphic variants can identify those patients requiring higher clinical doses of these agents.

2) Particular insensitivity to the adverse cardiovascular (including, yet not limited to; tachycardia, angina, palpitations, orthostatic hypotension, dyspnea, arrhythmias, and vasoconstriction), neuropsychiatric (including, yet not limited to; anxiety, confusion, hallucinations, and headache), renal (including, yet not limited to; azotemia), metabolic (including, yet not limited to; hyperglycemia), and other (including, yet not limited to; pleural pulmonary and retroperitoneal fibrosis) side effects of dopamine D1 receptor agonists including, yet not limited to; dopamine hydrochloride, fenoldopam, dopexamine, and pergolide. Genotyping individuals for these polymorphic variants can identify those patients that will exhibit a lesser propensity towards these side effects.

3) Particular susceptibility to, or malignant disease progression in, pathophysiological states in which dopamine D1 receptor agonist activity is a therapeutically useful intervention including, yet not limited to: shock, cardiopulmonary arrest, hepato-renal syndrome, and renal failure. Genotyping individuals for these polymorphic variants can identify those patients that will exhibit a greater susceptibility to, or malignant progression of, these disease states.

4) Particular sensitivity to the beneficial physiological effects of the dopamine D1 receptor antagonists including, yet not limited to; bromocriptine, and SCH23390. Genotyping individuals for these polymorphic variants can identify those patients requiring lower clinical doses of these agents.

Particular sensitivity to the adverse cardiovascular (including, yet not limited to; hypotension, and arrhythmias) and neuropsychiatric (including, yet not limited to; confusion, and hallucinations) side effects of the dopamine D1 receptor antagonists including, yet not limited to; bromocriptine and SCH23390. Genotyping individuals for these polymorphic variants can identify those patients that will exhibit a heightened sensitivity towards these side effects.

6) Particular resistance to, or benign disease progression in, pathophysiological states in which dopamine D1 receptor antagonist activity is a therapeutically useful intervention including, yet not limited to: neuropsychiatric diseases, including addiction and dependence behaviors. Genotyping individuals for these polymorphic variants can identify those patients that will exhibit a lesser susceptibility to, or benign progression of, these disease states.

Dopamine D2 Receptors (DRD2, Genbank # S69899)

A functional effect of polymorphic variation at amino acid position 40 was observed:

TABLE 6

| L40R Compound | Leucine 40 | | | Arginine 40 | | | |
|---|---|---|---|---|---|---|---|
| | Ave −Log EC50 | STD DEV | "n" | Ave −Log EC50 | STD DEV | "n" | FOLD |
| Pergolide | 9.87 | 0.26 | 7 | 7.65 | 0.12 | 7 | 166 |
| Lisuride | 10.68 | 0.18 | 4 | 8.89 | 0.20 | 4 | 62 |
| Bromocriptine | 9.35 | 0.53 | 4 | 7.32 | 0.45 | 4 | 107 |
| Dihydroergotamine | 10.29 | 0.30 | 4 | 7.61 | 0.39 | 3 | 479 |
| Trazodone | 6.39 | 0.10 | 4 | NR | | | NR |
| 8-OH-DPAT | 6.73 | 0.19 | 4 | 4.89 | 0.12 | 2 | 69 |
| Mesulergine | 8.45 | 0.14 | 5 | NR | | | NR |

A lysine to arginine transition at amino acid position 40 (L40R) in the dopamine D2 receptor protein was found to induce 62-479 fold shifts in functional potency for the reference and clinical agonists tested. This variant displays a loss of biological function, such that individuals that possess this variant will be particularly insensitive to the physiological effects of a therapeutic drug that activates the dopamine D2 receptor.

A functional effect of polymorphic variation at amino acid position 208 was observed:

TABLE 7

| V208L Compound | Valine 208 | | | Leucine 208 | | | |
|---|---|---|---|---|---|---|---|
| | Ave −Log EC50 | STD DEV | "n" | Ave −Log EC50 | STD DEV | "n" | FOLD |
| Pergolide | 9.28 | 0.13 | 11 | 9.65 | 0.14 | 11 | −2.3 |
| Lisuride | 10.69 | 0.11 | 5 | 11.14 | 0.18 | 4 | −2.8 |
| Bromocriptine | 8.78 | 0.14 | 3 | 9.53 | 0.54 | 3 | −5.6 |
| Dihydroergotamine | 9.57 | 0.12 | 5 | 10.29 | 0.15 | 4 | −5.2 |
| Trazodone | 6.20 | 0.10 | 5 | 6.28 | 0.08 | 5 | −1.2 |
| 8-OH-DPAT | 6.35 | 0.20 | 5 | 7.25 | 0.15 | 5 | −7.9 |
| Mesulergine | 8.16 | 0.22 | 5 | 8.67 | 0.32 | 5 | −3.2 |

A valine to lysine transition at amino acid position 208 (V208L) in the dopamine receptor protein was found to induce 2-6 fold shifts in functional potency for the reference and clinical agonists tested. This variant displays a gain of biological function, such that individuals that possess this variant will be particularly sensitive to the physiological effects of a therapeutic drug that activates the dopamine D2 receptor.

Dopamine D2 receptors mediate some of the varied physiological effects of the endogenous catecholamine dopamine. Therapeutic drugs with D2 receptor agonist activity are used clinically to Parkinson's disease, hyper-prolactinemia, acromegaly, neuroleptic malignant syndrome, as oxytoxics to induce uterine contractions in post-partum hemorrhage and uterine atony, hepato-renal syndrome, renal failure, and hypotension. Therapeutic drugs with dopamine D2 receptor antagonist activity are used to treat the psychosis associated with Schizophrenia, Schizoaffective disorder, and related psychoses, depression, the behavioral disturbances observed with neurodegenerative disorders such as Alzheimer's disease, as anti-emetics, to control symptoms of motion sickness, and as anti-diarrhea agents.

GPCR Variants # 8 and #9: Dopamine D2 Receptor L40R and V208L Polymorphisms

The presence in an individual of the genetic variant in the dopamine D2 receptor gene that introduces a arginine residue at amino acid position 40 or a leucine residue at amino acid position 208 will predispose that individual to one or more of the following clinical indications:

1) Particular insensitivity or sensitivity (variant #9), to the beneficial physiological effects of dopamine D2 receptor agonists including, yet not limited to; dopamine hydrochloride, bromocriptine mesylate, ergonovine maleate, methylergonovine maleate, metoprolol succinate, metoprolol tartrate, trihexyphenidyl hydrochloride, pramipexole, pergolide, and ropinirole. Genotyping individuals for the polymorphic variants, an arginine residue at amino acid position 40 or a leucine residue at amino acid position 208 (variant #9), can identify those patients requiring higher or lower (variant #9), respectively, clinical doses of these agents.

2) Particular insensitivity or sensitivity (variant #9), to the adverse cardiovascular (including, yet not limited to; tachycardia, angina, palpitations, orthostatic hypotension, syncope, shock, arrhythmias, and peripheral vasoconstriction), neuropsychiatric (including, yet not limited to; anxiety, confusion, hallucinations, psychosis, headache, dizziness, drowsiness, seizure, and stroke), renal (including, yet not limited to; azotemia), metabolic (including, yet not limited to; nausea, vomiting, epigastric pain, and hyperglycemia), and other (including, yet not limited to; erythromyalgia, pleural pulmonary and retroperitoneal fibrosis) side effects of dopamine D2 receptor agonists including, yet not limited to; dopamine hydrochloride, bromocriptine mesylate, ergonovine maleate, methylergonovine maleate, metoprolol succinate, metoprolol tartrate, trihexyphenidyl hydrochloride, pramipexole, pergolide, and ropinirole. Genotyping individuals for the polymorphic variants, an arginine residue at amino acid position 40 or a leucine residue at amino acid position 208 (variant #9), can identify those patients that will exhibit a lesser or greater (variant #9), respectively, propensity towards these side effects.

3) Particular susceptibility or resistance (variant #9) to, or malignant disease progression in, pathophysiological states in which dopamine D2 receptor agonist activity is a therapeutically useful intervention including, yet not limited to: Parkinson's disease, hyper-prolactinemia, acromegaly, neuroleptic malignant syndrome, post-partum hemorrhage and uterine atony, hepato-renal syndrome, renal failure, and hypotension. Genotyping individuals for the polymorphic variants, an arginine residue at amino acid position 40 or a leucine residue at amino acid position 208 (variant #9), can identify those patients that will exhibit a greater or lesser (variant #9), respectively, susceptibility to, or malignant progression of, these disease states.

4) Particular sensitivity or insensitivity (variant #9) to the beneficial physiological effects of the dopamine D2 receptor antagonists including, yet not limited to; all antipsychotics as a class exemplified by haloperidol, chlorpromazine, thiothixene, clozapine, respiridone, olanzapine, and quetiapine, anti-depressants including amoxapine, buspirone, and amitriptyline, nortriptyline, and imipramine, and anti-emetics including prochlorperazine edisylate, prochlorperazine maleate, meclizine hydrochloride, thiethylperazine malate, thiethylperazine maleate, and loperamide hydrochloride. Genotyping individuals for the polymorphic variants, an arginine residue at amino acid position 40 or a leucine residue at amino acid position 208 (variant #9), can identify those patients requiring lower or higher (variant #9), respectively, clinical doses of these agents.

5) Particular sensitivity or insensitivity (variant #9) to the adverse cardiovascular (including, yet not limited to; hypotension, and arrhythmias) and neuropsychiatric (including, yet not limited to; confusion, bradykinesia, tremors, tardive dyskinesias, cognitive impairment, and akithesias), endocrine (including, yet not limited to; prolactinemia) and other (including, yet not limited to; neuroleptics malignant syndrome, breast hypertrophy and hyperthermia) side effects of the dopamine D2 receptor antagonists including, yet not limited to; all antipsychotics as a class exemplified by haloperidol, chlorpromazine, thiothixene, clozapine, respiridone, olanzapine, and quetia pine, anti-depressants including amoxapine, buspirone, and amitriptyline, nortriptyline, and imipramine, and anti-emetics including prochlorperazine edisylate, prochlorperazine maleate, meclizine hydrochloride, thiethylperazine malate, thiethylperazine maleate, and loperamide hydrochloride. Genotyping individuals for the polymorphic variants, an arginine residue at amino acid position 40 or a leucine residue at amino acid position 208 (variant #9), can identify those patients that will exhibit a heightened sensitivity or lesser propensity (variant #9), respectively, towards these side effects.

6) Particular resistance or sensitivity (variant #9) to, or benign disease progression in, pathophysiological states in which dopamine D2 receptor antagonist activity is a therapeutically useful intervention including, yet not limited to: Schizophrenia, Schizo-affective disorder, and related psychoses, depression, as well as the behavioral disturbances observed with neurodegenerative disorders such as Alzheimer's disease, emesis, motion sickness, and diarrhea. Genotyping individuals for the polymorphic variants, an arginine residue at amino acid position 40 or a leucine residue at amino acid position 208 (variant #9), can identify those patients that will exhibit a lesser or greater (variant #9), respectively, susceptibility to, or benign progression of, these disease states.

Dopamine D3 Receptor (DRD3, Genbank # U32499)

A functional effect of polymorphic variation at amino acid position 50 was observed:

A valine to leucine transition at amino acid position 50 (V50L) in the dopamine D3 receptor protein was found to render the receptor unresponsive to the reference and clinical agonists tested. This variant displays a loss of biological function, such that individuals that possess this variant will be particularly insensitive to the physiological effects of a therapeutic drug that activates the dopamine D3 receptor. Dopamine D3 receptors mediate some of the varied physiological effects of the endogenous catecholamine dopamine. Therapeutic drugs with D3 receptor agonist activity are used clinically to Parkinson's disease, hyper-prolactinemia, acromegaly, neuroleptic malignant syndrome, as oxytoxics to induce uterine contractions in post-partum hemorrhage and uterine atony, hepato-renal syndrome, renal failure, and hypotension. Therapeutic drugs with dopamine D3 receptor antagonist activity are used to treat the psychosis associated with Schizophrenia, Schizo-affective disorder, and related psychoses, depression, the behavioral disturbances observed with neurodegenerative disorders such as Alzheimer's disease, as anti-emetics, to control symptoms of motion sickness, and as anti-diarrhea agents.

GPCR Variant # 10: Dopamine D3 Receptor V50L Polymorphism

The presence in an individual of the genetic variant in the dopamine D3 receptor gene that introduces a leucine residue at amino acid position 50 will predispose that individual to one or more of the following clinical indications:

1) Particular insensitivity to the beneficial physiological effects of dopamine D3 receptor agonists including, yet not limited to; dopamine hydrochloride, bromocriptine mesylate, ergonovine maleate, methylergonovine maleate, metoprolol succinate, metoprolol tartrate, trihexyphenidyl hydrochloride, pramipexole, pergolide, and ropinirole. Genotyping individuals for this polymorphic variant can identify those patients requiring higher clinical doses of these agents.

2) Particular insensitivity to the adverse cardiovascular (including, yet not limited to; tachycardia, angina, palpitations, orthostatic hypotension, syncope, shock, arrhythmias, and peripheral vasoconstriction), neuropsychiatric (including, yet not limited to; anxiety, confusion, hallucinations, psychosis, headache, dizziness, drowsiness, seizure, and stroke), renal (including, yet not limited to; azotemia), metabolic (including, yet not limited to; nausea, vomiting, epigastric pain, and hyperglycemia), and other (including, yet not limited to; erythromyalgia, pleural pulmonary and retroperitoneal fibrosis) side effects of dopamine D3 receptor agonists including, yet not limited to; dopamine hydrochloride, bromocriptine mesylate, ergonovine maleate, methylergonovine maleate, metoprolol succinate, metoprolol tartrate, trihexyphenidyl hydrochloride, pramipexole, pergolide, and ropinirole. Genotyping individuals for this polymorphic variant can identify those patients that will exhibit a lesser propensity towards these side effects.

3) Particular susceptibility to, or malignant disease progression in, pathophysiological states in which dopamine D3 receptor agonist activity is a therapeutically useful intervention including, yet not limited to: Parkinson's disease, hyper-prolactinemia, acromegaly, neuroleptic malignant syndrome, post-partum hemorrhage and uterine atony, hepato-renal syndrome, renal failure, and hypotension. Genotyping individuals for this polymorphic variant can identify those patients that will exhibit a greater susceptibility to, or malignant progression of, these disease states.

4) Particular sensitivity to the beneficial physiological effects of the dopamine D3 receptor antagonists including, yet not limited to; most antipsychotics as a class exemplified by haloperidol, chlorpromazine, thiothixene, clozapine, respiridone, olanzapine, and quetiapine, anti-depressants including amoxapine, buspirone, and amitriptyline, nortriptyline, and imipramine, and anti-emetics including prochlorperazine edisylate, prochlorperazine maleate, meclizine hydrochloride, thiethylperazine malate, thiethylperazine maleate, and loperamide hydrochloride. Genotyping individuals for this polymorphic variant can identify those patients requiring lower clinical doses of these agents.

5) Particular sensitivity to the adverse cardiovascular (including, yet not limited to; hypotension, and arrhythmias) and neuropsychiatric (including, yet not limited to; confusion, bradykinesia, tremors, tardive dyskinesias, cognitive impairment, and akithesias), endocrine (including, yet not limited to; prolactinemia) and other (including, yet not limited to; neuroleptics malignant syndrome, breast hypertrophy and hyperthermia, and agranulocystosis) side effects of the dopamine D3 receptor antagonists including, yet not limited to; most antipsychotics as a class exemplified by haloperidol, chlorpromazine, thiothixene, clozapine, respiridone, olanzapine, and quetiapine, anti-depressants including amoxapine, buspirone, and amitriptyline, nortriptyline, and imipramine, and anti-emetics including prochlorperazine edisylate, prochlorperazine maleate, meclizine hydrochloride, thiethylperazine malate, thiethylperazine maleate, and loperamide hydrochloride. Genotyping individuals for this polymorphic variant can identify those patients that will exhibit a heightened sensitivity towards these side effects.

6) Particular resistance to, or benign disease progression in, pathophysiological states in which dopamine D3 receptor antagonist activity is a therapeutically useful intervention including, yet not limited to: Schizophrenia, Schizo-affective affective disorder, and related psychoses, depression, as well as the behavioral disturbances observed with neurodegenerative disorders such as Alzheimer's disease, emesis, motion sickness, and diarrhea. Genotyping individuals for this polymorphic variant can identify those patients that will exhibit a lesser susceptibility to, or benign progression of, these disease states.

Histamine H1 Receptors (HRH1, Genbank # D14436)

A functional effect of polymorphic variation at amino acid 216 was observed:

TABLE 8

| A216G Compound | Alanine 216 | | | Glycine 216 | | | |
|---|---|---|---|---|---|---|---|
| | Ave −Log EC50 | STD DEV | "n" | Ave −Log EC50 | STD DEV | "n" | FOLD |
| Agonists | | | | | | | |
| HISTAMINE | 7.86 | 0.13 | 11 | 7.52 | 0.13 | 16 | 2.2 |
| LISURIDE | 8.70 | 0.15 | 11 | 8.18 | 0.11 | 14 | 3.3 |
| TERGURIDE | 7.07 | 0.14 | 8 | 6.43 | 0.09 | 11 | 4.4 |

An alanine to glycine transition at amino acid position 216 (A216G) in the histamine H1 receptor protein was found to induce 2-5 fold shifts in functional potency for the reference and clinical agonists tested. This variant displays a loss of biological function, such that individuals that possess this variant will be particularly insensitive to the physiological effects of a therapeutic drug that activates the histamine H1 receptor.

A functional effect of polymorphic variation at amino acid 226 was observed:

TABLE 9

| L226P Compound | Leucine 226 | | | Proline 226 | | | |
|---|---|---|---|---|---|---|---|
| | Ave −Log EC50 | STD DEV | "n" | Ave −Log EC50 | STD DEV | "n" | FOLD |
| Agonists | | | | | | | |
| HISTAMINE | 7.40 | 0.11 | 4 | 6.63 | 0.05 | 4 | 5.9 |
| LISURIDE | 8.03 | 0.07 | 4 | 7.49 | 0.13 | 4 | 3.5 |
| TERGURIDE | 6.46 | 0.09 | 3 | 5.87 | 0.17 | 4 | 3.9 |

A leucine to proline transition at amino acid position 226 (L226P) in the histamine H1 receptor protein was found to induce 4-6 fold shifts in functional potency for the reference and clinical agonists tested. This variant displays a loss of biological function, such that individuals that possess this variant will be particularly insensitive to the physiological effects of a therapeutic drug that activates the histamine H1 receptor.

Histamine H1 receptors mediate some of the varied physiological effects of the endogenous catecholamine histamine. Drugs with histamine H1 receptor agonist activity are currently in clinical use as anti-Parkinson agents. Therapeutic drugs with histamine H1 receptor antagonist activity are used clinically to induce sedation, to control acute dystonic reactions, as anti-emetics, and to manage the symptoms associated with allergic reactions.

GPCR Variants # 11 and # 12: Histamine H1 Receptor A216G and L226P Polymorphisms The presence in an individual of the genetic variant in the histamine H1 receptor gene that introduces an glycine residue at amino acid position 216, or a proline at amino acid residue 226, will predispose that individual to one or more of the following clinical indications:

1) Particular insensitivity to the beneficial physiological effects of histamine H1 receptor agonists including, yet not limited to: histamine, and lisuride. Genotyping individuals for this polymorphic variant can identify those patients requiring higher clinical doses of these agents.

2) Particular insensitivity to the adverse physiological effects including cardiovascular (including, yet not limited to; hypotension and edema), pulmonary (including, yet not limited to; bronchodilation), exocrine (including, yet not limited to; diffuse sweating, and salivation) and metabolic (including, yet not limited to; hyperglycemia) of histamine H1 receptor agonists including, yet not limited to; histamine and lisuride. Genotyping individuals for this polymorphic variant can identify those individuals that exhibit a lesser propensity towards these side effects.

3) Particular susceptibility to, or malignant disease progression, in pathophysiological states in which histamine H1 receptor agonist activity is a potentially therapeutically useful intervention including, yet not limited to: neuropsychiatric, cardiovascular, gastrointestinal, and oncogenic disorders. Genotyping individuals for this polymorphic variant can identify those patients that will exhibit a greater susceptibility to, or malignant progression of, these disease states.

4) Particular sensitivity to the beneficial physiological effects of histamine H1 receptor antagonists including, yet not limited to; acrivastine, azatadine maleate, brompheniramine maleate, dexbrompheniramine maleate, carbinoxamine maleate, cetrizine hydrochloride, chlorpheniramine maleate, clemastine fumarate, cyproheptadine hydrochloride, diphenhydramine hydrochloride, doxylamine succinate, fexofenadine hydrochloride, loratadine, promethazine hydrochloride, tripelennamine hydrochloride, triprolidine hydrochloride, azelastine hydrochloride, emedastine hydrochloride, ketotifen fumarate, levoclabastine hydrochloride, and olopatadine hydrochloride, dimenhydrinate, and trimethobenzamide hydrochloride. Genotyping individuals for this polymorphic variant can identify those patients requiring lower clinical doses of these agents.

5) Particular sensitivity to the adverse neuropsychiatric (including, yet not limited to; sedation, sleepiness, fatigue, headache, dizziness, confusion, agitation, psychosis, depression, anxiety, hallucinations, fever, restlessness, insomnia, tremor, bradykinesia, tardive dyskinesia, and delirium), gastrointestinal (including, yet not limited to; nausea, vomiting, diarrhea, cholestasis, and pancreatitis), dermatological (including, yet not limited to; rash and Steven's Johnson Syndrome), cardiovascular (including, yet not limited to; cardiac arrhythmias and hypotension), hepatic (including, yet not limited to; liver enzyme elevations), and other (including, yet not limited to; gynecomastia, arthralgias, leukopenia, thrombocytopenia, and myalgias) side effects of the histamine H1 receptor antagonists including, yet not limited to; acrivastine, azatadine maleate, brompheniramine maleate, dexbrompheniramine maleate, carbinoxamine maleate, cetrizine hydrochloride, chlorpheniramine maleate, clemastine fumarate, cyproheptadine hydrochloride, diphenhydramine hydrochloride, doxylamine succinate, fexofenadine hydrochloride, loratadine, promethazine hydrochloride, tripelennamine hydrochloride, triprolidine hydrochloride, azelastine hydrochloride, emedastine hydrochloride, ketotifen fumarate, levoclabastine hydrochloride, and olopatadine hydrochloride, dimenhydrinate, and trimethobenzamide hydrochloride. Genotyping individuals for this polymorphic variant can identify those patients that will exhibit a heightened sensitivity towards these side effects.

6) Particular resistance to, or benign disease progression in, pathophysiological states in which histamine H1 receptor antagonist activity is a therapeutically useful intervention including, yet not limited to: narcolepsy and related disorders of sleep, Parkinson's disease and related movement disorders, and atopy. Genotyping individuals for this polymorphic variant can identify those patients that will exhibit a lesser susceptibility to, or benign progression of, these disease states.

Histamine H2 Receptors (HRH2, Genbank # D49783)

A functional effect of polymorphic variation at amino acid position 175 was observed:

A lysine to asparagine transition at amino acid position 175 (K175N) in the histamine H2 receptor protein was found to significantly diminish constitutive receptor activity. This variant displays a loss of biological function, such that individuals that possess this variant will be particularly insensitive to the physiological effects of a therapeutic drug that activates the histamine H1. In addition, individuals that possess this variant will display a greater physiological response to therapeutic drugs that activate the histamine H2 receptor, as well as a diminished response to drugs that inactivate the histamine H2 receptor.

A functional effect of polymorphic variation at amino acid position 215 was observed:

TABLE 10

| R215G Compound | Arginine 215 | | | Glycine 215 | | | |
|---|---|---|---|---|---|---|---|
| | Ave −Log EC50 | STD DEV | "n" | Ave −Log EC50 | STD DEV | "n" | FOLD |
| Agonist | | | | | | | |
| HISTAMINE | 7.54 | 0.09 | 6 | 6.58 | 0.28 | 6 | 9.1 |
| DIMAPRIT | 6.63 | 0.25 | 3 | NR | | | NR |
| ROLIPRAM | 6.36 | 0.11 | 3 | NR | | | NR |
| ANTHAMINE | 7.81 | 0.18 | 3 | 7.11 | 0.52 | 3 | 5.0 |
| Inverse Agonist | | | | | | | |
| CIMETIDINE | 6.21 | 0.16 | 6 | 6.92 | 0.82 | 5 | −5.1 |
| RANITIDINE | 6.80 | 0.11 | 6 | 6.85 | 0.69 | 4 | −1.1 |

An arginine to glycine transition at amino acid position 215 (R215G) in the histamine H2 receptor protein was found to induce 5-10 fold shifts in functional potency for the reference and clinical agonists tested. This variant displays a loss of biological function, such that individuals that possess this variant will be particularly insensitive to the physiological effects of a therapeutic drug that activates the histamine H2 receptor, and particularly sensitive to therapeutic drugs that inactivate the histamine H2 receptor.

A functional effect of polymorphic variation at amino acid position 231 was observed:

TABLE 11

| K231R Compound | Lysine 231 | | | Arginine 231 | | | |
|---|---|---|---|---|---|---|---|
| | Ave −Log EC50 | STD DEV | "n" | Ave −Log EC50 | STD DEV | "n" | FOLD |
| Agonist | | | | | | | |
| HISTAMINE | 7.54 | 0.09 | 6 | 6.74 | 0.11 | 6 | 6.3 |
| DIMAPRIT | 6.63 | 0.25 | 3 | NR | | | NR |
| ROLIPRAM | 6.36 | 0.11 | 3 | 6.16 | 0.56 | 2 | 1.6 |
| ANTHAMINE | 7.82 | 0.13 | 4 | 7.29 | 0.13 | 3 | 3.4 |
| Inverse Agonist | | | | | | | |
| CIMETIDINE | 6.21 | 0.16 | 6 | 6.54 | 0.21 | 6 | −2.1 |
| RANITIDINE | 6.80 | 0.11 | 6 | 6.98 | 0.47 | 5 | −1.5 |

A lysine to arginine transition at amino acid position 231 (K231R) in the histamine H2 receptor protein was found to induce 3-6 fold shifts in functional potency for the reference and clinical compounds tested. This variant displays a loss of biological function, such that individuals that possess this variant will be particularly insensitive to the physiological effects of a therapeutic drug that activates the histamine H2 receptor, as well as particular sensitivity to therapeutic drugs that inactivate the histamine H2 receptor.

Histamine H2 receptors mediate some of the varied physiological effects of the endogenous catecholamine histamine. No therapeutic drugs with histamine H2 receptor agonist activity are currently in clinical use. Therapeutic drugs with histamine H2 receptor antagonist activity are used clinically to reduce gastric acid secretion associated with gastritis, duodenal and gastric ulcer disease, gastroesophageal reflux, prophylaxis of upper gastro-intestinal bleeding, Zollinger-Ellison Syndrome, multiple endocrine neoplasias, and systemic mastocytosis.

GPCR Variants # 13, # 14 and # 15: Histamine H2 Receptor K175N, R215G, and K231R Polymorphisms The presence in an individual of the genetic variant in the histamine H2 receptor gene that introduces an asparagine residue at amino acid position 175, a glycine residue at amino acid position 215, or an arginine residue at amino acid position 231 will predispose that individual to one or more of the following clinical indications:

1) Particular insensitivity to the beneficial physiological effects of histamine H2 receptor agonists including, yet not limited to: histamine. Genotyping individuals for this polymorphic variant can identify those patients requiring higher clinical doses of these agents.

2) Particular insensitivity to the adverse physiological effects including cardiovascular (including, yet not limited to; hypotension and edema), pulmonary (including, yet not limited to; bronchodilation), exocrine (including, yet not limited to; diffuse sweating, and salivation) and metabolic (including, yet not limited to; hyperglycemia) of histamine H2 receptor agonists including, yet not limited to; histamine hydrochloride. Genotyping individuals for this polymorphic variant can identify those individuals that exhibit a lesser propensity towards these side effects.

3) Particular susceptibility to, or malignant disease progression, in pathophysiological states in which histamine H2 receptor agonist activity is a potentially therapeutically useful intervention including, yet not limited to: neuropsychiatric, cardiovascular, gastrointestinal, and oncogenic disorders. Genotyping individuals for this polymorphic variant can identify those patients that will exhibit a greater susceptibility to, or malignant progression of, these disease states.

4) Particular sensitivity to the beneficial physiological effects of histamine H2 receptor antagonists including, yet not limited to; cimetidine hydrochloride, famotidine, nizatidine, and ranitidine hydrochloride. Genotyping individuals for this polymorphic variant can identify those patients requiring lower clinical doses of these agents.

5) Particular sensitivity to the adverse neuropsychiatric (including, yet not limited to; headache, dizziness, confusion, agitation, psychosis, depression, anxiety, hallucinations, fever, and delirium), gastrointestinal (including, yet not limited to; diarrhea and pancreatitis), dermatological (including, yet not limited to; rash and Steven's Johnson Syndrome), cardiovascular (including, yet not limited to; cardiac arrhythmias and hypotension), hematological (including, yet not limited to; neutropenia), renal (including, yet not limited to; interstitial nephritis), hepatic (including, yet not limited to; liver enzyme elevations), and other (including, yet not limited to; gynecomastia, arthralgias and myalgias) side effects of the histamine H2 receptor antagonists including, yet not limited to; cimetidine hydrochloride, famotidine, nizatidine, and ranitidine hydrochloride. Genotyping individuals for this polymorphic variant can identify those patients that will exhibit a heightened sensitivity towards these side effects.

6) Particular resistance to, or benign disease progression in, pathophysiological states in which histamine H2 receptor antagonist activity is a therapeutically useful intervention including, yet not limited to: gastritis, duodenal and gastric ulcer disease, gastro-esophageal refux, Zollinger-Ellison Syndrome, multiple endocrine neoplasias, and systemic mastocytosis. Genotyping individuals for this polymorphic variant can identify those patients that will exhibit a lesser susceptibility to, or benign progression of, these disease states.

Serotonin 1A Receptors (HTR1A, Genbank #M83181)

A functional effect of polymorphic variation at amino acid position 50 was observed:

TABLE 12

| Compound | Alanine 50 EC50 (-pKi) | Valine 50 EC50 (-pKi) | Fold |
|---|---|---|---|
| 8-OH-DPAT | 6.87 +/- 0.1 | 5.6 +/- 0.1 | 19 |
| Lisuride | 7.95 +/- 0.1 | 7.3 +/- 0.1 | 5 |
| Buspirone | 6.06 +/- 0.1 | 5.2 +/- 0.2 | 7 |

An alanine to valine transition at amino acid position 50 (A50V) in the serotonin 1A receptor protein was found to induce 5-19 fold shifts in functional potency for the reference and clinical agonists tested. This variant displays a loss of biological function, such that individuals that possess this variant will be particularly insensitive to the physiological effects of a therapeutic drug that activates the serotonin 1A receptor.

A functional effect of polymorphic variation at amino acid position 381 was observed:

TABLE 13

| Compound | Leucine 381 EC50 (-pKi) | Phenylalanine 381 EC50 (-pKi) | Fold |
|---|---|---|---|
| 8-OH-DPAT | 6.8 +/- 0.1 | 6.4 +/- 0.1 | 2 |
| Lisuride | 8.0 +/- 0.1 | 7.6 +/- 0.2 | 3 |
| Buspirone | 6.1 +/- 0.3 | 5.6 +/- 0.5 | 3 |

A leucine to phenylalanine transition at amino acid position 381 (L381F), in the serotonin 1A receptor protein was found to significantly reduce the maximal response for the reference and clinical agonists tested. This variant was found to induce 2-3 fold shifts in functional potency for the reference and clinical agonists tested. This variant displays a loss of biological function, such that individuals that possess this variant will be particularly insensitive to the physiological effects of a therapeutic drug that activates the serotonin 1A receptor.

A functional effect of polymorphic variation at amino acid position 172 was observed:

TABLE 14

| Compound | Methionine 172 EC50 (-pKi) | Isoleucine 172 EC50 (-pKi) | Fold |
|---|---|---|---|
| 8-OH-DPAT | 6.7 +/- 0.1 | 7.2 +/- 0.1 | -3.2 |
| Lisuride | 8.0 +/- 0.1 | 8.5 +/- 0.1 | -3.2 |
| Buspirone | 5.8 +/- 0.3 | 6.7 +/- 0.1 | -7.9 |

A methionine to isoleucine transition at amino acid position 172 (M172I), in the serotonin 1A receptor protein was found to induce 3-8 fold shifts in functional potency for the reference and clinical agonists tested. This variant displays a gain of biological function, such that individuals that possess this variant will be particularly sensitive to the physiological effects of a therapeutic drug that activates the serotonin 1A receptor.

Serotonin 1A receptors mediate some of the physiological effects of the endogenous hormone-neurotransmitter serotonin, including platelet, cardiovascular, and gastrointestinal functions. The most prominent physiological effects of serotonin occur in the central nervous system, where this neurotransmitter mediates such diverse processes as mood, cognition, memory, temperature regulation, feeding, sleep and wakefulness, and the production of cerebral spinal fluid. Serotonin 1A receptor agonists are used to treat anxiety, depression, headache, and psychosis, while serotonin 1A antagonists are in clinical development for various neuropsychiatric indications.

GPCR Variants # 16, # 17 and #18: Serotonin 1A Receptor A50V, L381F and M172I Polymorphisms The presence in an individual of the genetic variant in the serotonin 1A receptor gene that introduces a valine residue at amino acid position 50, or a phenylalanine at amino acid position 381 or an isoleucine residue at amino acid position 172 will predispose that individual to one or more of the following clinical indications:

1) Particular insensitivity or sensitivity (variant #18) to the beneficial physiological effects of serotonin 1A receptor agonists including, yet not limited to; buspirone hydrochloride, gepirone, ipsaperone, and sumatriptan succinate. Genotyping individuals for the polymorphic variants, a valine residue at amino acid position 50, or a phenylalanine at amino acid position 381 or an isoleucine residue at amino acid position 172, can identify those patients requiring higher or lower (variant #18) clinical doses of these agents.

2) Particular insensitivity or sensitivity (variant #18) to the adverse neuropsychiatric (including, yet not limited to; dizziness, headache, drowsiness, dream disturbances, akathisias, tremors, dystonia, involuntary movements, agitation, blurred vision, and sedation), gastrointestinal (including, yet not limited to; nausea, vomiting, diarrhea, constipation, and dry mouth), cardiovascular (including, yet not limited to; tachycardia, palpitations, syncope, hypotension, myocardial infarction, and congestive heart failure), dermatologic (including, yet not limited to; rash, edema, pruritis, flushing, and blisters), gynecological (including, yet not limited to; menstrual abnormalities), genitourinary (including, yet not limited to; urinary hesitancy, dysuria, and urinary frequency) and other (including, yet not limited to; cramps, arthralgias, dyspnea, and liver enzyme elevations) side effects of serotonin 1A receptor agonists including, yet not limited to; buspirone hydrochloride, gepirone, ipsaperone, and sumatriptan succinate. Genotyping individuals for the polymorphic variants, a valine residue at amino acid position 50, or a phenylalanine at amino acid position 381 or an isoleucine residue at amino acid position 172 (variant #18), can identify those patients that will exhibit a lesser or greater (variant #18) propensity towards these side effects.

3) Particular susceptibility or resistance (variant #18) to, or malignant disease progression in, pathophysiological states in which serotonin 1A receptor agonist activity is a therapeutically useful intervention including, yet not limited to: anxiety, depression, headache, and psychosis. Genotyping individuals for the polymorphic variants, a valine residue at amino acid position 50, or a phenylalanine at amino acid position 381 or an isoleucine residue at amino acid position 172 (variant #18), can identify those patients that will exhibit a greater or lesser (variant #18) susceptibility or to, or malignant progression of, these disease states.

4) Particular sensitivity or insensitivity (variant #18) to the beneficial effects of serotonin 1A receptor antagonists. Genotyping individuals for the polymorphic variants, a valine residue at amino acid position 50, or a phenylalanine at amino acid position 381 or an isoleucine residue at amino acid position 172, can identify those patients requiring lower or higher (variant #18) clinical doses of these agents.

5) Particular sensitivity or insensitivity (variant #18) to the adverse side effects of serotonin 1A receptor antagonists. Genotyping individuals for the polymorphic variants, a valine residue at amino acid position 50, or a phenylalanine at amino acid position 381 or an isoleucine residue at amino acid position 172, can identify those patients that will exhibit a heightened sensitivity or lesser propensity (variant #18) towards these side effects.

6) Particular resistance or susceptibility (variant #18) to, or benign disease progression in, pathophysiological states in which serotonin 1A receptor antagonist activity is a therapeutically useful intervention including, yet not limited to: neuropsychiatric diseases. Genotyping individuals for the polymorphic variants, a valine residue at amino acid position 50, or a phenylalanine at amino acid position 381 or an isoleucine residue at amino acid position 172, can identify those patients that will exhibit a lesser or greater (variant #18) susceptibility to, or benign progression of, these disease states.

Serotonin 1B Receptor (HTR1B, Genbank # M89478)

A threonine to asparagine transition at amino acid position 221 (T221N) in the serotonin 1B receptor protein was found to render the receptor protein non-functional. This variant displays a loss of biological function, such that individuals that possess this variant will be particularly insensitive to the physiological effects of a therapeutic drug that activates the serotonin 1B receptor. Serotonin 1B receptors mediate some of the varied physiological effects of the endogenous monoamine serotonin. Therapeutic drugs with serotonin 1B receptor agonist activity are used clinically to treat; migraines, vascular headaches, cluster headaches, hypertension, Parkinson's disease, and affective disorders including depression, and psychoses including Schizophrenia. Therapeutic drugs with serotonin 1B receptor antagonist activity are used clinically to treat; neuropsychiatric diseases including affective disorders, and Schizophrenia.

GPCR Variant # 19: Serotonin 1B Receptor T221N Polymorphism

The presence in an individual of the genetic variant in the serotonin 1B receptor gene that introduces a asparagine residue at amino acid position 221 will predispose that individual to one or more of the following clinical indications:

1) Particular insensitivity to the beneficial physiological effects of serotonin 1B receptor agonists, including, yet not limited to; serotonin, lisuride, oxymetazoline hydrochloride, pindolol, sumatriptan succinate, rizatriptan benzoate, naratriptan hydrochloride, zolmitriptan, and eletriptan, and a variety of clinically useful antipsychotics including perlapine. Genotyping individuals for this polymorphic variant can identify those patients who fail to respond to, or require higher clinical doses, of these agents.

2) Particular insensitivity to the adverse cardiovascular (including, yet not limited to; hypertension, syncope, tachycardia, bradycardia, angina, myocardial infarction, severe vasospasm, heart valvulopathies, flushing, chest pain, and arrhythmias), gastrointestinal (including, yet not limited to; nausea, vomiting, abdominal pain, hepatotoxicity, mouth and jaw discomfort, and diarrhea), neuropsychiatric (including, yet not limited to; anxiety, depression, irritability, headache, confusion, dizziness, vertigo, parasthesias, blurred vision, miosis, drowsiness, malaise, fatigue, and stroke), musculoskeletal (neck pain and stiffness), dermatological (erythema, pruritis), renal (dysuria), and hepatic (elevated liver enzymes), side effects of serotonin 1B receptor agonists including, yet not limited to; serotonin, lisuride, oxymetazoline hydrochloride, pindolol, sumatriptan succinate, rizatriptan benzoate, naratriptan hydrochloride, zolmitriptan, and eletriptan, and a variety of clinically useful antipsychotics including perlapine. Genotyping individuals for this polymorphic variant can identify those patients that will exhibit a lesser propensity towards these side effects.

3) Particular susceptibility to, or malignant disease progression in, pathophysiological states in which serotonin 1B agonist activity is a therapeutically useful intervention including, yet not limited to: migraines, vascular headaches, cluster headaches, hypertension, Parkinson's disease, affective disorders including depression, and Schizophrenia. Genotyping individuals for this polymorphic variant can identify those patients that will exhibit a greater susceptibility to, or malignant progression of, these disease states.

4) Particular sensitivity to the beneficial physiological effects of serotonin 1B receptor antagonists including, yet not limited to: a variety of clinically useful antidepressants including fluoxetine hydrochloride, and a variety of clinically useful antipsychotics including cis-flupenthixol, ocaperidone, tefludazine, and trilouperazine hydrochloride. Genotyping individuals for this polymorphic variant can identify those patients requiring lower clinical doses of these agents.

5) Particular sensitivity to the adverse cardiovascular (including, yet not limited to; hypertension, hypotension, syncope, tachycardia, bradycardia, angina, myocardial infarction, severe vasospasm, and arrhythmias), gastrointestinal (including, yet not limited to; nausea, vomiting, abdominal pain, hepatotoxicity, and diarrhea), neuropsychiatric (including, yet not limited to; anxiety, depression, irritability, headache, confusion, dizziness, parasthesias, blurred vision, miosis, drowsiness, fatigue, and stroke), and other (including, yet not limited to; muscle and joint pain, and rash) side effects of serotonin 1B receptor antagonists including, yet not limited to: a variety of clinically useful antidepressants including fluoxetine hydrochloride, and a variety of clinically useful antipsychotics including cis-flupenthixol, ocaperidone, tefludazine, and trilouperazine hydrochloride. Genotyping individuals for this polymorphic variant can identify those patients that will exhibit a heightened sensitivity towards these side effects.

6) Particular resistance to, or benign disease progression in, pathophysiological states in which serotonin 1B receptor antagonist activity is a therapeutically useful intervention including, yet not limited to: neuropsychiatric diseases including affective disorders and Schizophrenia. Genotyping individuals for this polymorphic variant can identify those patients that will exhibit a lesser susceptibility to, or benign progression of, these disease states.

Serotonin 1D Receptor (HTR1D, Genbank # M89955)

A functional effect of polymorphic variation at amino acid position 53 was observed:

TABLE 15

| V53L Compound | Valine 53 | | | Leucine 53 | | | |
|---|---|---|---|---|---|---|---|
| | Ave −Log EC50 | STD DEV | "n" | Ave −Log EC50 | STD DEV | "n" | FOLD |
| 5HT | 6.78 | 0.15 | 7 | 6.37 | 0.18 | 5 | 2.6 |
| 5CT | 8.70 | 0.24 | 6 | 7.85 | 0.52 | 4 | 7.1 |
| Lisuride | 10.37 | 0.06 | 2 | NR | | | NR |
| 8-OH-DPAT | 6.93 | 0.10 | 4 | 6.06 | 0.27 | 4 | 7.4 |
| Sumatriptan | 7.71 | 0.10 | 9 | 7.26 | 0.10 | 8 | 2.8 |

A valine to leucine transition at amino acid position 53 (V53L) in the serotonin 1D receptor protein was found to induce 3-8 fold shifts in functional potency for the reference and clinical agonists tested. This variant displays a loss of biological function, such that individuals that possess this variant will be particularly insensitive to the physiological effects of a therapeutic drug that activates the serotonin 1D receptor.

A functional effect of polymorphic variation at amino acid position 366 was observed:

TABLE 16

| A366G Compound | Alanine 366 | | | Glycine 366 | | | |
|---|---|---|---|---|---|---|---|
| | Ave −Log EC50 | STD DEV | "n" | Ave −Log EC50 | STD DEV | "n" | FOLD |
| 5HT | 6.79 | 0.13 | 8 | 6.29 | 0.10 | 8 | 3.2 |
| 5CT | 8.56 | 0.26 | 8 | 7.29 | 0.28 | 8 | 18.6 |
| Sumatriptan | 7.73 | 0.12 | 12 | 6.95 | 0.13 | 12 | 6.0 |
| Buspirone | 5.26 | 0.18 | 7 | 4.54 | 0.17 | 7 | 5.2 |
| Trazodone | 6.03 | 0.24 | 4 | 5.02 | 0.16 | 4 | 10.2 |

An alanine to glycine transition at amino acid position 366 (A366G) in the serotonin 1D receptor protein was found to induce 3 to 19 fold shifts in functional potency for the reference and clinical agonists tested. This variant displays a loss of biological function, such that individuals that possess this variant will be particularly insensitive to the physiological effects of a therapeutic drug that activate the serotonin 1D receptor.

Serotonin 1D receptors mediate some of the varied physiological effects of the endogenous monoamine serotonin. Therapeutic drugs with serotonin 1D receptor agonist activity are used clinically to treat; migraines, vascular headaches, cluster headaches, hypertension, Parkinson's disease, and affective disorders including depression and psychosis including Schizophrenia. Therapeutic drugs with serotonin 1D receptor antagonist activity are used clinically to treat; neuropsychiatric diseases including affective disorders, and Schizophrenia.

GPCR Variants # 20 and # 21: Serotonin 1D Receptor V53L and A366G Polymorphisms

The presence in an individual of the genetic variant in the serotonin 1D receptor gene that introduces a leucine residue at amino acid position 53, or a glycine at amino acid position 366 will predispose the individual to one or more of the following clinical indications:

1) Particular insensitivity to the beneficial physiological effects of serotonin 1D receptor agonists, including, yet not limited to; serotonin, lisuride, oxymetazoline hydrochloride, pindolol, timolol maleate, bromocriptine mesylate, methysergide maleate, sumatriptan succinate, rizatriptan benzoate, naratriptan hydrochloride, zolmitriptan, and eletriptan, a variety of clinically useful antipsychotics including perlapine, and a variety of clinically useful antidepressants including trazodone hydrochloride. Genotyping individuals for this polymorphic variant can identify those patients who may fail to respond to, or require higher clinical doses of, these agents.

2) Particular insensitivity to the adverse cardiovascular (including, yet not limited to; hypertension, syncope, tachycardia, bradycardia, angina, myocardial infarction, severe vasospasm, heart valvulopathies, flushing, chest pain, and arrhythmias), gastrointestinal (including, yet not limited to; nausea, vomiting, abdominal pain, hepatotoxicity, mouth and jaw discomfort, and diarrhea), neuropsychiatric (including, yet not limited to; anxiety, depression, irritability, headache, confusion, dizziness, vertigo, parasthesias, blurred vision, miosis, drowsiness, malaise, fatigue, and stroke), musculoskeletal (neck pain and stiffness), dermatological (erythema, pruritis), renal (dysuria), and hepatic (elevated liver enzymes), side effects of serotonin 1D receptor agonists including; yet not limited to; serotonin, lisuride, oxymetazoline hydrochloride, pindolol, timolol maleate, bromocriptine mesylate, methysergide maleate, sumatriptan succinate, rizatriptan benzoate, naratriptan hydrochloride, zolmitriptan, and eletriptan, a variety of clinically useful antipsychotics including perlapine, and a variety of clinically useful antidepressants including trazodone hydrochloride. Genotyping individuals for this polymorphic variant can identify those patients that will exhibit a lesser propensity towards these side effects.

3) Particular susceptibility to, or malignant disease progression in, pathophysiological states in which serotonin 1D agonist activity is a therapeutically useful intervention including, yet not limited to: migraines, vascular headaches, cluster headaches, hypertension, Parkinson's disease, affective disorders including depression, and Schizophrenia. Genotyping individuals for this polymorphic variant can identify those patients that will exhibit a greater susceptibility to, or malignant progression of, these disease states.

Particular sensitivity to the beneficial physiological effects of serotonin 1D receptor antagonists including, yet not limited to: a variety of clinically useful antipsychotics including rispiridone, and ocaperidone. Genotyping individuals for this polymorphic variant can identify those patients requiring lower clinical doses of these agents.

5) Particular sensitivity to the adverse cardiovascular (including, yet not limited to; hypertension, hypotension, syncope, tachycardia, bradycardia, angina, myocardial infarction, severe vasospasm, and arrhythmias), gastrointestinal (including, yet not limited to; nausea, vomiting, abdominal pain, hepatotoxicity, and diarrhea), neuropsychiatric (including, yet not limited to; anxiety, depression, irritability, headache, confusion, dizziness, parasthesias, blurred vision, miosis, drowsiness, fatigue, and stroke), and other (including, yet not limited to; muscle and joint pain, and rash) side effects of serotonin 1D receptor antagonists including, yet not limited to: a variety of clinically useful antipsychotics including respiridone, and ocaperidone. Genotyping individuals for this polymorphic variant can identify those patients that will exhibit a heightened sensitivity towards these side effects.

6) Particular resistance to, or benign disease progression in, pathophysiological states in which serotonin 1D receptor antagonist activity is a therapeutically useful intervention including, yet not limited to: neuropsychiatric diseases including affective disorders and Schizophrenia. Genotyping individuals for this polymorphic variant can identify those patients that will exhibit a lesser susceptibility to, or benign progression of, these disease states.

Serotonin 1E Receptor (HTR1E, Genbank # M91467)

A functional effect of polymorphic variation at amino acid position 44 was observed:

TABLE 17

| | Isoleucine 44 | | | Threonine 44 | | | |
|---|---|---|---|---|---|---|---|
| 144T Compound | Ave −Log EC50 | STD DEV | "n" | Ave −Log EC50 | STD DEV | "n" | FOLD |
| BRL54443 | 7.53 | 0.12 | 5 | 5.83 | 0.05 | 6 | 50 |
| Lisuride | 7.75 | 0.07 | 2 | 5.59 | 0.04 | 2 | 145 |

An isoleucine to threonine transition at amino acid position 44 (I44T) in the serotonin 1E receptor protein was found to induce 50-145 fold shifts in functional potency for the reference and clinical agonists tested. This variant displays a loss of biological function, such that individuals that possess this variant will be particularly insensitive to the physiological effects of a therapeutic drug that activates the serotonin 1E receptor.

A functional effect of polymorphic variation at amino acid position 262 was observed:

TABLE 18

| | Serine 262 | | | Phenylalanine 262 | | | |
|---|---|---|---|---|---|---|---|
| S262F Compound | Ave −Log EC50 | STD DEV | "n" | Ave −Log EC50 | STD DEV | "n" | FOLD |
| BRL54443 | 7.53 | 0.12 | 5 | 6.76 | 0.14 | 6 | 5.9 |
| Lisuride | 7.75 | 0.07 | 2 | 6.50 | 0.98 | 2 | 17.8 |

A serine to phenylalanine transition at amino acid position 262 (S262F) in the serotonin 1E receptor protein was found to induce 6 to 18 fold shifts in functional potency for the reference and clinical agonists tested. This variant displays a loss of biological function, such that individuals that possess this variant will be particularly insensitive to the physiological effects of a therapeutic drug that activates the serotonin 1E receptor.

Serotonin 1E receptors mediate some of the physiological effects of the endogenous hormone-neurotransmitter serotonin. The most prominent physiological effects of serotonin occur in the central nervous system, where this neurotransmitter mediates such diverse processes as mood, cognition, memory, temperature regulation, feeding, sleep and wakefulness, and the production of cerebral spinal fluid. No specific serotonin 1E receptor agonists or antagonists have been developed, yet known drugs with significant serotonin 1E receptor agonist activity are used to treat anxiety, depression, migraine, and psychosis, while serotonin 1E antagonists are in development for various neuropsychiatric indications.

GPCR Variants #22 and # 23: Serotonin 1E Receptor 144T and S262F Polymorphisms

The presence in an individual of the genetic variant in the serotonin 1E receptor, gene that introduces a threonine residue at amino acid position 44, or a phenylalanine at amino acid position 262 will predispose the individual to one or more of the following clinical indications:

1) Particular insensitivity to the beneficial physiological effects of serotonin 1E receptor agonists including, yet not limited to; buspirone hydrochloride, amitriptyline hydrochloride, desipramine hydrochloride, nortriptyline hydrochloride, fluoxetine hydrochloride, fluvoxamine maleate, mirtazepine, clozapine, olanzapine, loxapine hydrochloride, loxapine succinate, mesioridazine besylate, and sumatriptan succinate. Genotyping individuals for this polymorphic variant can identify those patients requiring higher clinical doses of these agents.

2) Particular insensitivity to the adverse neuropsychiatric (including, yet not limited to; dizziness, headache, drowsiness, dream disturbances, akathisias, tremors, dystonia, involuntary movements, agitation, blurred vision, seizures, decreased libido, and sedation), gastrointestinal (including, yet not limited to; nausea, vomiting, diarrhea, constipation, and dry mouth), cardiovascular (including, yet not limited to; tachycardia, palpitations, syncope, hypotension, myocardial infarction, and congestive heart failure), dermatologic (including, yet not limited to; rash, edema, pruritis, flushing, and blisters), gynecological (including, yet not limited to; menstrual abnormalities), genitourinary (including, yet not limited to; urinary hesitancy, dysuria, erection and ejaculatory disturbances, and urinary frequency) and other (including, yet not limited to; cramps, arthralgias, dyspnea, and liver enzyme elevations) side effects of serotonin 1E receptor agonists including, yet not limited to; buspirone hydrochloride, amitriptyline hydrochloride, desipramine hydrochloride, nortriptyline hydrochloride, fluoxetine hydrochloride, fluvoxamine maleate, mirtazepine, clozapine, olanzapine, loxapine hydrochloride, loxapine succinate, mesioridazine besylate, and sumatriptan succinate. Genotyping individuals for this polymorphic variant can identify those patients that will exhibit a lesser propensity towards these side effects.

3) Particular susceptibility to, or malignant disease progression in, pathophysiological states in which serotonin 1E receptor agonist activity is a therapeutically useful intervention including, yet not limited to: anxiety, depression, migraine, and psychosis. Genotyping individuals for this polymorphic variant can identify those patients that will exhibit a greater susceptibility to, or malignant progression of, these disease states.

4) Particular sensitivity to the beneficial effects of serotonin 1E receptor antagonists, including, yet not limited to: pindolol. Genotyping individuals for this polymorphic variant can identify those patients requiring lower clinical doses of these agents.

5) Particular sensitivity to the adverse neuropsychiatric (including, yet not limited to; dizziness, headache, drowsiness, dream disturbances, akathisias, tremors, dystonia, involuntary movements, agitation, blurred vision, seizures, parasthesias, weakness, catatonia, disorientation, decreased libido, fatigue, insomnia, and sedation) side effects of serotonin 1E receptor antagonists including, yet not limited to: pindolol. Genotyping individuals for this polymorphic variant can identify those patients that will exhibit a heightened sensitivity towards these side effects.

6) Particular resistance to, or benign disease progression in, pathophysiological states in which serotonin 1E receptor antagonist activity is a therapeutically useful intervention including, yet not limited to: neuropsychiatric diseases. Genotyping individuals for this polymorphic variant can identify those patients that will exhibit a lesser susceptibility to, or benign progression of, these disease states.

Serotonin 2B Receptor (HTR2B, Genbank #X77307)

A functional effect of polymorphic variation at amino acid position 388 was observed:

TABLE 19

| R388W Compound | Arginine 388 | | | Tryptophan 388 | | | |
| --- | --- | --- | --- | --- | --- | --- | --- |
| | Ave −Log EC50 | STD DEV | "n" | Ave −Log EC50 | STD DEV | "n" | FOLD |
| Serotonin | 6.79 | 0.13 | 14 | 6.27 | 0.29 | 3 | .3 |
| DHE | 10.03 | 0.29 | 8 | 8.93 | | 1 | 2.5 |
| mCPP | 7.84 | 0.13 | 10 | 7.46 | 0.16 | 3 | .4 |
| Methysergide | 9.26 | 0.39 | 4 | ND | | | |
| Nortryptiline | 7.40 | 0.12 | 5 | ND | | | |

An arginine to tryptophan transition at amino acid position 388 (R388W) in the serotonin 2B receptor protein was found to induce 3 to 13 fold shifts in functional potency for the reference and clinical agonists and inverse agonists tested. This variant displays a loss of biological function, such that individuals that possess this variant will be particularly insensitive to the physiological effects of a therapeutic drug that activates the serotonin 2B receptor, and particularly sensitivity to therapeutic drugs that inactivate the serotonin 2B receptor. Serotonin 2B receptors mediate some of the varied physiological effects of the endogenous hormone/neurotransmitter serotonin. Although no therapeutic drugs have yet been developed that specifically target the serotonin 2B receptor, many current therapeutic drugs possess potent serotonin 2B receptor agonist or inverse agonist activity. Therapeutic drugs with serotonin 2B receptor agonist activity are used to treat migraine, depression, obsessive-compulsive disorder, generalized anxiety disorder, panic disorder, eating disorders, attention deficit disorder, narcolepsy, Parkinson's disease, and irritable bowel syndrome. Therapeutic drugs with serotonin 2B receptor antagonist/inverse agonist activity are used to treat schizophrenia and psychosis.

GPCR Polymorphism # 24: Serotonin 2B Receptor R388W Polymorphism

The presence in an individual of the genetic variation in the serotonin 2B receptor gene that introduces an tryptophan residue at amino acid position 388 will predispose the individual to one or more of the following clinical indications:

1) Particular insensitivity to the beneficial physiological effects of serotonin 2B receptor agonists including, yet not limited to; serotonin hydrochloride, pergolide, bromocriptine mesylate, lisuride, dihydroergotamine methanosulfate, dihydroergotamine mesylate, methysergide maleate, modafinil, and a variety of anti-depressants including nortriptyline hydrochloride, protryptiline hydrochloride, amoxapine, buspirone, and trazodone hydrochloride. Genotyping individuals for this polymorphic variant can identify those patients requiring higher clinical doses of these agents.

2) Particular insensitivity to the adverse cardiovascular (including, yet not limited to; hypertension, hypotension, syncope, tachycardia, bradycardia, angina, palpitations, myocardial infarction, severe vasospasm, heart valvulopathies, and arrhythmias), gastrointestinal (including, yet not limited to; nausea, vomiting, anorexia, abdominal pain, hepatotoxicity, and diarrhea), neuropsychiatric (including, yet not limited to; anxiety, depression, confusion, hallucinations, delusions, headache, confusion, dizziness, blurred vision, insomnia, drowsiness, fatigue, ataxia, seizures, and stroke), and urologic (including, yet not limited to; urinary retention, priapism) and other (including, yet not limited to: retroperitoneal fibrosis, pleuropulmonary fibrosis, a constellation of symptoms referred to as serotonin syndrome, telangiectasias, prolactinemia, dry mouth, ileus, thrombocytopenia, and leg cramps) side effects of the serotonin 2B receptor agonists including, yet not limited to; serotonin hydrochloride, pergolide, bromocriptine mesylate, lisuride, dihydroergotamine methanosulfate, dihydroergotamine mesylate, methysergide maleate, modafinil, and a variety of anti-depressants including nortriptyline hydrochloride, protryptiline hydrochloride, amoxapine, buspirone, and trazodone hydrochloride. Genotyping individuals for this polymorphic variant can identify those patients that will exhibit a lesser propensity towards these side effects.

3) Particular susceptibility to, or malignant disease progression in, pathophysiological states in which serotonin 2B receptor agonist activity is a therapeutically useful intervention including, yet not limited to: migraine, depression, obsessive-compulsive disorder, generalized anxiety disorder, panic disorder, eating disorders, attention deficit disorder, narcolepsy, Parkinson's disease, and irritable bowel syndrome. Genotyping individuals for this polymorphic variant can identify those patients that will exhibit a heightened susceptibility to, or malignant progression of, these disease states.

4) Particular sensitivity to the beneficial effects of the serotonin 2B receptor antagonists/inverse agonists including, yet not limited to; a number of antipsychotics including clozapine, olanzapine, respiridone, loxapine, fluphenazine, fluspirilene and ziprasidone. Genotyping individuals for this polymorphic variant can identify those patients requiring lower clinical doses of these agents.

5) Particular sensitivity to the adverse cardiovascular (including, yet not limited to; hypotension, and arrhythmias) and neuropsychiatric (including, yet not limited to; confusion, bradykinesia, tremors, tardive dyskinesias, cognitive impairment, and akithesias), endocrine (including, yet not limited to; prolactinemia) and other (including, yet not limited to; neuroleptics malignant syndrome, breast hypertrophy and hyperthermia, and agranulocystosis) side effects of serotonin 2b receptor antagonists/inverse agonists including, yet not limited to: a number of antipsychotics including clozapine, olanzapine, respiridone, loxapine, fluphenazine, fluspirilene and ziprasidone. Genotyping individuals for this polymorphic variant can identify those patients that will exhibit a heightened sensitivity towards these side effects.

Particular resistance to, or benign disease progression in, pathophysiological states in which serotonin 2B receptor antagonist/inverse agonist activity is a therapeutically useful intervention including, yet not limited to: schizophrenia and psychosis. Genotyping individuals for this polymorphic variant can identify those patients that will exhibit a lesser susceptibility to, or benign progression of, these disease states.

Serotonin 7 Receptor (HTR7, Genbank #U68488)

A functional effect of polymorphic variation at amino acid position 92 was observed.

A threonine to lysine transition at amino acid position 92 (T92K) in the serotonin 7 receptor protein was found to significantly diminish constitutive receptor activity. This variant displays a loss of biological function, such that individuals that possess this variant will display a greater physiological response to therapeutic drugs that activate the serotonin 7 receptor, as well as a diminished response to drugs that inactivate the serotonin 7 receptor.

A functional effect of polymorphic variation at amino acid position 421 was observed:

TABLE 20

| L421P Compound | Leucine 421 | | | Proline 421 | | | |
|---|---|---|---|---|---|---|---|
| | Ave −Log EC50 | STD DEV | "n" | Ave −Log EC50 | STD DEV | "n" | FOLD |
| Clozapine | 8.21 | 0.15 | 10 | 7.43 | 0.14 | 4 | 6.0 |
| Fluphenazine | 8.17 | 0.19 | 10 | 7.41 | 0.13 | 4 | 5.8 |
| Cis-flupenthixol | 8.05 | 0.28 | 9 | 7.61 | 0.28 | 3 | 2.8 |
| Sertindole | 7.64 | 0.14 | 13 | 6.86 | 0.39 | 7 | 6.0 |
| Thiothixene | 8.16 | 0.18 | 8 | 7.66 | 0.15 | 2 | 3.2 |
| Tefludazine | 9.38 | 10.38 | 8 | 7.95 | 0.87 | 4 | 27.0 |

A leucine to proline transition at amino acid position 421 (L421P) in the serotonin 7 receptor protein was found to induce 3 to 27 fold shifts in functional potency for the reference and clinical inverse agonists tested. This variant displays a gain of biological function, such that individuals that possess this variant will be particularly sensitive to the physiological effects of a therapeutic drug that activates the serotonin 7 receptor, and particularly insensitivity to therapeutic drugs that inactivate the serotonin 7 receptor.

Serotonin 7 receptors mediate some of the varied physiological effects of the endogenous hormone/neurotransmitter serotonin. Although no therapeutic drugs have yet been developed that specifically target the serotonin 7 receptor, many current therapeutic drugs possess potent serotonin 7 receptor agonist or inverse agonist activity. Drugs with serotonin 7 receptor agonist activity are used to treat migraine, and Parkinson's disease. Drugs with serotonin 7 receptor antagonist/inverse agonist activity are used to treat depression, schizophrenia, and psychosis.

GPCR Polymorphisms # 25 and # 26: Serotonin 7 Receptor T92K and L421P Polymorphisms The presence in an individual of the genetic variation in the serotonin 7 receptor gene that introduces an lysine residue at amino acid position 92, or a proline at amino acid position 421 will predispose the individual to one or more of the following clinical indications:

1) Particular insensitivity to the beneficial physiological effects of serotonin 7 receptor agonists including, yet not limited to; serotonin hydrochloride, pergolide, bromocriptine mesylate, dihydroergotamine methanosulfate, and sumatriptan succinate. Genotyping individuals for this polymorphic variant can identify those patients requiring higher clinical doses of these agents.

2) Particular insensitivity to the adverse side effects of the serotonin 7 receptor agonists including, yet not limited to; serotonin hydrochloride, pergolide, bromocriptine mesylate, dihydroergotamine methanosulfate and sumatriptan succinate. Genotyping individuals for this polymorphic variant can identify those patients that will exhibit a lesser propensity towards these side effects.

Particular susceptibility to, or malignant disease progression in, pathophysiological states in which serotonin 7 receptor agonist activity is a therapeutically useful intervention including, yet not limited to: neuropsychiatric diseases. Genotyping individuals for this polymorphic variant can identify those patients that will exhibit a greater susceptibility to, or malignant progression of, these disease states.

4) Particular sensitivity to the beneficial effects of the serotonin 7 receptor antagonists including, yet not limited to; clozapine, chlorpromazine hydrochloride, risperidone, amitriptyline hydrochloride and amoxapine. Genotyping individuals for this polymorphic variant can identify those patients requiring lower clinical doses of these agents.

5) Particular sensitivity to the adverse side effects of the serotonin 7 receptor antagonists including, yet not limited to; clozapine, chlorpromazine hydrochloride, risperidone, amitriptyline hydrochloride and amoxapine. Genotyping individuals for this polymorphic variant can identify those patients that will exhibit a heightened sensitivity towards these side effects.

6) Particular resistance to, or benign disease progression in, pathophysiological states in which serotonin 7 receptor antagonist activity is a therapeutically useful intervention including, yet not limited to: neuropsychiatric diseases. Genotyping individuals this polymorphic variant can identify those patients that will exhibit a lesser susceptibility to, or benign progression of, these disease states.

Angiotensin II Type 1 Receptors (AGTR1, Genbank #XM_051470)

A functional effect of polymorphic variation at amino acid position 45 was observed:

A glycine to arginine transition at amino acid position 45 (G45W) in the angiotensin II Type 1 receptor protein was found to render the protein non-functional. This variant displays a loss of biological function, such that individuals that possess this variant will be particularly insensitive to the physiological effects of a therapeutic drug that activates the angiotensin II Type 1 receptor.

A functional effect of polymorphic variation at amino acid position 204:

TABLE 21

| Compound | Phenylalanine 204 EC50 (–pKi) | Serine 204 EC50 (–pKi) | FOLD |
|---|---|---|---|
| Angiotensin 2 | 6.9 +/– 0.1 | 5.1 +/– 0.3 | 63 |

A phenylalanine to serine transition at amino acid position 204 (F204S) in the angiotensin II Type 1 receptor protein was found to induce 63 fold shifts in functional potency for the reference agonist tested. This variant displays a loss of biological function, such that individuals that possess this variant will be particularly insensitive to the physiological effects of a therapeutic drug that activates the angiotensin II Type 1 receptor.

A functional effect of polymorphic variation at amino acid position 289 was observed:

TABLE 22

| Compound | Cysteine 289 EC50 (–pKi) | Tryptophan 289 EC50 (–pKi) | FOLD |
|---|---|---|---|
| Angiotensin 2 | 6.9 +/– 0.1 | 5.8 +/– 0.1 | 13 |

A cysteine to tryptophan transition at amino acid position 289 (C289W) in the angiotensin II Type 1 receptor protein was found to induce 13 fold shifts in functional potency for the reference agonist tested. This variant displays a loss of biological function, such that individuals that possess this variant will be particularly insensitive to the physiological effects of a therapeutic drug that activates the angiotensin IT Type 1 receptor.

Angiotensin II Type 1 receptor mediate some of the varied physiological effects of the endogenous hormone/neurotransmitter angiotensin II. No therapeutic drugs have yet been developed that are angiotensin II Type 1 receptor agonists. Many angiotensin II Type 1 receptor antagonists are used to treat hypertension, myocardial hypertrophy, congestive heart failure, hyperlipidemia, as renoprotective agents in diabetic nephropathy, and primary and secondary aldosteronism.

GPCR Polymorphisms # 27, # 28 and # 29: Angiotensin II Type 1 Receptor G45R, F204S and C289W Polymorphisms The presence in an individual of the genetic variation in the angiotensin II Type 1 receptor gene that introduces an arginine residue at amino acid position 45, or a serine at amino acid position 204, or a tryptophan at amino acid position 289 will predispose the individual to one or more of the following clinical indications:

1) Particular insensitivity to the beneficial physiological effects of angiotensin II Type 1 receptor agonists including, yet not limited to; angiotensin II. Genotyping individuals for this polymorphic variant can identify those patients requiring higher clinical doses of these agents.

2) Particular insensitivity to the adverse side effects of angiotensin II Type 1 receptor agonists including, yet not limited to; angiotensin II. Genotyping individuals for this polymorphic variant can identify those patients that will exhibit a lesser sensitivity towards these side effects.

3) Particular, susceptibility to, or malignant disease progression in, pathophysiological states in which angiotensin II Type 1 receptor agonist activity is a therapeutically useful intervention including, yet not limited to: hypotension, and aldosterone deficiency. Genotyping individuals for this polymorphic variant can identify those patients that will exhibit a greater susceptibility to, or malignant progression of, these disease states.

4) Particular sensitivity to the beneficial effects of angiotensin II Type 1 receptor antagonists including, yet not limited to; valsartan, irbesartan, candesartan, eprosartan, zolasartan, telmisartan, olmesartan, fonsartan, embusartan, saprisartan, and losartan potassium. Genotyping individuals for this polymorphic variant can identify those patients requiring lower clinical doses of these agents.

5) Particular sensitivity to adverse cardiovascular (including, yet not limited to; hypotension, and arrhythmias) neuropsychiatric (including, yet not limited to; headache and lightheadedness), gastrointestinal (including, yet not limited to; diarrhea and constipation), and other (including, yet not limited to; neonatal morbidity and mortality) side effects of the angiotensin II Type 1 receptor antagonists including, yet not limited to; valsartan, candesartan, eprosartan, zolasartan, tasosartan, telmisartan, olmesartan, fonsartan, embusartan, saprisartan, and losartan potassium. Genotyping individuals for this polymorphic variant can identify those patients that will exhibit a heightened sensitivity towards these side effects.

6) Particular resistance to, or benign disease progression in, pathophysiological states in which angiotensin II Type 1 receptor antagonist activity is a therapeutically useful intervention including, yet not limited to: hypertension, myocardial hypertrophy, congestive heart failure, hyperlipidemia, diabetic nephropathy, and primary and secondary aldosteronism hypertension. Genotyping individuals for this polymorphic variant can identify those patients that will exhibit a lesser susceptibility to, or benign progression of, these disease states.

Cannabinoid 1 Receptor (CNR1, Genbank # X54937)

A functional effect of polymorphic variation at amino acid position 200 was observed:

A phenylalanine to leucine transition at amino acid position 200 (F200L) in the cannabinoid 1 receptor was found to decrease the basal biological activity of the receptor protein. This variant displays a loss of biological function, such that individuals that possess this variant will be particularly insensitive to the physiological effects of a therapeutic drug that activates the cannabinoid 1 receptor. Cannabinoid 1 receptors mediate some of the varied physiological effects of the endogenous autocoid anandamide. Therapeutic drugs with cannabinoid 1 receptor agonist activity are used clinically to treat; nausea, anorexia, and pain, and novel cannabinoid 1 receptor agonists are in development to treat neuropsychiatric diseases including affective disorders. No current therapeutic drugs possess cannabinoid 1 receptor antagonist activity, however cannabinoid 1 receptor antagonists are in development for neuropsychiatric diseases including affective disorders, and psychoses including schizophrenia.

GPCR Variant # 30: Cannabinoid 1 Receptor F200L Polymorphism

The presence in an individual of the genetic variant in the cannabinoid 1 receptor gene that introduces a leucine residue at amino acid position 200 will predispose the individual to one or more of the following clinical indications:

1) Particular insensitivity to the beneficial physiological effects of cannabinoid 1 receptor agonists, including, yet not limited to; dronabinol, and nabilone. Genotyping individuals for this polymorphic variant can identify those patients who require higher clinical doses of these agents.

2) Particular insensitivity to the adverse cardiovascular (including, yet not limited to; hypertension, syncope, tachycardia, bradycardia, angina, myocardial infarction, severe vasospasm, heart valvulopathies, flushing, chest pain, and arrhythmias), gastrointestinal (including, yet not limited to; nausea, abdominal pain, hepatotoxicity, and diarrhea), neuropsychiatric (including, yet not limited to; anxiety, depression, irritability, headache, confusion, dizziness, vertigo, parasthesias, blurred vision, miosis, drowsiness, malaise, fatigue, delusions and frank psychosis), and hepatic (elevated liver enzymes), side effects of cannabinoid 1 receptor agonists including; yet not limited to; dronabinol and nabinole. Genotyping individuals for this polymorphic variant can identify those patients that will exhibit a lesser propensity towards these side effects.

3) Particular susceptibility to, or malignant disease progression in, pathophysiological states in which cannabinoid 1 receptor activity is a therapeutically useful intervention including, yet not limited to: anorexia, chronic pain, and neuropsychiatric diseases including affective disorders and Schizophrenia. Genotyping individuals for this polymorphic variant can identify those patients that will exhibit a greater susceptibility to, or malignant progression of, these disease states.

4) Particular sensitivity to the beneficial physiological effects of cannabinoid 1 receptor antagonists. Genotyping individuals for this polymorphic variant can identify those patients requiring lower clinical doses of these agents.

5) Particular sensitivity to the adverse side effects of cannabinoid 1 receptor antagonists. Genotyping individuals for this polymorphic variant can identify those patients that will exhibit a heightened sensitivity towards these side effects.

6) Particular resistance to, or benign disease progression in, pathophysiological states in which cannabinoid 1 receptor antagonist activity is a therapeutically useful intervention including, yet not limited to: neuropsychiatric diseases including affective disorders and Schizophrenia. Genotyping individuals for this polymorphic variant can identify those patients that will exhibit a lesser susceptibility to, or benign progression of, these disease states.

Cholecystokinin B Receptor (CCKRB Genbank # S70057)

A functional effect of polymorphic variation at amino acid position 224 was observed:

TABLE 23

| L224Q Compound | Leucine 224 | | | Glutamine 224 | | | |
| --- | --- | --- | --- | --- | --- | --- | --- |
| | Ave –Log EC50 | STD DEV | "n" | Ave –Log EC50 | STD DEV | "n" | FOLD |
| CCK-4 | 7.10 | 0.29 | 3 | 8.18 | 0.23 | 3 | −12.0 |
| CCK-8-Sulfated | 8.07 | 0.15 | 3 | 8.55 | 0.13 | 3 | −3.0 |
| CCK-8-desulfated | 7.11 | 0.35 | 3 | 8.05 | 0.53 | 3 | −8.7 |
| Gastrin | 8.71 | 0.01 | 3 | 9.78 | 0.04 | 3 | −11.7 |

A leucine to glutamine transition at amino acid position 224 (L224Q) in the cholecystokinin B receptor protein was found to induce 3 to 12 fold shifts in functional potency for the reference and clinical agonists tested. This variant displays a gain of biological function, such that individuals that possess this variant will be particularly sensitive to the physiological effects of a therapeutic drug that activates the cholecystokinin B receptor.

Cholecystokinin B receptors mediate some of the varied physiological effects of the endogenous hormones cholecystokinin and gastrin. Therapeutic drugs with cholecystokinin B receptor agonist activity are used clinically to treat disorders of bile secretion including cholecystitis, primary sclerosing cholangitis, and malabsorption syndromes including non-tropical sprue, and are in development for use as antiobesity agents, and to treat autism and chronic and acute pain. Therapeutic drugs with cholecystokinin B receptor antagonist activity are in development to treat anorexia nervosa and acute and chronic pain.

GPCR Variant # 31: Cholecystokinin B Receptor L224Q Polymorphism

The presence in an individual of the genetic variant in the cholecystokinin B receptor gene that introduces a glutamine residue at amino acid position 224 will predispose that individual to one or more of the following clinical indications:

1) Particular sensitivity to the beneficial physiological effects of cholecystokinin B receptor agonists, including, yet not limited to; Sincalide, CCK-4, CCK-8, and gastrin. Genotyping individuals for this polymorphic variant can identify those patients requiring lower clinical doses of these agents.

2) Particular sensitivity to the adverse gastrointestinal (including, yet not limited to; nausea, vomiting, abdominal pain, hepatotoxicity, and diarrhea), and neuropsychiatric (including, yet not limited to; dizziness and flushing) side effects of cholecystokinin B receptor agonists, including, yet not limited to; sincalide, CCK-4, CCK-8, and gastrin. Genotyping individuals for this polymorphic variant can identify those patients that will exhibit a heightened sensitivity towards these side effects.

3) Particular resistance to, or benign disease progression in, pathophysiological states in which cholecystokinin B receptor agonist activity is a therapeutically useful intervention including, yet not limited to: cholecystitis, primary sclerosing cholangitis, and malabsorption syndromes including non-tropical sprue, obesity, autism and chronic and acute pain. Genotyping individuals for this polymorphic variant can identify those patients that will exhibit a lesser susceptibility to, or benign progression of, these disease states.

4) Particular insensitivity to the beneficial physiological effects of cholecystokinin B receptor antagonists, including, yet not limited to; C1988, and L265260. Genotyping individuals for this polymorphic variant can identify those patients requiring lower clinical doses of these agents.

5) Particular insensitivity to the adverse side effects of cholecystokinin B receptor antagonists including, yet not limited to: C1988, and L265260. Genotyping individuals for this polymorphic variant can identify those patients that will exhibit a lesser propensity towards these side effects.

6) Particular susceptibility to, or malignant disease progression, in pathophysiological states in which cholecystokinin B receptor antagonists antagonist activity is a therapeutically useful intervention including, yet not limited to: anorexia nervosa and acute and chronic pain. Genotyping individuals for this polymorphic variant can identify those patients that will exhibit a greater susceptibility to, or malignant progression of, these disease states.

Gamma-Amino Butyric Acid Type B Receptors (GABBR1, Genbank #AJ012288)

A functional effect of polymorphic variation at amino acid position 93 was observed:

TABLE 24

| Compound | Proline 93 EC50 (–pKi) | Leucine 93 EC50 (–pKi) | Fold |
|---|---|---|---|
| R(+) Baclofen | 6.7 | 7.0 | –2.0 |
| AMPA | 7.2 | 7.6 | –2.5 |
| GABA | 6.3 | 7.6 | –20 |

A proline to leucine transition at amino acid position 93 (P93L) in the GABA-BR1 receptor protein was found to induced 2-20 fold shifts in potency to the reference and clinical agonists tested. This variant displays a gain of biological function, such that individuals that possess this variant will be particularly sensitive to the physiological effects of a therapeutic drug that activates the GABA-BR1 receptor, and particularly insensitivity to therapeutic drugs that inactivate the GABA-BR1 receptor.

A functional effect of polymorphic variation at amino acid position 542 was observed:

TABLE 25

| Compound | Leucine 542 EC50 (–pKi) | Proline 542 EC50 (–pKi) | Fold |
|---|---|---|---|
| R(+) Baclofen | 6.7 | 5.3 | 25 |
| AMPA | 7.2 | 5.7 | 32 |
| GABA | 6.3 | 4.7 | 40 |

A leucine to proline transition at amino acid position 542 (L542P) in the GABA-BR1 receptor protein was found to render the receptor protein significantly less responsive, and induced 25-40 fold shifts in potency to the reference and clinical agonists tested. This variant displays a loss of biological function, such that individuals that possess this variant will be particularly insensitive to the physiological effects of a therapeutic drug that activates the GABA-BR1 receptor, and particularly sensitivity to therapeutic drugs that inactivate the GABA-BR1 receptor.

GABA-BR1 receptors mediate some of the varied physiological effects of the endogenous hormone/neurotransmitter gamma-amino butyric acid. Therapeutic drugs with GABA-BR1 receptor agonist activity are used as skeletal muscle relaxants to treat spasticity, chorea, and trigeminal neuralgia. Therapeutic drugs with GABA-BR1 receptor antagonist activity are in development for treating neuropsychiatric disease.

GPCR Variants # 32 and #33: GABA-BR1 Receptor P93L and L542P Polymorphisms

The presence in an individual of the genetic variation in the GABA-BR1 receptor gene that introduces a leucine residue at amino acid position 93 or a proline residue at amino acid position 542 will predispose the individual to one or more of the following clinical indications:

1) Particular sensitivity or insensitivity (variant #33) to the beneficial physiological effects of GABA-BR1 receptor agonists including, yet not limited to; baclofen. Genotyping individuals for the polymorphic variants, a leucine residue at amino acid position 93 or a proline residue at amino acid position 542 (variant #33), can identify those patients requiring lower or higher (variant #33), respectively, clinical doses of these agents.

2) Particular sensitivity or resistance (variant #33) to the adverse cardiovascular (including, yet not limited to; bradycardia, dyspnea, palpitations, orthostatic hypotension), neuropsychiatric (including, yet not limited to; anxiety, depression, confusion, hallucinations, euphoria, psychosis, headache, weakness, hypotonia, dizziness, vertigo, fatigue, drowsiness, tremor, rigidity, and seizure), renal (including, yet not limited to; urinary frequency, dysuria, hematuria), metabolic (including, yet not limited to; nausea, vomiting, diarrhea, dry mouth), and other (including, yet not limited to; deep vein thrombosis, rash, weight gain, and transaminitis) side effects of GABA-BR1 receptor agonists including, yet not limited to; baclofen. Genotyping individuals for the polymorphic variants, a leucine residue at amino acid position 93 or a proline residue at amino acid position 542 (variant #33), can identify those patients that will exhibit a heightened sensitivity or lesser propensity (variant #33), respectively, towards these side effects.

3) Particular resistance or susceptibility (variant #33) to, or benign disease progression in, pathophysiological states in which GABA-BR1 receptor agonist activity is a therapeutically useful intervention including, yet not limited to: spasticity of any origin, and headache. Genotyping individuals for the polymorphic variants, a leucine residue at amino acid position 93 or a proline residue at amino acid position 542(variant #33), can identify those patients that will exhibit a lesser or greater susceptibility (variant #33), respectively, to, or benign progression of, these disease states.

4) Particular insensitivity or sensitivity (variant #33) to the beneficial physiological effects of the GABA-BR1 receptor antagonists. Genotyping individuals for the polymorphic variants, a leucine residue at amino acid position 93 or a proline residue at amino acid position 542 (variant #33), can identify those patients requiring higher or lower (variant #33), respectively, clinical doses of these agents.

5) Particular insensitivity or sensitivity (variant #33) to the adverse side effects of the GABA-BR1 receptor antagonists. Genotyping individuals for the polymorphic variants, a leucine residue at amino acid position 93 or a proline residue at amino acid position 542 (variant #33), can identify those patients that will exhibit a lesser propensity or heightened sensitivity (variant #33), respectively, towards these side effects.

6) Particular susceptibility or resistance (variant #33) to, or malignant disease progression in, pathophysiological states in which GABA-BR1 receptor antagonist activity is a therapeutically useful intervention including, yet not limited to: Schizophrenia, Schizo-affective disorder, and related psychoses, depression, as well as the behavioral disturbances observed with neurodegenerative disorders such as Alzheimer's disease. Genotyping individuals for the polymorphic variants, a leucine residue at amino acid position 93 or a proline residue at amino acid position 542 (variant #33), can identify those patients that will exhibit a greater or lesser (variant #33), respectively, susceptibility to, or malignant progression of, these disease states.

Thromboxane 2 Prostanoid Receptors (TBXA2R, Genbank #E03829)

A functional effect of polymorphic variation at amino acid position 80 was observed:

TABLE 26

| Compound | Valine 80 EC50 (-pKi) | Glutamic Acid 80 EC50 (-pKi) | Fold |
| --- | --- | --- | --- |
| U46619 | 8.04 +/- 0.2 | 6.24 +/- 0.4 | 63 |
| Thromboxane A2 | 6.41 +/- 0.2 | 5.39 +/- 0.1 | 11 |
| I-BOP | 9.49 +/- 0.3 | 7.52 +/- 0.1 | 93 |

A valine to glutamic acid transition at amino acid position 80 (V80E) in the thromboxane receptor protein was found to induce 11-93 fold shifts in functional potency for the reference agonists tested. This variant displays a loss of biological function, such that individuals that possess this variant will be particularly insensitive to the physiological effects of a therapeutic drug that activates the thromboxane receptor.

A functional effect of polymorphic variation at amino acid position 94 was observed:

TABLE 27

| Compound | Glutamine 94 EC50 (−pKi) | Valine 94 EC50 (−pKi) | Fold |
|---|---|---|---|
| U46619 | 8.34 +/− 0.2 | 7.56 +/− 0.1 | 6.0 |
| Thromboxane A2 | 6.12 +/− 0.2 | 6.48 +/− 0.2 | 2.3 |
| I-BOP | 9.50 +/− 0.2 | 8.95 +/− 0.1 | 3.5 |

A glutamine to valine transition at amino acid position 94 (E94V) in the thromboxane receptor protein was found to induce 3-6 fold shifts in functional potency for the reference agonists tested. This variant displays a loss of biological function, such that individuals that possess this variant will be particularly insensitive to the physiological effects of a therapeutic drug that activates the thromboxane receptor.

A functional effect of polymorphic variation at amino acid position 176 was observed:

| Compound | Valine 176 EC50 (−pKi) | Glutamic Acid 176 EC50 (−pKi) | Fold |
|---|---|---|---|
| U46619 | 8.04 +/− 0.2 | 7.33 +/− 0.3 | 5 |
| Thromboxane A2 | 6.41 +/− 0.2 | 5.58 +/− 0.3 | 7 |
| I-BOP | 9.49 +/− 0.3 | 8.39 +/− 0.1 | 13 |

A valine to glutamic acid transition at amino acid position 176 (V176E) in the thromboxane receptor protein was found to induce 5-13 fold shifts in functional potency for the reference agonists tested. This variant displays a loss of biological function, such that individuals that possess this variant will be particularly insensitive to the physiological effects of a therapeutic drug that activates the thromboxane receptor.

Thromboxane receptors mediate some of the varied physiological effects of the endogenous autocoid thromboxane A2. This receptor is an important mediator of platelet aggregation, vasoconstriction, leukocyte maturation, and has been shown to modulate atherosclerotic processes. No therapeutic drugs with thromboxane receptor agonist activity have yet been developed. Therapeutic drugs with thromboxane receptor antagonist activity are being developed to inhibit platelet aggregation, block vasoconstriction, and to treat nephrotic syndrome.

GPCR Polymorphisms # 34, # 35 and # 36: Thromboxane Receptor V80E, E94V and V176E Polymorphisms The presence in an individual of the genetic variation in the thromboxane receptor gene that introduces an glutamine residue at amino acid position 80, or a valine at amino acid position 94, or a glutamic acid at amino acid position 176 will predispose the individual to one or more of the following clinical indications:

1) Particular insensitivity to the beneficial physiological effects of thromboxane receptor agonists including, yet not limited to; thromboxane A2. Genotyping individuals for this polymorphic variant can identify those patients requiring higher clinical doses of these agents.

2) Particular insensitivity to the potential adverse side effects of thromboxane receptor agonists including, yet not limited to; thromboxane A2. Genotyping individuals for this polymorphic variant can identify those patients that will exhibit a lesser propensity towards these effects.

3) Particular susceptibility to, or malignant disease progression in, pathophysiological states in which thromboxane receptor agonist activity is a therapeutically useful intervention including, yet not limited to: hemorrhage, hypotension, and renal disorders including nephritic syndromes. Genotyping individuals for this polymorphic variant can identify those patients that will exhibit a greater susceptibility to, or malignant progression of, these disease states.

4) Particular sensitivity to the beneficial physiological effects of thromboxane receptor antagonists including, yet not limited to; sulotroban, and vapiprost. Genotyping individuals for this polymorphic variant can identify those patients requiring lower clinical doses of these agents.

5) Particular sensitivity to the potential adverse side effects of thromboxane receptor antagonists including, yet not limited to; sulotroban, and vapiprost. Genotyping individuals for this polymorphic variant can identify those patients that will exhibit a greater propensity towards these effects.

6) Particular resistance to, or benign disease progression in, pathophysiological states in which thromboxane receptor antagonist activity is a therapeutically useful intervention including, yet not limited to: thrombosis, hypertension, systemic vascular resistance syndromes, asthma, renal disorders including nephrotic syndrome, and atherosclerosis and its consequences including stroke, myocardial infarction, and peripheral vascular disease. Genotyping individuals for this polymorphic variant can identify those patients that will exhibit a lesser susceptibility to, or benign progression of, these disease states.

Neuropeptide Y1 Receptor (NPYR1, Genbank # A26481)

A functional effect of polymorphic variation at amino acid position 298 was observed:

TABLE 28

| | Histidine 298 | | | Proline 298 | | | |
|---|---|---|---|---|---|---|---|
| H298P Compound | Ave −Log EC50 | STD DEV | "n" | Ave −Log EC50 | STD DEV | "n" | FOLD |
| NPY | 6.36 | 0.09 | 4 | NR | | | NR |
| PYY | 9.94 | 0.80 | 3 | 6.91 | 0.2 | 3 | 1072 |
| Leu/Pro NPY | 7.50 | 0.11 | 4 | NR | | | NR |

A histidine to proline transition at amino acid position 298 (H298P) in the neuropeptide Y1 receptor protein was found to render the protein non-functional. This variant displays a loss of biological function, such that individuals that possess this variant will be particularly insensitive to the physiological effects of a therapeutic drug that activates the neuropeptide Y1 receptor.

Neuropeptide Y1 receptors mediate some the varied physiological effects of the endogenous hormone neuropeptide Y. No therapeutic drugs with neuropeptide Y1 receptor antagonist activity are currently in clinical use. Neuropeptide Y regulates a host physiological functions including vasomotor activity, fluid balance, hormonal release, and feeding and drinking behaviors.

GPCR Polymorphism # 37: Neuropeptide Y1 Receptor Polymorphism

The presence in an individual of the genetic variation in the neuropeptide Y1 receptor gene that introduces an arginine residue at amino acid position 298 will predispose the individual to one or more of the following clinical indications:

1) Particular insensitivity to the beneficial physiological effects of neuropeptide Y1 receptor agonists including, yet not limited to; NPY and PYY. Genotyping individuals for this polymorphic variant can identify those patients requiring higher clinical doses of these agents.

2) Particular insensitivity to the potential adverse side effects of neuropeptide Y1 receptor agonists including, yet not limited to; NPY and PYY. Genotyping individuals for this polymorphic variant can identify those patients that will exhibit a lesser propensity towards these effects.

3) Particular susceptibility to, or malignant disease progression in, pathophysiological states in which neuropeptide Y1 receptor agonist activity is a therapeutically useful intervention including, yet not limited to: hemorrhage, hypotension, neuropsychiatric disease, obesity and anorexia. Genotyping individuals for this polymorphic variant can identify those patients that will exhibit a greater susceptibility to, or malignant progression of, these disease states.

4) Particular sensitivity to the beneficial physiological effects of neuropeptide Y1 receptor antagonists. Genotyping individuals for this polymorphic variant can identify those patients requiring lower clinical doses of these agents.

5) Particular sensitivity to the potential adverse side effects of neuropeptide Y1 receptor antagonists. Genotyping individuals for this polymorphic variant can identify those patients that will exhibit a greater propensity towards these effects.

6) Particular resistance to, or benign disease progression in, pathophysiological states in which neuropeptide Y1 receptor antagonist activity is a therapeutically useful intervention including, yet not limited to: hemorrhage, hypotension, neuropsychiatric disease, obesity and anorexia. Genotyping individuals for this polymorphic variant can identify those patients that will exhibit a lesser susceptibility to, or benign progression of, these disease states.

Thus, in accordance with the invention, there are provided methods of screening a subject for the presence of GPCR variants, said variants providing clinical indications as set forth herein. In various embodiments, a method includes detecting the presence of one or more variants of alpha 1 adrenergic receptor, beta 3 adrenergic receptor, dopamine D1 receptor, dopamine D2 receptor, dopamine D3 receptor, histamine H1 receptor, histamine H2 receptor, serotonin 1A receptor, serotonin 1B receptor, serotonin 1D receptor, serotonin 1E receptor, serotonin 2B receptor, serotonin 7 receptor, angiotensin II type 1 receptor, CB1 cannabinoid receptor, cholecystokinin B receptor, gamma-amino-butyric acid Type B receptor, thromboxane A2 receptor, and neuropeptide Y1 receptor. In various aspects, a method includes screening a biological sample from a subject for one or more variants of: alpha 1 adrenergic receptor, beta 3 adrenergic receptor, dopamine D1 receptor, dopamine D2 receptor, dopamine D3 receptor, histamine H1 receptor, histamine H2 receptor, serotonin 1A receptor, serotonin 1B receptor, serotonin 1D receptor, serotonin 1E receptor, serotonin 2B receptor, serotonin 7 receptor, angiotensin II type 1 receptor, CB1 cannabinoid receptor, cholecystokinin B receptor, gamma-amino-butyric acid Type B receptor, thromboxane A2 receptor, and neuropeptide Y1 receptor.

In various aspects, the variants are selected from one or more of: alpha 1A/C adrenergic receptor having a cysteine residue at amino acid position 43 or a haplotype linked with a cysteine residue at amino acid position 43, or a serine residue at amino acid position 200 or a haplotype linked with a serine residue at amino acid position 200; beta 3 adrenergic receptor having a leucine residue at amino acid position 78 or a haplotype linked with a leucine residue at amino acid position 78; dopamine D1 receptor having a proline at amino acid position 37 or a haplotype linked with a proline at amino acid position 37, or an arginine at amino acid position 37 or a haplotype linked with an arginine at amino acid position 37, or a serine at amino acid position 79 or a haplotype linked with a serine at amino acid position 79, or an alanine at amino acid position 199 or a haplotype linked with an alanine at amino acid position 199; dopamine D2 receptor having an arginine at amino acid position 40 or a haplotype linked with an arginine at amino acid position 40, or a leucine at amino acid position 208 or a haplotype linked to a leucine at amino acid position 208; dopamine D3 receptor having a leucine at amino acid position 50 or a haplotype linked with a leucine at amino acid position 50; histamine H1 receptor having a glycine at amino acid position 216 or a haplotype linked to a glycine at amino acid position 216, or a proline at amino acid position 226 or a haplotype linked to a proline at amino acid position 226; histamine H2 receptor having an asparagine at amino acid 175 or a haplotype linked to an asparagine at amino acid 175, or a glycine at amino acid position 215 or a haplotype linked to a glycine at amino acid position 215, or an arginine at amino acid position 231 or a haplotype linked to an aspartic acid at amino acid 231; serotonin 1A receptor having a valine at amino acid position 50 or a haplotype linked to a valine at amino acid position 50, or an isoleucine at amino acid position 172 or a haplotype linked to an isoleucine at amino acid position 172, or a phenylalanine at amino acid position 381 or a haplotype linked to a phenylalanine at amino acid position 381; serotonin 1B receptor having an asparagine at amino acid position 221 or a haplotype linked to an asparagine at amino acid position 221; serotonin 1D receptor having a leucine at amino acid position 53 or a haplotype linked to a leucine at amino acid position 53, or a glycine at amino acid position 366 or a haplotype linked to a glycine at amino acid position 366; serotonin 1E receptor having a threonine at amino acid position 44 or a haplotype linked to a threonine at amino acid position 44, or a phenylalanine at amino acid position 262 or a haplotype linked to a phenylalanine at amino acid position 262; serotonin 2B receptor having a tryptophan at amino acid position 388 or a haplotype linked to a tryptophan at amino acid position 388; serotonin 7 receptor having a lysine at amino acid position 92 or a haplotype linked to a lysine at amino acid position 92, or a proline at amino acid position 421 or a haplotype linked to a proline at amino acid position 421; angiotensin II type 1 receptor having an arginine at amino acid position 45 or a haplotype linked to an arginine at amino acid position 45, or a serine at amino acid position 204 or a haplotype linked to a serine at amino acid position 204, or a tryptophan at amino acid position 289 or a haplotype linked to a tryptophan at amino acid position 289; CB1 cannabinoid receptor having a leucine at amino acid position 200 or a haplotype linked to a leucine at amino acid position 200; cholecystokinin B receptor having a glutamine at amino acid position 224 or a haplotype linked to a glutamine at amino acid position 224; gamma-amino-butyric acid B receptor having a leucine at amino acid position 93 or a haplotype linked to a leucine at amino acid position 93, or a proline at amino acid position 452 or a haplotype linked to a proline at amino acid position 452; thromboxane A2 receptor having a glutamic acid at amino acid position 80 or a haplotype linked to a glutamic acid at amino acid position 80, a valine at amino acid position 94 or a haplotype linked to a valine at amino acid position 94, or a glutamic acid at amino acid position 176 or a haplotype linked to a glutamic acid at amino acid position 176; or a neuropeptide Y1 receptor having a proline at amino acid position 298, or a haplotype linked to a proline at amino acid position 298.

The presence of the variant receptor or haplotype linked to the variant identifies the subject as having the corresponding receptor variant. Thus, further in accordance with the invention, there are provided methods for identifying individuals having increased or decreased sensitivity or insensitivity to beneficial physiological effects of GPCR agonists and antagonists; having increased or decreased sensitivity or insensitivity to adverse side effects produced by agonists or antagonists of GPCRs; having increased or decreased resistance or susceptibility to, or benign disease progression in, pathophysiological states in which GPCR agonist or antagonist activity is a therapeutically useful intervention.

In additional embodiments of the methods of the invention, the presence of the GPCR variants set forth herein may be detected by hybridization with polynucleotides that specifically hybridize to the variant sequence, i.e., the sequence that contains the nucleotide(s) polymorphism. Alternatively, direct nucleotide sequencing of the GPCR gene of interest will reveal whether the polymorphism is present. Thus, the invention methods may be practiced by hybridizing a polynucleotide to nucleic acid obtained from a subject, and the presence of the variant to which the polynucleotide specifically hybridizes detected using methods known in the art such as Northern or Southern blots or other methods, such as nucleotide sequencing.

The invention therefore also provides methods of screening for the presence of a GPCR variant employing polynucleotides that specifically hybridize to at least a portion of the GPCR sequence that encodes a variant amino acid residue of a GPCR variant disclosed herein. In one embodiment, a method includes contacting a sample that contains nucleic acid with a polynucleotide capable of specific hybridization to one or more GPCR sequences that encodes a variant sequence. Detecting a hybridization signal thereby detects the presence of a nucleic acid that encodes the variant. In various aspects, the hybridization signal is compared to a control polynucleotide that specifically hybridizes to a GPCR that does not contain the variant, e.g., a sequence that is wild type in respect to the particular polymorphism being detected. The hybridization signals of the polynucleotide that hybridizes to the GPCR variant sequence and the polynucleotide that hybridizes to a GPCR that does not contain the variant can be compared in order to confirm the presence or absence of the variant GPCR. In various aspects, the sample is from a subject, such as a mammal (human).

The methods of the invention directed to detecting one or more variant GPCRs, e.g. in a subject, generally require nucleic acid. Nucleic acid can be isolated from a biological sample such as cells, tissue or organ (e.g. biopsy) from a subject according to any well known method. The sample may be of any biological tissue or fluid. Samples include, but are not limited to, sputum, blood, blood cells (e.g., white cells), tissue or biopsy samples, stool, urine, peritoneal fluid, pleural fluid, spinal or cranial fluid or cells there from. Biological samples may also include sections of tissues such as frozen sections taken for histological purposes. Thus, essentially any sample that contains nucleic acid can be used for detecting variant GPCR.

The term "subject" refers to animals, typically mammalian animals, such as a non-human primate (gorillas, chimpanzees, orangutans, macaques, gibbons), a domestic animal (dogs and cats), a farm animal (horses, cows, goats, sheep, pigs), experimental animal (mouse, rat, rabbit, guinea pig) and humans that have or may have a GPCR variant. Human subjects include adults, and children, for example, newborns and older children, for example, between the ages of 1 and 5, 5 and 10 and 10 and 18. Subjects include disease model animals (e.g., such as mice and non-human primates) for studying the effect of a therapy on these animals having a GPCR variant sequences as disclosed herein.

Subjects that may be screened for the presence of a GPCR variant in accordance with the invention include, for example, any subject that is being treated or that is a candidate for treatment, for example, with any agent disclosed herein, or with any agent that exhibits activity on one or more of the GPCRs disclosed herein. For example, a subject being treated or a candidate for treatment with any alpha 1A/C adrenergic receptor agonist or antagonist, such as dobutamine, is a candidate subject to be screened in a method of the invention for the presence of a cysteine residue at amino acid position 43 or a serine residue at amino acid position 200 of alpha 1A/C adrenergic receptor. Likewise, a subject being treated or a candidate for treatment with any Beta 3 adrenergic receptor agonist or antagonist, such as albuterol, is a candidate subject to be screened in a method of the invention for the presence of a leucine residue at amino acid position 78 of Beta 3 adrenergic receptor. Thus, subjects that may be screened include subjects where GPCR variant screening may increase the likelihood of successful treatment with a drug that acts at least in part through the GPCR, diagnosis or identification of those with increased or decreased sensitivity or resistance to pathophysiological states in which GPCR agonists or antagonists are useful in treating, for tailoring the types and doses of particular drugs to that subject, and for identifying subjects having increased or decreased risk of an adverse side effect of the treatment.

The invention further provides compositions including, for example, polynucleotides that specifically hybridize to GPCR variant nucleic acids and antibodies that specifically bind to the variant GPCR polypeptides. In one embodiment, a polynucleotide of the invention specifically binds to a nucleic acid that includes a sequence (sense, antisense or RNA transcript) that codes for that portion of the GPCR sequence that contains the variant amino acid residue, or a haplotype linked with the variant amino acid residue. In particular aspects, the sequence codes for at least a portion of a polypeptide that includes a sequence selected, for example, from:

1) Alpha 1A/C adrenergic receptor having a cysteine residue at amino acid position 43 or a serine at amino acid position 200;

2) Beta 3 adrenergic receptor having a leucine residue at amino acid position 78;

3) D1 dopamine receptor having a proline at amino acid position 37 or an arginine at amino acid position 37 or a serine at amino acid position 79 or an alanine at amino acid position 199;

4) D2 dopamine receptor having an arginine at amino acid position 40 or a leucine at amino acid position 208;

5) D3 dopamine receptor having a leucine at amino acid position 50;

6) H1 Histamine receptor having a glycine at amino acid position 216 or a proline at amino acid 226;

7) H2 histamine receptor having an asparagine at amino acid position 175 or a glycine at amino acid position 215 or an arginine at amino acid position 231;

8) 1A serotonin receptor having a valine at amino acid position 50 or an isoleucine at amino acid position 172 or a phenylalanine at amino acid position 381;

9) 1B serotonin receptor having an asparagine at amino acid position 221;

10) 1D serotonin receptor having a leucine at amino acid position 53 or a glycine at amino acid position 366;

11) 1E serotonin receptor having a threonine at amino acid position 44 or a phenylalanine at amino acid position 262;

12) 2B serotonin receptor having a tryptophan at amino acid position 388;

13) serotonin 7 receptor having a lysine at amino acid position 92 or a proline at amino acid position 421;

14) angiotensin 2 type 1 receptor having an arginine at amino acid position 45 or a serine at amino acid position 204 or a tryptophan at amino acid position 289;

15) cannabinoid CB1 receptor having a leucine at amino acid position 200;

16) cholecystokinin B receptor having a glutamine at amino acid position 224;

17) gamma-amino-butyric acid B receptor having a leucine at amino acid position 93 or a proline at amino acid position 452;

18) thromboxane A2 receptor having a glutamic acid at amino acid position 80 or a valine at amino acid position 94 or a glutamic acid at amino acid position 176; and 19) neuropeptide Y1 receptor having a proline at amino acid position 298.

In more particular aspects, polynucleotides of the invention specifically hybridize to one or more nucleic acid sequences that encode the variant GPCR selected, or a portion of the sequence that contains the polymorphism, for example, from:

1) Alpha 1A/C adrenergic receptor having a thymine at position 564 or a guanine at position 1035 or a haplotype linked with thymine at position 564 or a guanine at position 1035;

2) Beta 3 adrenergic receptor having a thymine at nucleotide position 870, or a haplotype linked with a thymine at nucleotide position 870;

3) D1 dopamine receptor having a cytidine at nucleotide position 382 or a guanine at nucleotide position 383 or a thymine at nucleotide position 508 or a guanine at nucleotide position 868, or a haplotype linked with a cytidine at nucleotide position 382 or a guanine at nucleotide position 383 or a thymine at nucleotide position 508 or a guanine at nucleotide position 868;

4) D2 dopamine receptor having a guanine at nucleotide position 218 or a cytidine at nucleotide position 721, or a haplotype linked with a guanine at nucleotide position 218 or a cytidine at nucleotide position 721;

5) D3 dopamine receptor having a cytidine at nucleotide position 148, or a haplotype linked with a cytidine at nucleotide position 148;

6) H1 histamine receptor having a guanine at nucleotide position 2811 or a cytidine at nucleotide position 2841, or a haplotype linked to a guanine at nucleotide position 2811 or a cytidine at nucleotide position 2841;

7) H2 histamine receptor having a thymine at nucleotide position 2298 or a guanine at nucleotide position 2416 or a guanine at nucleotide position 2465;

8) 1A serotonin receptor having a thymine at nucleotide position 540 or a cytidine at nucleotide position 907 or a cytidine at nucleotide position 1534;

9) 1B serotonin receptor having an alanine at nucleotide position 1033;

10) 1D serotonin receptor having a cytidine at nucleotide position 427 or a guanine at nucleotide position 1367;

11) 1E serotonin receptor having a cytidine at nucleotide position 697 or a thymine at nucleotide position 1351;

12) 2B serotonin receptor having a thymine at nucleotide position 1217;

13) serotonin 7 receptor having a guanine at nucleotide position 302 or a cytidine at amino acid position 1289;

14) angiotensin II type 1 receptor having an alanine at nucleotide position 339 or a cytidine at nucleotide position 817 or a guanine at nucleotide position 1073;

15) cannabinoid CB1 receptor having a cytidine at nucleotide position 746;

16) cholecystokinin B receptor having a alanine at nucleotide position 856;

17) Gamma-amino-butyric acid B receptor having a thymine at nucleotide position 321 or a cytidine at nucleotide position 1698;

18) Thromboxane A2 receptor having an alanine at nucleotide position 1230 or a thymine at nucleotide position 1272 or an alanine at nucleotide position 1518; and 19) Neuropeptide Y1 receptor having a cytosine at nucleotide position 1068.

Of course, the methods of the invention may be performed using multiple polynucleotides capable of specifically hybridizing to multiple GPCR variants. For example, both alpha 1A/C adrenergic receptor variants can be simultaneously detected by using polynucleotides that specifically hybridize to sense or antisense nucleic acid coding for cysteine at amino acid position 43 and serine at position 200. If the variants are located closely enough to each other, a single polynucleotide that specifically hybridizes to GPCR sequences that include nucleotides that encode the variants can be used to detect two or more variants simultaneously. In this way, the presence of more than one GPCR variants may be detected affording economies of scale and additional clinical indication information for tailoring clinical treatment to the individual. Therefore, the invention also provides mixtures of polynucleotides (two or more polynucleotides, or a plurality) that specifically hybridize to GPCR variant nucleic acids and mixtures of antibodies (two or more antibodies, or a plurality) that specifically bind to the variant GPCR polypeptides. The term "polynucleotide," "oligonucleotide," "nucleic acid," "gene" and the like include linear oligomers of natural or modified monomers or linkages, including deoxyribonucleotides, ribonucleotides, α-anomeric forms thereof capable of specifically binding to a target sequence by way of a regular pattern of monomer-to-monomer interactions, such as Watson-Crick type of base pairing, base stacking, Hoogsteen or reverse Hoogsteen types of base pairing. Monomers are typically linked by phosphodiester bonds or analogs thereof to form the polynucleotides. Whenever a polynucleotide is represented by a sequence of letters, such as "ATGCCTG," it is understood that the nucleotides are in a 5'→3' orientation from left to right.

Polynucleotides can be a synthetic oligomer, a sense or antisense, single or double strand full-length cDNA encoding a variant GPCR, or a less-than full length cDNA that includes at least that portion of the sequence that contains the variant nucleotide(s), or a genomic sequence or subsequence which contains, for example, non-coding 5' and 3' regions and introns. Polynucleotides therefore include sequences that specifically hybridize to the portion of the GPCR variant that contains a sequence that codes for the variant amino acid residue. Thus, the polynucleotide need only hybridize to a region of the variant GPCR sequence that includes the polymorphism.

Polynucleotides also include for example, RNA, such as mRNA. Thus, polynucleotides include, but are not limited to, mRNA transcripts of the GPCR variant gene or genomic sequence, cDNA reverse transcribed from the mRNA, cRNA transcribed from the cDNA, DNA amplified from the GPCR genes or genomic sequences, RNA transcribed from amplified DNA, etc.

Polynucleotides of the invention include sequences suitable for hybridization or for attachment to a detection substrate. Typically polynucleotides for hybridization comprise the four natural nucleotides; however, they may also comprise non-natural nucleotide analogs, derivatized forms or mimetics. Analogs of phosphodiester linkages include phosphorothioate, phosphorodithioate, phosphoranilidate, phosphoramidate, for example. A particular example of a mimetic is protein nucleic acid (see, e.g., Egholm et al., Nature 365:566 (1993); see also U.S. Pat. No. 5,539,083.

Polynucleotides suitable for such applications are typically between 8 and 50 bases in length. Polynucleotides of the invention therefore can be of any length, but are more likely between about 8 and 50, for example, 8 to 12, 8 to 15, 12 to 15, 12 to 20, 15 to 20, 12 to 25, 15 to 25, 15 to 30, 15 to 35, 12 to 30, 18 to 25, 18 to 30, 12 to 35, 15 to 40, 20 to 30, 20 to 35, 20 to 40, 25 to 40, 30 to 40, 30 to 45, 30 to 50, 35 to 50, or any number between 8 and 50 nucleotides.

Polynucleotides of the invention will specifically hybridize to a sequence including a sequence encoding the variant GPCR, whether the sequence to which the polynucleotide hybridizes is the sense or antisense strand (genomic sequence or a cDNA sequence) or an RNA transcript transcribed from the variant GPCR. Therefore, polynucleotides of the invention include double or single strand, linear or circular, sequences that specifically hybridize to sense or antisense strands of regions of GPCRs that include the variant sequence, as well as polynucleotides that specifically hybridize to an RNA transcript that encodes a variant GPCR.

The term "hybridization" refers to the binding between complementary nucleic acids. The term "specific hybridization" or grammatical variations thereof, when used in reference to a polynucleotide capable of forming a non-covalent bond with another sequence, means that the hybridization is selective between 1) the polynucleotide and 2) a sequence that includes the variant nucleotide(s) that encodes at least a portion of the GPCR polypeptide that contains the variant amino acid residue. In other words, the polynucleotide will preferentially hybridize to the variant sequence over the wild type sequence, or other sequences (e.g., other variants) to the extent that one skilled in the art will be able to determine that the target GPCR variant is present. Suitable polynucleotide controls, for example, a polynucleotide that specifically hybridizes to GPCR encoding a wild-type amino acid residue instead of variant residue can be used for comparison in order to determine whether the GPCR variant is present or not.

For two nucleic acid sequences to bind, the temperature of a hybridization reaction must be less than the calculated TM for the sequences. As is understood by those skilled in the art, the TM (melting temperature) refers to the temperature at which binding between complementary sequences is no longer stable. The TM is influenced by the amount of sequence complementarity, length, composition (% GC), type of nucleic acid (RNA vs. DNA), and the amount of salt, detergent and other components in the reaction (e.g., formamide). For example, longer hybridizing sequences are stable at higher temperatures. Duplex stability between RNAs or DNAs is generally in the order of RNA:RNA>RNA:DNA>DNA:DNA. All of these factors are considered in establishing appropriate hybridization conditions (see, e.g., the hybridization techniques and formula for calculating TM described in Sambrook et al., 1989, supra). Generally, stringent conditions are selected to be about 5° C. lower than the melting point (Tm) for the specific sequence at a defined ionic strength and pH.

Typically, wash conditions are adjusted so as to attain the desired degree of hybridization stringency. Thus, hybridization stringency can be determined empirically, for example, by washing under particular conditions, e.g., at low stringency conditions or high stringency conditions. For example, a polynucleotide that specifically binds to a variant GPCR can be compared for hybridization to the variant GPCR sequence and the wild type GPCR sequence under the same hybridization conditions. A hybridization signal of at least two-fold greater for the variant than the wild type identifies appropriate hybridization conditions for differentiating between the variant and wild type GPCR sequence and, therefore, appropriate hybridization conditions for use in the methods of the invention. However, if the conditions are insufficient to detect differences in hybridization signal, stringency of the conditions can be increased.

Exemplary hybridization conditions include, for example, moderately stringent hybridization, 2×SSC/0.1% SDS at about 37° C. or 42° C. (hybridization); 0.5×SSC/0.1% SDS at about room temperature (low stringency wash); 0.5×SSC/0.1% SDS at about 42° C. (moderate stringency wash); moderately-high stringency hybridization: 2×SSC/0.1% SDS at about 37° C. or 42° C. (hybridization); 0.5×SSC/0.1% SDS at about room temperature (low stringency wash); 0.5×SSC/0.1% SDS at about 42° C. (moderate stringency wash); and 0.1×SSC/0.1% SDS at about 52° C. (moderately-high stringency wash); high stringency hybridization: 2×SSC/0.1% SDS at about 37° C. or 42° C. (hybridization); 0.5×SSC/0.1% SDS at about room temperature (low stringency wash); 0.5×SSC/0.1% SDS at about 42° C. (moderate stringency wash); and 0.1×SSC/0.1% SDS at about 65° C. (high stringency wash). Nucleic acid hybridization conditions using gene chips is described, for example, in U.S. Pat. No. 6,040,138.

Invention polynucleotide sequences will typically be highly homologous to the GPCR nucleotide sequence that encodes the variant. Examples of high homology depend on the length of the polynucleotide used for hybridization. For example, a 10 base polynucleotide may require 100% homology with the sequence it binds, i.e., the variant GPCR, because a single base mismatch may also allow it to bind to wild type GPCR sequence to the extent that they may not be distinguishable (i.e., less than a two-fold difference in hybridization signal between the variant and wild type GPCRs). However, longer sequences are able to tolerate mismatches; the longer the sequence, the greater the number of mismatches that may be tolerated without affecting specific hybridization. For example, a 12 to 15 base polynucleotide is likely to tolerate 1-2 mismatches; a 15 to 20 base polynucleotide is likely to tolerate 1-3 mismatches; a 20 to 25 base polynucleotide is likely to tolerate 1-4 mismatches; a 25 to 30 base polynucleotide is likely to tolerate 1-5 mismatches, and so forth. Thus, polynucleotides of the invention that specifically hybridize to variant GPCRs therefore are complementary to a portion of the variant GPCR nucleotide sequences disclosed herein that includes the sequence that codes for the variant amino acid residue to the extent that they are capable of distinguishing between the variant sequence and a GPCR sequence wild type in respect to the variant. Accordingly, invention polynucleotides need not be 100% homologous or 100% complementary to sequences that encode GPCR variant polypeptide sequence disclosed herein, or to the specific nucleic acid sequences disclosed herein that can encode the particular 37 GPCR variants.

Invention polynucleotides having less than 100% homology or complementarity to a GPCR variant nucleic acid sequence may be identified using routine assays. For example, a series of polynucleotides with less than 100% homology or complementarity to the variant GPCR sequence can be produced having various lengths. The polynucleotides can then be individually hybridized to the variant GPCR sequence; sequences that hybridize can then be compared for their ability to differentiate between the variant and the wild type GPCR sequence, for example, by comparing the hybridization signal when the polynucleotide hybridizes to the variant GPCR and vs. the wild type GPCR. Detecting a difference in hybridization signal, generally at least a two-fold or greater difference in the signal for the variant sequence than the wild type sequence identifies polynucleotides of the invention that specifically hybridize to the variant GPCR sequence.

The polynucleotides for hybridization may be labeled before, during, or after hybridization to a GPCR, although typically polynucleotides are labeled before hybridization. The labels may be incorporated by any of a number of means well known to those of skill in the art. For example, polymerase chain reaction (PCR) with labeled primers or labeled nucleotides will produce a labeled amplification product. Labels that may be employed include radioisotope labeled nucleotides (e.g., dCTP), fluorescein-labeled nucleotides (UTP or CTP). A label may be attached directly to the nucleic acid sample (e.g., mRNA, polyA mRNA, cDNA, etc.) or to the amplification product after the amplification is completed using methods well known to those of skill in the art including, for example nick translation or end-labeling (e.g. with a labeled RNA).

"Direct labels" are directly attached to or incorporated into the polynucleotides prior to hybridization. Indirect labels are attached to the hybrid duplex after hybridization. For example, an indirect label, such as biotin, can be attached to the polynucleotide prior to the hybridization. Following hybridization, an aviden-conjugated fluorophore will bind the biotin bearing hybrid duplexes to facilitate detection.

Labels therefore include any composition that can be attached to or incorporated into nucleic acid that is detectable by spectroscopic, photochemical, biochemical, immunochemical, electrical, optical or chemical means. Useful labels include biotin for staining with labeled streptavidin conjugate, magnetic beads (e.g., Dynabeads™), fluorescent dyes (e.g., 6-FAM, HEX, TET, TAMRA, ROX, JOE, 5-FAM, R110, fluorescein, texas red, rhodamine, lissamine, phycoerythrin (Perkin Elmer Cetus), Cy2, Cy3, Cy3.5, Cy5, Cy5.5, Cy7, FluorX (Amersham), radiolabels, enzymes (e.g., horse radish peroxidase, alkaline phosphatase and others used in ELISA), and colorimetric labels such as colloidal gold or colored glass or plastic beads (e.g., polystyrene, polypropylene, latex, etc.), fluorophore, a radioisotope or a chemiluminescent moiety.

Compositions further include detection substrates that include a two-dimensional array of polynucleotide sequences and a substrate; the polynucleotide sequences are typically attached to the surface of the substrate (e.g., via a covalent bond) at defined positions (addresses). In one aspect, the polynucleotides attached to the surface of the substrate encode at least a portion of a polypeptide that includes a sequence selected, for example, from: Alpha 1A/C adrenergic receptor having a cysteine residue at amino acid position 43 or a serine at amino acid position 200; Beta 3 adrenergic receptor having a leucine residue at amino acid position 78; D1 dopamine receptor having a proline at amino acid position 37 or an arginine at amino acid position 37 or a serine at amino acid position 79 or an alanine at amino acid position 199; D2 dopamine receptor having an arginine at amino acid position 40 or a leucine at amino acid position 208; D3 dopamine receptor having a leucine at amino acid position 50; H1 histamine receptor having a glycine at amino acid position 216 or a proline at amino acid 226; H2 histamine receptor having an asparagine at amino acid position 175 or a glycine at amino acid position 215 or an arginine at amino acid position 231; 1A serotonin receptor having a valine at amino acid position 50 or an isoleucine at amino acid position 172 or a phenylalanine at amino acid position 381; 1B serotonin receptor having an asparagine at amino acid position 221; 1D serotonin receptor having a leucine at amino acid position 53 or a glycine at amino acid position 366; 1E serotonin receptor having a threonine at amino acid position 44 or a phenylalanine at amino acid position 262; 2B serotonin receptor having a tryptophan at amino acid position 388; serotonin 7 receptor having a lysine at amino acid position 92 or a proline at amino acid position 421; angiotensin 2 type 1 receptor having an arginine at amino acid position 45 or a serine at amino acid position 204 or a tryptophan at amino acid position 289; cannabinoid CB1 receptor having a leucine at amino acid position 200; cholecystokinin B receptor having a glutamine at amino acid position 224; gamma-amino-butyric acid B receptor having a leucine at amino acid position 93 or a proline at amino acid position 452; thromboxane A2 receptor having a glutamic acid at amino acid position 80 or a valine at amino acid position 94 or a glutamic acid at amino acid position 176; and neuropeptide Y1 receptor having a proline at amino acid position 298.

In various aspects, the substrate includes a number of nucleic acid sequences greater than about 100, greater than about 1000, greater than about 10,000, greater than about 100,000, greater than about 1,000,000, or more. In additional aspects, the substrate includes a polynucleotide that codes for at least a portion of a polypeptide that includes a sequence selected, for example, from: Alpha 1A/C adrenergic receptor having a cysteine residue at amino acid position 43 or a serine at amino acid position 200; Beta 3 adrenergic receptor having a leucine residue at amino acid position 78; D1 dopamine receptor having a proline at amino acid position 37 or an arginine at amino acid position 37 or a serine at amino acid position 79 or an alanine at amino acid position 199; D2 dopamine receptor having an arginine at amino acid position 40 or a leucine at amino acid position 208; D3 dopamine receptor having a leucine at amino acid position 50; H1 histamine receptor having a glycine at amino acid position 216 or a proline at amino acid 226; H2 histamine receptor having an asparagine at amino acid position 175 or a glycine at amino acid position 215 or an arginine at amino acid position 231; 1A serotonin receptor having a valine at amino acid position 50 or an isoleucine at amino acid position 172 or a phenylalanine at amino acid position 381; 1B serotonin receptor having an asparagine at amino acid position 221; 1D serotonin receptor having a leucine at amino acid position 53 or a glycine at amino acid position 366; 1E serotonin receptor having a threonine at amino acid position 44 or a phenylalanine at amino acid position 262; 2B serotonin receptor having a tryptophan at amino acid position 388; serotonin 7 receptor having a lysine at amino acid position 92 or a proline at amino acid position 421; angiotensin 2 type 1 receptor having an arginine at amino acid position 45 or a serine at amino acid position 204 or a tryptophan at amino acid position 289; cannabinoid CB1 receptor having a leucine at amino acid position 200; cholecystokinin B receptor having a glutamine at amino acid position 224; gamma-amino-butyric acid B receptor having a leucine at amino acid position 93 or a proline at amino acid position 452; thromboxane A2 receptor having a glutamic acid at amino acid position 80 or a valine at amino acid position 94 or a glutamic acid at amino acid position 176; neuropeptide Y1 receptor having a proline at amino acid position 298; or subsequences thereof (e.g., from about 10-20, 20-30, 30-50, 50-100 or more nucleotides in length) that contain the variant. In yet additional aspects, the nucleic acid sequences include one or more GPCR sequences, e.g. one or more sequences that are wild type in respect to the variant GPCR nucleotide sequences.

Detection substrates that include a two-dimensional array of polynucleotide sequences of the invention, also referred to herein as "gene chips" or "arrays," and that are useful in the methods of the invention, are comprised of polynucleotide chains (e.g., DNA or RNA or combinations thereof) likely single stranded, or at least single stranded prior to hybridization. Arrays can comprise as few as about 25, 50, 100, 250, 500 or 1000 polynucleotides that are different in one or more nucleotides or 2500, 5000, 10,000, 20,000, 30,000, 40,000, 50,000, 75,000, 100,000, 250,000, 500,000, 1,000,000 or more polynucleotides. The greater the number of polynucleotides on the array representing different gene sequences, the more powerful the assay system. Thus, polynucleotides that hybridize to all or almost all GPCR variants are ideal for screening. However, such comprehensiveness is not required in order to practice the invention. Accordingly, polynucleotide arrays in which all or a subset of the polynucleotides represent or several GPCR variants may be used.

Arrays can have any polynucleotide density; the greater the density the greater the number of genes that can be screened on a given chip size. Density can be as few as 1-10 (e.g., 1, 2, 4, 5, 6, 8, 10) polynucleotides per $cm^2$. Density can be as many as 10-100 (e.g., 10-15, 15-20, 20-30, 30-40, 40-50, 50-60, 60-70, 70-80, 90-100) polynucleotides per cm2 or more. Greater density arrays afford economies of scale.

Purified or isolated variant GPCR polypeptides and fragments thereof that contain the variant amino acid sequence are also provided. Such variant polypeptides are useful for producing antibodies that specifically bind to the polypeptides. Such antibodies are useful for detecting the presence of variant GPCR in a sample. Thus, antibodies that specifically bind to variant GPCRs disclosed herein are further provided.

The term "antibody" refers to a protein that binds to other molecules (antigens) via heavy and light chain variable domains, $V_H$ and $V_L$, respectively. Antibodies include IgG, IgD, IgA, IgM and IgE. The antibodies may be intact immunoglobulin molecules, two full length heavy chains linked by disulfide bonds to two full length light chains, as well as subsequences (i.e. fragments) of immunoglobulin molecules, with our without constant region, that bind to an epitope of an antigen, or subsequences thereof (i.e. fragments) of immunoglobulin molecules, with or without constant region, that bind to an epitope of an antigen. Antibodies may comprise full length heavy and light chain variable domains, $V_H$ and $V_L$, individually or in any combination.

Polypeptide sequences can be produced by recombinant expression from a cell that produces the protein or alternatively, using a chemical synthesizer (see, e.g., Applied Biosystems, Foster City, Calif.). Antibodies and subsequences thereof can be expressed from recombinantly produced antibody-encoding nucleic acid, such as a polynucleotide isolated from hybridoma cells (see, e.g., Harlow and Lane, *Antibodies: A Laboratory Manual*, Cold Spring Harbor Laboratory, 1989; Harlow and Lane, *Using Antibodies: A Laboratory Manual*, Cold Spring Harbor Laboratory, 1999; Fitzgerald et al., *J.A.C.S.* 117:11075 (1995); Gram et al., *Proc. Natl. Acad. Sci. USA* 89:3576-80 (1992)). For antibody subsequences, pepsin or papain digestion of whole antibodies can be used to generate antibody fragments.

As used herein, the term "isolated," when used as a modifier of invention compositions (e.g., polynucleotides, polypeptides, antibodies, etc.), means that the compositions are separated from their naturally occurring in vivo environment. Generally, compositions so separated are substantially free of one or more materials with which they normally associate with in nature, for example, one or more protein, nucleic acid, lipid, carbohydrate, and cell membrane. An "isolated" polypeptide can also be "substantially pure" when free of most or all of the materials with which it normally associate with in nature. Thus, an isolated polypeptide that also is substantially pure does not include polypeptides or polynucleotides present among millions of other sequences, such as antibodies of an antibody library or nucleic acids in a genomic or cDNA library, for example. Purity can be at least about 60% or more by mass. The purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (nucleic acid and peptide).

In another embodiment, a detection substrate includes a two-dimensional array of polypeptide sequences and a substrate; the polypeptide sequences are attached to the substrate at defined positions. In one aspect, the polypeptide sequences attached to the surface of the substrate include one or more polypeptide sequences selected, for example, from: Alpha 1A/C adrenergic receptor having a cysteine residue at amino acid position 43 or a serine at amino acid position 200; Beta 3 adrenergic receptor having a leucine residue at amino acid position 78; D1 dopamine receptor having a proline at amino acid position 37 or an arginine at amino acid position 37 or a serine at amino acid position 79 or an alanine at amino acid position 199; D2 dopamine receptor having an arginine at amino acid position 40 or a leucine at amino acid position 208; D3 dopamine receptor having a leucine at amino acid position 50; H1 histamine receptor having a glycine at amino acid position 216 or a proline at amino acid position 226; H2 histamine receptor having an asparagine at amino acid position 175 or a glycine at amino acid position 215 or an arginine at amino acid position 231;

1A serotonin receptor having a valine at amino acid position 50 or an isoleucine at amino acid position 172 or a phenylalanine at amino acid position 381; 1B serotonin receptor having an asparagine at amino acid position 221; 1D serotonin receptor having a leucine at amino acid position 53 or a glycine at amino acid position 366; 1E serotonin receptor having a threonine at amino acid position 44 or a phenylalanine at amino acid position 262; 2B serotonin receptor having a tryptophan at amino acid position 388; serotonin 7 receptor having a lysine at amino acid position 92 or a proline at amino acid position 421; angiotensin 2 type 1 receptor having an arginine at amino acid position 45 or a serine at amino acid position 204 or a tryptophan at amino acid position 289; cannabinoid CB1 receptor having a leucine at amino acid position 200; cholecystokinin B receptor having a glutamine at amino acid position 224; gamma-amino-butyric acid B receptor having a leucine at amino acid position 93 or a proline at amino acid position 452; thromboxane A2 receptor having a glutamic acid at amino acid position 80 or a valine at amino acid position 94 or a glutamic acid at amino acid position 176; and neuropeptide Y1 receptor having a proline at amino acid position 298. The polypeptides attached to the substrate are useful for detecting molecules that bind to the variant GPCR proteins, such as agonists or antagonists of variant or wild type GPCRs.

The substrates to which the polynucleotides or polypeptides are attached include any impermeable or semi-permeable, rigid or semi-rigid, substance substantially inert so as not to interfere with the use of the array in hybridization reactions. The substrate may be a contiguous two-dimensional surface or may be perforated, for example. Exemplary substrates compatible with hybridization reactions include glass, plastic, polypropylene, polystyrene, nylon, polyacrylamide and nitrocellulose.

Arrays can include one or more polynucleotides for mismatch control or for expression level control. For example, each polynucleotide of the array that represents a known gene, that is, it specifically hybridizes to a GPCR gene transcript or nucleic acid produced from a transcript, can have a mismatch control oligonucleotide. The term "mismatch control" means a sequence that is not perfectly complementary to a particular oligonucleotide. The mismatch may comprise one or more mismatched bases. The mismatch(s) may be located at or near the center of the probe such that the mismatch is most likely to destabilize the duplex with the target sequence under hybridization conditions, but may be located anywhere, for example, a terminal mismatch. The mismatch control typically has a corresponding test probe that is perfectly complementary to the same particular target sequence. Mismatches are selected such that under appropriate hybridization conditions the test or control polynucleotide hybridizes with its target sequence, but the mismatch oligonucleotide does not. Mismatch polynucleotides therefore indicate whether hybridization is specific or not. For example, if the target variant GPCR is present the perfect match polynucleotide should provide a consistently stronger signal than the mismatch oligonucleotide.

Expression levels controls are polynucleotides that hybridize to constitutively expressed genes and may be included. Expression level controls are typically designed to control for cell health. Covariance of an expression level control with the expression of a target gene indicates whether measured changes in expression level of a gene is due to changes in transcription rate of that gene or to general variations in health of the cell. For example, when a cell is in poor health or lacking a critical metabolite the expression levels of both an active target gene and a constitutively expressed gene are expected to decrease. Thus, where the expression levels of an expression level control and the target gene appear to both decrease or to both increase, the change may be attributed to changes in the metabolic activity of the cell, not to differential expression of the target gene. Virtually any constitutively expressed gene is a suitable target for expression level controls. Typically expression level control genes are "housekeeping genes" including, but not limited to -actin gene, transferrin receptor and GAPDH.

Normalization controls are typically unnecessary for detection of GPCR variants as disclosed herein where polynucleotides that specifically hybridize to the target GPCR sequences has already been identified. Thus, the hybridization signal produced by the polynucleotide provides an accurate measure of the concentration of hybridized nucleic acid. Relative differences in gene expression can be detected without the use of such control polynucleotides. Therefore, the inclusion of control polynucleotides is optional.

Polynucleotides can be synthesized directly on the array by sequentially adding nucleotides to a particular position on the substrate until the desired sequence or length is achieved. For example, arrays containing thousands of polynucleotides complementary to particular sequences, at defined locations on a substrate are known (see, e.g., PCT Publication No. WO 90/15070.) and can be made by a variety of techniques known in the art including photolithography (see, Fodor et al., Science 251:767 (1991); Pease et al., Proc. Natl. Acad. Sci. USA 91:5022 (1994); Lockhart et al., Nature Biotech 14:1675 (1996); and U.S. Pat. Nos. 5,578,832; 5,556,752; and 5,510,270). Additional methods for rapid synthesis and deposition of defined oligonucleotides are described in Blanchard et al., Biosensors & Bioelectronics 11:687 (1996). Light-directed chemical coupling, and mechanically directed coupling, as described, for example, in U.S. Pat. No. 5,143,854 and PCT Publication Nos. WO 92/10092 and WO 93/09668 which disclose methods of forming vast arrays of oligonucleotides, peptides and other biomolecules. These procedures for biomolecule array synthesis are now referred to as VLSIPS.TM. procedures (see, also U.S. Pat. No. 6,040,138). U.S. Pat. No. 5,677,195 describes forming polynucleotides or peptides having diverse sequences on a single substrate by delivering various monomers or other reactants to multiple reaction sites on a single substrate where they are reacted in parallel. A series of channels, grooves, or spots are formed on or adjacent and reagents are selectively flowed through or deposited in the channels, grooves, or spots, forming the array on the substrate.

Alternatively, the polynucleotides can first be synthesized and then attached at defined positions on the substrate. Arrays made by first synthesizing the oligonucleotide and then attaching it to the surface of the substrate e.g., using N-phosphonate or phosphoramidite chemistries are described, for example, in Froehler et al., Nucleic Acid Res 14:5399 (1986); and McBride et al., Tetrahedron Lett. 24:245 (1983). In either case, the sequence and position (i.e., address) of all or a subset of the polynucleotides comprising the array will typically be known. The array produced may be redundant with respect to polynucleotide molecules that specifically hybridize to a single GPCR variant.

Any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989), could be used, although, microarrays allow the use of less hybridization reagents and can contain many more oligonucleotides.

Fluorescence emission of sequences hybridized to polynucleotides of an array can be detected by scanning confocal laser microscopy. Using the excitation line appropriate for the fluorophore, or for two fluorophores if used, will produce an emission signal whose intensity correlates with the amount of hybridized sequence. Alternatively, a laser that allows simultaneous specimen illumination at wavelengths specific to the two fluorophores and emissions from the two fluorophores can be used for simultaneously analyzing both (see Schena et al., Genome Research 6:639 (1996)).

In any case, hybridized arrays can be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Alternatively, the fiber-optic bundle described by Ferguson et al. (Nature Biotech. 14:1681 (1996)) may be used to monitor mRNA levels simultaneously. For any particular hybridization site on the array, a ratio of the emission of the two fluorophores may be calculated. The ratio is independent of the absolute expression level of the gene.

The invention provides kits including the polynucleotides that specifically hybridize to a GPCR variant sequence, antibodies that specifically bind to variant GPCR polypeptides and substrates containing the polynucleotides and antibodies, packaged into suitable packaging material. A kit typically includes a label or packaging insert including a description of the components or instructions for use (e.g., detecting the presence of a GPCR variant) in vitro, in vivo, or ex vivo, of the components therein. A kit can contain additional components, e.g., control polynucleotides that specifically hybridize to a GPCR sequence that is wild type in respect to a variant GPCR.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention.

Kits of the invention therefore can additionally include labels or instructions for using the kit components in a method of the invention. Instructions can include instructions for practicing any of the methods of the invention described herein. Thus, for example, a kit can include one or more polynucleotides that specifically hybridize to a GPCR variant sequence(s) together with instructions for screening a subject for the presence of one or more of the GPCR variant sequences, and providing one or more clinical indications for the subject based upon which of the GPCR variant(s) are present in the subject.

The instructions may be on "printed matter," e.g., on paper of cardboard within the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can include each component of the kit enclosed within an individual container and all of the various containers can be within a single package. Invention kits can be designed for cold storage.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "a variant GPCR" includes a plurality of such variant GPCRs and reference to "a polynucleotide that specifically hybridizes to a GPCR variant sequence" includes reference to one or more such polynucleotides, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes assaying the variant GPCR receptor activities.

R-SAT assays were performed with minor modifications from that previously described. In brief, NIH-3T3 cells were grown in 96 well tissue culture plates to 70-80% confluence in Delbecco's Modified Essential Media (DMEM) supplemented with 10% calf serum and 1% penicillin/streptomycin/glutamine (PSG). Cells were transfected for 12-16 hours with plasmid DNAs using Superfect Reagent (Qiagen) as per manufacturer's protocol. R-SAT's were generally performed with 1-50 ng/well of receptor and 20 ng/well of β galactosidase plasmid DNA. After overnight transfection, media was replaced with serum free DMEM containing 2% cyto-sf3 (Kemp Biotechnologies), and 1% PSG and varying concentrations of drug. Cells were then grown in a humidified atmosphere with 5% ambient CO2 for four to six days. Media was then removed from the plates and β-galactosidase activity was measured by the addition of o-nitrophenyl β-d-galactopyranoside (in phosphate buffered saline with 5% NP-40 detergent). The resulting colorimetric reaction was measured in a spectrophotometric plate reader (Titertek) at 420 nM. All data were analyzed using the computer programs Excel Fit and Graph Pad Prism software.

Example 2

This example lists wild type GPCR nucleotide (SEQ ID NOs: 1, 7, 11, 21, 27, 31, 37, 45, 53, 57, 63, 69, 73, 79, 87, 91, 95, 101, 109) and amino acid sequences (SEQ ID NOs:4, 9, 16, 24, 29, 34, 41, 49, 55, 60, 66, 71, 76, 83, 89, 93, 98, 105, 111) and the nucleotide (SEQ ID NOs:2, 3, 8, 12-15, 22, 23, 28, 32, 33, 38-40, 46-48, 54, 58, 59, 64, 65, 70, 74, 75, 80-82, 88, 92, 96, 97, 102-104, 110) and amino acid sequences (SEQ ID NOs:5, 6, 10, 17-20, 25, 26, 30, 35, 36, 42-44, 50-52, 56, 61, 62, 67, 68, 72, 77, 78, 84-86, 90, 94, 99, 100, 106-108, 112) of the 37 variant GPCRs which have biologically functional consequences.

What is claimed is:

1. A method for selecting an appropriate course of treatment for a human who is being treated with or is a candidate for treatment with an agonist of the 1A/C adrenergic receptor, comprising:
   a) providing a sample comprising nucleic acids or proteins from a human who is being treated with or is a candidate for treatment with an agonist of the 1A/C adrenergic receptor;
   b) determining whether the sample from the human comprises a variant alpha 1A/C adrenergic receptor having serine residue at amino acid position 200; and
   c) selecting an appropriate course of treatment using an agonist of the 1A/C adrenergic receptor for said human based on whether said sample comprises said variant alpha 1A/C adrenergic receptor;
   wherein said agonist of the 1A/C adrenergic receptor is selected from the group consisting of phenylephrine, dobutamine, cirazoline and oxymetazoline; and
   wherein said determining step comprises directly determining the nucleotide present at position 1035 of the gene encoding the alpha 1A/C adrenergic receptor or directly determining the amino acid present at position 200 of the alpha 1A/C adrenergic receptor.

2. The method of claim 1, wherein said appropriate course of treatment comprises a treatment selected from the group consisting of:
   administering said agonist of the alpha 1A/C adrenergic receptor if said human does not comprise said variant alpha 1A/C adrenergic receptor;
   selecting a treatment which does not involve administering said agonist of the alpha 1A/C adrenergic receptor if said human does comprise said variant alpha 1A/C adrenergic receptor; and
   selecting and administering a higher dose of said agonist of the alpha 1A/C adrenergic receptor if said human does comprise said variant alpha 1A/C adrenergic receptor.

3. The method of claim 2, wherein said variant alpha 1A/C adrenergic receptor confers in said human a decreased sensitivity to a beneficial physiological effect of said agonist of the alpha 1A/C adrenergic receptor.

4. The method of claim 1, wherein said determining step is selected from the group consisting of determining the nucleotide present at nucleotide position 1035 of the gene encoding ADRA1A by sequencing said gene and determining the nucleotide present at nucleotide position 1035 of the gene encoding ADRA1A by hybridizing a probe to said gene.

* * * * *